US012491265B2

(12) United States Patent
Rodino-Klapac et al.

(10) Patent No.: US 12,491,265 B2
(45) Date of Patent: Dec. 9, 2025

(54) ADENO-ASSOCIATED VIRUS VECTOR DELIVERY OF MUSCLE SPECIFIC MICRO-DYSTROPHIN TO TREAT MUSCULAR DYSTROPHY

(71) Applicant: RESEARCH INSTITUTE AT NATIONWIDE CHILDREN'S HOSPITAL, Columbus, OH (US)

(72) Inventors: Louise Rodino-Klapac, Grove City, OH (US); Jerry R. Mendell, Columbus, OH (US)

(73) Assignee: Research Institute at Nationwide Children's Hospital, Columbus, OH (US)

( * ) Notice: Subject to any disclaimer, the term of this patent is extended or adjusted under 35 U.S.C. 154(b) by 1207 days.

(21) Appl. No.: 17/253,956

(22) PCT Filed: Jun. 17, 2019

(86) PCT No.: PCT/US2019/037489

§ 371 (c)(1),
(2) Date: Dec. 18, 2020

(87) PCT Pub. No.: WO2019/245973

PCT Pub. Date: Dec. 26, 2019

(65) Prior Publication Data

US 2021/0260218 A1 Aug. 26, 2021

Related U.S. Application Data

(60) Provisional application No. 62/860,220, filed on Jun. 11, 2019, provisional application No. 62/823,649, filed on Mar. 25, 2019, provisional application No. 62/752,841, filed on Oct. 30, 2018, provisional application No. 62/740,402, filed on Oct. 2, 2018, provisional application No. 62/686,668, filed on Jun. 18, 2018.

(51) Int. Cl.

| | |
|---|---|
| ***A61K 48/00*** | (2006.01) |
| ***A61P 21/00*** | (2006.01) |
| ***C07K 14/47*** | (2006.01) |
| ***C12N 15/86*** | (2006.01) |

(52) U.S. Cl.

CPC ...... *A61K 48/0058* (2013.01); *A61K 48/0075* (2013.01); *A61P 21/00* (2018.01); *C07K 14/4716* (2013.01); *C12N 15/86* (2013.01)

(58) Field of Classification Search

CPC .................................................. C07K 14/4716

See application file for complete search history.

(56) References Cited

U.S. PATENT DOCUMENTS

| | | | |
|---|---|---|---|
| 5,173,414 | A | 12/1992 | Lebkowski et al. |
| 5,658,776 | A | 8/1997 | Flotte et al. |
| 5,786,211 | A | 7/1998 | Johnson |
| 5,871,982 | A | 2/1999 | Wilson et al. |
| 5,965,542 | A | 10/1999 | Wasan et al. |
| 6,258,595 | B1 | 7/2001 | Gao et al. |
| 6,310,196 | B1 | 10/2001 | Ricigliano et al. |
| 6,566,118 | B1 | 5/2003 | Atkinson et al. |
| 6,869,777 | B2 | 3/2005 | Chamberlain et al. |
| 7,001,761 | B2 | 2/2006 | Xiao |
| 7,282,199 | B2 | 10/2007 | Gao et al. |
| 7,790,449 | B2 | 9/2010 | Gao et al. |
| 8,569,256 | B2 | 10/2013 | Heyes et al. |
| 9,434,928 | B2 | 9/2016 | Mendell et al. |
| 10,166,272 | B2 | 1/2019 | Dickson et al. |
| 10,479,821 | B2 | 11/2019 | Chamberlain et al. |
| 11,338,045 | B2 | 5/2022 | Lochmuller et al. |
| 11,406,717 | B2 | 8/2022 | Rodino-Klapac et al. |
| 2004/0142025 | A1 | 7/2004 | MacLachlan et al. |
| 2005/0017054 | A1 | 1/2005 | Iverson et al. |
| 2005/0064595 | A1 | 3/2005 | MacLachlan et al. |
| 2005/0118253 | A1 | 6/2005 | MacLachlan et al. |
| 2005/0175682 | A1 | 8/2005 | Heyes et al. |
| 2006/0008910 | A1 | 1/2006 | MacLachlan et al. |
| 2006/0083780 | A1 | 4/2006 | Heyes et al. |
| 2006/0194265 | A1 | 8/2006 | Morris et al. |
| 2006/0240093 | A1 | 10/2006 | MacLachlan et al. |
| 2007/0042031 | A1 | 2/2007 | MacLachlan et al. |
| 2008/0044393 | A1 | 2/2008 | White et al. |
| 2008/0249052 | A1 | 10/2008 | Duan et al. |

(Continued)

FOREIGN PATENT DOCUMENTS

| | | | |
|---|---|---|---|
| CA | 2985000 | A1 | 11/2016 |
| CN | 101896186 | A | 11/2010 |

(Continued)

OTHER PUBLICATIONS

Nance et al. (2015, Human Gene Therapy, vol. 26(12), pp. 786-800) (Year: 2015).*

Cleveland Clinic Information Page, 2023—12 page web printout (Year: 2023).*

2005, Lovering et al., Phys. Ther., vol. 85(12), pp. 1372-1388 (Year: 2005).*

Bhosale et al., 2021, Chapter 2, Bhandari Pharmacology, pp. 1-4 (Year: 2021).*

Singh et al. (2022, Drug Delivery and Translational Res., vol. 12, pp. 2613-2633) (Year: 2022).*

(Continued)

*Primary Examiner* — Anoop K Singh
*Assistant Examiner* — David A Montanari
(74) *Attorney, Agent, or Firm* — Foley & Lardner LLP

(57) ABSTRACT

The invention provides gene therapy vectors, such as adeno-associated virus (AAV) vectors, expressing a miniaturized human micro-dystrophin gene and method of using these vectors to express micro-dystrophin in skeletal muscle s including diaphragm and cardiac muscle and to protect muscle fibers from injury, increase muscle strength and reduce and/or prevent fibrosis in subjects suffering from muscular dystrophy.

14 Claims, 30 Drawing Sheets

Specification includes a Sequence Listing.

(56) References Cited

U.S. PATENT DOCUMENTS

| | | | |
|---|---|---|---|
| 2010/0003218 | A1 | 1/2010 | Duan et al. |
| 2010/0130588 | A1 | 5/2010 | Yaworski et al. |
| 2010/0184209 | A1 | 7/2010 | Vermeulen et al. |
| 2011/0060032 | A1 | 3/2011 | MacLachlan et al. |
| 2011/0076335 | A1 | 3/2011 | Yaworski et al. |
| 2011/0091525 | A1 | 4/2011 | Heyes et al. |
| 2011/0117125 | A1 | 5/2011 | Hope et al. |
| 2011/0216622 | A1 | 9/2011 | MacLachlan et al. |
| 2011/0262527 | A1 | 10/2011 | Heyes et al. |
| 2011/0311582 | A1 | 12/2011 | Manoharan et al. |
| 2011/0311583 | A1 | 12/2011 | Manoharan et al. |
| 2012/0027803 | A1 | 2/2012 | Manoharan et al. |
| 2012/0058188 | A1 | 3/2012 | MacLachlan et al. |
| 2012/0172411 | A1 | 7/2012 | Heyes et al. |
| 2012/0183581 | A1 | 7/2012 | Yaworski et al. |
| 2012/0295832 | A1 | 11/2012 | Constien et al. |
| 2013/0017223 | A1 | 1/2013 | Hope et al. |
| 2013/0022649 | A1 | 1/2013 | Yaworski et al. |
| 2013/0086373 | A1 | 4/2013 | Rothkopf et al. |
| 2013/0123338 | A1 | 5/2013 | Heyes et al. |
| 2013/0195920 | A1 | 8/2013 | Maier et al. |
| 2013/0245107 | A1 | 9/2013 | De Fougerolles et al. |
| 2013/0323269 | A1 | 12/2013 | Manoharan et al. |
| 2013/0338210 | A1 | 12/2013 | Manoharan et al. |
| 2014/0200257 | A1 | 7/2014 | Rajeev et al. |
| 2014/0234255 | A1 | 8/2014 | Lai et al. |
| 2014/0256802 | A1 | 9/2014 | Boye et al. |
| 2014/0308304 | A1 | 10/2014 | Manoharan et al. |
| 2015/0005363 | A1 | 1/2015 | Ansell et al. |
| 2015/0203446 | A1 | 7/2015 | Manoharan et al. |
| 2015/0265708 | A1 | 9/2015 | Manoharan et al. |
| 2015/0273068 | A1 | 10/2015 | Maier et al. |
| 2015/0368647 | A1 | 12/2015 | Croce et al. |
| 2016/0009637 | A1 | 1/2016 | Manoharan et al. |
| 2016/0199485 | A1 | 7/2016 | Manoharan et al. |
| 2016/0317680 | A1 | 11/2016 | Liu et al. |
| 2017/0088837 | A1 | 3/2017 | Singer et al. |
| 2017/0368198 | A1 | 12/2017 | Xiao et al. |
| 2018/0250423 | A1 | 9/2018 | Martin |
| 2019/0117795 | A1 | 4/2019 | Rodino-Klapac et al. |
| 2019/0167762 | A1 | 6/2019 | Dickson et al. |

FOREIGN PATENT DOCUMENTS

| | | | |
|---|---|---|---|
| CN | 102459595 | A | 5/2012 |
| CN | 104520428 | A | 4/2015 |
| CN | 105324392 | A | 2/2016 |
| CO | 2018012084 | A2 | 2/2019 |
| CO | 2019000395 | A2 | 4/2019 |
| CO | 2021000227 | A2 | 1/2021 |
| EA | 201592014 | A1 | 6/2016 |
| JP | 11-512297 | A | 10/1999 |
| JP | 11-318467 | A | 11/1999 |
| JP | 2010-535247 | A | 11/2010 |
| JP | 2014-198728 | A | 10/2014 |
| WO | 1995/13365 | A1 | 5/1995 |
| WO | 1995/13392 | A1 | 5/1995 |
| WO | 1996/17947 | A1 | 6/1996 |
| WO | 1997/06243 | A1 | 2/1997 |
| WO | 1997/08298 | A1 | 3/1997 |
| WO | 1997/09441 | A2 | 3/1997 |
| WO | 1997/11190 | A2 | 3/1997 |
| WO | 1997/21825 | A1 | 6/1997 |
| WO | 1998/09657 | A2 | 3/1998 |
| WO | WO-99/09076 | A1 | 2/1999 |
| WO | 1999/11764 | A2 | 3/1999 |
| WO | WO-99/39741 | A2 | 8/1999 |
| WO | WO-01/07548 | A1 | 2/2001 |
| WO | 2001/83692 | A2 | 11/2001 |
| WO | 2002/06495 | A2 | 1/2002 |
| WO | 2002/53703 | A2 | 7/2002 |
| WO | WO-2008/014478 | A2 | 1/2008 |
| WO | WO-2008/066965 | A2 | 6/2008 |
| WO | 2008/088895 | A2 | 7/2008 |
| WO | 2009/018493 | A1 | 2/2009 |
| WO | WO-2009/054725 | A2 | 4/2009 |
| WO | 2010/071454 | A1 | 6/2010 |
| WO | WO-2010/123369 | A1 | 10/2010 |
| WO | WO-2011/004395 | A1 | 1/2011 |
| WO | WO-2011/141705 | A1 | 11/2011 |
| WO | WO-2011/143201 | A2 | 11/2011 |
| WO | 2013/016352 | A1 | 1/2013 |
| WO | WO-2013/016058 | A1 | 1/2013 |
| WO | WO-2013/016126 | A1 | 1/2013 |
| WO | 2013/078316 | A1 | 5/2013 |
| WO | WO-2013/086322 | A1 | 6/2013 |
| WO | WO-2013/086373 | A1 | 6/2013 |
| WO | 2013/102904 | A1 | 7/2013 |
| WO | WO-2013/123503 | A1 | 8/2013 |
| WO | WO-2014/008334 | A1 | 1/2014 |
| WO | WO-2014/172669 | A1 | 10/2014 |
| WO | 2015/107340 | A1 | 7/2015 |
| WO | 2015/110449 | A1 | 7/2015 |
| WO | 2015/161255 | A1 | 10/2015 |
| WO | 2015/197232 | A1 | 12/2015 |
| WO | 2015/197869 | A1 | 12/2015 |
| WO | WO-2015/199952 | A1 | 12/2015 |
| WO | WO-2016/025339 | A2 | 2/2016 |
| WO | 2016/115543 | A2 | 7/2016 |
| WO | 2016/177911 | A1 | 11/2016 |
| WO | WO-2017/004143 | A1 | 1/2017 |
| WO | WO-2017/049031 | A1 | 3/2017 |
| WO | WO-2017/075531 | A1 | 5/2017 |
| WO | WO-2017/083776 | A1 | 5/2017 |
| WO | WO-2017/117528 | A1 | 7/2017 |
| WO | 2017/165859 | A1 | 9/2017 |
| WO | 2017/180976 | A1 | 10/2017 |
| WO | 2017/181011 | A1 | 10/2017 |
| WO | 2017/181014 | A1 | 10/2017 |
| WO | 2017/181015 | A1 | 10/2017 |
| WO | 2017/221145 | A1 | 12/2017 |
| WO | WO-2018/170408 | A1 | 9/2018 |
| WO | WO-2019/015474 | A1 | 1/2019 |
| WO | WO-2019/018439 | A1 | 1/2019 |
| WO | WO-2019/078916 | A1 | 4/2019 |
| WO | WO-2019/089828 | A1 | 5/2019 |
| WO | WO-2019/118806 | A1 | 6/2019 |
| WO | WO-2019/152474 | A1 | 8/2019 |
| WO | WO-2019/177550 | A1 | 9/2019 |
| WO | WO-2019/195362 | A1 | 10/2019 |
| WO | WO-2019/209777 | A1 | 10/2019 |
| WO | 2019/245973 | A1 | 12/2019 |
| WO | WO-2020/006458 | A1 | 1/2020 |
| WO | WO-2020/081938 | A1 | 4/2020 |
| WO | WO-2020/123645 | A1 | 6/2020 |
| WO | WO-2020/176614 | A1 | 9/2020 |
| WO | WO-2021/035120 | A1 | 2/2021 |
| WO | WO-2021/257497 | A1 | 12/2021 |

OTHER PUBLICATIONS

Chamberlain et al. (2022, Human Gene Therapy, vol. 34(9/10), pp. 404-415) (Year: 2022).*

Gupta et al., Codon optimization, Project Report, 1-11 (2003).

Ambros, MicroRNA pathways in flies and worms: growth, death, fat, stress, and timing, Cell. 113:673-6 (2003).

Cacchiarelli et al., MicroRNAs involved in molecular circuitries relevant for the Duchenne muscular dystrophy pathogenesis are controlled by the dystrophin/nNOS pathway, Cell Metab. 12:341-51 (2010).

Chicoine et al., Plasmapheresis Eliminates the Negative Impact of AAV Antibodies on Microdystrophin Gene Expression Following Vascular Delivery, Mol. Ther. 22(2): 338-347 (2014).

Cushing et al., miR-29 is a major regulator of genes associated with pulmonary fibrosis, Am. J. Respir. Cell. Mol. Biol. 45:287-94 (2011).

Eisenberg et al. Distinctive Patterns of microRNA Expression in Primary Muscular Disorders, Proc. Natl. Acad. Sci. USA. 104:17016-21 (2007).

European Application No. 17783236, European Search Report and Opinion, mailed Oct. 24, 2019.

Extended European Search Report, Application No. 17783236.7 dated Oct. 24, 2019.

(56) References Cited

OTHER PUBLICATIONS

Foster et al., Codon and mRNA sequence optimization of microdystrophin transgenes improves expression and physiological outcome in dystrophic mdx mice following AAV2/8 gene transfer, Mol. Ther. 16(11):1825-1832 (2008).
Genbank Accession No. AF085716, Adena-associated virus 5 DNA binding trs helicase (Rep22) and capsid protein (VP1) aenes, complete eds. (1999).
GenBank Accession No. AX753246, Version AX753246, Sequence 1 from Patent EP1310571, located at < https://www.ncbi.nlm.nih.gov/nuccore/AX753246 > (2003).
Genbank Accession No. AX753249, Sequence 4 from Patent EP1310571, (2003).
Genbank Accession No. NC_001729, Adena-associated virus - 3, complete genome (2018).
GenBank Accession No. NC_001829, Version NC_001829, Adeno-associated virus-4, complete genome, located at < https://www.ncbi.nlm.nih.gov/nuccore/NC_001829 > (2018).
GenBank Accession No. NC_001862, Version NC_001862, Adeno-associated virus 6, complete genome, located at < https://www.ncbi.nlm.nih.gov/nuccore/NC_001862.1?report=genbank > (2004).
GenBank Accession No. NC_002077, Version NC_002077, Adeno-associated virus-1, complete genome, located at < https://www.ncbi.nlm.nih.gov/nuccore/NC_002077 > (2018).
Guan et al., Gene therapy in monogenic congenital myopathies, Methods. 99:91-8 (2015).
Hakim et al., Monitoring murine skeletal muscle function for muscle gene therapy, Methods. Mol. Biol. 709:75-89 (2011).
Hayashita-Kinoh et al., Intra-Amniotic rAAV-Mediated Microdystrophin Gene Transfer Improves Canine X-Linked Muscular Dystrophy and May Induce Immune Tolerance, Mol. Ther. 23(4):627-637 (2015).
Heller et al., MicroRNA-29 and Micro-Dystrophin Combinatorial Therapy Suppresses Fibrosis and Restores Function to mdx/utm+/- Mice, Mol. Ther. 24(1): S151 (2016).
Heller et al., MicroRNA-29 overexpression by adeno-associated virus suppresses fibrosis and restores muscle function in combination with micro-dystrophin, JCI Insight. 2(9): 1-13 (2017).
International Application No. PCT/US17/27630, International Preliminary Report on Patentability, mailed Oct. 25, 2018.
International Application No. PCT/US17/27630, International Search Report and Written Opinion, mailed Jul. 14, 2017.
International Application No. PCT/US17/27636, International Preliminary Report on Patentability, mailed Oct. 25, 2018.
International Application No. PCT/US17/27636, International Search Report and Written Opinion, mailed Jul. 5, 2017.
International Application No. PCT/US2018/022853, International Preliminary Report on Patentability, mailed May 28, 2020, 14 pages.
International Application No. PCT/US2018/022853, International Search Report and Written Opinion, mailed Jun. 6, 2018, 12 pages.
International Application No. PCT/IB18/001201, International Preliminary Report on Patentability, dated Sep. 26, 2019.
International Application No. PCT/US18/22881, International Preliminary Report on Patentability, dated Jan. 7, 2020.
International Application No. PCT/US2017/027635, International Preliminary Report on Patentability, dated Oct. 16, 2018.
International Application No. PCT/IB2018/001201, International Search Report and Written Opinion, dated Feb. 5, 2019.
International Application No. PCT/US18/22881, International Search Report and Written Opinion, dated May 22, 2018, 12 pages.
International Application No. PCT/US2017/027635, International Search Report and Written Opinion, dated Jul. 19, 2017.
Jaynes et al., Transcriptional Regulation of the Muscle Creatine Kinase Gene and Regulated Expression in Transfected Mouse Myoblasts, Mol. Cell. Biol. 6(8): 2855-64 (1986).
Jiang et al., MicroRNAs and the regulation of fibrosis, FEBS J. 277:2015-2021 (2010).
Kawecka et al., Adeno-Associated Virus (AAV) Mediated Dystrophin Gene Transfer Studies and Exon Skipping Strategies for Duchenne Muscular Dystrophy (DMD), Curr. Gene. Ther. 15(4):395-415 (2015).
Kim et al., microRNA-directed cleavage of ATHB15 mRNA regulates vascular development in *Arabidopsis* inflorescence stems, Plant J. 42:84-94 (2005).
Koo et al., Long-term functional adeno-associated virus-microdystrophin expression in the dystrophic CXMDj dog, J. Gene. Med. 13(9):497-506 (2011).
Kriegel et al., The miR-29 family: genomics, cell biology, and relevance to renal and cardiovascular injury, Physiological Genomics. 44:237-244 (2012).
Lederfein et al., Kilodalton Protein is a Major Product of the Duchenne Muscular Dystrophy Gene in Brain and Other Nonmuscle Tissues, Proc. Natl. Acad. Sci. USA. 89(12):5346-5350 (1992).
Meadows et al., Reducing skeletal muscle fibrosis with AAV-Oelivered miR-29 (P04.089), Neurology. 78:1-2 (2012).
Mendell et al., Evidence-based path to newborn screening for Ouchenne muscular dystrophy, Ann. Neural. 71:304-13 (2012).
Naso et al., Adeno-associated virus (AAV) as a vector for gene therapy, Bio. Drugs. 31:317-334 (2017).
Roderburg et al., Micro-RNA profiling reveals a role for miR-29 in human and murine liver fibrosis, Hepatology. 53:209-18 (2011).
Rooij et al., Dysregulation of microRNAs after myocardial infarction reveals a role of miR-29 in cardiac fibrosis, Proc. Natl. Acad. Sci. USA. 105:13027-32 (2008).
Pozsgai et al., Systemic AAV-mediated (Beta)-sarcoglycan delivery targeting cardiac and Skeletal muscle ameliorates histological and functional deficits in LGMD2E mice, Mol. Ther., 25(4):855-869 (2017).
Rafael et al., Skeletal muscle-specific expression of a utrophin transgene rescues utrophin-dystrophin deficient mice, Nat. Genet., 19:79-82 (1998).
Rodino-Klapac et al., A translational approach for limb vascular delivery of the micro-dystrophin gene without high volum or high pressure for treatment of Duchenne muscular dystrophy, J. Transl. Med., 5:45 (2007).
Rodino-Klapac et al., Micro-dystrophin and follistatin co-delivery restores muscle function in aged DMD model, Human Molecular Genetics., 22(24):4929-4937 (2013).
Rodino-Klapac et al., Persistent expression of Flag-tagged micro dystrophin in nonhuman primates following intramuscular and vascular delivery, Mol. Ther., 18:109-117 (2010).
Ruffing et al., Mutations in the carboxy terminus of adeno-associated virus 2 capsid proteins affect viral infectivity: Lack of an RGD integrin-binding motif, J. Gen. Virol., 75:3385-3392 (1994).
Sacco et al., Short telomeres and stem cell exhaustion model Duchenne muscular dystrophy in mdx/mTR mice, Cell., 143:1059-1071 (2010).
Salva et al., Design of tissue-specific regulatory cassettes for high-level rAAV-mediated expression in skeletal and cardiac muscle, Mol. Ther., 15(2):320-329 (2007).
Sambrook et al., Molecular cloning: A laboratory manual, 2nd Ed., Cold Spring Harbor Laboratory (1989).
Samulski et al., A recombinant plasmid from which an infectious adeno-associated virus genome can be excised in vitro and its use to study viral replication, J. Virol., 61(10):3096-3101 (1987).
Samulski et al., Cloning of adeno-associated virus into pBR322: rescue of intact virus from the recombinant plasmid in human cells, Proc. Natl. Acad. Sci. U.S.A., 79(6):2077-2081 (1982).
Samulski et al., Helper-free stocks of recombinant adeno-associated viruses: normal integration does not require viral gene expression, J. Virol., 63(9):3822-3828 (1989).
Schenpp et al., Highly purified recombinant adeno-associated virus vectors, Methods Mol. Med., 69:427-443 (2002).
Semenza et al., Hypoxia-inducible nuclear factors bind to an enhancer element located 3' to the human erythropoietin gene, Proc. Natl. Acad. Sci. U.S.A., 88(13):5680-5684 (1991).
Senapathy et al., Molecular cloning of adeno-associated virus variant genomes and generation of infectious virus by recombination in mammalian cells, J. Biol. Chem., 259:4661-4666 (1984).

(56) References Cited

OTHER PUBLICATIONS

Sicinski et al., The molecular basis of muscular dystrophy in the mdx mouse: a point mutation, Science, 244:1578-80 (1989).
Sondergaard et al., AAV. Dysferlin overlap vectors restore function in dysferlinopathy animal models, Annals of Clinical and Translational Neurology, 2:256-270 (2015).
Squire et al., Prevention of pathology in mdx mice by expression of utrophin: analysis using an inducible transgenic expression system, Hum. Mol. Genet., 11(26):3333-3344 (2002).
Srivastava et al., Nucleotide sequence and organization of the adeno-associated virus 2 genome, J. Virol., 45:555-564 (1983).
Stedman et al., The mdx mouse diaphragm reproduces the degenerative changes of duchenne muscular dystrophy, Nature, 352:536-539 (1991).
Straub et al., Muscular dystrophies and the dystrophinglycoprotein complex, Curr. Opin. Neurol., 10:168-175 (1997).
Tinsley et al., Expression of full-length utrophin prevents muscular dystrophy in mdx mice, Nat. Med., 4(2):1441-1444 (1998).
Tinsley et al., Primary structure of dystrophin-related protein, Nature, 360:591-593 (1992).
Tratschin et al., A human parvovirus, adeno-associated virus, as a eucaryotic vector: transient expression and encapsidation of the procaryotic gene for chloramphenicol acetyltransferase, Mol. Cell. Biol., 4(10):2072-2081 (1984).
Tratschin et al., Adeno-associated virus vector for high-frequency integration, expression, and rescue of genes in mammalian cells, Mol. Cell. Biol., 5(11):3251-3260 (1985).
Wallace et al., Mechanisms of muscle degeneration, regeneration, and repair in the muscular dystrophies, Annu. Rev. Physiol., 71:37-57 (2009).
Weintraub et al., The myoD gene family: nodal point during specification of the muscle cell lineage, Science, 251:761-766 (1991).
Xiao et al., Efficient long-term gene transfer in to muscle tissue of immunocompetent mice by adeno-associated virus vector, J. Virol., 70:8098-8108 (1996).
Xiao et al., Production of high-titer recombinant adeno-associated virus vectors in the absence of helper adenovirus, J. Virol., 72(3):2224-2232 (1998).
Zhou et al., Haploinsufficiency of utrophin gene worsens skeletal muscle inflammation and fibrosis in mdx mice, J. Neurol. Sci., 264:106-111 (2008).
Zhou et al., Targeting fibrosis in duchenne muscular dystrophy, J. Neuropathol. Exp. Neurol., 69(8):771-776 (2010).
Clemens et al., Recombinant truncated dystrophin minigenes: construction, expression, and adenoviral delivery, Hum. Gene Ther., 6:1477-1485 (1995).
Dong et al., Quantitative analysis of the packaging capacity of recombinant adeno-associated virus, Human Gene Therapy, 7:2101-2112 (1996).
Douglas Ingram, JP Morgan 39th Annual Healthcare Conference, Jan. 11, 2021.
Harper et al., Modular flexibility of dystrophin: implications for gene therapy of duchenne muscular dystrophy, Nat. Med., 8:253-261 (2002).
Hartigan-O'Connor et al., Progress toward gene therapy of duchenne muscular dystrophy, Seminars in Neurology, 19(3):323-332 (1999).
Hauser et al., Functional analysis of truncated dystrophin minigenes in the muscles of mdx mice, Abstract 2081, the American Journal of Human Genetics, S61(4) (1997).
Heller et al., Alternative to gene replacement for duchenne muscular dystrophy using human alpha7 integrin (ITGA7), Doctoral dissertation, Abstract only, 1-2 (2014).
Martin, Translational Studies of GALGT2 Gene Therapy for Duchenne Muscular Dystrophy, Annual Report, Approved for Public Release Distribution Unlimited the Research Institute at Nationwide Children's Hospital Columbus, (2013).
Mauro et al., A critical analysis of codon optimization in human therapeutics, Trends in Molecular Medicine, 20(11):604-13 (2014).
Mendell et al, A randomized, double blind, placebo-controlled, gene-delivery clinical trial of rAAVrh74.MHCK7 micro-dystrophin for Duchenne muscular dystrophy; ASGCT Virtual Annual Meeting, (2021).
Phelps et al., Expression of full-length and truncated dystrophin mini-genes in transgenic mdx mice, Human Molecular Genetics, 4(8):1251-1258 (1995).
Recan et al., Are cysteine-rich and COOH-terminal domains of dystrophin critical for sarcolemmal localization?, J. Clin. Invest., 89:712-716 (1992).
Rodino-Klapac et al., Development of AAVrh74 Micro-dystrophin gene transfer therapy for duchenne, Muscular dystrophy association (MDA) Virtual Clinical and Scientific Conference, (2021).
Sakamoto et al., Micro-dystrophin cDNA ameliorates dystrophic phenotypes when introduced into mdx mice as a transgene, Biochem. and Biophysical Research Comm., 293:1265-1272 (2002).
Wang et al., Adena-associated virus vector carrying human minidystrophin genes effectively ameliorates muscular dystrophy in mdx mouse model, PNAS, 97:13714-13719 (2000).
Wells et al., Expression of human full-length and minidystrophin in transgenic rndx mice: implications for gene therapy of duchenne muscular dystrophy, Hum. Mol. Gene., 4(8):1245-2250 (1995).
Yuasa et al., Effective restoration of dystrophin-associated proteins in vivo by adenovirus-mediated transfer of truncated dystrophin cDNAs, FEBS Letters, 425:329-336 (1998).
Aartsma-Rus et al., Entries in the Leiden Duchenne muscular dystrophy mutation database: an overview of mutation types and paradoxical cases that confirm the reading-frame rule, Muscle Nerve, 34(2):135-144 (2006).
Athanasopoulos et al., Codon optimization of the microdystrophin gene for Duchene muscular dystrophy gene therapy, Method Mol. Biol., 709:21-37 (2010).
Buskin et al., Identification of a myocyte nuclear factor that binds to the muscle-specific enhancer of the mouse muscle creatine kinase gene, Mol. Cell Biol., 9(6):2627-2640 (1989).
Calvo et al., Fiber-Type-Specific Transcription of the Troponin I Slow Gene Is Regulated by Multiple Elements, Molecular and Cellular Biology, 19(1):515-525 (1999).
Duan, Systemic AAV micro-dystrophin gene therapy for Duchenne muscular dystrophy, Jul. 18, 2018, Mol. Ther., 2337-2356, 26(1).
Fumoto et al., Targeted Gene Delivery: Importance of Administration Routes, Novel Gene Therapy Approaches, Chapter 1:3-31 (2013).
Gupta, Project Report, 2003 (https://www.guptalab.org/shubhg/pdf/shubhra_codon.pdf).
Hagstrom et al., Improved muscle-derived expression of human coagulation factor IX from a skeletal actin/CMV hybrid enhancer/promoter, Blood, 95:2536-2542 (2000).
Handbook of pharmaceutical excipients, 6th ed. / R.C. Rowe, P.J. Sheskey, M.E. Quinn (eds.) Pharmaceutical Press; American Pharmacists Association, 2009, 888 p. is accessible at: http://repositorio.ub.edu.ar/bitstream/handle/123456789/5143/handbook-of-pharmaceutical-excipients-6th-edition.pdf.
Liu et al., Adeno-associated virus type 4 (AAV4) targets ependyma and astrocytes in the subventricular zone and RMS, Gene. Therapy, 12:1503-1508 (2005).
Madigan et al., Engineering AAV receptor footprints for gene therapy, Curr. Opin. Virol., 18:89-96 (2016).
Molkentin et al., Alpha-myosin heavy chain gene regulation: delineation and characterization of the cardiac muscle-specific enhancer and muscle-specific promoter, J. Mol. Cell. Cardiol., 28:1211-1225 (1996).
Pleger et al., Stable Myocardial-Specific AAV6-S100A1 Gene Therapy Results in Chronic Functional Heart Failure Rescue, Circulation, 115:2506-2515 (2007).
Polyak et al., Identification of adeno-associated viral vectors suitable for intestinal gene delivery and modulation of experimental colitis, Am. J. Physiol. Gastrointest Liver Physiol., 302:G296-G308 (2012).
Sartorelli et al., Muscle-Specific Gene Expression a Comparison of Cardiac and Skeletal Muscle Transcription Strategies, Circulation Research, 72(5):925-931 (1993).

(56) References Cited

OTHER PUBLICATIONS

Schmidt et al., Adeno-associated virus type 12 (AAV12): a novel AAV serotype with sialic acid- and heparan sulfate proteoglycan-independent transduction activity, J. Virol., 82:1399-1406 (2008).
Semenza et al., Hypoxia-inducible nuclear factors bind to an enhancer element located 3' to the human erythropoietin gene, Proc. Natl. Acad. Sci. USA, 88:5680-5684 (1991).
Sondergaard et al., AAV.Dysferlin Overlap Vectors Restore Function in Dysferlinopathy Animal Models, Annals of Clinical and Transiational Neurology, 2(3):256-270 (2015).
Takeda, Gene therapy for muscular dystrophy, No to Hattatsu, 36(2):117-23 (2004).
Tanaka et al., A developmentally regulated switch from stem cells to dedifferentiation for limb muscle regeneration in newts, Nature Communications, 7:11069 (2016).
Wang et al., ?. , Systemic human minidystrophin gene transfer improves functions and life span of dystrophin and dystrophin/utrophin-deficient mice, J. Orthop. Res., 27(4):421-426 (2009).
Wang et al., Construction and analysis of compact muscle-specific promoters for AAV vectors, Gene. Therapy, 15:1489-1499 (2008).
Yin et al., Intravitreal Injection of AAV2 Transduces Macaque Inner Retina, Invest. Ophthalmol. Vis. Sci., 52(5):2775-2783 (2011).
Yoshimura et al., AAV Vector-Mediated Microdystrophin Expression in a Relatively Small Percentage of mdx Myofibers Improved the mdx Phenotype, Molecular Therapy, 10(5):821-828 (2004).
Zotova et al., Analysis of phenotype expressions of deletions in the dystrophin gene in terms of efficiency of exon skipping as a method for treatment of hereditary dystrophinopathies, Vestnik RGMU, 3:23-29 (2016).
Anderson et al., Nucleic acid hybridisation: A practical approach, Ch. 4, IRL press limited (Oxford, England).
Bulfield et al., X chromosome-linked muscular dystrophy (mdx) in the mouse, Proc. Natl. Acad. Sci. U.S.A., 81:1189-1192 (1984).
Carnwath et al., Muscular dystrophy in the mdx mouse: histopathology of the soleus and extensor digitorum longus muscles, J. Neurol. Sci., 80:39-54 (1987).
Carter, Adeno-associated virus vectors, Current Opinions in Biotechnology, 3(5):533-539 (1992).
Chao et al., Several log increase in therapeutic transgene delivery by distinct adeno-associated viral serotype vectors, Mol. Ther., 2:619-623 (2000).
Chao et al., Sustained and complete phenotype correction of hemophilia B mice following intramuscular injection of AAV1 serotype vectors, Mol. Ther., 4:217-222 (2001).
Clark et al., A stable cell line carrying adenovirus-inducible rep and cap genes allows for infectivity titration of adeno-associated virus vectors, Gene. Therapy, 3(12):1124-1132 (1996).
Clark et al., Highly purified recombinant adeno-associated virus vectors are biologically active and free of detectable helper and wild-type viruses, Hum. Gene. Ther., 10(6):1031-1039 (1999).
Clark et al., Recombinant adeno-associated viral vectors mediate long-term transgene expression in muscle, Hum. Gene. Ther., 8:659-669 (1997).
Coulton et al., The mdx mouse skeletal muscle myopathy: I. A histological, morphometric and biochemical investigation, Neuropathol. Appl. Neurobiol., 14:53-70 (1988).
Cserjesi et al., Myogenin induces the myocyte-specific enhancer binding factor MEF-2 independently of other muscle-specific gene products, Mol. Cell. Biol., 11(10):4854-4862 (1991).
Cullen et al., Ultrastructure of the skeletal muscle in the X chromosome-linked dystrophic (mdx) mouse comparison with duchenne muscular dystrophy, Acta. Neuropathol., 11:69-81 (1988).
De et al., High levels of persistent expression of alpha1-antitrypsin mediated by the nonhuman primate serotype rh.10 adeno-associated virus despite preexisting immunity to common human adeno-associated viruses, Mol. Ther., 13(1):67-76 (2006).
Deconinck et al., Utrophin-dystrophin-deficient mice as a model for duchenne muscular dystrophy, Cell., 90:717-727 (1997).
Desguerre et al., Endomysial fibrosis in duchenne muscular dystrophy: a marker of poor outcome associated with macrophage alternative activation, J. Neuropathol. Exp. Neurol., 68(7):762-773 (2009).
Diprimio et al., Adena-associated virus for the treatment of muscle diseases: toward clinical trials, Curr. Opin. Mol. Ther., 12:553-560 (2010).
Dupont-Versteegden et al., Differential expression of muscular dystrophy in diaphragm versus hindlimb muscles of mdx mice, Muscle Nerve., 15:1105-1110 (1992).
Flotte et al., Gene Expression from Adeno-associated Virus Vectors in Airway Epithelial Cells, Am. J. Respir. Cell Mol. Biol., 7:349-356, (1992).
Franz et al., Association of nonsense mutation of dystrophin gene with disruption of sarcoglycan complex in X-linked dilated cardiomyopathy, Lanc., 355(9217):1781-1785 (2000).
Gao et al., Clades of adeno-associated viruses are widely disseminated in human tissues, J. Virol., 78:6381-6388 (2004).
Grady et al., Skeletal and cardiac myopathies in mice lacking utrophin and dystrophin: a model for duchenne muscular dystrophy, Cell., 90:729-738 (1997).
Grose et al., Homologous recombination mediates functional recovery of dysferlin deficiency following AA VS gene transfer, PloS One, 7(6):e39233 (2012).
Gutpell et al., Skeletal muscle fibrosis in the mdx/utrn+/- mouse validates Its suitability as a murine model of duchenne muscular dystrophy, PloS One, 10:e0117306 (2015).
Harper et al., Modular flexibility of dystrophin: implications for gene therapy of Duchenne muscular dystrophy, Nature Medicine, 8(3):253-261 (2002).
Hermonat et al., Use of adeno-associated virus as a mammalian DNA cloning vector: transduction of neomycin resistance into mammalian tissue culture cells, Proc. Natl. Acad. Sci. U.S.A., 81(20):6466-6470 (1984).
Herzog et al., Stable gene transfer and expression of human blood coagulation factor IX after intramuscular injection of recombinant adeno-associated virus, Proc. Natl. Acad. Sci. U.S.A., 94(11):5804-5809 (1997).
Hoffman et al., Dystrophin: the protein product of the Duchenne muscular dystrophy locus, Cell., 51:919-928 (1987).
International Application No. PCT/US19/037489, International Search Report and Written Opinion, mailed Sep. 6, 2019.
International Application No. PCT/US19/37489, International Preliminary Report on Patentability, mailed Dec. 30, 2020.
Johnson et al., Muscle creatine kinase sequence elements regulating skeletal and cardiac muscle expression in transgenic mice, Mol. Cell. Biol., 9(8):3393-3399 (1989).
Kessler et al., Gene delivery to skeletal muscle results in sustained expression and systemic delivery of a therapeutic protein, Proc. Nat. Acad. Sc. U.S.A., 93:14082-14087 (1996).
Laughlin et al., Cloning of infectious adeno-associated virus genomes in bacterial plasmids, Gene., 23(1):65-73 (1983).
Lebkowski et al., Adena-associated virus: a vector system for efficient introduction and integration of DNA into a variety of mammalian cell types, Mol. Cell. Biol., 7:3988-96 (1988).
Lewis et al., Generation of neutralizing activity against human immunodeficiency virus type 1 in serum by antibody gene transfer, J. Virol., 76:8769-8775 (2002).
Liu et al., Adena-associated virus-mediated micro-dystrophin expression protects young mdx muscle from contraction-induced injury, Mol. Ther., 11(2):245-256 (2005).
Love et al., An autosomal transcript in skeletal muscle with homology to dystrophin, Nature, 339:55-58 (1989).
Mader et al., A steroid-inducible promoter for the controlled overexpression of cloned genes in eukaryotic cells, Proc. Natl. Acad. Sci. U.S.A., 90(12):5603-5607 (1993).
Marsic et al., Vector design tour de force: integrating combinatorial and rational approaches to derive novel adeno-associated virus variants, Mol. Ther., 22(11):1900-1909 (2014).
McLaughlin et al., Adeno-associated virus general transduction vectors: analysis of proviral structures, J. Virol., 62(6):1963-73 (1988).

(56) References Cited

OTHER PUBLICATIONS

Mendell et al., A phase 1/2a follistatin gene therapy trial for becker muscular dystrophy, Molecular Therapy : The Journal of the American Society of Gene Therapy, 23(1):192-201 (2015).
Mendell et al., Limb-girdle muscular dystrophy type 2D gene therapy restores alpha-sarcoglycan and associated proteins., Ann. Neurol., 66(3):290-297 (2009).
Mendell et al., Sustained alpha-sarcoglycan gene expression after gene transfer in limb-girdle muscular dystrophy, type 2D, Ann. Neurol., 68:629-638 (2010).
Mori et al., Two novel adeno-associated viruses from cynomolgus monkey: pseudotyping characterization of capsid protein, Virology, 330(2):375-383 (2004).
Mulieri et al., Protection of human left ventricular myocardium from cutting injury with 2,3-butanedione monoxime, Circ. Res., 65(5):1441-1449 (1989).
Murphy et al., Long-term correction of obesity and diabetes in genetically obese mice by a single intramuscular injection of recombinant adeno-associated virus encoding mouse leptin, Proc. Natl. Acad. Sci. U.S.A., 94:13921-13926 (1997).
Muscat et al., Multiple 5'-flanking regions of the human alpha-skeletal actin gene synergistically modulate muscle-specific expression, Mol. Cell Biol., 7(11):4089-4099 (1987).
Muzyczka, Use of adeno-associated virus as a general transduction vector for mammalian cells, Current topics in Microbiology and Immunology, 158:97-129 (1992).
Nevo et al., The Ras antagonist, famesylthiosalicylic acid (FTS), decreases fibrosis and improves muscle strength in dy/dy mouse model of muscular dystrophy, PloS One, 6(3):e18049 (2011).
Paul et al., Increased viral titer through concentration of viral harvests from retroviral packaging lines, Human Gene Therapy, 4(5):609-615 (1993).
Perrin et al., An experimental rabies vaccine produced with a new BHK-21 suspension cell culture process: use of serum-free medium and perfusion-reactor system, Vaccine, 13(13):1244-1250 (1995).
Chicoin et al., "Neuromuscular Therapeutic Strategies: Overcoming the Barriers from Microscope to Marketplace", Muscular Dystrophy Association National Scientific Conference, Mar. 13-16, 2011, Las Vegas, Nevada (Abstract Only).
Chu et al., "SV40 Dna transfection of cells in suspension: analysis of the efficiency of transcription and translation of T-antigen", Gene, 13, (1981) 197-202.
Inkley et al., "A study of methods for the prediction of plasma volume," J. Lab. Clin. Med. 45:841-850 (1955).
Rose, comprehensive Virology 3:1-61 (1974).
Scarabel et al., "Strategies to optimize siRNA delivery to hepatocellular carcinoma cells," Expert Opin. Drug Deliv., 17:1-14 (2017).
Tangsangasaksri et al., siRNA-Loaded Polyion Complex Micelle Decorated with Charge-Conversional Polymer Tuned to Undergo Stepwise Response to Intra-Tumoral and Intra-Endosomal pHs for Exerting Enhanced RNAi Efficacy, BioMacromolecules, 17:246-255 (2016).
Yang et al., Impact of PEG Chain Length on the Physical Properties and Bioactivity of PEGylated Chitosan/siRNA Nanoparticles in Vitro and in Vivo, ACS Appl. Mater. Interfaces, 9(14):12203-12216 (2017).
Athanasopoulos et al., "Recombinant adeno-associated viral (rAAV) vecors as therapeutic tools for Duchenne muscular dystrophy (DMD)," Gene Therapy, S109-S121 (2004).
Bengtsson et al., "Progress and prospects of gene therapy clinical trials for the muscular dystrophies", Human Molecular Genetics., 25:R9-R17 (2016).
Buyens et al., Liposome based systems for systemic siRNA delivery: Stability in blood sets the requirements for optimal carrier design, Journal of Controlled Release, 2012, vol. 158 (pp. 362-370).
Chalberg et al., GeneSeq Accession No. BAY70796, computer printout, 7-8 (2013).
Chamberlain et al., Geneseq accession No. AAL44606, Computer printout, 8-9 (2002).
Chicoine et al., "Vascular delivery of rAAVrh74.MCK.GALGT2 to the gastrocnemius muscle of the rhesus macaque stimulates the expression of dystrophin and laminin a2 surrogates", Mol. Ther., 22:713-24 (2014).
Corti et al., "B-cell depletion is protective against anti-AAV capsid immune response: a human subject case study," Molecular Therapy—Methods & Clinical Development, Aug. 13, 2014, vol. 1 (7 pages).
Danilov et al., "In vitro assay for the efficacy assessment of AAV vectors expressing microdystrophin," Exp Cell Res., 392:1-10 (2020).
Database "MCK exon 1 and intron DNA fragment," retrieved from EBI accession No. GSN:AEF99307, Database accession No. AEF99307, (Apr. 20, 2006).
Feldschuh et al., "Prediction of the normal blood volume. Relation of blood volume to body habitus," Circulation, 1977, vol. 56, No. 4 (pp. 605-612).
Forbes et al., "Skeletal muscles of ambulant children with Duchenne muscular dystrophy: validation of multicenter study of evaluation with MR imaging and MR spectroscopy", Radiology, 269:198-207 (2013).
Gao et al., The Dystrophin Complex: structure, function and implications for therapy, Compr Physiol, vol. 5, Issue 3. pp. 1223-1239.
GenBank Accession No. AF028704, Adeno-associated virus 6, complete genome, Jan. 12, 1998.
GenBank Accession No. NC_001401, Adena-associated virus-2, complete genome, Aug. 13, 2018.
Govoni et al., "Ongoing therapeutics trials and outcome measures for Duchenne muscular dystrophy", Cell Mol. Life Sci., 70:4585-602 (2013).
Graham et al., A new technique for the assay of infectivity of human adenovirus 5 DNA, Virology, 1973, vol. 52, Issue 2, pp. 456-467.
Griffin et al., "Adeno-associated Virus Serotype rh74 Prevalence in Muscular Dystrophy Population," American Society of Gene and Cell Therapy (ASGCT) 22nd Annual Meeting, Washington, DC, USA, Apr. 29-May 2, 2019 (1 page).
Groux-Degroote et al., "B4GALNT2 gene expression controls the biosynthesis of Sda and sialyl Lewis X antigens in healthy and cancer human gastrointestinal tract", Int. J_ Biochem. Cell Biol., 53:442-9 (2014).
Gupta et al., Codon optimization, Project Report, 2003. pp. 1-11.
Gurland et al., "A comparison of Centrifugal and Membrane-based Apheresis Formats," The International Journal of Artificial Organs, 1984, vol. 7, No. 1 (pp. 35-38).
Gurland et al., Comparative Evaluation of Filters Used in Membrane Plasmapheresis, Nephron, 1984, vol. 36, No. 3 (pp. 173-182).
Heller et al., Alternative to gene replacement for duchenne muscular dystrophy using human alpha7 integrin (ITGA7), Doctoral dissertation abstract only, 2014.
Hermonat et al., "Use of adeno-associated virus as a mammalian DNA cloning vector: Transduction of neomycin resistance into mammalian tissue culture cells", Proceedings of the National Academy of Sciences USA, Oct. 1984, vol. 81, pp. 6466-6470.
Howard MK, GeneSeq Accession No. AAF30284, computer printout, 7-8 (2001).
International Preliminary Report on Patentability on on PCT Application No. PCT/US2021/037470 dated Dec. 29, 2022 (8 pages).
International Search Report and Written Opinion on PCT Application No. PCT/US2021/037470 dated Oct. 1, 2021 (14 pages).
International Search Report and Written Opinion on PCT/US2016/052051 dtd Dec. 30, 2016.
Kaplan et al., "Plasma exchange with a rotating filter," Kidney International, 1990, vol. 38 (pp. 160-166).
Kaplan, A., "Therapeutic plasma exchange: a technical and operational review," Journal of Clinical Apheresis, Feb. 19, 2023, vol. 28 (pp. 3-10).
Koenig et al., Detailed Analysis of the Repeat Domain of Dystrophin Reveals Four Potential Hinge Segments That May Confer Flexibility, Journal of Biological Chemistry, vol. 265, Issue 8, pp. 4560-4566.
Lin et al., "Lipid-based nanoparticles in the systemic delivery of siRNA," Nanomedicine, 2014, vol. 9, No. 1 (pp. 105-120).
Marshall et al., "Sarcospan-dependent Aki activation is required for utrophin expression and muscle regeneration", J_Cell Biol., 197:1009-1027 (2012).

(56) References Cited

OTHER PUBLICATIONS

Martin et al, Translational Studies of GALGT2 Gene Therapy for Duchenne Muscular Dystrophy, Annual Report, Approved for Public Release Distribution Unlimited the Research Institute at Nationwide Children's Hospital Columbus, (2013).
Martin et al., Overexpression of Galgt2 in skeletal muscle prevents injury resulting from eccentric contractions in both mdx and wild-type mice, Am. J_ Physiol. Cell Physiol., vol. 296, pp. 476-488.
Martin et al., Translational Studies of GLAGT2 Gene Therapy for Duchenne Muscular Dystrophy, https://apps.dtic.mil/dtic/tr/fulltext/u2a613577.pdf (2018).
Martin, "Glycobiology of the neuromuscular junction", J_Neurocytol., 32:915-29 (2003).
Mateos-Aierdi, et al., "Advances in gene therapies for limb-girdle muscular dystrophies", Advances in Regenerative Biology, 1:25048, 6 pages, (2014).
Molecular Therapy Information for Authors, Feb. 1, 2019.
Montiel et al., Geneseq Accession No. AJ517771, computer printout, 11-14, direct submission, 11-14 (2002).
Nguyen et al., Overexpression of the cytotoxic T cell GalNAc transferase in skeletal muscle inhibits muscular dystrophy in mdx mice, Proc. Nall. Acad. Sci. USA., 99:5616-5621 (2002).
Padmanabhan et al., Guidelines on the Use of Therapeutic Apheresis in Clinical Practice—Evidence-Based 4 Approach from the Writing Committee of the American Society for Apheresis: The Eighth Special Issue, J. Clin. Apheresis, 34:171-354 (2019).
Patil et al., Polymeric nanoparticles for siRNA delivery and gene silencing, Pharmaceutical Nanotechnol., 367:195-203 (2009).
Perepelyuk et al., siRNA-Encapsulated Hybrid Nanoparticles Target Mutant K-ras and Inhibit Metastatic Tumor Burden in a Mouse Model of Lung Cancer, Mal. Ther. Nucleic Acids, 6, (2017), pp. 259-268.
Pham et al., "Therapeutic plasma exchange—A brief review of indications, urgency, schedule, and technical aspects," Transfusion and Apheresis Science, Jun. 2019, vol. 58, No. 3 (pp. 237-246).
Rabinowitz et al., Cross-packaging of a single adeno-associated virus (AAV) type 2 vector genome into multiple AAV serotypes enables transduction with broad specificity, J Virol., 2002, vol. 76, Issue 2, pp. 791-801.
Retzlaff et al., Erythrocyte vol. plasma vol. and lean body mass in adult men and women, Blood, 33:649-667 (1969).
Sahay et al., "Efficiency of siRNA delivery by lipid nanoparticles is limited by endocytic recycling," Nature Biotechnology, 2013, vol. 31 (pp. 653-658).
Samulski, GeneSeq Accession No. AOG17648, computer printout, 15-16 (2007).
Sawada et al., "Available removal systems: state of the art," Therapeutic Hemapheresis in the 1990s, Current Studies in Hematology and Blood Transfusion series, 1990, vol. 57:57-113.
Sprenger et al., "Predication of patient's plasma volume in plasma exchange therapy," Krager, 1986 (pp. 394-402).
Thomas et al., "B4GALNT2 (GALGT2) Gene Therapy Reduces Skeletal Muscle Pathology in the FKRP P448L Mouse Model of Limb Girdle Muscular Dystrophy 21", Am. J_ Pathol., 186(9):2429-2448 (2016).
Wang et al., Recombinant AAV serotype 1 transduction efficiency and tropism in the murine brain, Gene Ther., 2003, vol. 10, Issue 17, pp. 1528-1534.
White et al., GeneSeq Accession No. AEF99304, computer printout, 3-4 (2006).
Wu et al., "Improved siRNA Delivery Efficiency via Solvent-Induced Condensation of Micellar Nanoparticles," Nanotechnology, Apr. 25, 2017, vol. 28, No. 20.
Xu et al., "Postnatal overexpression of the CT GalNAc transferase inhibits muscular dystrophy in mdx mice without altering muscle growlh or neuromuscula development: evidence for a utrophin-independent mechanism", Neuromuscul. Disord., 17:209-20 (2007).
Xu et al., Deletion of Galgt2 (B4Galnl2) Reduces Muscle Growth in Response to Acute Injury and Increases Muscle Inflammation and Pathology in Dystrophin-Deficient Mice, American Journal of Pathology, 185:2668-2684 (2015).
Xu et al., Overexpression of GALGT2 in Skeletal Muscles via AAV Prevents Muscle Damage and Inhibits Muscle Pathology in Mouse Models of Muscular Dystrophy, Molecular Therapy, S201 (2009).
Xu et al., Overexpression of Galgt2 reduces dystrophic pathology in the skeletal muscles of alpha sarcoglycan-deficient mice, Am. J_ Pathol., 175:235-47 (2009).
Xu et al., Overexpression of the cytotoxic T cell {CT) carbohydrate inhibits muscular dystrophy in the dyW mouse model of congenital muscular dystrophy 1A, Am. J_ Pathol., 171:181-99 (2007).
You, GeneSeq Accession No. ARZ08701, computer printout, 10-11 (2008).
Le Rumeur, E., "Dystrophin and the two related genetic diseases, Duchenne and Becker muscular dystrophies," Bosnian Journal of Basic Medical Sciences, 15(3):14-20 (Jul. 20, 2015).
Meadows et al., Micro-RNA-29 Overexpression by adeno-associated virus suppresses fibrosis in mdx:utm+/- Mice (S61.003), Neurology, 82:S61.003 (Abstract) (2014).
Mendell et al., NCT03375164: A Gene Transfer Therapy Study to Evaluate the Safety of Delandistrogene Moxeparvovec (SRP-9001) in Participants With Duchenne Muscular Dystrophy (DMD). Version 2—Jan. 12, 2018. Found online [Sep. 25, 2024] URL: https://clinicaltrials.gov/study/NCT03375164?term=NCT03375164&viewType=Table&rank=1&tab=history&a=2#version-content-panel.
Mah, Jean K., "An overview of the other muscular dystrophies: underlying genetic and molecular mechanisms," Muscular Dystrophy: A Concise Guide, Raymond A. Huml Editor, Springer, Chapter 5, pp. 37-53 (2015).

* cited by examiner

Figure 2

SEQ ID NO: 3 rAAVrh74.MHCK7.microdystrophin

Main features:

ITR
MHCK7 promoter
Chimeric intron sequence
Human micro-dystrophin sequence
Poly A tail
Ampicillin resistance GCCCAATACGCAAACCGCCTCTCCCCGCGCGTTGGCCGATTCATTAATGCAGCTGCG
CGCTCGCTCGCTCACTGAGGCCGCCCGGGCAAAGCCCGGGCGTCGGGCGACC
TTTGGTCGCCCGGCCTCAGTGAGCGAGCGAGCGCGCAGAGAGGGAGTGGCCA
ACTCCATCACTAGGGGTTCCTTGTAGTTAATGATTAACCCGCCATGCTACTTATCT
ACGTAGCCATGCTCTAGAgtttaaacaagcttgcatgtctaagctagacccttcagattaaaaataactgaggtaagggcct
gggtaggggaggtggtgtgagacgctcctgtctctcctctatctgcccatcggccctttggggaggaggaatgtgcccaaggactaaaaa
aggccatggagccagaggggcgagggcaacagacctttcatgggcaaaccttggggccctgctgtctagcatgccccactacgggtcta
ggctgcccatgtaaggaggcaaggcctggggacacccgagatgcctggttataattaacccagacatgtggctgccccccccccccaac
acctgctgcctctaaaaataaccctgtccctggtggatcccctgcatgcgaagatcttcgaacaaggctgtgggggactgagggcaggctg
taacaggcttgggggccagggcttatacgtgcctgggactcccaaagtattactgttccatgttcccggcgaagggccagctgtcccccgc
cagctagactcagcacttagtttaggaaccagtgagcaagtcagcccttggggcagcccatacaaggccatggggctgggcaagctgcac
gcctgggtccggggtgggcacggtgcccgggcaacgagctgaaagctcatctgctctcaggggcccctccctggggacagcccctcctg
gctagtcacaccctgtaggctcctctatataacccaggggcacaggggctgccctcattctaccaccacctccacagcacagacagacact
caggagcagccagcggcgcgcccAGGTAAGTTTAGTCTTTTTGTCTTTTATTTCAGGTCCCGGAT
CCGGTGGTGGTGCAAATCAAAGAACTGCTCCTCAGTGGATGTTGCCTTTACTTCTAG
GCCTGTACGGAAGTGTTACTTCTGCTCTAAAAGCTGCGGAATTGTACCCGCGGCCGC
CACCATGCTGTGGTGGGAGGAGGTGGAGGATTGTTATGAAAGGGAGGACGTGCAGA
AGAAGACTTTTACCAAGTGGGTGAACGCTCAGTTCAGCAAATTTGGGAAGCAGCAC
ATCGAGAATCTGTTTTCCGACCTGCAGGATGGGAGACGGCTGCTGGATCTGCTGGAA
GGACTGACTGGCCAGAAGCTGCCCAAAGAGAAGGGGAGCACTAGGGTGCACGCCCT
GAACAACGTGAACAAAGCTCTGAGAGTGCTGCAGAACAACAACGTGGATCTGGTGA
ATATTGGCAGTACTGATATCGTGGACGGGAACCACAAACTGACACTGGGCCTGATCT
GGAACATTATTCTGCACTGGCAGGTGAAAAATGTGATGAAGAACATCATGGCCGGG
CTGCAGCAGACCAATTCCGAGAAGATCCTGCTGTCTTGGGTGCGGCAGAGCACCCG
CAACTATCCCCAGGTGAACGTGATTAACTTCACTACATCCTGGAGCGACGGGCTGGC
CCTGAATGCTCTGATTCACAGCCACAGGCCTGATCTGTTCGACTGGAATAGCGTGGT
GTGCCAGCAGTCTGCCACACAGCGCCTGGAACATGCCTTCAATATCGCTCGGTACCA
GCTGGGGATCGAAAAACTGCTGGACCCAGAGGATGTGGACACTACATACCCAGATA
AAAAGTCTATTCTGATGTACATTACTAGCCTGTTCCAGGTGCTGCCACAGCAGGTGT CTATTGAAGCCATTCAGGAGGTGGAAATGCTGCCCCGCCCCCCCAAAGTGACTAAA
GAGGAGCATTTTCAGCTGCATCATCAGATGCATTACAGCCAGCAGATTACCGTGAGC
CTGGCTCAGGGATATGAGCGCACCAGTAGTCCAAAACCACGGTTCAAGTCCTACGC
TTATACCCAGGCTGCCTACGTGACAACTAGCGACCCTACTAGATCCCCCTTTCCATC
CCAGCACCTGGAGGCCCCAGAGGACAAGAGCTTTGGGTCCAGCCTGATGGAAAGCG
AGGTGAATCTGGATCGGTACCAGACAGCCCTGGAGGAGGTGCTGAGCTGGCTGCTG
AGTGCTGAAGACACACTGCAGGCCCAGGGCGAAATTTCCAATGACGTGGAAGTGGT
GAAGGATCAGTTCCACACACACGAGGGCTATATGATGGACCTGACAGCTCACCAGG
GGCGCGTGGGCAATATCCTGCAGCTGGGCTCTAAACTGATCGGCACCGGGAAACTG
AGTGAGGACGAGGAAACAGAAGTGCAGGAGCAGATGAACCTGCTGAACAGCCGCT
GGGAGTGTCTGAGAGTGGCTAGTATGGAGAAGCAGTCCAACCTGCACCGGGTGCTG
ATGGACCTGCAGAACCAGAAACTGAAAGAGCTGAACGACTGGCTGACAAAGACTGA
GGAACGCACAAGGAAGATGGAGGAGGAGCCACTGGGACCCGACCTGGAGGATCTG
AAGAGACAGGTGCAGCAGCATAAGGTGCTGCAGGAGGATCTGGAACAGGAGCAGG
TGCGGGTGAACTCCCTGACACATATGGTGGTGGTGGTGGACGAATCTAGTGGAGAT
CACGCCACCGCCGCCCTGGAGGAACAGCTGAAGGTGCTGGGGGACCGGTGGGCCAA
CATTTGCCGGTGGACCGAGGACAGGTGGGTGCTGCTGCAGGACATCCTGCTGAAAT
GGCAGAGGCTGACCGAGGAGCAGTGTCTGTTTAGTGCTTGGCTGAGCGAGAAAGAG
GACGCCGTGAACAAGATCCACACAACCGGCTTTAAGGATCAGAACGAAATGCTGTC
TAGCCTGCAGAAACTGGCTGTGCTGAAGGCCGATCTGGAGAAAAAGAAGCAGAGCA
TGGGCAAACTGTATAGCCTGAAACAGGACCTGCTGAGCACCCTGAAGAACAAGAGC
GTGACCCAGAAGACAGAAGCCTGGCTGGATAACTTTGCCCGCTGCTGGGACAACCT
GGTGCAGAAACTGGAGAAAAGTACAGCTCAGATCTCTCAGGCTGTGACCACAACCC
AGCCTAGCCTGACCCAGACAACCGTGATGGAAACCGTGACCACCGTGACAACCCGC
GAACAGATCCTGGTGAAACATGCCCAGGAAGAGCTGCCACCTCCACCTCCCCAGAA
GAAGAGAACCCTGGAGCGGCTGCAGGAGCTGCAGGAAGCCACTGACGAACTGGAC
CTGAAGCTGAGGCAGGCCGAAGTGATTAAGGGGTCTTGGCAGCCTGTGGGCGATCT
GCTGATTGATTCCCTGCAGGACCACCTGGAAAAGGTGAAGGCTCTGAGAGGCGAAA
TTGCTCCACTGAAGGAGAACGTGAGTCATGTGAACGATCTGGCTAGACAGCTGACA
ACACTGGGCATCCAGCTGAGCCCATACAATCTGAGCACACTGGAGGACCTGAATAC
CAGGTGGAAGCTGCTGCAGGTGGCTGTGGAAGACCGGGTGCGGCAGCTGCATGAGG
CCCATCGCGACTTCGGACCAGCCAGCCAGCACTTTCTGAGCACATCCGTGCAGGGGC
CCTGGGAGAGGGCCATTTCTCCCAACAAGGTGCCCTACTATATTAATCACGAGACCC
AGACCACTTGTTGGGACCATCCCAAGATGACAGAACTGTACCAGTCCCTGGCCGATC
TGAACAACGTGAGGTTTAGCGCTTACAGAACCGCTATGAAGCTGAGACGGCTGCAG
AAGGCCCTGTGCCTGGATCTGCTGTCCCTGTCCGCCGCCTGCGATGCCCTGGATCAG
CATAATCTGAAGCAGAACGATCAGCCAATGGATATCCTGCAGATCATCAACTGCCTG
ACCACTATCTACGACAGGCTGGAGCAGGAGCACAACAACCTGGTGAACGTGCCTCT
GTGCGTGGATATGTGCCTGAACTGGCTGCTGAACGTGTATGACACTGGGCGCACCGG
CCGGATCAGAGTGCTGAGTTTTAAAACTGGGATTATCTCCCTGTGTAAGGCCCACCT
GGAGGACAAGTACAGGTACCTGTTCAAGCAGGTGGCTAGTAGCACTGGATTTTGTG
ACCAGCGCCGCCTGGGACTGCTGCTGCATGATAGTATCCAGATTCCTAGACAGCTGG
GAGAGGTGGCTAGTTTCGGAGGATCTAACATCGAACCCAGCGTGCGCAGCTGTTTCC
AGTTTGCCAATAACAAACCTGAAATCGAGGCTGCTCTGTTCCTGGATTGGATGCGCC
TGGAACCACAGAGCATGGTGTGGCTGCCTGTGCTGCACAGAGTGGCTGCCGCCGAA
ACTGCCAAGCACCAGGCTAAATGCAACATCTGCAAGGAATGTCCCATTATCGGCTTT

Figure 2 (continued)

CGCTACAGGAGTCTGAAACATTTTAACTACGATATTTGCCAGAGCTGCTTCTTTTCCG
GAAGAGTGGCCAAAGGACACAAGATGCACTACCCTATGGTGGAATATTGCACCCCA
ACTACATCTGGCGAAGATGTGCGCGATTTTGCCAAGGTGCTGAAGAATAAGTTTCGG
ACTAAGAGGTACTTCGCCAAGCACCCCCGCATGGGGTATCTGCCAGTGCAGACAGT
GCTGGAAGGAGACAATATGGAGACCGATACAATGtgaGCGGCCGCAATAAAAGATCT
TTATTTTCATTAGATCTGTGTGTTGGTTTTTTGTGTGTCTAGAGCATGGCTACGTAGA
TAAGTAGCATGGCGGGTTAATCATTAACTACAAGGAACCCCTAGTGATGGAGTTG
GCCACTCCCTCTCTGCGCGCTCGCTCGCTCACTGAGGCCGGGCGACCAAAGGT
CGCCCGACGCCCGGGCTTTGCCCGGGCGGCCTCAGTGAGCGAGCGAGCGCGC
AGCTGGCGTAATAGCGAAGAGGCCCGCACCGATCGCCCTTCCCAACAGTTGCGCAG
CCTGAATGGCGAATGGCGATTCCGTTGCAATGGCTGGCGGTAATATTGTTCTGGATA
TTACCAGCAAGGCCGATAGTTTGAGTTCTTCTACTCAGGCAAGTGATGTTATTACTA
ATCAAAGAAGTATTGCGACAACGGTTAATTTGCGTGATGGACAGACTCTTTTACTCG
GTGGCCTCACTGATTATAAAAACACTTCTCAGGATTCTGGCGTACCGTTCCTGTCTA
AAATCCCTTTAATCGGCCTCCTGTTTAGCTCCCGCTCTGATTCTAACGAGGAAAGCA
CGTTATACGTGCTCGTCAAAGCAACCATAGTACGCGCCCTGTAGCGGCGCATTAAGC
GCGGCGGGTGTGGTGGTTACGCGCAGCGTGACCGCTACACTTGCCAGCGCCCTAGC
GCCCGCTCCTTTCGCTTTCTTCCCTTCCTTTCTCGCCACGTTCGCCGGCTTTCCCCGTC
AAGCTCTAAATCGGGGGCTCCCTTTAGGGTTCCGATTTAGTGCTTTACGGCACCTCG
ACCCCAAAAAACTTGATTAGGGTGATGGTTCACGTAGTGGGCCATCGCCCTGATAGA
CGGTTTTTCGCCCTTTGACGTTGGAGTCCACGTTCTTTAATAGTGGACTCTTGTTCCA
AACTGGAACAACACTCAACCCTATCTCGGTCTATTCTTTTGATTTATAAGGGATTTTG
CCGATTTCGGCCTATTGGTTAAAAAATGAGCTGATTTAACAAAAATTTAACGCGAAT
TTTAACAAAATATTAACGCTTACAATTTAAATATTTGCTTATACAATCTTCCTGTTTT
TGGGGCTTTTCTGATTATCAACCGGGGTACATATGATTGACATGCTAGTTTTACGATT
ACCGTTCATCGATTCTCTTGTTTGCTCCAGACTCTCAGGCAATGACCTGATAGCCTTT
GTAGAGACCTCTCAAAAATAGCTACCCTCTCCGGCATGAATTTATCAGCTAGAACGG
TTGAATATCATATTGATGGTGATTTGACTGTCTCCGGCCTTTCTCACCCGTTTGAATC
TTTACCTACACATTACTCAGGCATTGCATTTAAAATATATGAGGGTTCTAAAAATTTT
TATCCTTGCGTTGAAATAAAGGCTTCTCCCGCAAAAGTATTACAGGGTCATAATGTT
TTTGGTACAACCGATTTAGCTTTATGCTCTGAGGCTTTATTGCTTAATTTTGCTAATT
CTTTGCCTTGCCTGTATGATTTATTGGATGTTGGAATCGCCTGATGCGGTATTTTCTC
CTTACGCATCTGTGCGGTATTTCACACCGCATATGGTGCACTCTCAGTACAATCTGCT
CTGATGCCGCATAGTTAAGCCAGCCCCGACACCCGCCAACACCCGCTGACGCGCCCT
GACGGGCTTGTCTGCTCCCGGCATCCGCTTACAGACAAGCTGTGACCGTCTCCGGGA
GCTGCATGTGTCAGAGGTTTTCACCGTCATCACCGAAACGCGCGAGACGAAAGGGC
CTCGTGATACGCCTATTTTTATAGGTTAATGTCATGATAATAATGGTTTCTTAGACGT
CAGGTGGCACTTTTCGGGGAAATGTGCGCGGAACCCCTATTTGTTTATTTTTCTAAAT
ACATTCAAATATGTATCCGCTCATGAGACAATAACCCTGATAAATGCTTCAATAATA
TTGAAAAAGGAAGAGTATGAGTATTCAACATTTCCGTGTCGCCCTTATTCCCTTTTTT
GCGGCATTTTGCCTTCCTGTTTTTGCTCACCCAGAAACGCTGGTGAAAGTAAAAGAT
GCTGAAGATCAGTTGGGTGCACGAGTGGGTTACATCGAACTGGATCTCAACAGCGG
TAAGATCCTTGAGAGTTTTCGCCCCGAAGAACGTTTTCCAATGATGAGCACTTTTAA
AGTTCTGCTATGTGGCGCGGTATTATCCCGTATTGACGCCGGGCAAGAGCAACTCGG
TCGCCGCATACACTATTCTCAGAATGACTTGGTTGAGTACTCACCAGTCACAGAAAA
GCATCTTACGGATGGCATGACAGTAAGAGAATTATGCAGTGCTGCCATAACCATGA

Figure 2 (continued)

GTGATAACACTGCGGCCAACTTACTTCTGACAACGATCGGAGGACCGAAGGAGCTA
ACCGCTTTTTTGCACAACATGGGGGATCATGTAACTCGCCTTGATCGTTGGGAACCG
GAGCTGAATGAAGCCATACCAAACGACGAGCGTGACACCACGATGCCTGTAGCAAT
GGCAACAACGTTGCGCAAACTATTAACTGGCGAACTACTTACTCTAGCTTCCCGGCA
ACAATTAATAGACTGGATGGAGGCGGATAAAGTTGCAGGACCACTTCTGCGCTCGG
CCCTTCCGGCTGGCTGGTTTATTGCTGATAAATCTGGAGCCGGTGAGCGTGGGTCTC
GCGGTATCATTGCAGCACTGGGGCCAGATGGTAAGCCCTCCCGTATCGTAGTTATCT
ACACGACGGGGAGTCAGGCAACTATGGATGAACGAAATAGACAGATCGCTGAGATA
GGTGCCTCACTGATTAAGCATTGGTAACTGTCAGACCAAGTTTACTCATATATACTTT
AGATTGATTTAAAACTTCATTTTTAATTTAAAAGGATCTAGGTGAAGATCCTTTTTGA
TAATCTCATGACCAAAATCCCTTAACGTGAGTTTTCGTTCCACTGAGCGTCAGACCC
CGTAGAAAAGATCAAAGGATCTTCTTGAGATCCTTTTTTTCTGCGCGTAATCTGCTGC
TTGCAAACAAAAAAACCACCGCTACCAGCGGTGGTTTGTTTGCCGGATCAAGAGCT
ACCAACTCTTTTTCCGAAGGTAACTGGCTTCAGCAGAGCGCAGATACCAAATACTGT
TCTTCTAGTGTAGCCGTAGTTAGGCCACCACTTCAAGAACTCTGTAGCACCGCCTAC
ATACCTCGCTCTGCTAATCCTGTTACCAGTGGCTGCTGCCAGTGGCGATAAGTCGTG
TCTTACCGGGTTGGACTCAAGACGATAGTTACCGGATAAGGCGCAGCGGTCGGGCT
GAACGGGGGGTTCGTGCACACAGCCCAGCTTGGAGCGAACGACCTACACCGAACTG
AGATACCTACAGCGTGAGCTATGAGAAAGCGCCACGCTTCCCGAAGGGAGAAAGGC
GGACAGGTATCCGGTAAGCGGCAGGGTCGGAACAGGAGAGCGCACGAGGGAGCTT
CCAGGGGGAAACGCCTGGTATCTTTATAGTCCTGTCGGGTTTCGCCACCTCTGACTT
GAGCGTCGATTTTTGTGATGCTCGTCAGGGGGGCGGAGCCTATGGAAAAACGCCAG
CAACGCGGCCTTTTTACGGTTCCTGGCCTTTTGCTGGCCTTTTGCTCACATGTTCTTTC
CTGCGTTATCCCCTGATTCTGTGGATAACCGTATTACCGCCTTTGAGTGAGCTGATAC
CGCTCGCCGCAGCCGAACGACCGAGCGCAGCGAGTCAGTGAGCGAGGAAGCGGAA
GAGC

Figure 2 (continued)

Figure 6

SEQ ID NO: 5 rAAVrh74.MCK.micro-dystrophin

Main features:
ITR
MCK promoter
Chimeric intron sequence
Human codon optimized micro-dystrophin sequence -
Poly A tail
Ampicillin resistance
pGEX plasmid backbone with pBR322 origin or replication

GCCCAATACGCAAACCGCCTCTCCCCGCGCGTTGGCCGATTCATTAATGCAGCTGGCGCGCTCGCTCGCTCACTGA

GGCCGCCCGGGCAAAGCCCGGGCGTCGGGCGACCTTTGGTCGCCCGGCCTCAGTGAGCGAGCGAGCGCGCAGA

GAGGGAGTGGCCAACTCCATCACTAGGGGTTCCTTGTAGTTAATGATTAACCCGCCATGCTAATTATCTACGTAGC

CATGTCTAGACAGCCACTATGGGTCTAGGCTGCCCATGTAAGGAGGCAAGGCCTGGGGACACCCGAGATGCCTG

GTTATAATTAACCCAGACATGTGGCTGCTCCCCCCCCCCAACACCTGCTGCCTGAGCCTCACCCCCACCCCGGTGCC

TGGGTCTTAGGCTCTGTACACCATGGAGGAGAAGCTCGCTCTAAAAATAACCCTGTCCCTGGTGGGCTGTGGGGG

ACTGAGGGCAGGCTGTAACAGGCTTGGGGGCCAGGGCTTATACGTGCCTGGGACTCCCAAAGTATTACTGTTCCA

TGTTCCCGGCGAAGGGCCAGCTGTCCCCCGCCAGCTAGACTCAGCACTTAGTTTAGGAACCAGTGAGCAAGTCAG

CCCTTGGGGCAGCCCATACAAGGCCATGGGGCTGGGCAAGCTGCACGCCTGGGTCCGGGGTGGGCACGGTGCCC

GGGCAACGAGCTGAAAGCTCATCTGCTCTCAGGGGCCCCTCCCTGGGGACAGCCCCTCCTGGCTAGTCACACCCT

GTAGGCTCCTCTATATAACCCAGGGGCACAGGGGCTGCCCCCGGGTCACCACCACCTCCACAGCACAGACAGACA

CTCAGGAGCCAGCCAGCCAGGTAAGTTTAGTCTTTTTGTCTTTTATTTCAGGTCCCGGATCCGGTGGTGGTGCAAA

TCAAAGAACTGCTCCTCAGTGGATGTTGCCTTTACTTCTAGGCCTGTACGGAAGTGTTACTTCTGCTCTAAAAGCTG

CGGAATTGTACCCGCGGCCGCCACCATGCTGTGGTGGGAGGAGGTGGAGGATTGTTATGAAAGGGAGGACGTGC

AGAAGAAGACTTTTACCAAGTGGGTGAACGCTCAGTTCAGCAAATTTGGGAAGCAGCACATCGAGAATCTGTTTT

CCGACCTGCAGGATGGGAGACGGCTGCTGGATCTGCTGGAAGGACTGACTGGCCAGAAGCTGCCCAAAGAGAAG

GGGAGCACTAGGGTGCACGCCCTGAACAACGTGAACAAAGCTCTGAGAGTGCTGCAGAACAACAACGTGGATCT

GGTGAATATTGGCAGTACTGATATCGTGGACGGGAACCACAAACTGACACTGGGCCTGATCTGGAACATTATTCT

GCACTGGCAGGTGAAAAATGTGATGAAGAACATCATGGCCGGGCTGCAGCAGACCAATTCCGAGAAGATCCTGC

TGTCTTGGGTGCGGCAGAGCACCCGCAACTATCCCCAGGTGAACGTGATTAACTTCACTACATCCTGGAGCGACG
GGCTGGCCCTGAATGCTCTGATTCACAGCCACAGGCCTGATCTGTTCGACTGGAATAGCGTGGTGTGCCAGCAGT
CTGCCACACAGCGCCTGGAACATGCCTTCAATATCGCTCGGTACCAGCTGGGGATCGAAAAACTGCTGGACCCAG
AGGATGTGGACACTACATACCCAGATAAAAAGTCTATTCTGATGTACATTACTAGCCTGTTCCAGGTGCTGCCACA
GCAGGTGTCTATTGAAGCCATTCAGGAGGTGGAAATGCTGCCCCGCCCCCCCAAAGTGACTAAAGAGGAGCATTT
TCAGCTGCATCATCAGATGCATTACAGCCAGCAGATTACCGTGAGCCTGGCTCAGGGATATGAGCGCACCAGTAG
TCCAAAACCACGGTTCAAGTCCTACGCTTATACCCAGGCTGCCTACGTGACAACTAGCGACCCTACTAGATCCCCCT
TTCCATCCCAGCACCTGGAGGCCCCAGAGGACAAGAGCTTTGGGTCCAGCCTGATGGAAAGCGAGGTGAATCTG
GATCGGTACCAGACAGCCCTGGAGGAGGTGCTGAGCTGGCTGCTGAGTGCTGAAGACACACTGCAGGCCCAGGG
CGAAATTTCCAATGACGTGGAAGTGGTGAAGGATCAGTTCCACACACACGAGGGCTATATGATGGACCTGACAGC
TCACCAGGGGCGCGTGGGCAATATCCTGCAGCTGGGCTCTAAACTGATCGGCACCGGGAAACTGAGTGAGGACG
AGGAAACAGAAGTGCAGGAGCAGATGAACCTGCTGAACAGCCGCTGGGAGTGTCTGAGAGTGGCTAGTATGGA
GAAGCAGTCCAACCTGCACCGGGTGCTGATGGACCTGCAGAACCAGAAACTGAAAGAGCTGAACGACTGGCTGA
CAAAGACTGAGGAACGCACAAGGAAGATGGAGGAGGAGCCACTGGGACCCGACCTGGAGGATCTGAAGAGACA
GGTGCAGCAGCATAAGGTGCTGCAGGAGGATCTGGAACAGGAGCAGGTGCGGGTGAACTCCCTGACACATATGG
TGGTGGTGGTGGACGAATCTAGTGGAGATCACGCCACCGCCGCCCTGGAGGAACAGCTGAAGGTGCTGGGGGAC
CGGTGGGCCAACATTTGCCGGTGGACCGAGGACAGGTGGGTGCTGCTGCAGGACATCCTGCTGAAATGGCAGAG
GCTGACCGAGGAGCAGTGTCTGTTTAGTGCTTGGCTGAGCGAGAAAGAGGACGCCGTGAACAAGATCCACACAA
CCGGCTTTAAGGATCAGAACGAAATGCTGTCTAGCCTGCAGAAACTGGCTGTGCTGAAGGCCGATCTGGAGAAAA
AGAAGCAGAGCATGGGCAAACTGTATAGCCTGAAACAGGACCTGCTGAGCACCCTGAAGAACAAGAGCGTGACC
CAGAAGACAGAAGCCTGGCTGGATAACTTTGCCCGCTGCTGGGACAACCTGGTGCAGAAACTGGAGAAAAGTAC
AGCTCAGATCTCTCAGGCTGTGACCACAACCCAGCCTAGCCTGACCCAGACAACCGTGATGGAAACCGTGACCACC
GTGACAACCCGCGAACAGATCCTGGTGAAACATGCCCAGGAAGAGCTGCCACCTCCACCTCCCCAGAAGAAGAGA
ACCCTGGAGCGGCTGCAGGAGCTGCAGGAAGCCACTGACGAACTGGACCTGAAGCTGAGGCAGGCCGAAGTGAT
TAAGGGGTCTTGGCAGCCTGTGGGCGATCTGCTGATTGATTCCCTGCAGGACCACCTGGAAAAGGTGAAGGCTCT
GAGAGGCGAAATTGCTCCACTGAAGGAGAACGTGAGTCATGTGAACGATCTGGCTAGACAGCTGACAACACTGG
GCATCCAGCTGAGCCCATACAATCTGAGCACACTGGAGGACCTGAATACCAGGTGGAAGCTGCTGCAGGTGGCTG
TGGAAGACCGGGTGCGGCAGCTGCATGAGGCCCATCGCGACTTCGGACCAGCCAGCCAGCACTTTCTGAGCACAT
CCGTGCAGGGGCCCTGGGAGAGGGCCATTTCTCCCAACAAGGTGCCCTACTATATTAATCACGAGACCCAGACCA
CTTGTTGGGACCATCCCAAGATGACAGAACTGTACCAGTCCCTGGCCGATCTGAACAACGTGAGGTTTAGCGCTTA
CAGAACCGCTATGAAGCTGAGACGGCTGCAGAAGGCCCTGTGCCTGGATCTGCTGTCCCTGTCCGCCGCCTGCGA
TGCCCTGGATCAGCATAATCTGAAGCAGAACGATCAGCCAATGGATATCCTGCAGATCATCAACTGCCTGACCACT

Figure 6 (continued)

ATCTACGACAGGCTGGAGCAGGAGCACAACAACCTGGTGAACGTGCCTCTGTGCGTGGATATGTGCCTGAACTGG
CTGCTGAACGTGTATGACACTGGGCGCACCGGCCGGATCAGAGTGCTGAGTTTTAAAACTGGGATTATCTCCCTGT
GTAAGGCCCACCTGGAGGACAAGTACAGGTACCTGTTCAAGCAGGTGGCTAGTAGCACTGGATTTTGTGACCAGC
GCCGCCTGGGACTGCTGCTGCATGATAGTATCCAGATTCCTAGACAGCTGGGAGAGGTGGCTAGTTTCGGAGGAT
CTAACATCGAACCCAGCGTGCGCAGCTGTTTCCAGTTTGCCAATAACAAACCTGAAATCGAGGCTGCTCTGTTCCT
GGATTGGATGCGCCTGGAACCACAGAGCATGGTGTGGCTGCCTGTGCTGCACAGAGTGGCTGCCGCCGAAACTG
CCAAGCACCAGGCTAAATGCAACATCTGCAAGGAATGTCCCATTATCGGCTTTCGCTACAGGAGTCTGAAACATTT
TAACTACGATATTTGCCAGAGCTGCTTCTTTTCCGGAAGAGTGGCCAAAGGACACAAGATGCACTACCCTATGGTG
GAATATTGCACCCCAACTACATCTGGCGAAGATGTGCGCGATTTTGCCAAGGTGCTGAAGAATAAGTTTCGGACTA
AGAGGTACTTCGCCAAGCACCCCCGCATGGGGTATCTGCCAGTGCAGACAGTGCTGGAAGGAGACAATATGGAG
ACCGATACAATGTGAGCGGCCGCAATAAAAGATCTTTATTTTCATTAGATCTGTGTGTTGGTTTTTTGTGTGTCTA
GAGCATGGCTACGTAGATAAGTAGCATGGCGGGTTAATCATTAACTACAAGGAACCCCTAGTGATGGAGTTGGC
CACTCCCTCTCTGCGCGCTCGCTCGCTCACTGAGGCCGGGCGACCAAAGGTCGCCCGACGCCCGGGCTTTGCCCG
GGCGGCCTCAGTGAGCGAGCGAGCGCGCCAGCTGGCGTAATAGCGAAGAGGCCCGCACCGATCGCCCTTCCCAA
CAGTTGCGCAGCCTGAATGGCGAATGGAAGTTCCAGACGATTGAGCGTCAAAATGTAGGTATTTCCATGAGCGTT
TTTCCTGTTGCAATGGCTGGCGGTAATATTGTTCTGGATATTACCAGCAAGGCCGATAGTTTGAGTTCTTCTACTCA
GGCAAGTGATGTTATTACTAATCAAAGAAGTATTGCGACAACGGTTAATTTGCGTGATGGACAGACTCTTTTACTC
GGTGGCCTCACTGATTATAAAAACACTTCTCAGGATTCTGGCGTACCGTTCCTGTCTAAAATCCCTTTAATCGGCCT
CCTGTTTAGCTCCCGCTCTGATTCTAACGAGGAAAGCACGTTATACGTGCTCGTCAAAGCAACCATAGTACGCGCC
CTGTAGCGGCGCATTAAGCGCGGCGGGTGTGGTGGTTACGCGCAGCGTGACCGCTACACTTGCCAGCGCCCTAGC
GCCCGCTCCTTTCGCTTTCTTCCCTTCCTTTCTCGCCACGTTCGCCGGCTTTCCCCGTCAAGCTCTAAATCGGGGGCT
CCCTTTAGGGTTCCGATTTAGTGATTTACGGCACCTCGACCCCAAAAAACTTGATTAGGGTGATGGTTCACGTAGT
GGGCCATCGCCCTGATAGACGGTTTTTCGCCCTTTGACGTTGGAGTCCACGTTCTTTAATAGTGGACTCTTGTTCCA
AACTGGAACAACACTCAACCCTATCTCGGTCTATTCTTTTGATTTATAAGGGATTTTGCCGATTTCGGCCTATTGGTT
AAAAAATGAGCTGATTTAACAAAAATTTAACGCGAATTTTAACAAAATATTAACGTTTACAATTTAAATATTTGCTT
ATACAATCTTCCTGTTTTTGGGGCTTTTCTGATTATCAACCGGGGTACATATGATTGACATGCTAGTTTTACGATTAC
CGTTCATCGATTCTCTTGTTTGCTCCAGACTCTCAGGCAATGACCTGATAGCCTTTGTAGAGACCTCTCAAAAATAG
CTACCCTCTCCGGCATGAATTTATCAGCTAGAACGGTTGAATATCATATTGATGGTGATTTGACTGTCTCCGGCCTT
TCTCACCCGTTTGAATCTTTACCTACACATTACTCAGGCATTGCATTTAAAATATATGAGGGTTCTAAAAATTTTTAT
CCTTGCGTTGAAATAAAGGCTTCTCCCGCAAAAGTATTACAGGGTCATAATGTTTTTGGTACAACCGATTTAGCTTT
ATGCTCTGAGGCTTTATTGCTTAATTTTGCTAATTCTTTGCCTTGCCTGTATGATTTATTGGATGTTGGAAGTTCCTG
ATGCGGTATTTTCTCCTTACGCATCTGTGCGGTATTTCACACCGCATATGGTGCACTCTCAGTACAATCTGCTCTGAT

Figure 6 (continued)

GCCGCATAGTTAAGCCAGCCCCGACACCCGCCAACACCCGCTGACGCGCCCTGACGGGCTTGTCTGCTCCCGGCAT
CCGCTTACAGACAAGCTGTGACCGTCTCCGGGAGCTGCATGTGTCAGAGGTTTTCACCGTCATCACCGAAACGCGC
GAGACGAAAGGGCCTCGTGATACGCCTATTTTTATAGGTTAATGTCATGATAATAATGGTTTCTTAGACGTCAGGT
GGCACTTTTCGGGGAAATGTGCGCGGAACCCCTATTTGTTTATTTTTCTAAATACATTCAAATATGTATCCGCTCAT
GAGACAATAACCCTGATAAATGCTTCAATAATATTGAAAAAGGAAGAGTATGAGTATTCAACATTTCCGTGTCGCC
CTTATTCCCTTTTTTGCGGCATTTTGCCTTCCTGTTTTTGCTCACCCAGAAACGCTGGTGAAAGTAAAAGATGCTGAA
GATCAGTTGGGTGCACGAGTGGGTTACATCGAACTGGATCTCAACAGCGGTAAGATCCTTGAGAGTTTTCGCCCC
GAAGAACGTTTTCCAATGATGAGCACTTTTAAAGTTCTGCTATGTGGCGCGGTATTATCCCGTATTGACGCCGGGC
AAGAGCAACTCGGTCGCCGCATACACTATTCTCAGAATGACTTGGTTGAGTACTCACCAGTCACAGAAAAGCATCT
TACGGATGGCATGACAGTAAGAGAATTATGCAGTGCTGCCATAACCATGAGTGATAACACTGCGGCCAACTTACTT
CTGACAACGATCGGAGGACCGAAGGAGCTAACCGCTTTTTTGCACAACATGGGGGATCATGTAACTCGCCTTGAT
CGTTGGGAACCGGAGCTGAATGAAGCCATACCAAACGACGAGCGTGACACCACGATGCCTGTAGCAATGGCAAC
AACGTTGCGCAAACTATTAACTGGCGAACTACTTACTCTAGCTTCCCGGCAACAATTAATAGACTGGATGGAGGCG
GATAAAGTTGCAGGACCACTTCTGCGCTCGGCCCTTCCGGCTGGCTGGTTTATTGCTGATAAATCTGGAGCCGGTG
AGCGTGGGTCTCGCGGTATCATTGCAGCACTGGGGCCAGATGGTAAGCCCTCCCGTATCGTAGTTATCTACACGAC
GGGGAGTCAGGCAACTATGGATGAACGAAATAGACAGATCGCTGAGATAGGTGCCTCACTGATTAAGCATTGGT
AACTGTCAGACCAAGTTTACTCATATATACTTTAGATTGATTTAAAACTTCATTTTTAATTTAAAAGGATCTAGGTGA
AGATCCTTTTTGATAATCTCATGACCAAAATCCCTTAACGTGAGTTTTCGTTCCACTGAGCGTCAGACCCCGTAGAA
AAGATCAAAGGATCTTCTTGAGATCCTTTTTTTCTGCGCGTAATCTGCTGCTTGCAAACAAAAAAACCACCGCTACC
AGCGGTGGTTTGTTTGCCGGATCAAGAGCTACCAACTCTTTTTCCGAAGGTAACTGGCTTCAGCAGAGCGCAGATA
CCAAATACTGTCCTTCTAGTGTAGCCGTAGTTAGGCCACCACTTCAAGAACTCTGTAGCACCGCGTACATACCTCGC
TCTGCTAATCCTGTTACCAGTGGCTGCTGCCAGTGGCGATAAGTCGTGTCTTACCGGGTTGGACTCAAGACGATAG
TTACCGGATAAGGCGCAGCGGTCGGGCTGAACGGGGGGTTCGTGCACACAGCCCAGCTTGGAGCGAACGACCTA
CACCGAACTGAGATACCTACAGCGTGAGCTATGAGAAAGCGCCACGCTTCCCGAAGGGAGAAAGGCGGACAGGT
ATCCGGTAAGCGGCAGGGTCGGAACAGGAGAGCGCACGAGGGAGCTTCCAGGGGGAAACGCCTGGTATCTTTAT
AGTCCTGTCGGGTTTCGCCACCTCTGACTTGAGCGTCGATTTTTGTGATGCTCGTCAGGGGGGCGGAGCCTATGGA
AAAACGCCAGCAACGCGGCCTTTTTACGGTTCCTGGCCTTTTGCTGGCCTTTTGCTCACATGTTCTTTCCTGCGTTAT
CCCCTGATTCTGTGGATAACCGTATTACCGGGTTTGAGTGAGCTGATACCGCTCGCCGCAGCCGAACGACCGAGC
GCAGCGAGTCAGTGAGCGACCAAGCGGAAGAGC

Figure 6 (continued)

Micro-dystrophin Expression (IHC)

| Western Quantitation Method | Mean Micro-dystrophin Expression (N=4) vs Normal |
|---|---|
| Method 1 | 74.3% (not adjusted for fat and fibrotic tissue) |
| Method 2 | 95.8% (adjusted for fat and fibrotic tissue) |

Figure 11: Mean CK Levels Significantly Decreases Over time

Mean NSAA change significantly increases over time while mean CK levels significantly decrease over time.

Figure 13

SEQ ID NO: 9
rAAVrh74.MHCK7.microdystrophin

Main Features:
ITR
MHCK7 promoter
Chimeric Intron sequence
Human micro-dystrophin sequence
Poly A tail

GCGCGCTCGCTCGCTCACTGAGGCCGCCCGGGCAAAGCCCGGGCGTCGGGCG
ACCTTTGGTCGCCCGGCCTCAGTGAGCGAGCGAGCGCGCAGAGAGGGAGTGG
CCAACTCCATCACTAGGGGTTCCTTGTAGTTAATGATTAACCCGCCATGCTACTT
ATCTACGTAGCCATGCTCTAGAgtttaaacaagcttgcatgtctaagctagacccttcagattaaaaataactgaggtaa
gggcctgggtaggggaggtggtgtgagacgctcctgtctctcctctatctgcccatcggccctttggggaggaggaatgtgcccaaggact
aaaaaaaggccatggagccagaggggcgagggcaacagacctttcatgggcaaaccttggggccctgctgtctagcatgccccactacg
ggtctaggctgcccatgtaaggaggcaaggcctggggacacccgagatgcctggttataattaacccagacatgtggctgcccccccccc
cccaacacctgctgcctctaaaaataaccctgtccctggtggatcccctgcatgcgaagatcttcgaacaaggctgtgggggactgagggc
aggctgtaacaggcttgggggccagggcttatacgtgcctgggactcccaaagtattactgttccatgttcccggcgaagggccagctgtcc
cccgccagctagactcagcacttagtttaggaaccagtgagcaagtcagcccttggggcagcccatacaaggccatggggctgggcaag
ctgcacgcctgggtccggggtgggcacggtgcccgggcaacgagctgaaagctcatctgctctcaggggcccctccctggggacagcc
cctcctggctagtcacaccctgtaggctcctctatataacccaggggcacaggggctgccctcattctaccaccacctccacagcacagaca
gacactcaggagcagccagcggcgcgcccAGGTAAGTTTAGTCTTTTTGTCTTTTATTTCAGGTCCCG
GATCCGGTGGTGGTGCAAATCAAAGAACTGCTCCTCAGTGGATGTTGCCTTTACTTC
TAGGCCTGTACGGAAGTGTTACTTCTGCTCTAAAAGCTGCGGAATTGTACCCGCGGC
CGCCACCATGCTGTGGTGGGAGGAGGTGGAGGATTGTTATGAAAGGGAGGACGTGC
AGAAGAAGACTTTTACCAAGTGGGTGAACGCTCAGTTCAGCAAATTTGGGAAGCAG
CACATCGAGAATCTGTTTTCCGACCTGCAGGATGGGAGACGGCTGCTGGATCTGCTG
GAAGGACTGACTGGCCAGAAGCTGCCCAAAGAGAAGGGGAGCACTAGGGTGCACG
CCCTGAACAACGTGAACAAAGCTCTGAGAGTGCTGCAGAACAACAACGTGGATCTG
GTGAATATTGGCAGTACTGATATCGTGGACGGGAACCACAAACTGACACTGGGCCT
GATCTGGAACATTATTCTGCACTGGCAGGTGAAAAATGTGATGAAGAACATCATGG
CCGGGCTGCAGCAGACCAATTCCGAGAAGATCCTGCTGTCTTGGGTGCGGCAGAGC
ACCCGCAACTATCCCCAGGTGAACGTGATTAACTTCACTACATCCTGGAGCGACGGG
CTGGCCCTGAATGCTCTGATTCACAGCCACAGGCCTGATCTGTTCGACTGGAATAGC
GTGGTGTGCCAGCAGTCTGCCACACAGCGCCTGGAACATGCCTTCAATATCGCTCGG
TACCAGCTGGGGATCGAAAAACTGCTGGACCCAGAGGATGTGGACACTACATACCC
AGATAAAAAGTCTATTCTGATGTACATTACTAGCCTGTTCCAGGTGCTGCCACAGCA
GGTGTCTATTGAAGCCATTCAGGAGGTGGAAATGCTGCCCCGCCCCCCCAAAGTGA
CTAAAGAGGAGCATTTTCAGCTGCATCATCAGATGCATTACAGCCAGCAGATTACCG
TGAGCCTGGCTCAGGGATATGAGCGCACCAGTAGTCCAAAACCACGGTTCAAGTCC
TACGCTTATACCCAGGCTGCCTACGTGACAACTAGCGACCCTACTAGATCCCCCTTT
CCATCCCAGCACCTGGAGGCCCCAGAGGACAAGAGCTTTGGGTCCAGCCTGATGGA AAGCGAGGTGAATCTGGATCGGTACCAGACAGCCCTGGAGGAGGTGCTGAGCTGGC
TGCTGAGTGCTGAAGACACACTGCAGGCCCAGGGCGAAATTTCCAATGACGTGGAA
GTGGTGAAGGATCAGTTCCACACACACGAGGGCTATATGATGGACCTGACAGCTCA
CCAGGGGCGCGTGGGCAATATCCTGCAGCTGGGCTCTAAACTGATCGGCACCGGGA
AACTGAGTGAGGACGAGGAAACAGAAGTGCAGGAGCAGATGAACCTGCTGAACAG
CCGCTGGGAGTGTCTGAGAGTGGCTAGTATGGAGAAGCAGTCCAACCTGCACCGGG
TGCTGATGGACCTGCAGAACCAGAAACTGAAAGAGCTGAACGACTGGCTGACAAAG
ACTGAGGAACGCACAAGGAAGATGGAGGAGGAGCCACTGGGACCCGACCTGGAGG
ATCTGAAGAGACAGGTGCAGCAGCATAAGGTGCTGCAGGAGGATCTGGAACAGGA
GCAGGTGCGGGTGAACTCCCTGACACATATGGTGGTGGTGGTGGACGAATCTAGTG
GAGATCACGCCACCGCCGCCCTGGAGGAACAGCTGAAGGTGCTGGGGGACCGGTGG
GCCAACATTTGCCGGTGGACCGAGGACAGGTGGGTGCTGCTGCAGGACATCCTGCT
GAAATGGCAGAGGCTGACCGAGGAGCAGTGTCTGTTTAGTGCTTGGCTGAGCGAGA
AAGAGGACGCCGTGAACAAGATCCACACAACCGGCTTTAAGGATCAGAACGAAATG
CTGTCTAGCCTGCAGAAACTGGCTGTGCTGAAGGCCGATCTGGAGAAAAAGAAGCA
GAGCATGGGCAAACTGTATAGCCTGAAACAGGACCTGCTGAGCACCCTGAAGAACA
AGAGCGTGACCCAGAAGACAGAAGCCTGGCTGGATAACTTTGCCCGCTGCTGGGAC
AACCTGGTGCAGAAACTGGAGAAAAGTACAGCTCAGATCTCTCAGGCTGTGACCAC
AACCCAGCCTAGCCTGACCCAGACAACCGTGATGGAAACCGTGACCACCGTGACAA
CCCGCGAACAGATCCTGGTGAAACATGCCCAGGAAGAGCTGCCACCTCCACCTCCC
CAGAAGAAGAGAACCCTGGAGCGGCTGCAGGAGCTGCAGGAAGCCACTGACGAAC
TGGACCTGAAGCTGAGGCAGGCCGAAGTGATTAAGGGGTCTTGGCAGCCTGTGGGC
GATCTGCTGATTGATTCCCTGCAGGACCACCTGGAAAAGGTGAAGGCTCTGAGAGG
CGAAATTGCTCCACTGAAGGAGAACGTGAGTCATGTGAA
CGATCTGGCTAGACAGCTGACAACACTGGGCATCCAGCTGAGCCCATACAATCTGA
GCACACTGGAGGACCTGAATACCAGGTGGAAGCTGCTGCAGGTGGCTGTGGAAGAC
CGGGTGCGGCAGCTGCATGAGGCCCATCGCGACTTCGGACCAGCCAGCCAGCACTT
TCTGAGCACATCCGTGCAGGGGCCCTGGGAGAGGGCCATTTCTCCCAACAAGGTGC
CCTACTATATTAATCACGAGACCCAGACCACTTGTTGGGACCATCCCAAGATGACAG
AACTGTACCAGTCCCTGGCCGATCTGAACAACGTGAGGTTTAGCGCTTACAGAACCG
CTATGAAGCTGAGACGGCTGCAGAAGGCCCTGTGCCTGGATCTGCTGTCCCTGTCCG
CCGCCTGCGATGCCCTGGATCAGCATAATCTGAAGCAGAACGATCAGCCAATGGAT
ATCCTGCAGATCATCAACTGCCTGACCACTATCTACGACAGGCTGGAGCAGGAGCA
CAACAACCTGGTGAACGTGCCTCTGTGCGTGGATATGTGCCTGAACTGGCTGCTGAA
CGTGTATGACACTGGGCGCACCGGCCGGATCAGAGTGCTGAGTTTTAAAACTGGGA
TTATCTCCCTGTGTAAGGCCCACCTGGAGGACAAGTACAGGTACCTGTTCAAGCAGG
TGGCTAGTAGCACTGGATTTTGTGACCAGCGCCGCCTGGGACTGCTGCTGCATGATA
GTATCCAGATTCCTAGACAGCTGGGAGAGGTGGCTAGTTTCGGAGGATCTAACATCG
AACCCAGCGTGCGCAGCTGTTTCCAGTTTGCCAATAACAAACCTGAAATCGAGGCTG
CTCTGTTCCTGGATTGGATGCGCCTGGAACCACAGAGCATGGTGTGGCTGCCTGTGC
TGCACAGAGTGGCTGCCGCCGAAACTGCCAAGCACCAGGCTAAATGCAACATCTGC
AAGGAATGTCCCATTATCGGCTTTCGCTACAGGAGTCTGAAACATTTTAACTACGAT
ATTTGCCAGAGCTGCTTCTTTTCCGGAAGAGTGGCCAAAGGACACAAGATGCACTAC
CCTATGGTGGAATATTGCACCCCAACTACATCTGGCGAAGATGTGCGCGATTTTGCC
AAGGTGCTGAAGAATAAGTTTCGGACTAAGAGGTACTTCGCCAAGCACCCCCGCAT
GGGGTATCTGCCAGTGCAGACAGTGCTGGAAGGAGACAATATGGAGACCGATACAA Figure 13 (continued)

TGTGAGCGGCCGCAATAAAAGATCTTTATTTTCATTAGATCTGTGTGTTGGTTTTTTG
TGTGtctagagtcgaccagagcatggctacgtagataagtagcatggcgggttaatcattaactacaAGGAACCCCTAG
TGATGGAGTTGGCCACTCCCTCTCTGCGCGCTCGCTCGCTCACTGAGGCCGGG
CGACCAAAGGTCGCCCGACGCCCGGGCTTTGCCCGGGCGGCCTCAGTGAGCG
AGCGAGCGCGC

Figure 13 (continued)

Figure 15

SEQ ID NO: 8

Main Features:
ITR
MHCK7 promoter
Chimeric Intron sequence
Human micro-dystrophin sequence
Poly A tail
Kanamycin resistance

GCGCGCTCGCTCGCTCACTGAGGCCGCCCGGGCAAAGCCCGGGCGTCGGGCG
ACCTTTGGTCGCCCGGCCTCAGTGAGCGAGCGAGCGCGCAGAGAGGGAGTGG
CCAACTCCATCACTAGGGGTTCCTTGTAGTTAATGATTAACCCGCCATGCTACTT
ATCTACGTAGCCATGCTCTAGAgtttaaacaagcttgcatgtctaagctagacccttcagattaaaaataactgaggtaa
gggcctgggtaggggaggtggtgtgagacgctcctgtctctcctctatctgcccatcggccctttggggaggaggaatgtgcccaaggact
aaaaaaaggccatggagccagaggggcgagggcaacagacctttcatgggcaaaccttggggccctgctgtctagcatgccccactacg
ggtctaggctgcccatgtaaggaggcaaggcctggggacacccgagatgcctggttataattaacccagacatgtggctgcccccccccc
cccaacacctgctgcctctaaaaataaccctgtccctggtggatcccctgcatgcgaagatcttcgaacaaggctgtgggggactgagggc
aggctgtaacaggcttgggggccagggcttatacgtgcctgggactcccaaagtattactgttccatgttcccggcgaagggccagctgtcc
cccgccagctagactcagcacttagtttaggaaccagtgagcaagtcagcccttggggcagcccatacaaggccatggggctgggcaag
ctgcacgcctgggtccggggtgggcacggtgcccgggcaacgagctgaaagctcatctgctctcaggggcccctccctggggacagcc
cctcctggctagtcacaccctgtaggctcctctatataacccaggggcacaggggctgccctcattctaccaccacctccacagcacagaca
gacactcaggagcagccagcggcgcgcccAGGTAAGTTTAGTCTTTTTGTCTTTTATTTCAGGTCCCG
GATCCGGTGGTGGTGCAAATCAAAGAACTGCTCCTCAGTGGATGTTGCCTTTACTTC
TAGGCCTGTACGGAAGTGTTACTTCTGCTCTAAAAGCTGCGGAATTGTACCCGCGGC
CGCCACCATGCTGTGGTGGGAGGAGGTGGAGGATTGTTATGAAAGGGAGGACGTGC
AGAAGAAGACTTTTACCAAGTGGGTGAACGCTCAGTTCAGCAAATTTGGGAAGCAG
CACATCGAGAATCTGTTTTCCGACCTGCAGGATGGGAGACGGCTGCTGGATCTGCTG
GAAGGACTGACTGGCCAGAAGCTGCCCAAAGAGAAGGGGAGCACTAGGGTGCACG
CCCTGAACAACGTGAACAAAGCTCTGAGAGTGCTGCAGAACAACAACGTGGATCTG
GTGAATATTGGCAGTACTGATATCGTGGACGGGAACCACAAACTGACACTGGGCCT
GATCTGGAACATTATTCTGCACTGGCAGGTGAAAAATGTGATGAAGAACATCATGG
CCGGGCTGCAGCAGACCAATTCCGAGAAGATCCTGCTGTCTTGGGTGCGGCAGAGC
ACCCGCAACTATCCCCAGGTGAACGTGATTAACTTCACTACATCCTGGAGCGACGGG
CTGGCCCTGAATGCTCTGATTCACAGCCACAGGCCTGATCTGTTCGACTGGAATAGC
GTGGTGTGCCAGCAGTCTGCCACACAGCGCCTGGAACATGCCTTCAATATCGCTCGG
TACCAGCTGGGGATCGAAAAACTGCTGGACCCAGAGGATGTGGACACTACATACCC
AGATAAAAAGTCTATTCTGATGTACATTACTAGCCTGTTCCAGGTGCTGCCACAGCA
GGTGTCTATTGAAGCCATTCAGGAGGTGGAAATGCTGCCCCGCCCCCCCAAAGTGA
CTAAAGAGGAGCATTTTCAGCTGCATCATCAGATGCATTACAGCCAGCAGATTACCG TGAGCCTGGCTCAGGGATATGAGCGCACCAGTAGTCCAAAACCACGGTTCAAGTCC
TACGCTTATACCCAGGCTGCCTACGTGACAACTAGCGACCCTACTAGATCCCCCTTT
CCATCCCAGCACCTGGAGGCCCCAGAGGACAAGAGCTTTGGGTCCAGCCTGATGGA
AAGCGAGGTGAATCTGGATCGGTACCAGACAGCCCTGGAGGAGGTGCTGAGCTGGC
TGCTGAGTGCTGAAGACACACTGCAGGCCCAGGGCGAAATTTCCAATGACGTGGAA
GTGGTGAAGGATCAGTTCCACACACACGAGGGCTATATGATGGACCTGACAGCTCA
CCAGGGGCGCGTGGGCAATATCCTGCAGCTGGGCTCTAAACTGATCGGCACCGGGA
AACTGAGTGAGGACGAGGAAACAGAAGTGCAGGAGCAGATGAACCTGCTGAACAG
CCGCTGGGAGTGTCTGAGAGTGGCTAGTATGGAGAAGCAGTCCAACCTGCACCGGG
TGCTGATGGACCTGCAGAACCAGAAACTGAAAGAGCTGAACGACTGGCTGACAAAG
ACTGAGGAACGCACAAGGAAGATGGAGGAGGAGCCACTGGGACCCGACCTGGAGG
ATCTGAAGAGACAGGTGCAGCAGCATAAGGTGCTGCAGGAGGATCTGGAACAGGA
GCAGGTGCGGGTGAACTCCCTGACACATATGGTGGTGGTGGTGGACGAATCTAGTG
GAGATCACGCCACCGCCGCCCTGGAGGAACAGCTGAAGGTGCTGGGGGACCGGTGG
GCCAACATTTGCCGGTGGACCGAGGACAGGTGGGTGCTGCTGCAGGACATCCTGCT
GAAATGGCAGAGGCTGACCGAGGAGCAGTGTCTGTTTAGTGCTTGGCTGAGCGAGA
AAGAGGACGCCGTGAACAAGATCCACACAACCGGCTTTAAGGATCAGAACGAAATG
CTGTCTAGCCTGCAGAAACTGGCTGTGCTGAAGGCCGATCTGGAGAAAAAGAAGCA
GAGCATGGGCAAACTGTATAGCCTGAAACAGGACCTGCTGAGCACCCTGAAGAACA
AGAGCGTGACCCAGAAGACAGAAGCCTGGCTGGATAACTTTGCCCGCTGCTGGGAC
AACCTGGTGCAGAAACTGGAGAAAAGTACAGCTCAGATCTCTCAGGCTGTGACCAC
AACCCAGCCTAGCCTGACCCAGACAACCGTGATGGAAACCGTGACCACCGTGACAA
CCCGCGAACAGATCCTGGTGAAACATGCCCAGGAAGAGCTGCCACCTCCACCTCCC
CAGAAGAAGAGAACCCTGGAGCGGCTGCAGGAGCTGCAGGAAGCCACTGACGAAC
TGGACCTGAAGCTGAGGCAGGCCGAAGTGATTAAGGGGTCTTGGCAGCCTGTGGGC
GATCTGCTGATTGATTCCCTGCAGGACCACCTGGAAAAGGTGAAGGCTCTGAGAGG
CGAAATTGCTCCACTGAAGGAGAACGTGAGTCATGTGAACGATCTGGCTAGACAGC
TGACAACACTGGGCATCCAGCTGAGCCCATACAATCTGAGCACACTGGAGGACCTG
AATACCAGGTGGAAGCTGCTGCAGGTGGCTGTGGAAGACCGGGTGCGGCAGCTGCA
TGAGGCCCATCGCGACTTCGGACCAGCCAGCCAGCACTTTCTGAGCACATCCGTGCA
GGGGCCCTGGGAGAGGGCCATTTCTCCCAACAAGGTGCCCTACTATATTAATCACGA
GACCCAGACCACTTGTTGGGACCATCCCAAGATGACAGAACTGTACCAGTCCCTGG
CCGATCTGAACAACGTGAGGTTTAGCGCTTACAGAACCGCTATGAAGCTGAGACGG
CTGCAGAAGGCCCTGTGCCTGGATCTGCTGTCCCTGTCCGCCGCCTGCGATGCCCTG
GATCAGCATAATCTGAAGCAGAACGATCAGCCAATGGATATCCTGCAGATCATCAA
CTGCCTGACCACTATCTACGACAGGCTGGAGCAGGAGCACAACAACCTGGTGAACG
TGCCTCTGTGCGTGGATATGTGCCTGAACTGGCTGCTGAACGTGTATGACACTGGGC
GCACCGGCCGGATCAGAGTGCTGAGTTTTAAAACTGGGATTATCTCCCTGTGTAAGG
CCCACCTGGAGGACAAGTACAGGTACCTGTTCAAGCAGGTGGCTAGTAGCACTGGA
TTTTGTGACCAGCGCCGCCTGGGACTGCTGCTGCATGATAGTATCCAGATTCCTAGA Figure 15 (continued)

CAGCTGGGAGAGGTGGCTAGTTTCGGAGGATCTAACATCGAACCCAGCGTGCGCAG
CTGTTTCCAGTTTGCCAATAACAAACCTGAAATCGAGGCTGCTCTGTTCCTGGATTG
GATGCGCCTGGAACCACAGAGCATGGTGTGGCTGCCTGTGCTGCACAGAGTGGCTG
CCGCCGAAACTGCCAAGCACCAGGCTAAATGCAACATCTGCAAGGAATGTCCCATT
ATCGGCTTTCGCTACAGGAGTCTGAAACATTTTAACTACGATATTTGCCAGAGCTGC
TTCTTTTCCGGAAGAGTGGCCAAAGGACACAAGATGCACTACCCTATGGTGGAATAT
TGCACCCCAACTACATCTGGCGAAGATGTGCGCGATTTTGCCAAGGTGCTGAAGAAT
AAGTTTCGGACTAAGAGGTACTTCGCCAAGCACCCCCGCATGGGGTATCTGCCAGTG
CAGACAGTGCTGGAAGGAGACAATATGGAGACCGATACAATGTGAGCGGCCGCAAT
AAAAGATCTTTATTTTCATTAGATCTGTGTGTTGGTTTTTTGTGTGtctagagtcgaccagagcat
ggctacgtagataagtagcatggcgggttaatcattaactacaAGGAACCCCTAGTGATGGAGTTGGCCA
CTCCCTCTCTGCGCGCTCGCTCGCTCACTGAGGCCGGGCGACCAAAGGTCGCC
CGACGCCCGGGCTTTGCCCGGGCGGCCTCAGTGAGCGAGCGAGCGCGCagctgcat
taatgaatcggccaacgcgcggggagaggcggtttgcgtattgggcgctcttccgcttcctcgctcactgactcgctgcgctcggtcgttcg
gctgcggcgagcggtatcagctcactcaaaggcggtaatacggttatccacagaatcaggggataacgcaggaaagaaCATGTGA
GCAAAAGGCCAGCAAAAGGCCAGGAACCGTAAAAAGGCCGCGTTGCTGGCGTTTTT
CCATAGGCTCCGCCCCCCTGACGAGCATCACAAAAATCGACGCTCAAGTCAGAGGT
GGCGAAACCCGACAGGACTATAAAGATACCAGGCGTTTCCCCCTGGAAGCTCCCTC
GTGCGCTCTCCTGTTCCGACCCTGCCGCTTACCGGATACCTGTCCGCCTTTCTCCCTT
CGGGAAGCGTGGCGCTTTCTCATAGCTCACGCTGTAGGTATCTCAGTTCGGTGTAGG
TCGTTCGCTCCAAGCTGGGCTGTGTGCACGAACCCCCCGTTCAGCCCGACCGCTGCG
CCTTATCCGGTAACTATCGTCTTGAGTCCAACCCGGTAAGACACGACTTATCGCCAC
TGGCAGCAGCCACTGGTAACAGGATTAGCAGAGCGAGGTATGTAGGCGGTGCTACA
GAGTTCTTGAAGTGGTGGCCTAACTACGGCTACACTAGAAGAACAGTATTTGGTATC
TGCGCTCTGCTGAAGCCAGTTACCTTCGGAAAAAGAGTTGGTAGCTCTTGATCCGGC
AAACAAACCACCGCTGGTAGCGGTGGTTTTTTTGTTTGCAAGCAGCAGATTACGCGC
AGAAAAAAAGGATCTCAAGAAGATCCTTTGATCTTTTCTACGGGGTCTGACGCTCAG
TGGAACGAAAACTCACGTTAAGGGATTTTGGTCATGAGATTATCAAAAAGGATCTTC
ACCTAGATCCTTTTAAATTAAAAATGAAGTTTTAAATCAATCTAAAGTATATATGAG
TAAAAATATTCCGGAATTGCCAGCTGGGGCGCCCTCTGGTAAGGTTGGGAAGCCCTG
CAAAGTAAACTGGATGGCTTTCTTGCCGCCAAGGATCTGATGGCGCAGGGGATCAA
GATCTGATCAAGAGACAGGATGAGGATCGTTTCGCATGATTGAACAAGATGGATTG
CACGCAGGTTCTCCGGCCGCTTGGGTGGAGAGGCTATTCGGCTATGACTGGGCACAA
CAGACAATCGGCTGCTCTGATGCCGCCGTGTTCCGGCTGTCAGCGCAGGGGCGCCCG
GTTCTTTTTGTCAAGACCGACCTGTCCGGTGCCCTGAATGAACTGCAGGACGAGGCA
GCGCGGCTATCGTGGCTGGCCACGACGGGCGTTCCTTGCGCAGCTGTGCTCGACGTT
GTCACTGAAGCGGGAAGGGACTGGCTGCTATTGGGCGAAGTGCCGGGGCAGGATCT
CCTGTCATCCCACCTTGCTCCTGCCGAGAAAGTATCCATCATGGCTGATGCAATGCG
GCGGCTGCATACGCTTGATCCGGCTACCTGCCCATTCGACCACCAAGCGAAACATCG
CATCGAGCGAGCACGTACTCGGATGGAAGCCGGTCTTGTCGATCAGGATGATCTGG Figure 15 (continued)

ACGAAGAGCATCAGGGGCTCGCGCCAGCCGAACTGTTCGCCAGGCTCAAGGCGCGC
ATGCCCGACGGCGAGGATCTCGTCGTGACCCATGGCGATGCCTGCTTGCCGAATATC
ATGGTGGAAAATGGCCGCTTTTCTGGATTCATCGACTGTGGCCGGCTGGGTGTGGCG
GACCGCTATCAGGACATAGCGTTGGCTACCCGTGATATTGCTGAAGAGCTTGGCGGC
GAATGGGCTGACCGCTTCCTCGTGCTTTACGGTATCGCCGCTCCCGATTCGCAGCGC
ATCGCCTTCTATCGCCTTCTTGACGAGTTCTTCTGAACCGGTAATATTATTGAAGCAT
TTATCAGGGTTATTGTCTCATGAGCGGATACATATTTGAATGTATTTAGAAAAATAA
ACAAATAGGGGTTCCGCGCACATTTCCCCGAAAAGTGCCACCTGACGTctaagaaaccattat
tatcatgacattaacctataaaaataggcgtatcacgaggccctttcgtctcgcgcgtttcggtgatgacggtgaaaacctctgacacatgcag
ctcccggagacggtcacagcttgtctgtaagcggatgccgggagcagacaagcccgtcagggcgcgtcagcgggtgttggcgggtgtc
ggggctggcttaactatgcggcatcagagcagattgtactgagagtgcaccatatgcggtgtgaaataccgcacagatgcgtaaggagaa
aataccgcatcaggCGAttccaacatccaataaatcatacaggcaaggcaaagaattagcaaaattaagcaataaagcctcagagcataa
agctaaatcggttgtaccaaaaacattatgaccctgtaatacttttgcgggagaagcctttatttcaacgcaaggataaaaatttttagaacccctc
atatattttaaatgcaatgcctgagtaatgtgtaggtaaagattcaaacgggtgagaaaggccggagacagtcaaatcaccatcaatatgatat
tcaaccgttctagctgataaattcatgccggagagggtagctatttttgagaggtctctacaaaggctatcaggtcattgcctgagagtctgga
gcaaacaagagaatcgatgaacggtaatcgtaaaactagcatgtcaatcatatgtaccccggttgataatcagaaaagccccaaaaacagg
aagattgtataagcaaatatttaaattgtaaGcgttaatattttgttaaaattcgcgttaaatttttgttaaatcagctcattttttaaccaataggccg
aaatcggcaaaatcccttataaatcaaaagaatagaccgagatagggttgagtgttgttccagtttggaacaagagtccactattaaagaacg
tggactccaacgtcaaagggcgaaaaaccgtctatcagggcgatggcccactacgtgaaccatcaccctaatcaagttttttggggtcgag
gtgccgtaaaGcactaaatcggaaccctaaagggagcccccgatttagagcttgacggggaaagccggcgaacgtggcgagaaagga
agggaagaaagcgaaaggagcgggcgctagggcgctggcaagtgtagcggtcacgctgcgcgtaaccaccacacccgccgcgcttaa
tgcgccgctacagggcgcgtactatggttgctttgacgagcacgtataacgtgctttcctcgttagaatcagagcgggagctaaacaggagg
ccgattaaagggattttagacaggaacggtacgccagaatcctgagaagtgtttttataatcagtgaggccaccgagtaaaagagtctgtcca
tcacgcaaattaaccgttgtcgcaatacttctttgattagtaataacatcacttgcctgagtagaagaactcaaactatcggccttgctggtaatat
ccagaacaatattaccgccagccattgcaacggaatcgccattcgccattcaggctgcgcaactgttgggaagggcgatcggtgcgggcc
tcttcgctattacgccagct Figure 15 (continued)

ADENO-ASSOCIATED VIRUS VECTOR DELIVERY OF MUSCLE SPECIFIC MICRO-DYSTROPHIN TO TREAT MUSCULAR DYSTROPHY

This application is as a U.S. National Phase Application under 35 U.S.C. § 371 of International Application No. PCT/US2019/037489, filed on Jun. 17, 2019, which claims priority benefit to U.S. Provisional Patent Application No. 62/686,668, filed Jun. 18, 2018; U.S. Provisional Patent Application No. 62/740,402, filed Oct. 2, 2018; U.S. Provisional Patent Application No. 62/752,841, filed Oct. 30, 2018; U.S. Provisional Patent Application No. 62/823,649, filed Mar. 25, 2019; and U.S. Provisional Patent Application No. 62/860,220 filed Jun. 11, 2019 each of which are incorporated by reference herein in their entirety.

INCORPORATION BY REFERENCE OF MATERIAL SUBMITTED ELECTRONICALLY

This application contains, as a separate part of the disclosure, a Sequence Listing in computer-readable form which is incorporated by reference in its entirety and identified as follows: Filename: 53169_Seqlisting.txt; Size: 60,056 bytes, created; Jun. 17, 2019.

FIELD OF INVENTION

The invention provides gene therapy vectors, such as adeno-associated virus (AAV) vectors, expressing a miniaturized human micro-dystrophin gene and method of using these vectors to express micro-dystrophin in skeletal muscles including diaphragm and cardiac muscle and to protect muscle fibers from injury, increase muscle strength and reduce and/or prevent fibrosis in subjects suffering from muscular dystrophy.

BACKGROUND

The importance of muscle mass and strength for daily activities, such as locomotion and breathing, and for whole body metabolism is unequivocal. Deficits in muscle function produce muscular dystrophies (MDs) that are characterized by muscle weakness and wasting and have serious impacts on quality of life. The most well-characterized MDs result from mutations in genes encoding members of the dystrophin-associated protein complex (DAPC). These MDs result from membrane fragility associated with the loss of sarcolemmal-cytoskeleton tethering by the DAPC. Duchenne Muscular Dystrophy (DMD) is one of the most devastating muscle disease affecting 1 in 5000 newborn males.

DMD is caused by mutations in the DMD gene leading to reductions in mRNA and the absence of dystrophin, a 427 kD sarcolemmal protein associated with the dystrophin-associated protein complex (DAPC) (Hoffman et al., *Cell* 51 (6): 919-28, 1987). The DAPC is composed of multiple proteins at the muscle sarcolemma that form a structural link between the extra-cellular matrix (ECM) and the cytoskeleton via dystrophin, an actin binding protein, and alpha-dystroglycan, a laminin-binding protein. These structural links act to stabilize the muscle cell membrane during contraction and protect against contraction-induced damage. With dystrophin loss, membrane fragility results in sarcolemmal tears and an influx of calcium, triggering calcium-activated proteases and segmental fiber necrosis (Straub et al., *Curr Opin. Neurol.* 10 (2): 168-75, 1997). This uncontrolled cycle of muscle degeneration and regeneration ultimately exhausts the muscle stem cell population (Sacco et al., *Cell,* 2010. 143 (7): p. 1059-71; Wallace et al., *Annu Rev Physiol,* 2009. 71: p. 37-57), resulting in progressive muscle weakness, endomysial inflammation, and fibrotic scarring.

Without membrane stabilization from dystrophin or a micro-dystrophin, DMD will manifest uncontrolled cycles of tissue injury and repair ultimately replace lost muscle fibers with fibrotic scar tissue through connective tissue proliferation. Fibrosis is characterized by the excessive deposits of ECM matrix proteins, including collagen and elastin. ECM proteins are primarily produced from cytokines such as TGFβ that is released by activated fibroblasts responding to stress and inflammation. Although the primary pathological feature of DMD is myofiber degeneration and necrosis, fibrosis as a pathological consequence has equal repercussions. The over-production of fibrotic tissue restricts muscle regeneration and contributes to progressive muscle weakness in the DMD patient. In one study, the presence of fibrosis on initial DMD muscle biopsies was highly correlated with poor motor outcome at a 10-year follow-up (Desguerre et al., *J Neuropathol Exp Neurol,* 2009. 68 (7): p. 762-7). These results point to fibrosis as a major contributor to DMD muscle dysfunction and highlight the need for early intervention prior to overt fibrosis.

There is a need for treatments that increase muscle strength and protect against muscle injury in patients suffering from DMD.

SUMMARY OF INVENTION

The present invention is directed to gene therapy vectors, e.g. AAV, expressing the micro-dystrophin gene to skeletal muscles including diaphragm and cardiac muscle to protect muscle fibers from injury, increase muscle strength and reduce and/or prevent fibrosis.

The invention provides for therapies and approaches for increasing muscular force and/or increasing muscle mass using gene therapy vectors to deliver micro-dystrophin to address the gene defect observed in DMD. Example 2 describes a systemic gene delivery clinical trial for Duchenne muscular dystrophy, in this study the subjects received 2×1014 vg/kg AAVrh74.MHCK7.micro-dystrophin. The clinical study described in Example 3 provides a novel pivotal clinical protocol that includes a randomized double-blind placebo controlled design. At study initiation, subjects are randomized and either receive $2\times10^{14}$ vg/kg AAVrh74.MHCK7.micro-dystrophin or lactated ringers.

The invention provides for nucleic acid molecules comprising the nucleotide sequence of SEQ ID NO: 3, 8 or 9. The invention also provides for rAAV comprising the nucleic acid sequence of SEQ ID NO: 9 or nucleotides 1-4977 of SEQ ID NO: 8 or nucleotides 55-5021 of SEQ ID NO: 3, and rAAV particles comprising the nucleic acid sequence of SEQ ID NO: 9 or nucleotides 1-4977 of SEQ ID NO: 8 or nucleotides 55-5021 of SEQ ID NO: 3.

Another aspect of the invention provides for compositions comprising a nucleic acid molecule comprising the nucleotide sequence of SEQ ID NO: 3, 8 or 9, rAAV comprising the nucleic acid sequence of SEQ ID NO: 9 or nucleotides 1-4977 of SEQ ID NO: 8 or nucleotides 55-5021 of SEQ ID NO: 3, and rAAV particles comprising the nucleic acid sequence of SEQ ID NO: 9 or nucleotides 1-4977 of SEQ ID NO: 8 or nucleotides 55-5021 of SEQ ID NO: 3. Any of the methods disclosed herein may be carried out with these compositions.

The invention provides for methods of treating a muscular dystrophy in a human subject in need thereof comprising the step of administering a recombinant adeno-virus associated (rAAV) rAAV.MHCK7.microdystrophin, wherein the rAAV is administered by a systemic route of administration at a dose of about $5.0\times10^{12}$ vg/kg to about $1.0\times10^{15}$ vg/kg. The muscular dystrophy may be Duchenne muscular dystrophy or Becker's muscular dystrophy.

For example, the dose of rAAV administered is about $5.0\times10^{12}$ vg/kg to about $1.0\times10^{14}$ vg/kg, or about $5.0\times10^{12}$ vg/kg to $1.0\times10^{14}$ vg/kg, or about $5.0\times10^{12}$ vg/kg to about $2.0\times10^{14}$ vg/kg, or about $5.0\times10^{12}$ vg/kg to about $1.0\times10^{14}$ vg/kg, or about $5.0\times10^{12}$ vg/kg to about $5.0\times10^{13}$ vg/kg, or about $5.0\times10^{12}$ vg/kg to about $2.0\times10^{13}$ vg/kg, or about $5.0\times10^{12}$ vg/kg to about $1.0\times10^{13}$ vg/kg, or $1.0\times10^{14}$ vg/kg to about $1.0\times10^{15}$ vg/kg, or $1.0\times10^{13}$ vg/kg to about $1.0\times10^{14}$ vg/kg, or about $1.0\times10^{13}$ vg/kg to $1.0\times10^{14}$ vg/kg, or about $1.0\times10^{13}$ vg/kg to about $2.0\times10^{14}$ vg/kg, or about $1.0\times10^{13}$ vg/kg to about $1.0\times10^{14}$ vg/kg, or about $1.0\times10^{13}$ vg/kg to about $5.0\times10^{13}$ vg/kg, or about $1.0\times10^{13}$ vg/kg to about $3.0\times10^{14}$ vg/kg, or about $1.0\times10^{13}$ vg/kg to about $5.0\times10^{14}$ vg/kg, or about $1.0\times10^{13}$ vg/kg to about $6.0\times10^{14}$ vg/kg, or $1.0\times10^{13}$ vg/kg to about $1.0\times10^{15}$ vg/kg, or $5.0\times10^{13}$ vg/kg to about $1.0\times10^{14}$ vg/kg, or about $5.0\times10^{13}$ vg/kg to $1.0\times10^{14}$ vg/kg, or about $5.0\times10^{13}$ vg/kg to about $2.0\times10^{14}$ vg/kg, or about $5.0\times10^{13}$ vg/kg to about $1.0\times10^{14}$ vg/kg, or about $5.0\times10^{13}$ vg/kg to about $3.0\times10^{14}$ vg/kg, or about $5.0\times10^{13}$ vg/kg to about $5.0\times10^{14}$ vg/kg, or about $5.0\times10^{13}$ vg/kg to about $6.0\times10^{14}$ vg/kg, or $5.0\times10^{13}$ vg/kg to about $1.0\times10^{15}$ vg/kg, or $1.0\times10^{14}$ vg/kg to about $6.0\times10^{14}$ vg/kg, or $1.0\times10^{14}$ vg/kg to about $5.0\times10^{14}$ vg/kg, or $1.0\times10^{14}$ vg/kg to about $4.0\times10^{14}$ vg/kg, or $1.0\times10^{14}$ vg/kg to about $1.0\times10^{15}$ vg/kg, or $1.0\times10^{14}$ vg/kg to about $3.0\times10^{14}$ vg/kg, or about $1.0\times10^{14}$ vg/kg to about $2.5\times10^{14}$ vg/kg, or $1.0\times10^{14}$ vg/kg to about $2.0\times10^{14}$ vg/kg, or about $1.25\times10^{14}$ vg/kg to about $3.75\times10^{14}$ vg/kg, or about $1.25\times10^{14}$ vg/kg to $6.0\times10^{14}$, or about $1.25\times10^{14}$ vg/kg to $5.0\times10^{14}$, or about $1.25\times10^{14}$ vg/kg to $4.0\times10^{14}$, or about $1.25\times10^{14}$ vg/kg to $1.0\times10^{15}$, or about $1.25\times10^{14}$ vg/kg to about $3.5\times10^{14}$ vg/kg, or about $1.25\times10^{14}$ vg/kg to about $3.0\times10^{14}$ vg/kg, or about $1.25\times10^{14}$ vg/kg to about $2.75\times10^{14}$ vg/kg, or about $1.25\times10^{14}$ vg/kg to about $2.5\times10^{14}$ vg/kg, or about $1.25\times10^{14}$ vg/kg to about $2.0\times10^{14}$ vg/kg, or $1.25\times10^{14}$ vg/kg to about $3.75\times10^{14}$ vg/kg, or about $1.25\times10^{14}$ vg/kg to about $3.5\times10^{14}$ vg/kg, or $1.5\times10^{14}$ vg/kg to about $1.0\times10^{15}$ vg/kg, or about $1.5\times10^{14}$ vg/kg to $6.0\times10^{14}$, or about $1.5\times10^{14}$ vg/kg to $5.0\times10^{14}$, or about $1.5\times10^{14}$ vg/kg to $4.0\times10^{14}$, or about $1.5\times10^{14}$ vg/kg to about $3.75\times10^{14}$ vg/kg, or about $1.5\times10^{14}$ vg/kg to about $3.5\times10^{14}$ vg/kg, or about $1.5\times10^{14}$ vg/kg to about $3.25\times10^{14}$ vg/kg, or about $1.5\times10^{14}$ vg/kg to about $3.0\times10^{14}$ vg/kg, or about $1.5\times10^{14}$ vg/kg to about $2.75\times10^{14}$ vg/kg, or about $1.5\times10^{14}$ vg/kg to about $2.5\times10^{14}$ vg/kg, or about $1.5\times10^{14}$ vg/kg to about $2.0\times10^{14}$ vg/kg, or $1.75\times10^{14}$ vg/kg to about $1.0\times10^{15}$ vg/kg, or about $1.75\times10^{14}$ vg/kg to $6.0\times10^{14}$, or about $1.75\times10^{14}$ vg/kg to $5.0\times10^{14}$, or about $1.75\times10^{14}$ vg/kg to $4.0\times10^{14}$, or about $1.75\times10^{14}$ vg/kg to about $3.75\times10^{14}$ vg/kg, or about $1.75\times10^{14}$ vg/kg to about $3.5\times10^{14}$ vg/kg, or about $1.75\times10^{14}$ vg/kg to about $3.25\times10^{14}$ vg/kg, or about $1.75\times10^{14}$ vg/kg to about $3.0\times10^{14}$ vg/kg, or about $1.75\times10^{14}$ vg/kg to about $2.75\times10^{14}$ vg/kg, or about $1.75\times10^{14}$ vg/kg to about $2.5\times10^{14}$ vg/kg, or about $1.75\times10^{14}$ vg/kg to about $2.25\times10^{14}$ vg/kg, or about $1.75\times10^{14}$ vg/kg to about $2.0\times10^{14}$ vg/kg, or about $2.0\times10^{14}$ vg/kg to $1.0\times10^{15}$, or about $2.0\times10^{14}$ vg/kg to $6.0\times10^{14}$, or about $2.0\times10^{14}$ vg/kg to $5.0\times10^{14}$, or about $2.0\times10^{14}$ vg/kg to about $4.0\times10^{14}$ vg/kg, or about $2.0\times10^{14}$ vg/kg to about $3.75\times10^{14}$ vg/kg, or about $2.0\times10^{14}$ vg/kg to about $3.5\times10^{14}$ vg/kg, or about $2.0\times10^{14}$ vg/kg to about $3.25\times10^{14}$ vg/kg.

In one embodiment, the methods of the invention comprise systemically administering rAAV wherein the systemic route of administration is an intravenous route and the dose of the rAAV administered is about $2.0\times10^{14}$ vg/kg. In another embodiment, the methods of the invention comprise systemically administering rAAV wherein the systemic route of administration is an intravenous route and the dose of the rAAV administered is about $5.0\times10^{12}$ vg/kg, or about $6.0\times10^{12}$ vg/kg, or about $7.0\times10^{12}$ vg/kg, or about $8.0\times10^{12}$ vg/kg, or about $9.0\times10^{12}$ vg/kg, or about $1.0\times10^{13}$ vg/kg, or about $1.25\times10^{13}$ vg/kg, or about $1.5\times10^{13}$ vg/kg, or about $1.75\times10^{13}$ vg/kg, or about $2.25\times10^{13}$ vg/kg, or about $2.5\times10^{13}$ vg/kg, or about $2.75\times10^{13}$ vg/kg, or about $3.0\times10^{13}$ vg/kg, or about $3.25\times10^{13}$ vg/kg, or about $3.5\times10^{13}$ vg/kg, or about $3.75\times10^{13}$ vg/kg, or about $4.0\times10^{13}$ vg/kg, or about $5.0\times10^{13}$ vg/kg, or about $6.0\times10^{13}$ vg/kg, or about $7.0\times10^{13}$ vg/kg, or about $8.0\times10^{13}$ vg/kg, or about $9.0\times10^{13}$ vg/kg, or about $1.0\times10^{14}$ vg/kg, or about $1.25\times10^{14}$ vg/kg, or about $1.5\times10^{14}$ vg/kg, or about $1.75\times10^{14}$ vg/kg, or about $2.25\times10^{14}$ vg/kg, or about $2.5\times10^{14}$ vg/kg, or about $2.75\times10^{14}$ vg/kg, or about $3.0\times10^{14}$ vg/kg, or about $3.25\times10^{14}$ vg/kg, or about $3.5\times10^{14}$ vg/kg, or about $3.75\times10^{14}$ vg/kg, or about $4.0\times10^{14}$ vg/kg, or about $5.0\times10^{14}$ vg/kg, or about $6.0\times10^{14}$ vg/kg, or about $1\times10^{15}$ vg/kg. In one embodiment, the rAAV is AAVrh74.MHCK7.microdystrophin or AAVrh74.MCK.microdystrophin. In one embodiment, the rAAV is the AAVrh74.MHCK7.microdystrophin of SEQ ID NO: 9, nucleotides 55-5021 of SEQ ID NO: 3, nucleotides 1-4977 of SEQ ID NO: 8 or nucleotides 56-5022 of SEQ ID NO: 6. In one embodiment, the rAAV is the AAVrh74.MCK.microdystrophin of nucleotides 56-4820 of SEQ ID NO: 5.

In any of the methods of the invention, the dose of rAAV can be administered at about 5 mL/kg to about 15 mL/kg, or about 8 mL/kg to about 12 mL/kg, or 8 mL/kg to about 10 mL/kg, or 5 mL/kg to about 10 mL/kg or about 10 mL/kg to 12 mL/k, or about 10 mL/kg to 15 mL/kg or 10 mL/kg to about 20 mL/kg. In a particular embodiment, the dose or the rAAV is administered in about 10 mL/kg. In one embodiment, the rAAV is AAVrh74.MHCK7.microdystrophin or AAVrh74.MCK.microdystrophin. In one embodiment, the rAAV is the AAVrh74.MHCK7.microdystrophin of SEQ ID NO: 9, nucleotides 55-5021 of SEQ ID NO: 3, nucleotides 1-4977 of SEQ ID NO: 8 or nucleotides 56-5022 of SEQ ID NO: 6. In one embodiment, the rAAV is the AAVrh74.MCK.microdystrophin of nucleotides 56-4820 of SEQ ID NO: 5.

In any of the methods of the invention, the dose of rAAV can be administered by injection, infusion or implantation. For example, the dose of rAAV is administered by infusion over approximately one hour. In addition, the dose of rAAV is administered by an intravenous route through a peripheral limb vein, such as a peripheral arm vein or a peripheral leg vein. Alternatively, the infusion may be administered over approximately 30 minutes, or approximately 1.5 hours, or approximately 2 hours, or approximately 2.5 hours or approximately 3 hours. In one embodiment, the rAAV is AAVrh74.MHCK7.microdystrophin. In one embodiment, the AAVrh74.MHCK7.microdystrophin is the AAVrh74.MHCK7.microdystrophin of SEQ ID NO: 9, nucleotides 55-5021 of SEQ ID NO: 3, nucleotides 1-4977 of SEQ ID NO: 8 or nucleotides 56-5022 of SEQ ID NO: 6. In one embodiment, the rAAV is AAVrh74.MCK.microdystrophin. In one embodiment, the AAVrh74.MCK.microdystrophin is the AAVrh74.MCK.microdystrophin of nucleotides 56-4820 of SEQ ID NO: 5.

The rAAV administered by any of the methods of the invention can comprise the human micro-dystrophin nucleotide sequence of SEQ ID NO: 1, the MHCK7 promoter sequence of SEQ ID NO: 2 or SEQ ID NO:7. In addition, the rAAV administered by any of the methods of the invention comprises the human micro-dystrophin nucleotide sequence of SEQ ID NO: 1 and the MHCK7 promoter sequence of SEQ ID NO: 2 or SEQ ID NO:7. For example, the rAAV can comprise the AAVrh74.MHCK7.micro-dystrophin construct nucleotide sequence of SEQ ID NO: 9, nucleotides 55-5021 of SEQ ID NO: 3, nucleotides 1-4977 of SEQ ID NO: 8, or nucleotides 56-5022 of SEQ ID NO: 6. In one embodiment, the rAAV is AAVrh74.MHCK7.microdystrophin. In one embodiment, the AAVrh74.MHCK7.microdystrophin is the AAVrh74.MHCK7.microdystrophin of SEQ ID NO: 9, nucleotides 55-5021 of SEQ ID NO: 3, nucleotides 1-4977 of SEQ ID NO: 8, or nucleotides 56-5022 of SEQ ID NO: 6.

In one embodiment, the rAAV is AAVrh74.MCK.microdystrophin. In one embodiment, the AAVrh74.MCK.microdystrophin is the AAVrh74.MCK.microdystrophin of nucleotides 56-4820 of SEQ ID NO: 5.

In any of the methods of the invention, the rAAV administered is of the serotype AAVrh7.4.

In some embodiments, the methods of the invention treat Duchenne muscular dystrophy or Becker's muscular dystrophy. An exemplary embodiment is a method of treating Duchenne muscular dystrophy or Becker's muscular dystrophy in a human subject in need thereof comprising the step of administering a dose recombinant adeno-virus associated (rAAV) rAAV.MHCK7.microdystrophin, wherein the route of administration is intravenous infusion and the dose of the rAAV administered is about $2\times10^{14}$ vg/kg over approximately one hour, and wherein the rAAV vector comprises the AAVrh74.MHCK7.micro-dystrophin construct nucleotide sequence of SEQ ID NO: 9 or of nucleotides 55-5021 of SEQ ID NO: 3, nucleotides 1-4977 of SEQ ID NO: 8, or nucleotides 56-5022 of SEQ ID NO: 6. In one embodiment, the rAAV is AAVrh74.MHCK7.microdystrophin. In one embodiment, the AAVrh74.MHCK7.microdystrophin is the AAVrh74.MHCK7.microdystrophin of SEQ ID NO: 9 or of nucleotides 55-5021 of SEQ ID NO: 3, nucleotides 1-4977 of SEQ ID NO: 8, or nucleotides 56-5022 of SEQ ID NO: 6. In one embodiment, the rAAV is AAVrh74.MCK.microdystrophin. In one embodiment, the AAVrh74.MCK.microdystrophin is the AAVrh74.MCK.microdystrophin of nucleotides 56-4820 of SEQ ID NO: 5.

In one embodiment, the invention provides for a rAAV comprising a muscle specific control element nucleotide sequence, and a nucleotide sequence encoding the micro-dystrophin protein. For example, the nucleotide sequence encodes a functional micro-dystrophin protein, wherein the nucleotide has, e.g., at least 65%, at least 70%, at least 75%, at least 80%, 81%, 82%, 83%, 84%, 85%, 86%, 87%, 88%, or 89%, more typically at least 90%, 91%, 92%, 93%, or 94% and even more typically at least 95%, 96%, 97%, 98%, 99%, or 100% sequence identity to SEQ ID NO: 1, wherein the protein retains micro-dystrophin activity. The micro-dystrophin protein provides stability to the muscle membrane during muscle contraction, e.g. micro-dystrophin acts as a shock absorber during muscle contraction. In one embodiment, the rAAV is AAVrh74.MHCK7.microdystrophin. In one embodiment, the AAVrh74.MHCK7.microdystrophin is the AAVrh74.MHCK7.microdystrophin of SEQ ID NO: 9 or of nucleotides 55-5021 of SEQ ID NO: 3, nucleotides 1-4977 of SEQ ID NO: 8, or nucleotides 56-5022 of SEQ ID NO: 6. In one embodiment, the rAAV is AAVrh74.MCK.microdystrophin. In one embodiment, the AAVrh74.MCK.microdystrophin is the AAVrh74.MCK.microdystrophin of nucleotides 56-4820 of SEQ ID NO: 5.

The invention also provides for rAAV wherein the nucleotide sequence comprises a nucleotide sequence that hybridizes under stringent conditions to the nucleic acid sequence of SEQ ID NO: 1, or compliments thereof, and encodes a functional micro-dystrophin protein.

In one embodiment, the rAAV is a non-replicating, recombinant adeno-associated virus (AAV) termed AAVrh74.MHCK7.micro-dystrophin of SEQ ID NO: 9, nucleotides 55-5021 of SEQ ID NO: 3, nucleotides 1-4977 of SEQ ID NO: 8, or nucleotides 56-5022 of SEQ ID NO: 6. This vector genome contains minimal elements required for gene expression, including AAV2 inverted terminal repeats (ITR), the micro-dystrophin, SV40 intron (SD/SA), and synthetic polyadenylation (Poly A) signal, all under the control of the MHCK7 promoter/enhancer. The schematic of the vector genome and expression cassette is shown FIG. 1. The AAVrh74 serotype can be employed to achieve efficient gene transfer in skeletal and cardiac muscle following IV administration.

The term "stringent" is used to refer to conditions that are commonly understood in the art as stringent. Hybridization stringency is principally determined by temperature, ionic strength, and the concentration of denaturing agents such as formamide. Examples of stringent conditions for hybridization and washing are 0.015 M sodium chloride, 0.0015 M sodium citrate at 65-68° C. or 0.015 M sodium chloride, 0.0015M sodium citrate, and 50% formamide at 42° C. See Sambrook et al., *Molecular Cloning: A Laboratory Manual,* 2nd Ed., Cold Spring Harbor Laboratory, (Cold Spring Harbor, N.Y. 1989). More stringent conditions (such as higher temperature, lower ionic strength, higher formamide, or other denaturing agent) may also be used, however, the rate of hybridization will be affected. In instances wherein hybridization of deoxyoligonucleotides is concerned, additional exemplary stringent hybridization conditions include washing in 6×SSC 0.05% sodium pyrophosphate at 37° C. (for 14-base oligos), 48° C. (for 17-base oligos), 55° C. (for 20-base oligos), and 60° C. (for 23-base oligos).

Other agents may be included in the hybridization and washing buffers for the purpose of reducing non-specific and/or background hybridization. Examples are 0.1% bovine serum albumin, 0.1% polyvinyl-pyrrolidone, 0.1% sodium pyrophosphate, 0.1% sodium dodecylsulfate, NaDodSO4, (SDS), ficoll, Denhardt's solution, sonicated salmon sperm DNA (or other non-complementary DNA), and dextran sulfate, although other suitable agents can also be used. The concentration and types of these additives can be changed without substantially affecting the stringency of the hybridization conditions. Hybridization experiments are usually carried out at pH 6.8-7.4, however, at typical ionic strength conditions, the rate of hybridization is nearly independent of pH. See Anderson et al., *Nucleic Acid Hybridisation: A Practical Approach*, Ch. 4, IRL Press Limited (Oxford, England). Hybridization conditions can be adjusted by one skilled in the art in order to accommodate these variables and allow DNAs of different sequence relatedness to form hybrids.

The term "muscle specific control element" refers to a nucleotide sequence that regulates expression of a coding sequence that is specific for expression in muscle tissue. These control elements include enhancers and promoters. The invention provides for constructs comprising the muscle specific control elements MCKH7 promoter, the MCK promoter and the MCK enhancer.

The term "operably linked" refers to the positioning of the regulatory element nucleotide sequence, e.g. promoter nucleotide sequence, to confer expression of said nucleotide sequence by said regulatory element.

In one aspect, the invention provides for a rAAV wherein the muscle specific control element is a human skeletal actin gene element, cardiac actin gene element, myocyte-specific enhancer binding factor (MEF), muscle creatine kinase (MCK), truncated MCK (tMCK), myosin heavy chain (MHC), hybrid α-myosin heavy chain enhancer-/MCK enhancer-promoter (MHCK7), C5-12, murine creatine kinase enhancer element, skeletal fast-twitch troponin c gene element, slow-twitch cardiac troponin c gene element, the slow-twitch troponin i gene element, hypoxia-inducible nuclear factors, steroid-inducible element or glucocorticoid response element (GRE).

For example, the muscle specific control element is the MHCK7 promoter nucleotide sequence SEQ ID NO: 2 or SEQ ID NO: 7, or the muscle specific control element is MCK nucleotide sequence SEQ ID NO: 4. In addition, in any of the rAAV vectors of the invention, the muscle specific control element nucleotide sequence, e.g. MHCK7 or MCK nucleotide sequence, is operably linked to the nucleotide sequence encoding the micro-dystrophin protein. For example, the MHCK7 promoter nucleotide sequence (SEQ ID NO: 2 or SEQ ID NO: 7) is operably linked to the human micro-dystrophin coding sequence (SEQ ID NO: 1) as set out in the construct provided in FIG. 1 or FIG. 2 (SEQ ID NO: 3) or FIG. 13 (SEQ ID NO: 9). In another example, the MCK promoter (SEQ ID NO: 4) is operably linked to the human micro-dystrophin coding sequence (SEQ ID NO: 1) as set out in the construct provided in FIG. 5 or FIG. 6 (SEQ ID NO: 5). In another aspect, the invention provides for a rAAV vector comprising the nucleotide sequence of SEQ ID NO: 1 and SEQ ID NO: 2, or SEQ ID NO: 1 and SEQ ID NO: 7. The invention also provides for a rAAV vector comprising the nucleotide sequence of SEQ ID NO: 1 and SEQ ID NO: 4.

In a further aspect, the invention provides for an rAAV construct contained in the plasmid comprising the nucleotide sequence of SEQ ID NO: 3, SEQ ID NO: 5, SEQ ID NO: 6, or SEQ ID NO: 8. For example, the AAVrh74.MHCK7.microdystrophin vector comprises the nucleotide sequence within and inclusive of the ITR's of SEQ ID NO: 3 and shown in FIG. 2. The rAAV vector comprises the 5' ITR, MHCK7 promoter, a chimeric intron sequence, the coding sequence for the human micro-dystrophin gene, polyA, and 3' ITR. In one embodiment, the vector comprises nucleotides 55-5021 of SEQ ID NO:3. The plasmid set forth in SEQ ID NO:3 further comprises ampicillin resistance and the pGEX plasmid backbone with pBR322 origin of replication.

In another aspect, the invention provides for a rAAV comprising the nucleotide sequence of SEQ ID NO: 9. For example, the AAVrh74.MHCK7.microdystrophin vector construct comprises the nucleotide sequence of SEQ ID NO: 9 and shown in FIG. 13. This rAAV vector construct comprises the MHCK7 promoter, a chimeric intron sequence, the coding sequence for the human micro-dystrophin gene, and polyA. In one embodiment, the rAAV vector construct further comprises an ITR 5' to the promoter, and an ITR 3' to the polyA. In one embodiment, the rAAV is AAVrh74.

In another aspect, the AAVrh74.MHCK7.microdystrophin vector comprises the nucleotide sequence within and inclusive of the ITR's of SEQ ID NO: 8 and shown in FIG. 15. The rAAV vector comprises the 5' ITR, MHCK7 promoter, a chimeric intron sequence, the coding sequence for the human micro-dystrophin gene, polyA, and 3' ITR. In one embodiment, the vector comprises nucleotides 1-4977 of SEQ ID NO:9. The plasmid set forth in SEQ ID NO:3 further comprises kanamycin resistance and the pGEX plasmid backbone with pBR322 origin of replication.

In another aspect, the invention provides for a plasmid comprising the AAVrh74.MHCK7.microdystrophin vector construct. In one embodiment, the plasmid comprises the 5' ITR, MHCK7 promoter, a chimeric intron sequence, the coding sequence for the human micro-dystrophin gene, polyA, and 3' ITR. In one embodiment, the plasmid comprises kanamycin resistance and optionally comprises the pGEX plasmid backbone with pBR322 origin of replication. In a particular embodiment, the plasmid is set forth in SEQ ID NO:8, and shown in FIGS. 14 and 15.

The invention provides for a recombinant AAV vector comprising the human micro-dystrophin nucleotide sequence of SEQ ID NO: 1 and the MHCK7 promoter nucleotide sequence of SEQ ID NO: 2 or SEQ ID NO:7. This rAAV vector is the AAV serotype AAVrh.74.

The invention also provides for a rAAV comprising the AAVrh74.MHCK7.micro-dystrophin construct nucleotide sequence within and inclusive of the ITR's in SEQ ID NO: 3, the nucleotide sequence within and inclusive of the ITR's in SEQ ID NO: 8 or the nucleotide sequence as set forth in SEQ ID NO: 9. This rAAV vector is the AAV serotype AAVrh.74.

The rAAV vectors of the invention may be any AAV serotype, such as the serotype AAVrh.74, AAV1, AAV2, AAV4, AAV5, AAV6, AAV7, AAV8, AAV9, AAV10, AAV11, AAV12 or AAV13.

The invention also provides for pharmaceutical compositions (or sometimes referred to herein as simply "compositions") comprising any of the rAAV vectors of the invention.

In another embodiment, the invention provides for methods of producing a rAAV vector particle comprising culturing a cell that has been transfected with any rAAV vector of the invention and recovering rAAV particles from the supernatant of the transfected cells. The invention also provides for viral particles comprising any of the recombinant AAV vectors of the invention.

In any of the methods of treating a muscular dystrophy, the level of micro-dystrophin gene expression in a cell of the subject is increased after administration of the rAAV. Expression of the micro-dystrophin gene in the cell is detected by measuring the micro-dystrophin protein level by Western blot in muscle biopsied before and after administration of the rAAV. In particular, the level of micro-dystrophin protein is increased by at least about 70% to at least about 80%, or at least about 70% to at least about 90%, or at least about 80% to at least about 90% after administration of rAAV compared to the level of micro-dystrophin before administration of rAAV. For example, the level of micro-dystrophin protein is increased by at least about 70% or at least about 71% or at least about 72% or at least about 73% or at least about 74% or at least about 75% or at least about 76% or at least about 77% or at least about 78% or at least about 79% or at least about 80%, or at least about 81%, or at least about 82%, or at least about 83%, or at least about 84%, or at least about 85% after administration of rAAV compared to the level of micro-dystrophin before administration of rAAV.

In addition, expression of the micro-dystrophin gene in the cell is detected by measuring the micro-dystrophin protein level by immunohistochemistry in muscle biopsies before and after administration of the rAAV. The level of micro-dystrophin protein is increased by at least about 70% to at least about 80%, or at least about 70% to at least about 90%, or at least about 80% to at least about 90% after administration of rAAV compared to the level of micro-dystrophin before administration of rAAV. For example, the level of micro-dystrophin protein is increased by at least about 70% or at least about 71% or at least about 72% or at least about 73% or at least about 74% or at least about 75% or at least about 76% or at least about 77% or at least about 78% or at least about 79% or at least about 80%, or at least about 81%, or at least about 82%, or at least about 83%, or at least about 84%, or at least about 85% after administration of rAAV compared to the level of micro-dystrophin before administration of rAAV.

In any of the methods of treating a muscular dystrophy, the serum CK level in the subject is decreased after administration of the rAAV as compared to serum CK level before administration of the rAAV. For example, the serum CK level in the subject is decreased by about 65% to about 90% or about 65% to about 95% or about 75% to about 90% or about 80% to about 90% or about 85% to about 95% or about 87% to about 95% or about 87% to about 90% by 60 days after administration of the rAAV as compared to the serum CK level before administration of the rAAV. In particular, in any of the methods of treating a muscular dystrophy of the invention, the serum CK level in the subject is decreased by about 87% by 60 days after administration of the rAAV as compared to the serum CK level before administration of the rAAV or in any of the methods of treating a muscular dystrophy of the invention, the serum CK level in the subject is decreased by about 72% by 60 days after administration of the rAAV as compared to the serum CK level before administration of the rAAV, or in any of the methods of treating a muscular dystrophy of the invention, the serum CK level in the subject is decreased by about 73% by 60 days after administration of the rAAV as compared to the serum CK level before administration of the rAAV, or in any of the methods of treating a muscular dystrophy of the invention, the serum CK level in the subject is decreased by about 78% by 60 days after administration of the rAAV as compared to the serum CK level before administration of the rAAV, or in any of the methods of treating a muscular dystrophy of the invention, the serum CK level in the subject is decreased by about 95% by 60 days after administration of the rAAV as compared to the serum CK level before administration of the rAAV. In any of the methods of treating a muscular dystrophy, the number of micro-dystrophin positive fibers in the muscle tissue of the subject is increased after administration of the rAAV as compared to the number of micro-dystrophin positive fibers before administration of the rAAV. For example, the number of micro-dystrophin positive fibers is detected by measuring the micro-dystrophin protein level by Western blot or immunohistochemistry on muscle biopsies before and after administration of the rAAV.

In any of the methods of treating a muscular dystrophy, administration of the rAAV upregulates expression of DAPC proteins such as alpha-sarcoglycan or beta-sarcoglycan. For example, the level of alpha-sarcoglycan in the subject is increased after administration of the rAAV as compared to the level of alpha-sarcoglycan before administration of the rAAV. In addition, the level of beta-sarcoglycan in the subject is increased after administration of the rAAV as compared to the level of the beta-sarcoglycan before administration of the rAAV. The level of alpha-sarcoglycan or beta-sarcoglycan is detected by measuring the alpha-sarcoglycan or beta-sarcoglycan protein level by Western blot or immunohistochemistry on muscle biopsies before and after administration of the rAAV.

In any of the methods of the treating a muscular dystrophy, disease progression in the subject is delayed after administration of the rAAV as measured by any of: the six minute walk test, time to rise, ascend 4 steps, ascend and descend 4 steps, North Star Ambulatory Assessment (NSAA), 10 meter timed test, 100 meter timed test, hand held dynamometry (HHD), Timed Up and Go, and/or Gross Motor Subtest Scaled (Bayley-III) score.

For example, in any of the methods, the subject has at least a 6-point improvement in NSAA score at least 270 days after administration of the rAAV as compared to NSAA score before administration of the rAAV. Further, in any of the methods, the subject has at least about 0.8 second improvement in time to rise at least 270 days after administration of the rAAV as compared to time to rise before administration of the rAAV. In addition, in any of the methods, the subject has at least about 1.2 second improvement in time to ascend 4 steps test at least 270 days after administration of the rAAV as compared to time to ascend 4 steps test before administration of the rAAV. In addition, in any of the methods, the subject has at least about 7 second improvement in the 100 m timed test at least 270 days after administration of the rAAV as compared to the 100 m timed test before administration of the rAAV.

In another embodiment, the invention provides for methods of expressing micro-dystrophin gene in a patient cell comprising administering to the patient the AAVrh74.MHCK7.micro-dystrophin construct nucleotide sequence of SEQ ID NO: 9, nucleotides 55-5021 of SEQ ID NO: 3, nucleotides 1-4977 of SEQ ID NO: 8 or nucleotides 56-5022 of SEQ ID NO: 6. For example, expression of the micro-dystrophin gene in the patient cell is detected by measuring the micro-dystrophin protein level by Western blot or immunohistochemistry in muscle biopsies before and after administration of the rAAV.MHCK7.micro-dystrophin construct. In addition, the expression of the micro-dystrophin gene is measured in the patient by detecting greater the number of vector genomes per nucleus, wherein 1 vector genome per nucleus is about 50% micro-dystrophin expression and great than 1 copy per nucleus is consistent with micro-dystrophin expression level. For example, the cells have 1.2 vector copies per nucleus, or 1.3 vector copies per nucleus, or 1.4 vector copies per nucleus, or 1.5 vector copies per nucleus, or 1.6 vector copies per nucleus, or 1.7 vector copies per nucleus, or 1.8 vector copies per nucleus, or 1.9 vector copies per nucleus.

In a further embodiment, the invention provides for methods of decreasing serum CK levels in a patient in need thereof, the method comprising administering to the patient the AAVrh74.MHCK7.micro-dystrophin construct nucleotide sequence of SEQ ID NO: 9, nucleotides 55-5021 of SEQ ID NO: 3, nucleotides 1-4977 of SEQ ID NO: 8, or nucleotides 56-5022 of SEQ ID NO: 6. For example, the serum CK level in the patient is decreased by at least about 65% to about 90% or about 65% to about 95% or about 75% to about 90% or about 80% to about 90% or about 85% to about 95% or about 87% to about 95% or about 87% to about 90% by 60 days after administration of the rAAV as compared to the serum CK level before administration of the rAAV. In particular, the serum CK level in the subject is decreased by about 87% by 60 days after administration of the rAAV as compared to the serum CK level before administration of the rAAV or in any of the methods of treating a muscular dystrophy of the invention, the serum CK level in the subject is decreased by about 72% by 60 days after administration of the rAAV as compared to the serum CK level before administration of the rAAV, or in any of the methods of treating a muscular dystrophy of the invention, the serum CK level in the subject is decreased by about 73% by 60 days after administration of the rAAV as compared to the serum CK level before administration of the rAAV, or in any of the methods of treating a muscular dystrophy of the invention, the serum CK level in the subject is decreased by about 78% by 60 days after administration of the rAAV as compared to the serum CK level before administration of the rAAV, or in any of the methods of treating a muscular dystrophy of the invention, the serum CK level in the subject is decreased by about 95% by 60 days after administration of the rAAV as compared to the serum CK level before administration of the rAAV.

The invention also provides for methods of increasing micro-dystrophin positive fibers in a patient muscle tissue comprising administering to the patient the AAVrh74.MHCK7.micro-dystrophin construct nucleotide sequence of SEQ ID NO: 9, nucleotides 55-5021 of SEQ ID NO: 3, nucleotides 1-4977 of SEQ ID NO: 8, or nucleotides 56-5022 of SEQ ID NO: 6. For example, the number of micro-dystrophin positive fibers is detected by measuring the dystrophin protein level by Western blot or immunohistochemistry on muscle biopsies before and after administration of the rAAV. In addition, the expression of the micro-dystrophin gene is measured in the patient by detecting greater the number of vector genomes per nucleus, wherein 1 vector genome per nucleus is about 50% micro-dystrophin expression and great than 1 copy per nucleus is consistent with micro-dystrophin expression level. For example, the cells have 1.2 vector copies per nucleus, or 1.3 vector copies per nucleus, or 1.4 vector copies per nucleus, or 1.5 vector copies per nucleus, or 1.6 vector copies per nucleus, or 1.7 vector copies per nucleus, or 1.8 vector copies per nucleus, or 1.9 vector copies per nucleus.

In another embodiment, the invention provides for methods of increasing the expression of alpha-sarcoglycan in a patient in need thereof comprising administering to the patient the AAVrh74.MHCK7.micro-dystrophin construct nucleotide sequence of SEQ ID NO: 9, nucleotides 55-5021 of SEQ ID NO: 3, nucleotides 1-4977 of SEQ ID NO: 8, or nucleotides 56-5022 of SEQ ID NO: 6. For example, the level of alpha-sarcoglycan is detected by measuring the alpha-sarcoglycan protein level by Western blot or immunohistochemistry on muscle biopsies before and after administration of the rAAV.

In addition, the invention provides for methods of increasing the expression of beta-sarcoglycan in a patient in need thereof comprising administering to the patient the AAVrh74.MHCK7.micro-dystrophin construct nucleotide sequence of SEQ ID NO: 9, nucleotides 55-5021 of SEQ ID NO: 3, nucleotides 1-4977 of SEQ ID NO: 8, or nucleotides 56-5022 of SEQ ID NO: 6. For example, the level of beta-sarcoglycan is detected by measuring the beta-sarcoglycan protein level by Western blot or immunohistochemistry on muscle biopsies before and after administration of the rAAV.

The invention also provides for methods of treating a patient with Duchenne muscular dystrophy or Becker muscular dystrophy comprising administering to the patient the AAVrh74.MHCK7.micro-dystrophin construct nucleotide sequence of SEQ ID NO: 9, nucleotides 55-5021 of SEQ ID NO: 3, nucleotides 1-4977 of SEQ ID NO: 8, or nucleotides 56-5022 of SEQ ID NO: 6, such that disease progression in the patient is delayed as measured by any of: the six minute walk test, time to rise, ascend 4 steps, ascend and descend 4 steps, North Star Ambulatory Assessment (NSAA), 10 meter timed test, 100 meter timed test, hand held dynamometry (HHD), Timed Up and Go, and/or Gross Motor Subtest Scaled (Bayley-III) score.

For example, in any of the methods, the subject has at least a 6-point improvement in NSAA score at least 270 days after administration of the rAAV as compared to NSAA score before administration of the rAAV. Further, in any of the methods, the subject has at least about 0.8 second improvement in time to rise at least 270 days after administration of the rAAV as compared to time to rise before administration of the rAAV. In addition, in any of the methods, the subject has at least about 1.2 second improvement in time to ascend 4 steps test at least 270 days after administration of the rAAV as compared to time to ascend 4 steps test before administration of the rAAV. In addition, in any of the methods, the subject has at least about 7 second improvement in the 100 m timed test at least 270 days after administration of the rAAV as compared to the 100 m timed test before administration of the rAAV.

"Fibrosis" refers to the excessive or unregulated deposition of extracellular matrix (ECM) components and abnormal repair processes in tissues upon injury, including skeletal muscle, cardiac muscle, liver, lung, kidney, and pancreas. The ECM components that are deposited include fibronectin and collagen, e.g. collagen 1, collagen 2 or collagen 3.

The invention also provides for methods of reducing or preventing fibrosis in a subject suffering from muscular dystrophy comprising administering a therapeutically effective amount of a rAAV comprising the human micro-dystrophin nucleotide sequence of SEQ ID NO: 1 and the MHCK7 promoter nucleotide sequence of SEQ ID NO: 2 or SEQ ID NO: 7; or a rAAV vector comprising the AAVrh74.MHCK7.micro-dystrophin construct nucleotide sequence of SEQ ID NO: 9, nucleotides 55-5021 of SEQ ID NO: 3, nucleotides 1-4977 of SEQ ID NO: 8, or nucleotides 56-5022 of SEQ ID NO: 6. In one embodiment, the rAAV is AAVrh74.MHCK7.microdystrophin. In one embodiment, the AAVrh74.MHCK7.microdystrophin is the AAVrh74.MHCK7.microdystrophin of nucleotides 55-5021 of SEQ ID NO: 3. In another embodiment, the AAVrh74.MHCK7.microdystrophin is the AAVrh74.MHCK7.microdystrophin of SEQ ID NO: 9. In another embodiment, the AAVrh74.MHCK7.microdystrophin is the AAVrh74.MHCK7.microdystrophin of nucleotides 1-4977 of SEQ ID NO: 8 or nucleotides 56-5066 of SEQ ID NO: 6. In a further embodiment, the rAAV is AAVrh74.MCK.microdystrophin. In one embodiment, the AAVrh74.MCK.microdystrophin is the AAVrh74.MCK.microdystrophin of nucleotides 56-4820 of SEQ ID NO: 5.

In another embodiment, the invention provides for methods of preventing fibrosis in a subject in need thereof, comprising administering a therapeutically effective amount of the human micro-dystrophin nucleotide sequence of SEQ ID NO: 1 and the MHCK7 promoter nucleotide sequence of SEQ ID NO: 2 or SEQ ID NO:7; or rAAV vector comprising the AAV74.MHCK7.micro-dystrophin construct nucleotide sequence of SEQ ID NO: 9, nucleotides 55-5021 of SEQ ID NO: 3, nucleotides 1-4977 of SEQ ID NO: 8, or nucleotides 56-5022 of SEQ ID NO: 6. For example, any of the rAAV of the invention can be administered to subjects suffering from muscular dystrophy to prevent fibrosis, e.g. the rAAV of the invention expressing a human micro-dystrophin protein administered before fibrosis is observed in the subject. In addition, the rAAV of the invention expressing a human micro-dystrophin gene can be administered to a subject at risk of developing fibrosis, such as those suffering or diagnosed with muscular dystrophy, e.g. DMD. The rAAV of the invention can be administered to the subject suffering from muscular dystrophy in order to prevent new fibrosis in these subjects.

The invention contemplates administering rAAV before fibrosis is observed in the subject. In addition, the rAAV can be administered to a subject at risk of developing fibrosis, such as those suffering or diagnosed with a muscular dystrophy, e.g. DMD. The rAAV can be administered to the subject suffering from muscular dystrophy who already has developed fibrosis in order to prevent new fibrosis in these subjects.

The invention also provides for methods of increasing muscular force and/or muscle mass in a subject suffering from a muscular dystrophy comprising administering a therapeutically effective amount of the human micro-dystrophin nucleotide sequence of SEQ ID NO: 1 and the MHCK7 promoter nucleotide sequence of SEQ ID NO: 2 or SEQ ID NO: 7; or a rAAV comprising the AAVrh74.MHCK7.micro-dystrophin construct nucleotide sequence of SEQ ID NO: 9, nucleotides 55-5021 of SEQ ID NO: 3, nucleotides 1-4977 of SEQ ID NO: 8, or nucleotides 56-5022 of SEQ ID NO: 6.

The invention contemplates administering rAAV vectors to subjects diagnosed with DMD before fibrosis is observed in the subject or before the muscle force has been reduced or before the muscle mass has been reduced.

The invention also contemplates administering the human micro-dystrophin nucleotide sequence of SEQ ID NO: 1 and the MHCK7 promoter nucleotide sequence of SEQ ID NO: 2 or SEQ ID NO:7; or a rAAV comprising the AAVrh74.MHCK7.micro-dystrophin construct nucleotide sequence of SEQ ID NO: 9, nucleotides 55-5021 of SEQ ID NO: 3, nucleotides 1-4977 of SEQ ID NO: 8, or nucleotides 56-5022 of SEQ ID NO: 6 to a subject suffering from a muscular dystrophy who already has developed fibrosis, in order to prevent new fibrosis in these subjects or to reduce fibrosis in these subjects. The invention also provides for administering the human micro-dystrophin nucleotide sequence of SEQ ID NO: 1 and the MHCK7 promoter nucleotide sequence of SEQ ID NO: 2 or SEQ ID NO:7; or a rAAV vector comprising the AAVrh74.MHCK7.micro-dystrophin construct nucleotide sequence of SEQ ID NO: 9, nucleotides 55-5021 of SEQ ID NO: 3, nucleotides 1-4977 of SEQ ID NO: 8, or nucleotides 56-5022 of SEQ ID NO: 6 to the subject suffering from a muscular dystrophy who already has reduced muscle force or has reduced muscle mass in order to protect the muscle from further injury.

In any of the methods of the invention, the subject may be suffering from a muscular dystrophy such as DMD or any other dystrophin-associated muscular dystrophy.

In other embodiments of any of the methods of the invention described herein, the serum CK level in the subject is decreased after administration of the rAAV as compared to the serum CK level before administration of the rAAV by a percentage level selected from the group consisting of:

a) at least 78% by 90, 180, or 270 days after the administration;
b) at least 46, 55, 56, 57, 58, 59, 60, 61, 62, 63, 64, 65, 66, 67, 68, 69, 70 or 85% by 270 days after the administration;
c) at least 72, 73, 74, or 95% by 180 days after the administration;
d) at least 87, 88, 93 or 95% by 90 days after the administration;
e) at least 70% by 270 days after the administration;
f) 70 to 95% by 90, 180, or 270 days after the administration;
g) at least 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, or 95% by 90, 180, or 270 days after the administration; and
h) at least 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, or 95% by 90, 180, or 270 days after the administration.

In another embodiment, the invention provides for compositions for treating a muscular dystrophy in a human subject in need, wherein the composition comprises a dose of recombinant adeno-virus associated (rAAV) rAAV.MHCK7.microdystrophin, wherein composition is formulated for a systemic route of administration and the dose of the rAAV is about $1\times10^{14}$ vg/kg to about $4\times10^{14}$ vg/kg. In one embodiment, the rAAV is AAVrh74.MHCK7.microdystrophin. In one embodiment, the AAVrh74.MHCK7.microdystrophin is the AAVrh74.MHCK7.microdystrophin of SEQ ID NO: 9, nucleotides 55-5021 of SEQ ID NO: 3, nucleotides 1-4977 of SEQ ID NO: 8, or nucleotides 56-5022 of SEQ ID NO: 6. In one embodiment, the rAAV is AAVrh74.MCK.microdystrophin. In one embodiment, the AAVrh74.MCK.microdystrophin is the AAVrh74.MCK.microdystrophin of nucleotides 56-4820 of SEQ ID NO: 5.

For example, the composition of the invention comprises a dose of rAAV of about $5.0\times10^{12}$ vg/kg to about $1.0\times10^{14}$ vg/kg, or about $5.0\times10^{12}$ vg/kg to $1.0\times10^{14}$ vg/kg, or about $5.0\times10^{12}$ vg/kg to about $2.0\times10^{14}$ vg/kg, or about $5.0\times10^{12}$ vg/kg to about $1.0\times10^{14}$ vg/kg, or about $5.0\times10^{12}$ vg/kg to about $5.0\times10^{13}$ vg/kg, or about $5.0\times10^{12}$ vg/kg to about $2.0\times10^{13}$ vg/kg, or about $5.0\times10^{12}$ vg/kg to about $1.0\times10^{13}$ vg/kg, or $1.0\times10^{14}$ vg/kg to about $1.0\times10^{15}$ vg/kg, or $1.0\times10^{13}$ vg/kg to about $1.0\times10^{14}$ vg/kg, or about $1.0\times10^{13}$ vg/kg to $1.0\times10^{14}$ vg/kg, or about $1.0\times10^{13}$ vg/kg to about $2.0\times10^{14}$ vg/kg, or about $1.0\times10^{13}$ vg/kg to about $1.0\times10^{14}$ vg/kg, or about $1.0\times10^{13}$ vg/kg to about $5.0\times10^{13}$ vg/kg, or about $1.0\times10^{13}$ vg/kg to about $3.0\times10^{14}$ vg/kg, or about $1.0\times10^{13}$ vg/kg to about $5.0\times10^{14}$ vg/kg, or about $1.0\times10^{13}$ vg/kg to about $6.0\times10^{14}$ vg/kg, or $1.0\times10^{13}$ vg/kg to about $1.0\times10^{15}$ vg/kg, or $5.0\times10^{13}$ vg/kg to about $1.0\times10^{14}$ vg/kg, or about $5.0\times10^{13}$ vg/kg to $1.0\times10^{14}$ vg/kg, or about $5.0\times10^{13}$ vg/kg to about $2.0\times10^{14}$ vg/kg, or about $5.0\times10^{13}$ vg/kg to about $1.0\times10^{14}$ vg/kg, or about $5.0\times10^{13}$ vg/kg to about $3.0\times10^{14}$ vg/kg, or about $5.0\times10^{13}$ vg/kg to about $5.0\times10^{14}$ vg/kg, or about $5.0\times10^{13}$ vg/kg to about $6.0\times10^{14}$ vg/kg, or $5.0\times10^{13}$ vg/kg to about $1.0\times10^{15}$ vg/kg, or $1.0\times10^{14}$ vg/kg to about $6.0\times10^{14}$ vg/kg, or $1.0\times10^{14}$ vg/kg to about $5.0\times10^{14}$ vg/kg, or $1.0\times10^{14}$ vg/kg to about $4.0\times10^{14}$ vg/kg, or $1.0\times10^{14}$ vg/kg to about $1.0\times10^{15}$ vg/kg, or $1.0\times10^{14}$ vg/kg to about $3.0\times10^{14}$ vg/kg, or about $1.0\times10^{14}$ vg/kg to about $2.5\times10^{14}$ vg/kg, or $1.0\times10^{14}$ vg/kg to about $2.0\times10^{14}$ vg/kg, or about $1.25\times10^{14}$ vg/kg to about $3.75\times10^{14}$ vg/kg, or about $1.25\times10^{14}$ vg/kg to $6.0\times10^{14}$, or about $1.25\times10^{14}$ vg/kg to $5.0\times10^{14}$, or about $1.25\times10^{14}$ vg/kg to $4.0\times10^{14}$, or about $1.25\times10^{14}$ vg/kg to $1.0\times10^{15}$, or about $1.25\times10^{14}$ vg/kg to about $3.5\times10^{14}$ vg/kg, or about $1.25\times10^{14}$ vg/kg to about $3.0\times10^{14}$ vg/kg, or about $1.25\times10^{14}$ vg/kg to about $2.75\times10^{14}$ vg/kg, or about $1.25\times10^{14}$ vg/kg to about $2.5\times10^{14}$ vg/kg, or about $1.25\times10^{14}$ vg/kg to about $2.0\times10^{14}$ vg/kg, or $1.25\times10^{14}$ vg/kg to about $3.75\times10^{14}$ vg/kg, or about $1.25\times10^{14}$ vg/kg to about $3.5\times10^{14}$ vg/kg, or $1.5\times10^{14}$ vg/kg to about $1.0\times10^{15}$ vg/kg, or about $1.5\times10^{14}$ vg/kg to $6.0\times10^{14}$, or about $1.5\times10^{14}$ vg/kg to $5.0\times10^{14}$, or about $1.5\times10^{14}$ vg/kg to $4.0\times10^{14}$, or about $1.5\times10^{14}$ vg/kg to about $3.75\times10^{14}$ vg/kg, or about $1.5\times10^{14}$ vg/kg to about $3.5\times10^{14}$ vg/kg, or about $1.5\times10^{14}$ vg/kg to about $3.25\times10^{14}$ vg/kg, or about $1.5\times10^{14}$ vg/kg to about $3.0\times10^{14}$ vg/kg, or about $1.5\times10^{14}$ vg/kg to about $2.75\times10^{14}$ vg/kg, or about $1.5\times10^{14}$ vg/kg to about $2.5\times10^{14}$ vg/kg, or about $1.5\times10^{14}$ vg/kg to about $2.0\times10^{14}$ vg/kg, or $1.75\times10^{14}$ vg/kg to about $1.0\times10^{15}$ vg/kg, or about $1.75\times10^{14}$ vg/kg to $6.0\times10^{14}$, or about $1.75\times10^{14}$ vg/kg to $5.0\times10^{14}$, or about $1.75\times10^{14}$ vg/kg to $4.0\times10^{14}$, or about $1.75\times10^{14}$ vg/kg to about $3.75\times10^{14}$ vg/kg, or about $1.75\times10^{14}$ vg/kg to about $3.5\times10^{14}$ vg/kg, or about $1.75\times10^{14}$ vg/kg to about $3.25\times10^{14}$ vg/kg, or about $1.75\times10^{14}$ vg/kg to about $3.0\times10^{14}$ vg/kg, or about $1.75\times10^{14}$ vg/kg to about $2.75\times10^{14}$ vg/kg, or about $1.75\times10^{14}$ vg/kg to about $2.5\times10^{14}$ vg/kg, or about $1.75\times10^{14}$ vg/kg to about $2.25\times10^{14}$ vg/kg, or about $1.75\times10^{14}$ vg/kg to about $2.0\times10^{14}$ vg/kg, or about $2.0\times10^{14}$ vg/kg to $1.0\times10^{15}$, or about $2.0\times10^{14}$ vg/kg to $6.0\times10^{14}$, or about $2.0\times10^{14}$ vg/kg to $5.0\times10^{14}$, or about $2.0\times10^{14}$ vg/kg to about $4.0\times10^{14}$ vg/kg, or about $2.0\times10^{14}$ vg/kg to about $3.75\times10^{14}$ vg/kg, or about $2.0\times10^{14}$ vg/kg to about $3.5\times10^{14}$ vg/kg, or about $2.0\times10^{14}$ vg/kg to about $3.25\times10^{14}$ vg/kg. In one embodiment, the rAAV is AAVrh74.MHCK7.microdystrophin. In one embodiment, the AAVrh74.MHCK7.microdystrophin is the AAVrh74.MHCK7.microdystrophin of SEQ ID NO: 9, nucleotides 55-5021 of SEQ ID NO: 3, nucleotides 1-4977 of SEQ ID NO: 8, or nucleotides 56-5022 of SEQ ID NO: 6. In one embodiment, the rAAV is AAVrh74.MCK.microdystrophin. In one embodiment, the AAVrh74.MCK.microdystrophin is the AAVrh74.MCK.microdystrophin of nucleotides 56-4820 of SEQ ID NO: 5.

In one embodiment, the compositions of the invention are formulated for intravenous administration and comprise a dose of rAAV that is about $2.0\times10^{14}$ vg/kg. In another embodiment, the compositions of the invention are formulated for intravenous administration and comprise a dose of rAAV that is about $5.0\times10^{12}$ vg/kg, or about $6.0\times10^{12}$ vg/kg, or about $7.0\times10^{12}$ vg/kg, or about $8.0\times10^{12}$ vg/kg, or about $9.0\times10^{12}$ vg/kg, or about $1.0\times10^{13}$ vg/kg, or about $1.25\times10^{13}$ vg/kg, or about $1.5\times10^{13}$ vg/kg, or about $1.75\times10^{13}$ vg/kg, or about $2.25\times10^{13}$ vg/kg, or about $2.5\times10^{13}$ vg/kg, or about $2.75\times10^{13}$ vg/kg, or about $3.0\times10^{13}$ vg/kg, or about $3.25\times10^{13}$ vg/kg, or about $3.5\times10^{13}$ vg/kg, or about $3.75\times10^{13}$ vg/kg, or about $4.0\times10^{13}$ vg/kg, or about $5.0\times10^{13}$ vg/kg, or about $6.0\times10^{13}$ vg/kg, or about $7.0\times10^{13}$ vg/kg, or about $8.0\times10^{13}$ vg/kg, or about $9.0\times10^{13}$ vg/kg, or about $1.0\times10^{14}$ vg/kg, or about $1.25\times10^{14}$ vg/kg, or about $1.5\times10^{14}$ vg/kg, or about $1.75\times10^{14}$ vg/kg, or about $2.25\times10^{14}$ vg/kg, or about $2.5\times10^{14}$ vg/kg, or about $2.75\times10^{14}$ vg/kg, or about $3.0\times10^{14}$ vg/kg, or about $3.25\times10^{14}$ vg/kg, or about $3.5\times10^{14}$ vg/kg, or about $3.75\times10^{14}$ vg/kg, or about $4.0\times10^{14}$ vg/kg, or about $5.0\times10^{14}$ vg/kg, or about $6.0\times10^{14}$ vg/kg, or about $1\times10^{15}$. In one embodiment, the rAAV is AAVrh74.MHCK7.microdystrophin. In one embodiment, the AAVrh74.MHCK7.microdystrophin is the AAVrh74.MHCK7.microdystrophin of SEQ ID NO: 9, nucleotides 55-5021 of SEQ ID NO: 3, nucleotides 1-4977 of SEQ ID NO: 8, or nucleotides 56-5022 of SEQ ID NO: 6. In another embodiment, the rAAV is AAVrh74.MCK.microdystrophin. In one embodiment, the AAVrh74.MCK.microdystrophin is the AAVrh74.MCK.microdystrophin of nucleotides 56-4820 of SEQ ID NO: 5.

In any of the compositions of the invention, the dose of rAAV is delivered in about 5 mL/kg to about 15 mL/kg, or about 8 mL/kg to about 12 mL/kg, or 8 mL/kg to about 10 mL/kg, or 5 mL/kg to about 10 mL/kg or about 10 mL/kg to 12 mL/kg, or about 10 mL/kg to 15 mL/kg or 10 mL/kg to about 20 mL/kg. In a particular embodiment, the composition comprises a dose of the rAAV delivered in about 10 mL/kg. In one embodiment, the rAAV is AAVrh74.MHCK7.microdystrophin. In one embodiment, the AAVrh74.MHCK7.microdystrophin is the AAVrh74.MHCK7.microdystrophin of SEQ ID NO: 9, nucleotides 55-5021 of SEQ ID NO: 3, nucleotides 1-4977 of SEQ ID NO: 8, or nucleotides 56-5022 of SEQ ID NO: 6. In another embodiment, the rAAV is AAVrh74.MCK.microdystrophin. In one embodiment, the AAVrh74.MCK.microdystrophin is the AAVrh74.MCK.microdystrophin of nucleotides 56-4820 of SEQ ID NO: 5.

The compositions of the invention are formulated for administration by injection, infusion or implantation. For example, the compositions are formulated for administration by infusion over approximately one hour. In addition, the compositions of the invention are formulated for intravenous administration through a peripheral limb vein such as a peripheral arm vein or a peripheral leg vein. Alternatively, the infusion may be administered over approximately 30 minutes, or approximately 1.5 hours, or approximately 2 hours, or approximately 2.5 hours or approximately 3 hours.

Any of the compositions of the invention comprise a rAAV comprising the human micro-dystrophin nucleotide sequence of SEQ ID NO: 1 and the MHCK7 promoter sequence of SEQ ID NO: 2 or SEQ ID NO:7 or a rAAV vector comprising the AAVrh74.MHCK7.micro-dystrophin construct nucleotide sequence of SEQ ID NO: 9, nucleotides 55-5021 of SEQ ID NO: 3, nucleotides 1-4977 of SEQ ID NO: 8, or nucleotides 56-5022 of SEQ ID NO: 6.

In particular, the compositions of the invention are for treating Duchenne muscular dystrophy or Becker's muscular dystrophy. For example, the invention provides for compositions for treating Duchenne muscular dystrophy or Becker's muscular dystrophy in a human subject in need thereof wherein the composition comprises a dose of recombinant adeno-virus associated (rAAV) rAAV.MHCK7.microdystrophin, wherein the composition is formulated for administration by intravenous infusion over approximately one hour and the dose of the rAAV administered is about $2\times10^{14}$ vg/kg, and wherein the rAAV comprises the AAVrh74.MHCK7.micro-dystrophin construct nucleotide sequence of SEQ ID NO: 9, nucleotides 55-5021 of SEQ ID NO: 3, nucleotides 1-4977 of SEQ ID NO: 8, or nucleotides 56-5022 of SEQ ID NO: 6.

In another embodiment, the invention also provides a composition comprising rAAV for reducing fibrosis in a subject in need thereof. In addition, the invention provides a composition comprising a rAAV vectors for preventing fibrosis in a subject suffering from a muscular dystrophy.

The invention also provides for compositions comprising rAAV for increasing muscular force and/or muscle mass in a subject suffering from a muscular dystrophy. In a further embodiment, the invention provides for compositions comprising any of the rAAV of the invention for treatment of muscular dystrophy.

In other embodiments of any of the compositions of the invention, after administration of said composition to a human subject in need of treatment for muscular dystrophy, the serum CK level in the subject is decreased as compared to the serum CK level before administration of the composition by a percentage level selected from the group consisting of:

a) at least 78% by 90, 180, or 270 days after the administration;
b) at least 46, 55, 70, or 85% by 270 days after the administration;
c) at least 72, 73, 74, or 95% by 180 days after the administration;
d) at least 87, 99, 93 or 95% by 90 days after the administration;
e) at least 70% by 270 days after the administration;
f) 70 to 95% by 90, 180, or 270 days after the administration;
g) at least 69, 70, 71, 72, 73, 74, 75, 76, 77, 78, 79, 80, 81, 82, 83, 84, 85, 86, 87, 88, 89, 90, 91, 92, 93, 94, or 95% by 90, 180, or 270 days after the administration; and
h) 69, 70, 71, 72, 73, 74, 75, 76, 77, 78, 79, 80, 81, 82, 83, 84, 85, 86, 87, 88, 89, 90, 91, 92, 93, 94, or 95% by 90, 180, or 270 days after the administration.

In another embodiment, the invention provides for use of a dose of recombinant adeno-virus associated (rAAV) rAAV.MHCK7.microdystrophin for the preparation of a medicament for the treatment of muscular dystrophy in a human subject in need thereof, wherein the medicament is formulated for a systemic route of administration and the dose of the rAAV is about $1\times10^{14}$ vg/kg to about $4\times10^{14}$ vg/kg. In one embodiment, the rAAV is AAVrh74.MHCK7.microdystrophin. In one embodiment, the AAVrh74.MHCK7.microdystrophin is the AAVrh74.MHCK7.microdystrophin of SEQ ID NO: 9, nucleotides 55-5021 of SEQ ID NO: 3, nucleotides 1-4977 of SEQ ID NO: 8, or nucleotides 56-5022 of SEQ ID NO: 6. In one embodiment, the rAAV is AAVrh74.MCK.microdystrophin. In one embodiment, the AAVrh74.MCK.microdystrophin is the AAVrh74.MCK.microdystrophin of nucleotides 56-4820 of SEQ ID NO: 5.

For example, the medicament comprises a dose of rAAV of about $5.0\times10^{12}$ vg/kg to about $1.0\times10^{14}$ vg/kg, or about $5.0\times10^{12}$ vg/kg to $1.0\times10^{14}$ vg/kg, or about $5.0\times10^{12}$ vg/kg to about $2.0\times10^{14}$ vg/kg, or about $5.0\times10^{12}$ vg/kg to about $1.0\times10^{14}$ vg/kg, or about $5.0\times10^{12}$ vg/kg to about $5.0\times10^{13}$ vg/kg, or about $5.0\times10^{12}$ vg/kg to about $2.0\times10^{13}$ vg/kg, or about $5.0\times10^{12}$ vg/kg to about $1.0\times10^{13}$ vg/kg, or $1.0\times10^{14}$ vg/kg to about $1.0\times10^{15}$ vg/kg, or $1.0\times10^{13}$ vg/kg to about $1.0\times10^{14}$ vg/kg, or about $1.0\times10^{13}$ vg/kg to $1.0\times10^{14}$ vg/kg, or about $1.0\times10^{13}$ vg/kg to about $2.0\times10^{14}$ vg/kg, or about $1.0\times10^{13}$ vg/kg to about $1.0\times10^{14}$ vg/kg, or about $1.0\times10^{13}$ vg/kg to about $5.0\times10^{13}$ vg/kg, or about $1.0\times10^{13}$ vg/kg to about $3.0\times10^{14}$ vg/kg, or about $1.0\times10^{13}$ vg/kg to about $5.0\times10^{14}$ vg/kg, or about $1.0\times10^{13}$ vg/kg to about $6.0\times10^{14}$ vg/kg, or $1.0\times10^{13}$ vg/kg to about $1.0\times10^{15}$ vg/kg, or $5.0\times10^{13}$ vg/kg to about $1.0\times10^{14}$ vg/kg, or about $5.0\times10^{13}$ vg/kg to $1.0\times10^{14}$ vg/kg, or about $5.0\times10^{13}$ vg/kg to about $2.0\times10^{14}$ vg/kg, or about $5.0\times10^{13}$ vg/kg to about $1.0\times10^{14}$ vg/kg, or about $5.0\times10^{13}$ vg/kg to about $3.0\times10^{14}$ vg/kg, or about $5.0\times10^{13}$ vg/kg to about $5.0\times10^{14}$ vg/kg, or about $5.0\times10^{13}$ vg/kg to about $6.0\times10^{14}$ vg/kg, or $5.0\times10^{13}$ vg/kg to about $1.0\times10^{15}$ vg/kg, or $1.0\times10^{14}$ vg/kg to about $6.0\times10^{14}$ vg/kg, or $1.0\times10^{14}$ vg/kg to about $5.0\times10^{14}$ vg/kg, or $1.0\times10^{14}$ vg/kg to about $4.0\times10^{14}$ vg/kg, or $1.0\times10^{14}$ vg/kg to about $1.0\times10^{15}$ vg/kg, or $1.0\times10^{14}$ vg/kg to about $3.0\times10^{14}$ vg/kg, or about $1.0\times10^{14}$ vg/kg to about $2.5\times10^{14}$ vg/kg, or $1.0\times10^{14}$ vg/kg to about $2.0\times10^{14}$ vg/kg, or about $1.25\times10^{14}$ vg/kg to about $3.75\times10^{14}$ vg/kg, or about $1.25\times10^{14}$ vg/kg to $6.0\times10^{14}$, or about $1.25\times10^{14}$ vg/kg to $5.0\times10^{14}$, or about $1.25\times10^{14}$ vg/kg to $4.0\times10^{14}$, or about $1.25\times10^{14}$ vg/kg to $1.0\times10^{15}$, or about $1.25\times10^{14}$ vg/kg to about $3.5\times10^{14}$ vg/kg, or about $1.25\times10^{14}$ vg/kg to about $3.0\times10^{14}$ vg/kg, or about $1.25\times10^{14}$ vg/kg to about $2.75\times10^{14}$ vg/kg, or about $1.25\times10^{14}$ vg/kg to about $2.5\times10^{14}$ vg/kg, or about $1.25\times10^{14}$ vg/kg to about $2.0\times10^{14}$ vg/kg, or $1.25\times10^{14}$ vg/kg to about $3.75\times10^{14}$ vg/kg, or about $1.25\times10^{14}$ vg/kg to about $3.5\times10^{14}$ vg/kg, or $1.5\times10^{14}$ vg/kg to about $1.0\times10^{15}$ vg/kg, or about $1.5\times10^{14}$ vg/kg to $6.0\times10^{14}$, or about $1.5\times10^{14}$ vg/kg to $5.0\times10^{14}$, or about $1.5\times10^{14}$ vg/kg to $4.0\times10^{14}$, or about $1.5\times10^{14}$ vg/kg to about $3.75\times10^{14}$ vg/kg, or about $1.5\times10^{14}$ vg/kg to about $3.5\times10^{14}$ vg/kg, or about $1.5\times10^{14}$ vg/kg to about $3.25\times10^{14}$ vg/kg, or about $1.5\times10^{14}$ vg/kg to about $3.0\times10^{14}$ vg/kg, or about $1.5\times10^{14}$ vg/kg to about $2.75\times10^{14}$ vg/kg, or about $1.5\times10^{14}$ vg/kg to about $2.5\times10^{14}$ vg/kg, or about $1.5\times10^{14}$ vg/kg to about $2.0\times10^{14}$ vg/kg, or $1.75\times10^{14}$ vg/kg to about $1.0\times10^{15}$ vg/kg, or about $1.75\times10^{14}$ vg/kg to $6.0\times10^{14}$, or about $1.75\times10^{14}$ vg/kg to $5.0\times10^{14}$, or about $1.75\times10^{14}$ vg/kg to $4.0\times10^{14}$, or about $1.75\times10^{14}$ vg/kg to about $3.75\times10^{14}$ vg/kg, or about $1.75\times10^{14}$ vg/kg to about $3.5\times10^{14}$ vg/kg, or about $1.75\times10^{14}$ vg/kg to about $3.25\times10^{14}$ vg/kg, or about $1.75\times10^{14}$ vg/kg to about $3.0\times10^{14}$ vg/kg, or about $1.75\times10^{14}$ vg/kg to about $2.75\times10^{14}$ vg/kg, or about $1.75\times10^{14}$ vg/kg to about $2.5\times10^{14}$ vg/kg, or about $1.75\times10^{14}$ vg/kg to about $2.25\times10^{14}$ vg/kg, or about $1.75\times10^{14}$ vg/kg to about $2.0\times10^{14}$ vg/kg, or about $2.0\times10^{14}$ vg/kg to $1.0\times10^{15}$, or about $2.0\times10^{14}$ vg/kg to $6.0\times10^{14}$, or about $2.0\times10^{14}$ vg/kg to $5.0\times10^{14}$, or about $2.0\times10^{14}$ vg/kg to about $4.0\times10^{14}$ vg/kg, or about $2.0\times10^{14}$ vg/kg to about $3.75\times10^{14}$ vg/kg, or about $2.0\times10^{14}$ vg/kg to about $3.5\times10^{14}$ vg/kg, or about $2.0\times10^{14}$ vg/kg to about $3.25\times10^{14}$ vg/kg. In one embodiment, the rAAV is AAVrh74.MHCK7.microdystrophin. In one embodiment, the AAVrh74.MHCK7.microdystrophin is the AAVrh74.MHCK7.microdystrophin of SEQ ID NO: 9, nucleotides 55-5021 of SEQ ID NO: 3, nucleotides 1-4977 of SEQ ID NO: 8, or nucleotides 56-5022 of SEQ ID NO: 6. In one embodiment, the rAAV is AAVrh74.MCK.microdystrophin. In one embodiment, the AAVrh74.MCK.microdystrophin is the AAVrh74.MCK.microdystrophin of nucleotides 56-4820 of SEQ ID NO: 5.

In one embodiment, the medicaments of the invention are formulated for systemic administration of a dose of rAAV wherein the systemic route of administration is an intravenous route and the dose of the rAAV administered is about $2.0\times10^{14}$ vg/kg. In another embodiment, the medicament of the invention is formulated for systemic administration of a dose of rAAV wherein the systemic route of administration is an intravenous route and the dose of the rAAV is about $5.0\times10^{12}$ vg/kg, or about $6.0\times10^{12}$ vg/kg, or about $7.0\times10^{12}$ vg/kg, or about $8.0\times10^{12}$ vg/kg, or about $9.0\times10^{12}$ vg/kg, or about $1.0\times10^{13}$ vg/kg, or about $1.25\times10^{13}$ vg/kg, or about $1.5\times10^{13}$ vg/kg, or about $1.75\times10^{13}$ vg/kg, or about $2.25\times10^{13}$ vg/kg, or about $2.5\times10^{13}$ vg/kg, or about $2.75\times10^{13}$ vg/kg, or about $3.0\times10^{13}$ vg/kg, or about $3.25\times10^{13}$ vg/kg, or about $3.5\times10^{13}$ vg/kg, or about $3.75\times10^{13}$ vg/kg, or about $4.0\times10^{13}$ vg/kg, or about $5.0\times10^{13}$ vg/kg, or about $6.0\times10^{13}$ vg/kg, or about $7.0\times10^{13}$ vg/kg, or about $8.0\times10^{13}$ vg/kg, or about $9.0\times10^{13}$ vg/kg, or about $1.0\times10^{14}$ vg/kg, or about $1.25\times10^{14}$ vg/kg, or about $1.5\times10^{14}$ vg/kg, or about $1.75\times10^{14}$ vg/kg, or about $2.25\times10^{14}$ vg/kg, or about $2.5\times10^{14}$ vg/kg, or about $2.75\times10^{14}$ vg/kg, or about $3.0\times10^{14}$ vg/kg, or about $3.25\times10^{14}$ vg/kg, or about $3.5\times10^{14}$ vg/kg, or about $3.75\times10^{14}$ vg/kg, or about $4.0\times10^{14}$ vg/kg, or about $5.0\times10^{14}$ vg/kg, or about $6.0\times10^{14}$ vg/kg, or about $1\times10^{15}$ vg/kg. In one embodiment, the rAAV is AAVrh74.MHCK7.microdystrophin. In one embodiment, the AAVrh74.MHCK7.microdystrophin is the AAVrh74.MHCK7.microdystrophin of SEQ ID NO: 9, nucleotides 55-5021 of SEQ ID NO: 3, nucleotides 1-4977 of SEQ ID NO: 8, or nucleotides 56-5022 of SEQ ID NO: 6. In one embodiment, the rAAV is AAVrh74.MCK.microdystrophin. In one embodiment, the AAVrh74.MCK.microdystrophin is the AAVrh74.MCK.microdystrophin of nucleotides 56-4820 of SEQ ID NO: 5.

In any of the uses of the invention, the medicament comprises a dose of rAAV in about 5 mL/kg to about 15 mL/kg, or about 8 mL/kg to about 12 mL/kg, or 8 mL/kg to about 10 mL/kg, or 5 mL/kg to about 10 mL/kg or about 10 mL/kg to 12 mL/k, or about 10 mL/kg to 15 mL/kg or 10 mL/kg to about 20 mL/kg. In a particular embodiment, the dose or the rAAV is in about 10 mL/kg. In one embodiment, the rAAV is AAVrh74.MHCK7.microdystrophin. In one embodiment, the AAVrh74.MHCK7.microdystrophin is the AAVrh74.MHCK7.microdystrophin of SEQ ID NO: 9, nucleotides 55-5021 of SEQ ID NO: 3, nucleotides 1-4977 of SEQ ID NO: 8, or nucleotides 56-5022 of SEQ ID NO: 6. In one embodiment, the rAAV is AAVrh74.MCK.microdystrophin. In one embodiment, the AAVrh74.MCK.microdystrophin is the AAVrh74.MCK.microdystrophin of nucleotides 56-4820 of SEQ ID NO: 5.

In any of the uses of the invention, the medicament is formulated for administration by injection, infusion or implantation. For example, the medicament is formulated for administration by infusion over approximately one hour. In addition, the medicament is formulated for intravenous administration through a peripheral limb vein, such as a peripheral arm vein or a peripheral leg vein. Alternatively, the infusion may be administered over approximately 30 minutes, or approximately 1.5 hours, or approximately 2 hours, or approximately 2.5 hours or approximately 3 hours.

In any of the uses of the invention, the medicament comprises an rAAV comprising the human micro-dystrophin nucleotide sequence of SEQ ID NO: 1 and the MHCK7 promoter sequence of SEQ ID NO: 2 or SEQ ID NO:7 or the AAVrh74.MHCK7.micro-dystrophin construct nucleotide sequence of SEQ ID NO: 9, nucleotides 55-5021 of SEQ ID NO: 3, nucleotides 1-4977 of SEQ ID NO: 8, or nucleotides 56-5022 of SEQ ID NO: 6.

A particular use of the invention is for preparation of a medicament for the treatment of Duchenne muscular dystrophy or Becker's muscular dystrophy. For example, the invention provides for use of a dose of recombinant adenovirus associated (rAAV) rAAV.MHCK7.microdystrophin for the preparation of a medicament for treating Duchenne muscular dystrophy in a or Becker's muscular dystrophy human subject in need thereof, wherein the medicament is formulated for administration by intravenous infusion over approximately one hour and the dose of the rAAV administered is about $2\times10^{14}$ vg/kg, and wherein the rAAV comprises the AAVrh74.MHCK7.micro-dystrophin construct nucleotide sequence of SEQ ID NO: 9, nucleotides 55-5021 of SEQ ID NO: 3, nucleotides 1-4977 of SEQ ID NO: 8, or nucleotides 56-5022 of SEQ ID NO: 6.

In a further embodiment, the invention provides for use of a rAAV for preparation of a medicament for reducing fibrosis in a subject in need thereof. For example, the subject in need can be suffering from a muscular dystrophy, such as DMD or any other dystrophin associated muscular dystrophy.

In another embodiment, the invention provides for use of a rAAV for the preparation of a medicament to prevent fibrosis in a subject suffering from a muscular dystrophy.

In addition, the invention provides for use of a rAAV for the preparation of a medicament to increase muscular strength and/or muscle mass in a subject suffering from muscular dystrophy.

The invention also provides for use of the rAAV for the preparation of a medicament for treatment of muscular dystrophy.

The invention provides for use of a rAAV vector comprising the human micro-dystrophin nucleotide sequence of SEQ ID NO: 1 and the MHCK7 promoter nucleotide sequence of SEQ ID NO: 2 or SEQ ID NO:7 for preparation of a medicament for the treatment of a muscular dystrophy or a rAAV vector comprising the AAVrf74.MHCK7.micro-dystrophin construct nucleotide sequence of SEQ ID NO: 9, nucleotides 55-5021 of SEQ ID NO: 3, nucleotides 1-4977 of SEQ ID NO: 8, or nucleotides 56-5022 of SEQ ID NO: 6 for treatment of muscular dystrophy.

In other embodiments of any of the uses of the invention, the serum CK level in the subject is decreased after administration of the rAAV to the subject as compared to the serum CK level before administration of the rAAV by a percentage level selected from the group consisting of:

a) at least 78% by 90, 180, or 270 days after the administration;
b) at least 46, 55, 70, or 95% by 270 days after the administration;
c) at least 72, 73, 74, or 95% by 180 days after the administration;
d) at least 87, 88, 93 or 95% by 90 days after the administration;
e) at least 70% by 270 days after the administration;
f) 70 to 95% by 90, 180, or 270 days after the administration;
g) at least 69, 70, 71, 72, 73, 74, 75, 76, 77, 78, 79, 80, 81, 82, 83, 84, 85, 86, 87, 88, 89, 90, 91, 92, 93, 94, or 95% by 90, 180, or 270 days after the administration; and
h) 69, 70, 71, 72, 73, 74, 75, 76, 77, 78, 79, 80, 81, 82, 83, 84, 85, 86, 87, 88, 89, 90, 91, 92, 93, 94, or 95% by 90, 180, or 270 days after the administration.

In any of the compositions for treating a muscular dystrophy or the uses of a medicament for treating a muscular dystrophy, the level of micro-dystrophin gene expression in a cell of the subject is increased after administration of the composition or medicament. Expression of the micro-dystrophin gene in the cell is detected by measuring the micro-dystrophin protein level by Western blot in muscle biopsied before and after administration of the composition or medicament. In particular, the level of micro-dystrophin protein is increased by at least about 70% to at least about 80%, or at least about 70% to at least about 90%, or at least about 80% to at least about 90% after administration of the composition or medicament compared to the level of micro-dystrophin before administration of the composition or medicament. For example, the level of micro-dystrophin protein is increased by at least about 70% or at least about 71% or at least about 72% or at least about 73% or at least about 74% or at least about 75% or at least about 76% or at least about 77% or at least about 78% or at least about 79% or at least about 80%, or at least about 81%, or at least about 82%, or at least about 83%, or at least about 84%, or at least about 85% after administration of the composition compared to the level of micro-dystrophin before administration of the composition or medicament.

In addition, expression of the micro-dystrophin gene in the cell is detected by measuring the micro-dystrophin protein level by immunohistochemistry in muscle biopsies before and after administration of the composition or medicament. The level of micro-dystrophin protein is increased by at least about 70% to at least about 80%, or at least about 70% to at least about 90%, or at least about 80% to at least about 90% after administration of rAAV compared to the level of micro-dystrophin before administration of the composition or medicament. For example, the level of micro-dystrophin protein is increased by at least about 70% or at least about 71% or at least about 72% or at least about 73% or at least about 74% or at least about 75% or at least about 76% or at least about 77% or at least about 78% or at least about 79% or at least about 80%, or at least about 81%, or at least about 82%, or at least about 83%, or at least about 84%, or at least about 85% after administration of the composition or medicament compared to the level of micro-dystrophin before administration of the composition or medicament.

In any of the compositions for treating a muscular dystrophy, the serum CK level in the subject is decreased after administration of the rAAV as compared to serum CK level before administration of the composition or medicament. For example, the serum CK level in the subject is decreased by about 65% to about 90% or about 65% to about 95% or about 75% to about 90% or about 80% to about 90% or about 85% to about 95% or about 87% to about 95% or about 87% to about 90% by 60 days after administration of the composition or medicament as compared to the serum CK level before administration of the composition or medicament. In particular, in any of the compositions for treating a muscular dystrophy of the invention, the serum CK level in the subject is decreased by about 87% by 60 days after administration of the composition or medicament as compared to the serum CK level before administration of the composition or medicament or in any of the compositions for treating a muscular dystrophy or the uses of a medicament for treating a muscular dystrophy of the invention, the serum CK level in the subject is decreased by about 72% by 60 days after administration of the composition or medicament as compared to the serum CK level before administration of the composition or medicament, or in any of the compositions for treating a muscular dystrophy of the invention, the serum CK level in the subject is decreased by about 73% by 60 days after administration of the composition or medicament as compared to the serum CK level before administration of the composition or medicament, or in any of the compositions for treating a muscular dystrophy or the uses of a medicament for treating a muscular dystrophy of the invention, the serum CK level in the subject is decreased by about 78% by 60 days after administration of the composition or medicament as compared to the serum CK level before administration of the composition or in any of the compositions for treating a muscular dystrophy or the uses of a medicament for treating a muscular dystrophy of the invention, the serum CK level in the subject is decreased by about 95% by 60 days after administration of the composition or medicament as compared to the serum CK level before administration of the composition or medicament. In any of the composition s for treating a muscular dystrophy or the uses of a medicament for treating a muscular dystrophy, the number of micro-dystrophin positive fibers in the muscle tissue of the subject is increased after administration of the composition or medicament as compared to the number of micro-dystrophin positive fibers before administration of the composition or medicament. For example, the number of micro-dystrophin positive fibers is detected by measuring the micro-dystrophin protein level by Western blot or immunohistochemistry on muscle biopsies before and after administration of the composition or medicament.

In any of the compositions for treating a muscular dystrophy or the uses of a medicament for treating a muscular dystrophy, administration of the composition or medicament upregulates expression of DAPC proteins such as alpha-sarcoglycan or beta-sarcoglycan. For example, the level of alpha-sarcoglycan in the subject is increased after administration of the composition or medicament as compared to the level of alpha-sarcoglycan before administration of the composition or medicament. In addition, the level of beta-sarcoglycan in the subject is increased after administration of the composition or medicament as compared to the level of the beta-sarcoglycan before administration of the composition or medicament. The level of alpha-sarcoglycan or beta-sarcoglycan is detected by measuring the alpha-sarcoglycan or beta-sarcoglycan protein level by Western blot or immunohistochemistry on muscle biopsies before and after administration of the composition or medicament.

In any of the compositions for treating a muscular dystrophy or the uses of a medicament for treating a muscular dystrophy, disease progression in the subject is delayed after administration of the composition or medicament as measured by any of: the six minute walk test, time to rise, ascend 4 steps, ascend and descend 4 steps, North Star Ambulatory Assessment (NSAA), 10 meter timed test, 100 meter timed test, hand held dynamometry (HHD), Timed Up and Go, and/or Gross Motor Subtest Scaled (Bayley-III) score.

For example, after administration of any of the compositions for treating a muscular dystrophy or the uses of a medicament for treating a muscular dystrophy, the subject has at least a 6-point improvement in NSAA score at least 270 days after administration of the composition or medicament as compared to NSAA score before administration of the rAAV. Further, in any of the methods, the subject has at least about 0.8 second improvement in time to rise at least 270 days after administration of the composition or medicament as compared to time to rise before administration of the composition or medicament. In addition, in any of the methods or uses of the invention, the subject has at least about 1.2 second improvement in time to ascend 4 steps test at least 270 days after administration of the composition or medicament as compared to time to ascend 4 steps test before administration of the composition or medicament. In addition, in any of the methods or uses of the invention, the subject has at least about 7 second improvement in the 100 m timed test at least 270 days after administration of the composition or medicament as compared to the 100 m timed test before administration of the composition or medicament.

In another embodiment, the invention provides for compositions for expressing micro-dystrophin gene in a patient cell comprising the AAVrh74.MHCK7.micro-dystrophin construct nucleotide sequence of SEQ ID NO: 9, nucleotides 55-5021 of SEQ ID NO: 3, nucleotides 1-4977 of SEQ ID NO: 8 or nucleotides 56-5022 of SEQ ID NO: 6. In a further embodiment, the invention provides for use of a dose of a AAVrh74.MHCK7.micro-dystrophin construct nucleotide sequence of SEQ ID NO: 9, nucleotides 55-5021 of SEQ ID NO: 3, nucleotides 1-4977 of SEQ ID NO: 8 or nucleotides 56-5022 of SEQ ID NO: 6 for the preparation of a medicament for expressing micro-dystrophin gene in a patient cell. For example, expression of the micro-dystrophin gene in the patient cell is detected by measuring the micro-dystrophin protein level by Western blot or immunohistochemistry in muscle biopsies before and after administration of the rAAV.MHCK7.micro-dystrophin construct. In addition, the expression of the micro-dystrophin gene is measured in the patient by detecting greater the number of vector genomes per nucleus, wherein 1 vector genome per nucleus is about 50% micro-dystrophin expression and great than 1 copy per nucleus is consistent with micro-dystrophin expression level. For example, the cells have 1.2 vector copies per nucleus, or 1.3 vector copies per nucleus, or 1.4 vector copies per nucleus, or 1.5 vector copies per nucleus, or 1.6 vector copies per nucleus, or 1.7 vector copies per nucleus, or 1.8 vector copies per nucleus, or 1.9 vector copies per nucleus.

In a further embodiment, the invention provides for compositions for decreasing serum CK levels in a patient in need thereof, the composition comprising the AAVrh74.MHCK7.micro-dystrophin construct nucleotide sequence of SEQ ID NO: 9, nucleotides 55-5021 of SEQ ID NO: 3, nucleotides 1-4977 of SEQ ID NO: 8, or nucleotides 56-5022 of SEQ ID NO: 6. In addition, the invention provides for use of a dose of AAVrh74.MHCK7.micro-dystrophin construct nucleotide sequence of SEQ ID NO: 9, nucleotides 55-5021 of SEQ ID NO: 3, nucleotides 1-4977 of SEQ ID NO: 8, or nucleotides 56-5022 of SEQ ID NO: 6 for the preparation of a medicament for decreasing serum CK levels in a patient in need thereof. For example, the serum CK level in the patient is decreased by at least about 65% to about 90% or about 65% to about 95% or about 75% to about 90% or about 80% to about 90% or about 85% to about 95% or about 87% to about 95% or about 87% to about 90% by 60 days after administration of the composition or medicament as compared to the serum CK level before administration of the composition or medicament. In particular, the serum CK level in the subject is decreased by about 87% by 60 days after administration of the composition or medicament as compared to the serum CK level before administration of the composition or medicament, or decreased by about 72% by 60 days after administration of the composition or medicament as compared to the serum CK level before administration of the composition or medicament, or decreased by about 73% by 60 days after administration of the composition or medicament as compared to the serum CK level before administration of the composition or medicament, or decreased by about 78% by 60 days after administration of the composition or medicament as compared to the serum CK level before administration of the composition or medicament, or decreased by about 95% by 60 days after administration of the composition or medicament as compared to the serum CK level before administration of the composition or medicament.

The invention also provides for compositions for increasing micro-dystrophin positive fibers in a patient muscle tissue comprising the AAVrh74.MHCK7.micro-dystrophin construct nucleotide sequence of SEQ ID NO: 9, nucleotides 55-5021 of SEQ ID NO: 3, nucleotides 1-4977 of SEQ ID NO: 8, or nucleotides 56-5022 of SEQ ID NO: 6. In addition, the invention provides for use of a dose of AAVrh74.MHCK7.micro-dystrophin construct nucleotide sequence of SEQ ID NO: 9, nucleotides 55-5021 of SEQ ID NO: 3, nucleotides 1-4977 of SEQ ID NO: 8, or nucleotides 56-5022 of SEQ ID NO: 6 for the preparation of a medicament for increasing micro-dystrophin positive fibers in a patient muscle tissue. For example, the number of micro-dystrophin positive fibers is detected by measuring the dystrophin protein level by Western blot or immunohistochemistry on muscle biopsies before and after administration of the composition or medicament. In addition, the expression of the micro-dystrophin gene is measured in the patient by detecting greater the number of vector genomes per nucleus, wherein 1 vector genome per nucleus is about 50% micro-dystrophin expression and great than 1 copy per nucleus is consistent with micro-dystrophin expression level. For example, the cells have 1.2 vector copies per nucleus, or 1.3 vector copies per nucleus, or 1.4 vector copies per nucleus, or 1.5 vector copies per nucleus, or 1.6 vector copies per nucleus, or 1.7 vector copies per nucleus, or 1.8 vector copies per nucleus, or 1.9 vector copies per nucleus.

In another embodiment, the invention provides for compositions for increasing the expression of alpha-sarcoglycan in a patient in need thereof comprising the AAVrh74.MHCK7.micro-dystrophin construct nucleotide sequence of SEQ ID NO: 9, nucleotides 55-5021 of SEQ ID NO: 3, nucleotides 1-4977 of SEQ ID NO: 8, or nucleotides 56-5022 of SEQ ID NO: 6. The invention also provides for use of a dose of AAVrh74.MHCK7.micro-dystrophin construct nucleotide sequence of SEQ ID NO: 9, nucleotides 55-5021 of SEQ ID NO: 3, nucleotides 1-4977 of SEQ ID NO: 8, or nucleotides 56-5022 of SEQ ID NO: 6 for the preparation of a medicament for increasing the expression of alpha-sarcoglycan in a patient in need thereof. For example, the level of alpha-sarcoglycan is detected by measuring the alpha-sarcoglycan protein level by Western blot or immunohistochemistry on muscle biopsies before and after administration of the composition or medicament.

In addition, the invention provides for compositions for increasing the expression of beta-sarcoglycan in a patient in need thereof comprising the AAVrh74.MHCK7.micro-dystrophin construct nucleotide sequence of SEQ ID NO: 9, nucleotides 55-5021 of SEQ ID NO: 3, nucleotides 1-4977 of SEQ ID NO: 8, or nucleotides 56-5022 of SEQ ID NO: 6. The invention also provides for use of the AAVrh74.MHCK7.micro-dystrophin construct nucleotide sequence of SEQ ID NO: 9, nucleotides 55-5021 of SEQ ID NO: 3, nucleotides 1-4977 of SEQ ID NO: 8, or nucleotides 56-5022 of SEQ ID NO: 6 for the preparation of a medicament for increasing the expression of beta-sarcoglycan in a patient in need thereof. For example, the level of beta-sarcoglycan is detected by measuring the beta-sarcoglycan protein level by Western blot or immunohistochemistry on muscle biopsies before and after administration of the composition or medicament.

The invention also provides for use of a dose of AAVrh74.MHCK7.micro-dystrophin construct nucleotide sequence of SEQ ID NO: 9, nucleotides 55-5021 of SEQ ID NO: 3, nucleotides 1-4977 of SEQ ID NO: 8, or nucleotides 56-5022 of SEQ ID NO: 6 for the preparation of a medicament for treating a patient with Duchenne muscular dystrophy or Becker muscular dystrophy, such that administration of the medicament results in disease progression in the patient is delayed as measured by any of: the six minute walk test, time to rise, ascend 4 steps, ascend and descend 4 steps, North Star Ambulatory Assessment (NSAA), 10 meter timed test, 100 meter timed test, hand held dynamometry (HHD), Timed Up and Go, and/or Gross Motor Subtest Scaled (Bayley-III) score.

For example, the subject has at least a 6-point improvement in NSAA score at least 270 days after administration of the composition or medicament as compared to NSAA score before administration of the composition or medicament. Further, the subject has at least about 0.8 second improvement in time to rise at least 270 days after administration of the composition or medicament as compared to time to rise before administration of the composition or medicament. In addition, the subject has at least about 1.2 second improvement in time to ascend 4 steps test at least 270 days after administration of the composition or medicament as compared to time to ascend 4 steps test before administration of the composition or medicament. In addition, the subject has at least about 7 second improvement in the 100 m timed test at least 270 days after administration of the composition or medicament as compared to the 100 m timed test before administration of the composition or medicament.

BRIEF DESCRIPTION OF THE DRAWINGS

FIG. 2 provides the nucleic acid sequence (SEQ ID NO: 3) AAVrh74.MHCK7.micro-dystrophin.

FIG. 6 provides the nucleic acid sequence (SEQ ID NO: 5) rAAVrh74.MCK.micro-dystrophin.

In FIG. 8C, Subject 4 samples (*) were diluted 1:4 (to linear range) as ULDQ (>80%) exceeded in initial analysis, and mean values were multiplied by the dilution correction factor for final value in comparison to normal. Mean Micro-dystrophin Expression Vs. Normal was 182.7% in Method 1 and 222.0% in Method 2.

FIG. 13 provides the nucleic acid sequence (SEQ ID NO: 9) AAVrh74.MHCK7.micro-dystrophin.

FIG. 15 provides the nucleic acid sequence (SEQ ID NO: 9) of the AAVrh74.MHCK7.micro-dystrophin plasmid construct, which comprises kanamycin resistance gene.

DETAILED DESCRIPTION

Figure 1:
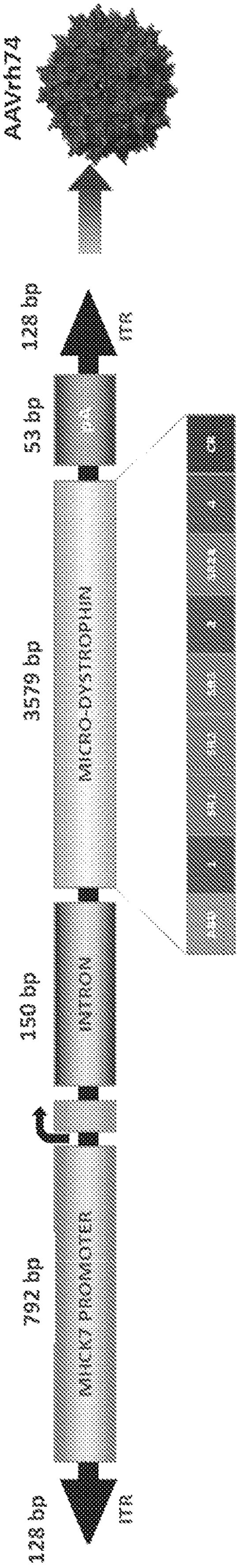
FIG. 1 illustrates the rAAV.MHCK7.micro-dystrophin construct. In this construct, the cDNA expression cassette is flanked by AAV2 inverted terminal repeat sequences (ITR). The construct is characterized by an in-frame rod deletion (R4-R23), while hinges 1, 2 and 4 ($H_1$, $H_2$ and $H_4$) and the cysteine rich domain remain producing a 138 kDa protein. The expression of the micro-dystrophin protein (3579 bp) is guided by a MHCK7 promoter (795 bp). The intron and 5' UTR are derived from plasmid pCMVß (Clontech). The micro-dystrophin cassette had a consensus Kozak immediately in front of the ATG start and a small 53 bp synthetic polyA signal for mRNA termination. The human micro-dystrophin cassette contained the (R4-R23/Δ71-78) domains as previously described by Harper et al. (*Nature Medicine* 8, 253-261 (2002)).

The present invention provides for gene therapy vectors, e.g. rAAV vectors, overexpressing human micro-dystrophin and methods of reducing and preventing fibrosis in muscular dystrophy patients. Muscle biopsies taken at the earliest age of diagnosis of DMD reveal prominent connective tissue proliferation. Muscle fibrosis is deleterious in multiple ways. It reduces normal transit of endomysial nutrients through connective tissue barriers, reduces the blood flow and deprives muscle of vascular-derived nutritional constituents, and functionally contributes to early loss of ambulation through limb contractures. Over time, treatment challenges multiply as a result of marked fibrosis in muscle. This can be observed in muscle biopsies comparing connective tissue proliferation at successive time points. The process continues to exacerbate leading to loss of ambulation and accelerating out of control, especially in wheelchair-dependent patients.

Without early treatment including a parallel approach to reduce fibrosis it is unlikely that the benefits of exon skipping, stop-codon read-through, or gene replacement therapies can ever be fully achieved. Even small molecules or protein replacement strategies are likely to fail without an approach to reduce muscle fibrosis. Previous work in aged mdx mice with existing fibrosis treated with AAV.micro-dystrophin demonstrated that we could not achieve full functional restoration (Liu, M., et al., *Mol Ther* 11, 245-256 (2005)). It is also known that progression of DMD cardiomyopathy is accompanied by scarring and fibrosis in the ventricular wall.

As used herein, the term "AAV" is a standard abbreviation for adeno-associated virus. Adeno-associated virus is a single-stranded DNA parvovirus that grows only in cells in which certain functions are provided by a co-infecting helper virus. There are currently thirteen serotypes of AAV that have been characterized. General information and reviews of AAV can be found in, for example, Carter, 1989, Handbook of Parvoviruses, Vol. 1, pp. 169-228, and Berns, 1990, Virology, pp. 1743-1764, Raven Press, (New York). However, it is fully expected that these same principles will be applicable to additional AAV serotypes since it is well known that the various serotypes are quite closely related, both structurally and functionally, even at the genetic level. (See, for example, Blacklowe, 1988, pp. 165-174 of Parvoviruses and Human Disease, J. R. Pattison, ed.; and Rose, Comprehensive Virology 3:1-61 (1974)). For example, all AAV serotypes apparently exhibit very similar replication properties mediated by homologous rep genes; and all bear three related capsid proteins such as those expressed in AAV2. The degree of relatedness is further suggested by heteroduplex analysis which reveals extensive cross-hybridization between serotypes along the length of the genome; and the presence of analogous self-annealing segments at the termini that correspond to "inverted terminal repeat sequences" (ITRs). The similar infectivity patterns also suggest that the replication functions in each serotype are under similar regulatory control.

An "AAV vector" as used herein refers to a vector comprising one or more polynucleotides of interest (or transgenes) that are flanked by AAV terminal repeat sequences (ITRs). Such AAV vectors can be replicated and packaged into infectious viral particles when present in a host cell that has been transfected with a vector encoding and expressing rep and cap gene products.

An "AAV virion" or "AAV viral particle" or "AAV vector particle" refers to a viral particle composed of at least one AAV capsid protein and an encapsidated polynucleotide AAV vector. If the particle comprises a heterologous polynucleotide (i.e. a polynucleotide other than a wild-type AAV genome such as a transgene to be delivered to a mammalian cell), it is typically referred to as an "AAV vector particle" or simply an "AAV vector". Thus, production of AAV vector particle necessarily includes production of AAV vector, as such a vector is contained within an AAV vector particle.

AAV

Adeno-associated virus (AAV) is a replication-deficient parvovirus, the single-stranded DNA genome of which is about 4.7 kb in length including 145 nucleotide inverted terminal repeat (ITRs). There are multiple serotypes of AAV. The nucleotide sequences of the genomes of the AAV serotypes are known. For example, the nucleotide sequence of the AAV serotype 2 (AAV2) genome is presented in Srivastava et al., *J Virol,* 45:555-564 (1983) as corrected by Ruffing et al., *J Gen Virol,* 75:3385-3392 (1994). As other examples, the complete genome of AAV-1 is provided in GenBank Accession No. NC_002077; the complete genome of AAV-3 is provided in GenBank Accession No. NC_1829; the complete genome of AAV-4 is provided in GenBank Accession No. NC_001829; the AAV-5 genome is provided in GenBank Accession No. AF085716; the complete genome of AAV-6 is provided in GenBank Accession No. NC_00 1862; at least portions of AAV-7 and AAV-8 genomes are provided in GenBank Accession Nos. AX753246 and AX753249, respectively (see also U.S. Pat. Nos. 7,282,199 and 7,790,449 relating to AAV-8); the AAV-9 genome is provided in Gao et al., *J. Virol.,* 78:6381-6388 (2004); the AAV-10 genome is provided in *Mol. Ther.,* 13 (1): 67-76 (2006); and the AAV-11 genome is provided in *Virology,* 330 (2): 375-383 (2004). Cloning of the AAVrh.74 serotype is described in Rodino-Klapac, et al. *Journal of translational medicine* 5, 45 (2007). Cis-acting sequences directing viral DNA replication (rep), encapsidation/packaging and host cell chromosome integration are contained within the ITRs. Three AAV promoters (named p5, p19, and p40 for their relative map locations) drive the expression of the two AAV internal open reading frames encoding rep and cap genes. The two rep promoters (p5 and p19), coupled with the differential splicing of the single AAV intron (e.g., at AAV2 nucleotides 2107 and 2227), result in the production of four rep proteins (rep 78, rep 68, rep 52, and rep 40) from the rep gene. Rep proteins possess multiple enzymatic properties that are ultimately responsible for replicating the viral genome. The cap gene is expressed from the p40 promoter and it encodes the three capsid proteins VP1, VP2, and VP3. Alternative splicing and non-consensus translational start sites are responsible for the production of the three related capsid proteins. A single consensus polyadenylation site is located at map position 95 of the AAV genome. The life cycle and genetics of AAV are reviewed in Muzyczka, *Current Topics in Microbiology and Immunology,* 158:97-129 (1992).

AAV possesses unique features that make it attractive as a vector for delivering foreign DNA to cells, for example, in gene therapy. AAV infection of cells in culture is noncytopathic, and natural infection of humans and other animals is silent and asymptomatic. Moreover, AAV infects many mammalian cells allowing the possibility of targeting many different tissues in vivo. Moreover, AAV transduces slowly dividing and non-dividing cells, and can persist essentially for the lifetime of those cells as a transcriptionally active nuclear episome (extrachromosomal element). The AAV proviral genome is infectious as cloned DNA in plasmids which makes construction of recombinant genomes feasible. Furthermore, because the signals directing AAV replication, genome encapsidation and integration are contained within the ITRs of the AAV genome, some or all of the internal approximately 4.3 kb of the genome (encoding replication and structural capsid proteins, rep-cap) may be replaced with foreign DNA such as a gene cassette containing a promoter, a DNA of interest and a polyadenylation signal. The rep and cap proteins may be provided in trans. Another significant feature of AAV is that it is an extremely stable and hearty virus. It easily withstands the conditions used to inactivate adenovirus (56° C. to 65° C. for several hours), making cold preservation of AAV less critical. AAV may even be lyophilized. Finally, AAV-infected cells are not resistant to superinfection.

Multiple studies have demonstrated long-term (>1.5 years) recombinant AAV-mediated protein expression in muscle. See, Clark et al., *Hum Gene Ther,* 8: 659-669 (1997); Kessler et al., *Proc Nat. Acad Sc. USA,* 93:14082-14087 (1996); and Xiao et al., *J Virol,* 70:8098-8108 (1996). See also, Chao et al., *Mol Ther,* 2:619-623 (2000) and Chao et al., *Mol Ther,* 4:217-222 (2001). Moreover, because muscle is highly vascularized, recombinant AAV transduction has resulted in the appearance of transgene products in the systemic circulation following intramuscular injection as described in Herzog et al., *Proc Natl Acad Sci USA,* 94:5804-5809 (1997) and Murphy et al., *Proc Natl Acad Sci USA,* 94:13921-13926 (1997). Moreover, Lewis et al., *J Virol,* 76:8769-8775 (2002) demonstrated that skeletal myofibers possess the necessary cellular factors for correct antibody glycosylation, folding, and secretion, indicating that muscle is capable of stable expression of secreted protein therapeutics.

Recombinant AAV genomes of the invention comprise nucleic acid molecule of the invention and one or more AAV ITRs flanking a nucleic acid molecule. AAV DNA in the rAAV genomes may be from any AAV serotype for which a recombinant virus can be derived including, but not limited to, AAV serotypes AAVrh.74, AAV-1, AAV-2, AAV-3, AAV-4, AAV-5, AAV-6, AAV-7, AAV-8, AAV-9, AAV-10, AAV-11, AAV-12 and AAV-13. Production of pseudotyped rAAV is disclosed in, for example, WO 01/83692. Other types of rAAV variants, for example rAAV with capsid mutations, are also contemplated. See, for example, Marsic et al., *Molecular Therapy,* 22 (11): 1900-1909 (2014). As noted in the Background section above, the nucleotide sequences of the genomes of various AAV serotypes are known in the art. To promote skeletal muscle specific expression, AAV1, AAV6, AAV8 or AAVrh.74 can be used.

DNA plasmids of the invention comprise rAAV genomes of the invention. The DNA plasmids are transferred to cells permissible for infection with a helper virus of AAV (e.g., adenovirus, E1-deleted adenovirus or herpesvirus) for assembly of the rAAV genome into infectious viral particles. Techniques to produce rAAV particles, in which an AAV genome to be packaged, rep and cap genes, and helper virus functions are provided to a cell are standard in the art. Production of rAAV requires that the following components are present within a single cell (denoted herein as a packaging cell): a rAAV genome, AAV rep and cap genes separate from (i.e., not in) the rAAV genome, and helper virus functions. The AAV rep and cap genes may be from any AAV serotype for which recombinant virus can be derived and may be from a different AAV serotype than the rAAV genome ITRs, including, but not limited to, AAV serotypes AAV-1, AAV-2, AAV-3, AAV-4, AAV-5, AAV-6, AAV-7, AAVrh.74, AAV-8, AAV-9, AAV-10, AAV-11, AAV-12 and AAV-13. Production of pseudotyped rAAV is disclosed in, for example, WO 01/83692 which is incorporated by reference herein in its entirety.

A method of generating a packaging cell is to create a cell line that stably expresses all the necessary components for AAV particle production. For example, a plasmid (or multiple plasmids) comprising a rAAV genome lacking AAV rep and cap genes, AAV rep and cap genes separate from the rAAV genome, and a selectable marker, such as a neomycin resistance gene, are integrated into the genome of a cell. AAV genomes have been introduced into bacterial plasmids by procedures such as GC tailing (Samulski et al., 1982, *Proc. Natl. Acad. S6. USA,* 79:2077-2081), addition of synthetic linkers containing restriction endonuclease cleavage sites (Laughlin et al., 1983, Gene, 23:65-73) or by direct, blunt-end ligation (Senapathy & Carter, 1984, J. Biol. Chem., 259:4661-4666). The packaging cell line is then infected with a helper virus such as adenovirus. The advantages of this method are that the cells are selectable and are suitable for large-scale production of rAAV. Other examples of suitable methods employ adenovirus or baculovirus rather than plasmids to introduce rAAV genomes and/or rep and cap genes into packaging cells.

General principles of rAAV production are reviewed in, for example, Carter, 1992, Current Opinions in Biotechnology, 1533-539; and Muzyczka, 1992, Curr. Topics in Microbial. and Immunol., 158:97-129). Various approaches are described in Ratschin et al., *Mol. Cell. Biol.* 4:2072 (1984); Hermonat et al., *Proc. Natl. Acad. Sci. USA,* 81:6466 (1984); Tratschin et al., *Mol. Cell. Biol.* 5:3251 (1985); McLaughlin et al., *J. Virol.,* 62:1963 (1988); and Lebkowski et al., *Mol. Cell. Biol.,* 7:349 (1988). Samulski et al., *J. Virol.,* 63:3822-3828 (1989); U.S. Pat. No. 5,173,414; WO 95/13365 and corresponding U.S. Pat. No. 5,658,776; WO 95/13392; WO 96/17947; PCT/US98/18600; WO 97/09441 (PCT/US96/14423); WO 97/08298 (PCT/US96/13872); WO 97/21825 (PCT/US96/20777); WO 97/06243 (PCT/FR96/01064); WO 99/11764; Perrin et al. *Vaccine* 13:1244-1250 (1995); Paul et al. *Human Gene Therapy* 4:609-615 (1993); Clark et al. *Gene Therapy* 3:1124-1132 (1996); U.S. Pat. Nos. 5,786,211; 5,871,982; and 6,258,595. The foregoing documents are hereby incorporated by reference in their entirety herein, with particular emphasis on those sections of the documents relating to rAAV production.

The invention thus provides packaging cells that produce infectious rAAV. In one embodiment packaging cells may be stably transformed cancer cells such as HeLa cells, 293 cells and PerC.6 cells (a cognate 293 line). In another embodiment, packaging cells are cells that are not transformed cancer cells, such as low passage 293 cells (human fetal kidney cells transformed with E1 of adenovirus), MRC-5 cells (human fetal fibroblasts), WI-38 cells (human fetal fibroblasts), Vero cells (monkey kidney cells) and FRhL-2 cells (rhesus fetal lung cells).

Recombinant AAV (i.e., infectious encapsidated rAAV particles) of the invention comprise a rAAV genome. In exemplary embodiments, the genomes of both rAAV lack AAV rep and cap DNA, that is, there is no AAV rep or cap DNA between the ITRs of the genomes. Examples of rAAV that may be constructed to comprise the nucleic acid molecules of the invention are set out in International Patent Application No. PCT/US2012/047999 (WO 2013/016352) incorporated by reference herein in its entirety.

In an exemplary embodiment, the recombinant AAV vector of the invention is produced by the triple transfection method (Xiao et al., *J Virol* 72, 2224-2232 (1998) using the AAV vector plasmids rAAV.MHCK7.micro-dystrophin, pNLRep2-Caprh74 and pHelp, rAAV contains the micro-dystrophin gene expression cassette flanked by AAV2 inverted terminal repeat sequences (ITR). It is this sequence that is encapsidated into AAVrh74 virions. The plasmid contains the micro-dystrophin sequence and the MHCK7 enhancer and core promoter elements of the muscle specific promoter to drive gene expression. The expression cassette also contains an SV40 intron (SD/SA) to promote high-level gene expression and the bovine growth hormone polyadenylation signal is used for efficient transcription termination.

Figure 3:
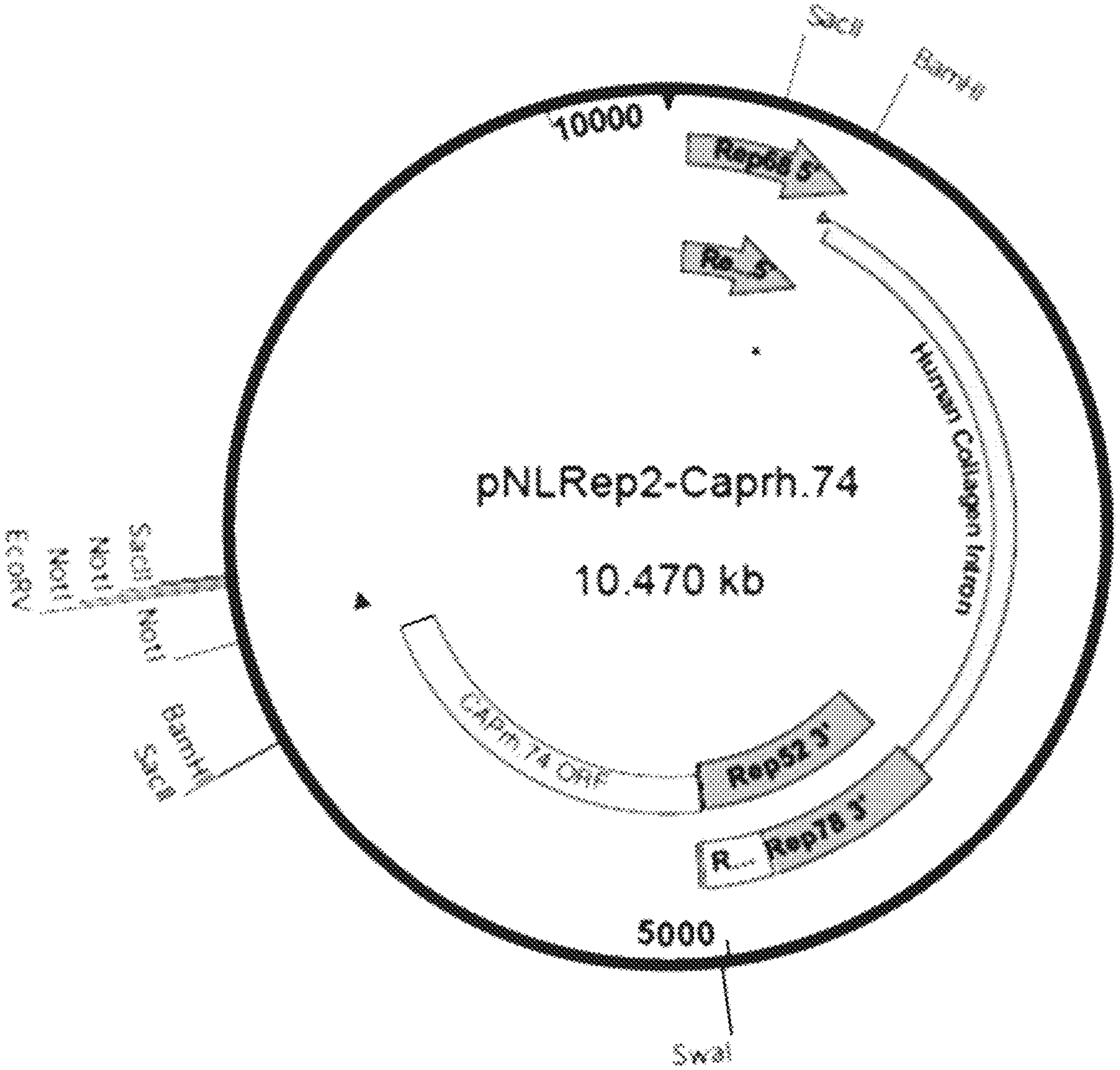
FIG. 3 provides the pNLREP2-Caprh74 AAV helper plasmid map.

The pNLREP2-Caprh74 is an AAV helper plasmid that encodes the 4 wild-type AAV2 rep proteins and the 3 wild-type AAV VP capsid proteins from serotype rh74. A schematic map of the pNLREP2-Caprh74 plasmid is shown in FIG. 3.

Figure 4:
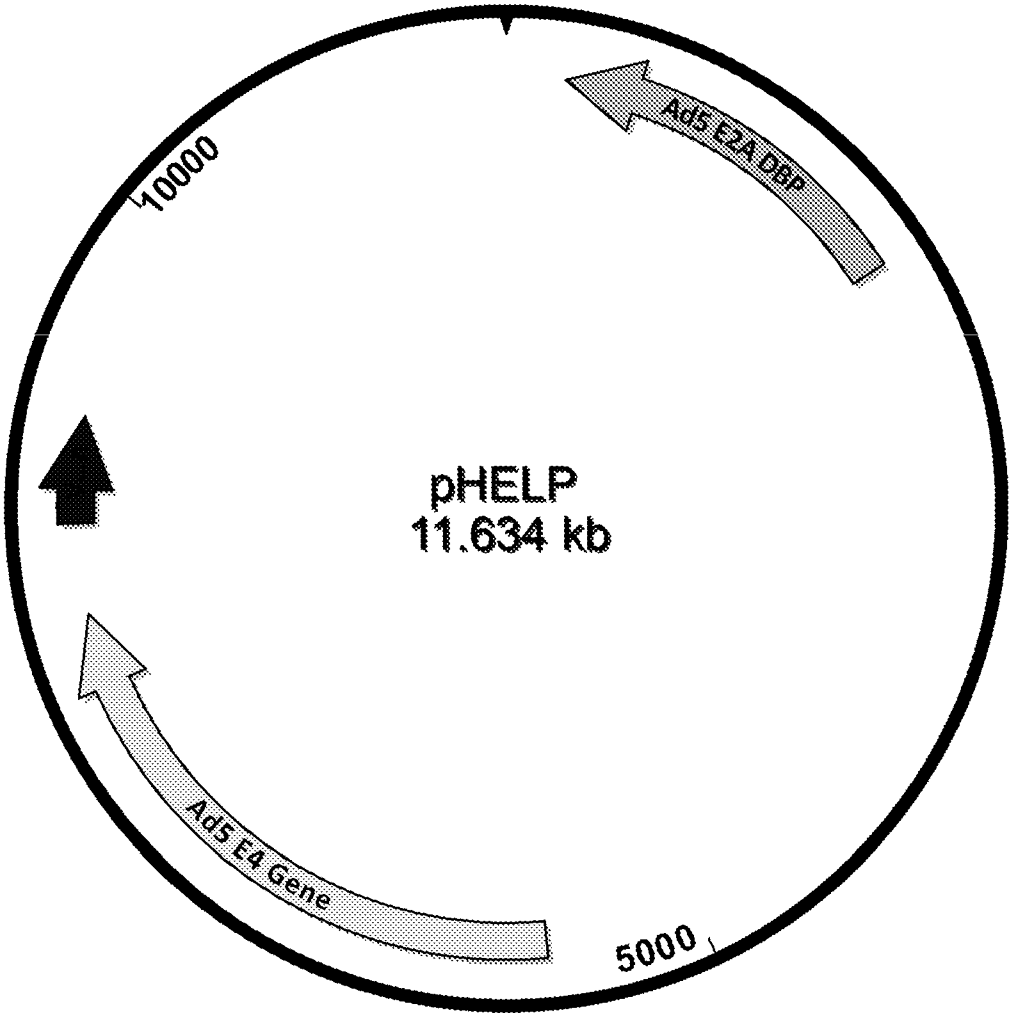
FIG. 4 provides the Ad Helper plasmid pHELP.

The pHELP adenovirus helper plasmid is 11,635 bp and was obtained from Applied Viromics. The plasmid contains the regions of adenovirus genome that are important for AAV replication, namely E2A, E4ORF6, and VA RNA (the adenovirus E1 functions are provided by the 293 cells). The adenovirus sequences present in this plasmid only represents ~40% of the adenovirus genome, and does not contain the cis elements critical for replication such as the adenovirus terminal repeats. Therefore, no infectious adenovirus is expected to be generated from such a production system. A schematic map of the pHELP plasmid is shown in FIG. 4.

The rAAV may be purified by methods standard in the art such as by column chromatography or cesium chloride gradients. Methods for purifying rAAV vectors from helper virus are known in the art and include methods disclosed in, for example, Clark et al., *Hum. Gene Ther.,* 10 (6): 1031-1039 (1999); Schenpp and Clark, *Methods Mol. Med.,* 69 427-443 (2002); U.S. Pat. No. 6,566,118 and WO 98/09657.

In another embodiment, the invention contemplates compositions comprising rAAV of the present invention. Compositions of the invention comprise rAAV and a pharmaceutically acceptable carrier. The compositions may also comprise other ingredients such as diluents and adjuvants. Acceptable carriers, diluents and adjuvants are nontoxic to recipients and are preferably inert at the dosages and concentrations employed and include buffers and surfactants such as pluronics.

Titers of rAAV to be administered in methods of the invention will vary depending, for example, on the particular rAAV, the mode of administration, the treatment goal, the individual, and the cell type(s) being targeted, and may be determined by methods standard in the art. Titers of rAAV may range from about $1\times10^6$, about $1\times10^7$, about $1\times10^8$, about $1\times10^9$, about $1\times10^{10}$, about $1\times10^{11}$, about $1\times10^{12}$, about $1\times10^{13}$ to about $1\times10^{14}$ or more DNase resistant particles (DRP) per ml. Dosages may also be expressed in units of viral genomes (vg). One exemplary method of determining encapsilated vector genome titer uses quantitative PCR such as the methods described in (Pozsgai et al., Mol. Ther. 25 (4): 855-869, 2017).

Methods of transducing a target cell with rAAV, in vivo or in vitro, are contemplated by the invention. The in vivo methods comprise the step of administering an effective dose, or effective multiple doses, of a composition comprising a rAAV of the invention to an animal (including a human being) in need thereof. If the dose is administered prior to development of a disorder/disease, the administration is prophylactic. If the dose is administered after the development of a disorder/disease, the administration is therapeutic. In embodiments of the invention, an effective dose is a dose that alleviates (eliminates or reduces) at least one symptom associated with the disorder/disease state being treated, that slows or prevents progression to a disorder/disease state, that slows or prevents progression of a disorder/disease state, that diminishes the extent of disease, that results in remission (partial or total) of disease, and/or that prolongs survival. An example of a disease contemplated for prevention or treatment with methods of the invention is DMD.

Combination therapies are also contemplated by the invention. Combination as used herein includes both simultaneous treatment and sequential treatments. Combinations of methods of the invention with standard medical treatments (e.g., corticosteroids) are specifically contemplated, as are combinations with novel therapies.

Administration of an effective dose of the compositions may be by routes standard in the art including, but not limited to, intramuscular, parenteral, intravenous, oral, buccal, nasal, pulmonary, intracranial, intraosseous, intraocular, rectal, or vaginal. Route(s) of administration and serotype(s) of AAV components of the rAAV (in particular, the AAV ITRs and capsid protein) of the invention may be chosen and/or matched by those skilled in the art taking into account the infection and/or disease state being treated and the target cells/tissue(s) that are to express the micro-dystrophin protein.

The invention provides for local administration and systemic administration of an effective dose of rAAV and compositions of the invention. For example, systemic administration is administration into the circulatory system so that the entire body is affected. Systemic administration includes enteral administration such as absorption through the gastrointestinal tract and parenteral administration through injection, infusion or implantation.

In particular, actual administration of rAAV of the present invention may be accomplished by using any physical method that will transport the rAAV recombinant vector into the target tissue of an animal. Administration according to the invention includes, but is not limited to, injection into muscle and injection into the bloodstream. Simply resuspending a rAAV in phosphate buffered saline has been demonstrated to be sufficient to provide a vehicle useful for muscle tissue expression, and there are no known restrictions on the carriers or other components that can be co-administered with the rAAV (although compositions that degrade DNA should be avoided in the normal manner with rAAV). Capsid proteins of a rAAV may be modified so that the rAAV is targeted to a particular target tissue of interest such as muscle. See, for example, WO 02/053703, the disclosure of which is incorporated by reference herein. Pharmaceutical compositions can be prepared as injectable formulations or as topical formulations to be delivered to the muscles by transdermal transport. Numerous formulations for both intramuscular injection and transdermal transport have been previously developed and can be used in the practice of the invention. The rAAV can be used with any pharmaceutically acceptable carrier for ease of administration and handling.

In one embodiment of the invention, the AAVrh74.MHCK7.microdystrophin described herein is formulated in a buffer containing 20 mM Tris (pH 8.0), 1 mM magnesium chloride ($MgCl_2$), 200 mM sodium chloride (NaCl), and 0.001% poloxamer 188.

The dose of rAAV to be administered in methods disclosed herein will vary depending, for example, on the particular rAAV, the mode of administration, the treatment goal, the individual, and the cell type(s) being targeted, and may be determined by methods standard in the art. Titers of each rAAV administered may range from about $1\times10^6$, about $1\times10^7$, about $1\times10^8$, about $1\times10^9$, about $1\times10^{10}$, about $1\times10^{11}$, about $1\times10^{12}$, about $1\times10^{13}$, about $1\times10^{14}$, about $2\times10^{14}$, or to about $1\times10^{15}$ or more DNase resistant particles (DRP) per ml. Dosages may also be expressed in units of viral genomes (vg) (i.e., $1\times10^7$ vg, $1\times10^8$ vg, $1\times10^9$ vg, $1\times10^{10}$ vg, $1\times10^{11}$ vg, $1\times10^{12}$ vg, $1\times10^{13}$ vg, $1\times10^{14}$ vg, $2\times10^{14}$ vg, $1\times10^{15}$ vg respectively). Dosages may also be expressed in units of viral genomes (vg) per kilogram (kg) of bodyweight (i.e., $1\times10^{10}$ vg/kg, $1\times10^{11}$ vg/kg, $1\times10^{12}$ vg/kg, $1\times10^{13}$ vg/kg, $1\times10^{14}$ vg/kg, $1.25\times10^{14}$ vg/kg, $1.5\times10^{14}$ vg/kg, $1.75\times10^{14}$ vg/kg, $2.0\times10^{14}$ vg/kg, $2.25\times10^{14}$ vg/kg, $2.5\times10^{14}$ vg/kg, $2.75\times10^{14}$ vg/kg, $3.0\times10^{14}$ vg/kg, $3.25\times10^{14}$ vg/kg, $3.5\times10^{14}$ vg/kg, $3.75\times10^{14}$ vg/kg, $4.0\times10^{14}$ vg/kg, $1\times10^{15}$ vg/kg respectively). Methods for titering AAV are described in Clark et al., *Hum. Gene Ther.,* 10:1031-1039 (1999).

In particular, actual administration of rAAV of the present invention may be accomplished by using any physical method that will transport the rAAV recombinant vector into the target tissue of an animal. Administration according to the invention includes, but is not limited to, injection into muscle and injected into the bloodstream. Simply resuspending a rAAV in phosphate buffered saline has been demonstrated to be sufficient to provide a vehicle useful for muscle tissue expression, and there are no known restrictions on the carriers or other components that can be co-administered with the rAAV (although compositions that degrade DNA should be avoided in the normal manner with rAAV). Capsid proteins of a rAAV may be modified so that the rAAV is targeted to a particular target tissue of interest such as muscle. See, for example, WO 02/053703, the disclosure of which is incorporated by reference herein. Pharmaceutical compositions can be prepared as injectable formulations or as topical formulations to be delivered to the muscles by transdermal transport. Numerous formulations for both intramuscular injection and transdermal transport have been previously developed and can be used in the practice of the invention. The rAAV can be used with any pharmaceutically acceptable carrier for ease of administration and handling.

For purposes of intramuscular injection, solutions in an adjuvant such as sesame or peanut oil or in aqueous propylene glycol can be employed, as well as sterile aqueous solutions. Such aqueous solutions can be buffered, if desired, and the liquid diluent first rendered isotonic with saline or glucose. Solutions of rAAV as a free acid (DNA contains acidic phosphate groups) or a pharmacologically acceptable salt can be prepared in water suitably mixed with a surfactant such as hydroxpropylcellulose. A dispersion of rAAV can also be prepared in glycerol, liquid polyethylene glycols and mixtures thereof and in oils. Under ordinary conditions of storage and use, these preparations contain a preservative to prevent the growth of microorganisms. In this connection, the sterile aqueous media employed are all readily obtainable by standard techniques well-known to those skilled in the art.

The pharmaceutical carriers, diluents or excipients suitable for injectable use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating actions of microorganisms such as bacteria and fungi. The carrier can be a solvent or dispersion medium containing, for example, water, ethanol, polyol (for example, glycerol, propylene glycol, liquid polyethylene glycol and the like), suitable mixtures thereof, and vegetable oils. The proper fluidity can be maintained, for example, by the use of a coating such as lecithin, by the maintenance of the required particle size in the case of a dispersion and by the use of surfactants. The prevention of the action of microorganisms can be brought about by various antibacterial and antifungal agents, for example, parabens, chlorobutanol, phenol, sorbic acid, thimerosal and the like. In many cases it will be preferable to include isotonic agents, for example, sugars or sodium chloride. Prolonged absorption of the injectable compositions can be brought about by use of agents delaying absorption, for example, aluminum monostearate and gelatin.

Sterile injectable solutions are prepared by incorporating rAAV in the required amount in the appropriate solvent with various other ingredients enumerated above, as required, followed by filter sterilization. Generally, dispersions are prepared by incorporating the sterilized active ingredient into a sterile vehicle which contains the basic dispersion medium and the required other ingredients from those enumerated above. In the case of sterile powders for the preparation of sterile injectable solutions, the preferred methods of preparation are vacuum drying and the freeze drying technique that yield a powder of the active ingredient plus any additional desired ingredient from the previously sterile-filtered solution thereof.

Transduction with rAAV may also be carried out in vitro. In one embodiment, desired target muscle cells are removed from the subject, transduced with rAAV and reintroduced into the subject. Alternatively, syngeneic or xenogeneic muscle cells can be used where those cells will not generate an inappropriate immune response in the subject.

Suitable methods for the transduction and reintroduction of transduced cells into a subject are known in the art. In one embodiment, cells can be transduced in vitro by combining rAAV with muscle cells, e.g., in appropriate media, and screening for those cells harboring the DNA of interest using conventional techniques such as Southern blots and/or PCR, or by using selectable markers. Transduced cells can then be formulated into pharmaceutical compositions, and the composition introduced into the subject by various techniques, such as by intramuscular, intravenous, subcutaneous and intraperitoneal injection, or by injection into smooth and cardiac muscle, using e.g., a catheter.

Transduction of cells with rAAV of the invention results in sustained expression of the micro-dystrophin protein. The present invention thus provides methods of administering/delivering rAAV which express micro-dystrophin protein to an animal, preferably a human being. These methods include transducing tissues (including, but not limited to, tissues such as muscle, organs such as liver and brain, and glands such as salivary glands) with one or more rAAV of the present invention. Transduction may be carried out with gene cassettes comprising tissue specific control elements. For example, one embodiment of the invention provides methods of transducing muscle cells and muscle tissues directed by muscle specific control elements, including, but not limited to, those derived from the actin and myosin gene families, such as from the myoD gene family (See Weintraub et al., *Science,* 251:761-766 (1991)), the myocyte-specific enhancer binding factor MEF-2 (Cserjesi and Olson, *Mol Cell Biol* 11:4854-4862 (1991)), control elements derived from the human skeletal actin gene (Muscat et al., *Mol Cell Biol,* 7:4089-4099 (1987)), the cardiac actin gene, muscle creatine kinase sequence elements (See Johnson et al., *Mol Cell Biol,* 9:3393-3399 (1989)) and the murine creatine kinase enhancer (mCK) element, control elements derived from the skeletal fast-twitch troponin C gene, the slow-twitch cardiac troponin C gene and the slow-twitch troponin I gene: hypoxia-inducible nuclear factors (Semenza et al., *Proc Natl Acad Sci USA,* 88:5680-5684 (1991)), steroid-inducible elements and promoters including the glucocorticoid response element (GRE) (See Mader and White, *Proc. Natl. Acad. Sci. USA* 90:5603-5607 (1993)), and other control elements.

Muscle tissue is an attractive target for in vivo DNA delivery, because it is not a vital organ and is easy to access. The invention contemplates sustained expression of micro-dystrophin from transduced myofibers.

By "muscle cell" or "muscle tissue" is meant a cell or group of cells derived from muscle of any kind (for example, skeletal muscle and smooth muscle, e.g. from the digestive tract, urinary bladder, blood vessels or cardiac tissue). Such muscle cells may be differentiated or undifferentiated, such as myoblasts, myocytes, myotubes, cardiomyocytes and cardiomyoblasts.

The term "transduction" is used to refer to the administration/delivery of the coding region of the micro-dystrophin to a recipient cell either in vivo or in vitro, via a replication-deficient rAAV of the invention resulting in expression of micro-dystrophin by the recipient cell.

Thus, the invention provides methods of administering an effective dose (or doses, administered essentially simultaneously or doses given at intervals) of rAAV that encode micro-dystrophin to a subject in need thereof.

The following EXAMPLES are provided by way of illustration and not limitation. Described numerical ranges are inclusive of each integer value within each range and inclusive of the lowest and highest stated integer.

EXAMPLES

Example 1

A) Generation of the AAVrh74.MHCK7.Micro-Dystrophin Construct

The AAVrh74.MHCK7.micro-dystrophin plasmid contains a human micro-dystrophin cDNA expression cassette flanked by AAV2 inverted terminal repeat sequences (ITR) (see FIG. 1). The micro-dystrophin construct was characterized by an in-frame rod deletion (R4-R23), while hinges 1, 2 and 4 and cysteine rich domain remain producing a 138 kDa protein. The expression of the micro-dystrophin protein (3579 bp) was guided by a MHCK7 promoter (792 bp). The plasmid was constructed from the rAAV.MCK.micro-dystrophin plasmid by removing the MCK promoter and inserting the MHCK7 promoter. After the core promoter, the 53 bp endogenous mouse MCK Exon1 (untranslated) is present for efficient transcription initiation, followed by the SV40 late 16S/19S splice signals (150 bp) and a small 5'UTR (61 bp). The intron and 5' UTR are derived from plasmid pCMVB (Clontech). The micro-dystrophin cassette had a consensus Kozak immediately in front of the ATG start and a small 53 bp synthetic polyA signal for mRNA termination. The human micro-dystrophin cassette contained the (R4-R23/471-78) domains as previously described by Harper et al. (*Nature Medicine* 8, 253-261 (2002)). The complementary DNA was codon optimized for human usage and synthesized by GenScript (Piscataway, NJ) (*Mol Ther* 18, 109-117 (2010)). The only viral sequences included in this vector were the inverted terminal repeats of AAV2, which are required for both viral DNA replication and packaging. The micro-dystrophin cassette has a small 53 bp synthetic polyA signal for mRNA termination.

Previous studies have validated cardiac expression using MHCK7 promoter (Salva et al. *Mol Ther* 15, 320-329 (2007) and AAVrh74 achieving skeletal, diaphragm, and cardiac muscle expression (Sondergaard et al. *Annals of clinical and Transl Neurology* 2, 256-270 (2015)), The sequence of construct of FIG. 1 was encapsidated into AAVrh.74 virions. The molecular clone of the AAVrh.74 serotype was cloned from a rhesus macaque lymph node and is discussed in in Rodino-Klapac et al. *Journal of Translational medicine* 5, 45 (2007).

Table 1 shows the molecular features of the plasmid AAVrh74.MHCK7.micro-dystrophin (SEQ ID NO: 3)

TABLE 1

Molecular Features of plasmid rAAV•MHCK7•micro-dystrophin

| TYPE | START | END | NAME | DESCRIPTION |
|---|---|---|---|---|
| REGION | 55 | 182 | 5' ITR | Wild-type AAV2 inverted terminal repeat |
| REGION | 244 | 1035 | MHCK7 | Mouse myosin heavy chain complex - E box muscle creatine kinase fusion enhancer/promoter |
| REGION | 1045 | 1194 | Chimeric intron | 5' donor site from human β-globin gene and the branchpoint and 3' splice acceptor site from IgG heavy chain variable region |
| GENE | 1205 | 4783 | huDys cDNA | Human micro-dystrophin cDNA |
| REGION | 4786 | 4838 | PolyA | Synthetic PolyA |
| REGION | 4894 | 5021 | 3' ITR | Wild-type AAV2 inverted terminal repeat |
| GENE | 6760 | 7619 | AmpR | β-lactamase gene |
| REGION | 7823 | 8442 | Ori | Plasmid origin of replication |

Figure 14:
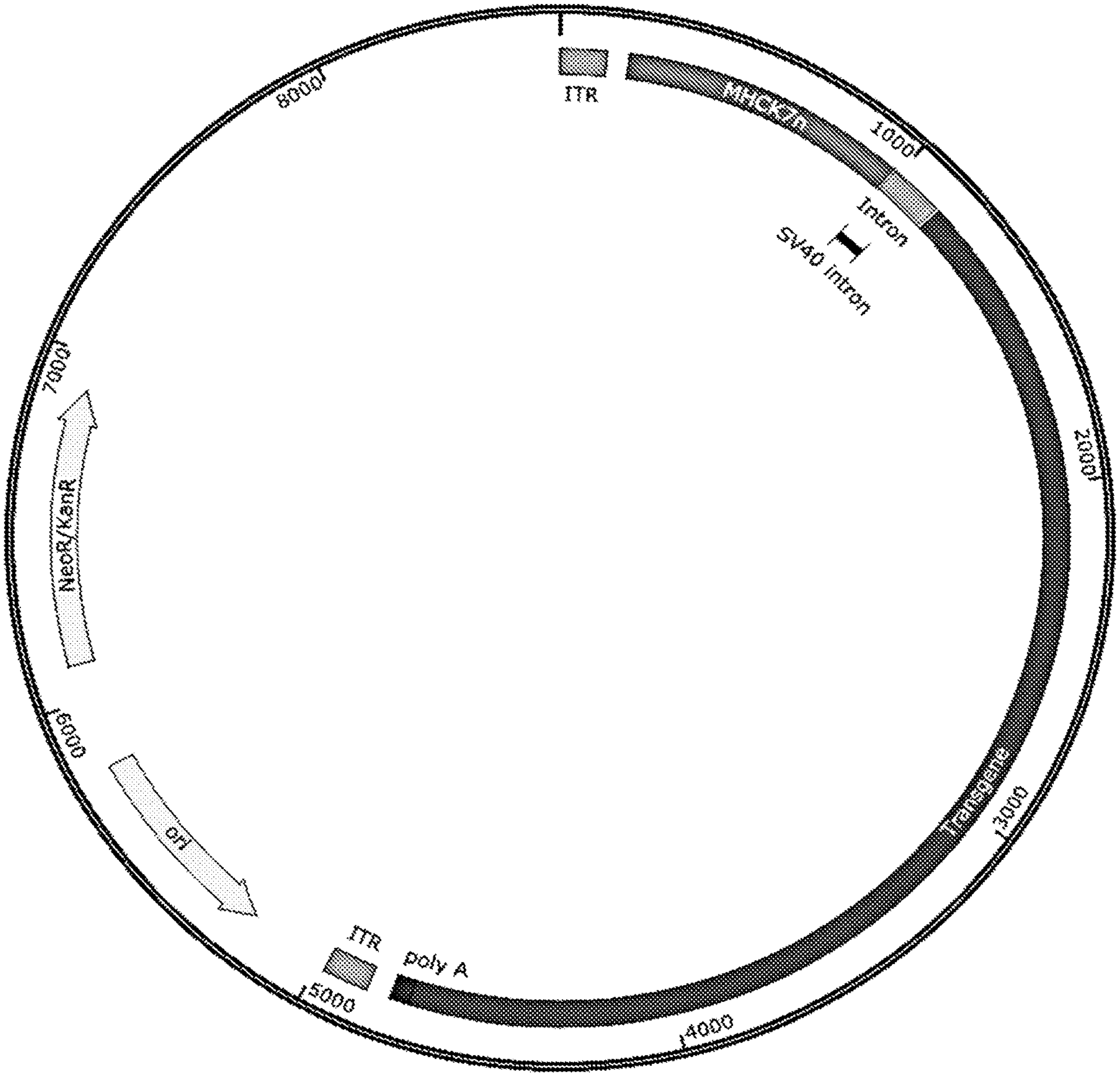
FIG. 14 illustrates the AAVrh74.MHCK7.micro-dystrophin plasmid construct.

B) Generation of the AAVrh74.MHCK7.Micro-Dystrophin Construct from and Plasmid Encoding Kanamycin (Kan) Resistance Cloning of MHCK7.μDys.KAN was achieved by isolating the MHCK7.μDys fragment from an MHCK7.μDys.AMP plasmid and the Kanamycin Backbone, and annealing them using the NEBuilder cloning workflow. The MHCK7.μDys fragment was isolated via restriction enzyme digestion with SnaBI. The digestion was performed in a 50 μL total reaction in 1× CutSmart Buffer (NEB) and 1 μL SnaBI, at 37° C. for 1 hour. The resulting fragment was isolated via electrophoresis using a 1% Agarose gel, running at 105 volts for 1.5 hours. The band corresponding to the MHCK7.μDys insert was cut out and purified using a gel purification kit (Macherey-Nagel). The resulting fragment had a DNA concentration of 10 ng/μL. The Kan backbone fragment was isolated via XbaI restriction enzyme digestion in a 50 μL reaction with 1× CutSmart Buffer (NEB) and 1 μL XbaI, at 37° C. for 1 hour. The resulting fragment was isolated via electrophoresis using a 1% Agarose gel, running at 105 volts for 1.5 hours. The band corresponding to the Kan Backbone was cut out and purified via gel purification kit (Macherey-Nagel). The resulting fragment had a DNA concentration of 8.1 ng/μL. The two fragments were annealed using the NEB Builder cloning workflow, which has the ability to join two fragments with overlapping sequences. The NEBuilder cloning reaction was performed per manufacturer protocol at 50° C. for 15 minutes, using a 1:1 ratio of MHCK7.μDys to Kanamycin backbone in 1× NEBuilder HiFi DNA Assembly Master Mix for a total reaction volume of 20 μL. The resulting clone was transformed into NEB® Stable Competent *E. coli* (C3040) by adding 2.5 μL cloning product to the cells followed by 30 minutes on ice, then 30 seconds at 42° C. and an additional 5 minutes on ice. After transformation, 950 μL of outgrowth media was added to the cells and allowed to grow at 30° C. for 1.5 hours, shaking at 225 rpm. Following outgrowth, 450 μL of these cells was plated on a 50 μg/mL kanamycin LB agar plate and incubated overnight at 30° C. in a dry incubator. A colony was picked from this plate and grown up overnight in LB containing 50 μg/mL kanamycin. DNA was isolated from 3 mL of this culture using QIAprep® Spin Miniprep Kit (Qiagen). This DNA was used to confirm the cloning product. The cloning product was confirmed via restriction enzyme digestion with PmeI, MscI, and SmaI followed by gel electrophoresis. The cloning product was additionally confirmed via sequencing. The resultant plasmid is set forth in SEQ ID NO:8, and shown in FIGS. 14 and 15. The sequence of construct of FIG. 13 which corresponds to that of SEQ ID NO:9, and nucleotides 1-4977 of SEQ ID NO: 8, was encapsidated into AAVrh.74 virions as described above.

Example 2

Systemic Gene Delivery Clinical Trial for Duchenne Muscular Dystrophy

This is a single-dose controlled trial using the rAAVrh74.MHCK7.micro-dystrophin of SEQ ID NO: 3, nucleotides 55-5021, for DMD subjects. Cohort A will include six subjects of ages 3 months to 3 years, and Cohort B will include six subjects of ages 4 years to 7 years old. All subjects will receive intravenous micro-dystrophin vector ($2\times10^{14}$ vg/kg in 10 mL/kg). The rAAVrh74.MHCK7.micro-dystrophin is formulated in a buffer containing 20 mM Tris (pH 8.0), 1 mM magnesium chloride ($MgCl_2$), 200 mM sodium chloride (NaCl), and 0.001% poloxamer 188.

In the study, the rAAVrh74.MHCK7.micro-dystrophin was infused via peripheral arm vein so that it can reach all the muscles in the body. Six DMD subjects ages 3 months to 3 years in Cohort A, and six DMD subjects ages 4 years to age 7 years in Cohort B, were enrolled. All subjects received intravenous micro-dystrophin vector ($2\times10^{14}$ vg/kg in 10 mL/kg). The encapsilated vector genome titer for the administered dose was determined using quantitative PCR using a Prism 7500 Taqman detector system (PE Applied Biosystems) with primers directed against the MHCK7 promoter compared to a supercoiled DNA plasmid standard (Pozsgai et al. Mol. Ther. 25 (4): 855-869, 2017).

Subjects received infusions over 1 hour in the Pediatric Intensive Care Unit (PICU) at Nationwide Children's Hospital. Before the gene therapy, a muscle biopsy was performed at the screening visit. Subjects will have a second muscle biopsy to determine if the gene allowed for replacement of the missing dystrophin protein at 90 days post-delivery. After the gene transfer, patients were carefully monitored for any side effects of the treatment. This monitoring included blood and urine tests, as well as physical examination during the screening visits and on days 0, 1, 7, 14, 30, 60, 90, and 180, and at months 9, 12, 18, 24, 30 and 36 to make sure that there are no side effects from the gene injection.

The subjects of Cohort A (n=6) were between 3 months to 3 years of age, and received intravenous rAAVrh74.MHCK7.micro-dystrophin vector ($2\times10^{14}$ vg/kg in 10 mL/kg). One-day prior to gene transfer subjects in Cohort A were started on prednisone or deflazacort 1 mg/kg and maintained for 30 days while monitoring immune response. If negative at day 30, steroids were weaned over 1 week. If T cell response to AAV or micro-dys was >125 SFC/106 PBMCs, steroids were maintained until levels drop below this threshold.

The subjects of Cohort B (n=6) were between 4 years to 7 years of age, and received intravenous rAAVrh74.MHCK7.micro-dystrophin vector ($2\times10^{14}$ vg/kg in 10 mL/kg). These subjects were maintained on stable dose of corticosteroids throughout trial but may have been increased for short time if T cell response to AAV or micro-dystrophin was >125 SFC/106 PBMCs.

Eligibility Criteria

Inclusion criteria for the study were as follows:

- Age of enrollment: Cohort A: 3 months to 7 years of age and Cohort B: between 4-7 years of age, inclusive.
- Molecular characterization of the DMD gene with frame-shift (deletion or duplication), or premature stop codon mutation between exons 18 to 58.
- CK elevation>1000 U/L
- Cohort A subjects: below average on the Bayley-III motor assessment for gross motor defined as a scaled score of ≤9
- Cohort B: Below average on 100 meter timed test defined as <80% predicted.
- Males of any ethnic group.
- Ability to cooperate with motor assessment testing.
- Cohort A subjects: No previous treatment with corticosteroids.
- Cohort B subjects: Stable dose equivalent of oral corticosteroids for at least 12 weeks prior to screening and the dose is expected to remain constant (except for modifications to accommodate changes in weight) throughout the stud Exclusion criteria for the study were as follows:

- Active viral infection based on clinical observations.
- Signs of cardiomyopathy, including echocardiogram with ejection fraction below 40%.
- Serological evidence of HIV infection, or Hepatitis B or C infection.
- Diagnosis of (or ongoing treatment for) an autoimmune disease.
- Abnormal laboratory values considered clinically significant.
- Concomitant illness or requirement for chronic drug treatment that in the opinion of the PI creates unnecessary risks for gene transfer.
- Subjects with AAVrh74 or AAV8 antibody titers>1:400 as determined by ELISA immunoassay.
- Medical condition or extenuating circumstance that, in the opinion of the investigator, might compromise the subject's ability to comply with the protocol required testing or procedures or compromise the subject's wellbeing, safety, or clinical interpretability.
- Severe infection (e.g., pneumonia, pyelonephritis, or meningitis) within 4 weeks before gene transfer visit (enrollment may be postponed).
- Received any investigational medication (other than corticosteroids) or exon skipping medications (including ExonDys 51®), experimental or otherwise, in the last 6 months prior to screening for this study.
- Has had any type of gene therapy, cell based therapy (e.g. stem cell transplantation), or CRISPR/Cas9 therapy.
- Family does not want to disclose patient's study participation with primary care physician and other medical providers.

Outcome Measures

The primary outcome measure was safety based on number of participants with adverse events (time frame: 3 years). Adverse effects were monitored and scored for severity and relatedness to the study article.

The secondary outcome measures were as follows:

Gross Motor Subtest Scaled (Bayley-III) score (time frame: screening, Day 30-3 Years): The Gross Motor Scaled Score measured motor development. The Bayley-III Gross Motor Subtest was scored for Cohort A on every follow up visit starting at Day 30 through 3 years. Any subject that was 43-47 months of age, inclusive, at time of screening had the scaled score calculated compared to normative data for 42 month old children. The Bayley-III provided normative data for children 1-42 months of age.

Physical Therapy Assessments The 100 Meter Timed Test (100 m) (time frame: screening, Day 30-3 Years): The 100 m was the primary motor outcome for Cohort B. The 100 Meter Timed Test was an exploratory outcome initiated for Cohort A as soon as the child was 3 years of age.

Physical Therapy Assessments North Star Ambulatory Assessment (NSAA) (time frame: screening, Day 30-3 Years): The North Star Ambulatory Assessment (NSAA) was an exploratory outcome initiated for Cohort A as soon as the child was four years of age and for cohort B. The NSAA measures the quality of ambulation in young boys with Duchenne Muscular Dystrophy.

Physical Therapy Assessments Timed Up and Go modified for children (TUG) (time frame: screening, Day 30-3 Years): Exploratory outcomes for Cohort B included the Timed Up and Go modified for children (TUG).

Physical Therapy Assessments Ascend and Descend of 4 steps (time frame: screening, Day 30-3 Years): Exploratory outcomes for Cohort B will include ascend and descend of 4 steps.

Physical Therapy Assessments Hand Held Dynamometry (HHD) (time frame: screening, Day 30-3 Years): Exploratory outcomes for Cohort B included hand held dynamometry (HHD) for knee extensors and knee flexors, and elbow flexors and elbow extensors.

Micro-dystrophin gene expression quantification by immunofluorescence (time frame: screening, Day 90): Micro-dystrophin gene expression levels were quantified by immunofluorescence and compared in pre and post muscle biopsies.

Micro-dystrophin gene expression quantification by western blot (time frame: screening, Day 90): Micro-dystrophin gene expression levels were quantified by western blot analysis and compared in pre and post muscle biopsies.

A decrease in CK following gene therapy (time frame: 3 years): Decrease in CK levels in circulating blood.

Cardiac magnetic resonance imaging (at 1 year).

Micro-Dystrophin Gene Expression

Figure 7:
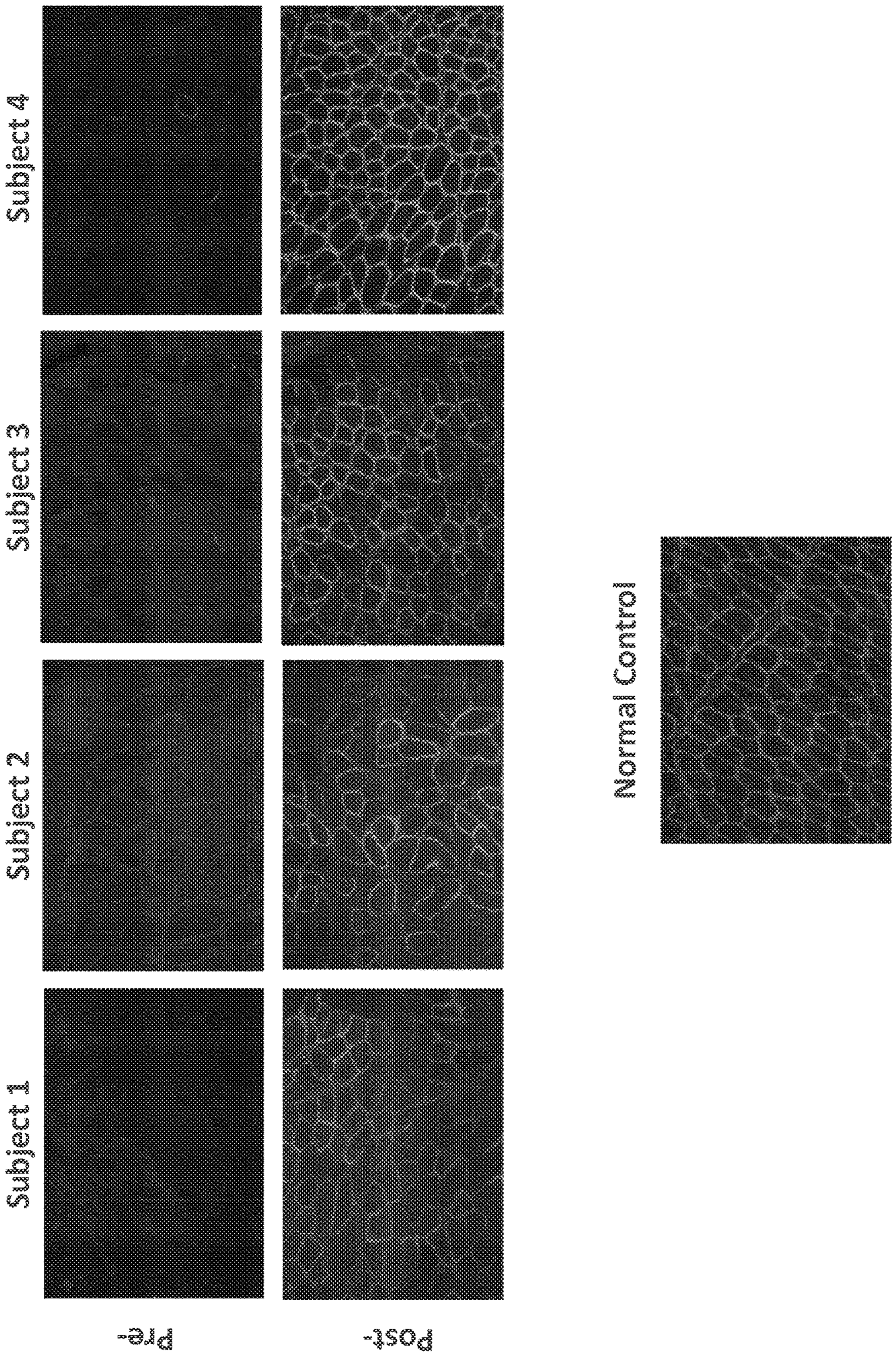
FIG. 7 demonstrates micro-dystrophin gene expression in muscle fibers of gastrocnemius muscle biopsy as measured by immunocytochemistry.

Change from Baseline in micro-dystrophin expression via immunofluorescence (IF) fiber intensity was analyzed and quantitated. As shown in FIG. 7, Subject 1 (age 5) demonstrated 78% expression, of micro-dystrophin protein in the muscle fibers of the gastrocnemius muscle biopsy after administration of the rAAVrh74.MHCK7.micro-dystrophin, Subject 2 (age 4) demonstrated 73.5% expression of micro-dystrophin protein in the muscle fibers of the gastrocnemius muscle biopsy after administration of the rAAVrh74.MHCK7.micro-dystrophin, and Subject 3 (age 6) demonstrated 77.0% expression of micro-dystrophin protein in the muscle fibers of the gastrocnemius muscle biopsy after administration of the rAAVrh74.MHCK7.micro-dystrophin. Subject 4 (age 4) demonstrated 96.2% expression of micro-dystrophin in the muscle fibers of the gastrocnemius muscle biopsy after administration of the rAAVrh74.MHCK7.micro-dystrophin. All patients showed robust expression of transduced micro-dystrophin, which is properly localized to the muscle sarcolemma, as measured by immunohistochemistry. Mean gene expression, as measured by percentage of micro-dystrophin positive fibers was 76.2% and the mean intensity of the fibers was 74.5% compared to normal control.

| Subject | Mean Intensity | Percentage of Dystrophin-Positive Fibers |
|---|---|---|
| 1 | 82.0% | 78.0% |
| 2 | 59.0% | 73.5% |
| 3 | 83.0% | 77.0% |
| 4 | 160.0% | 96.2% |
| Mean | 96.0% | 81.2% |

Figure 8A:
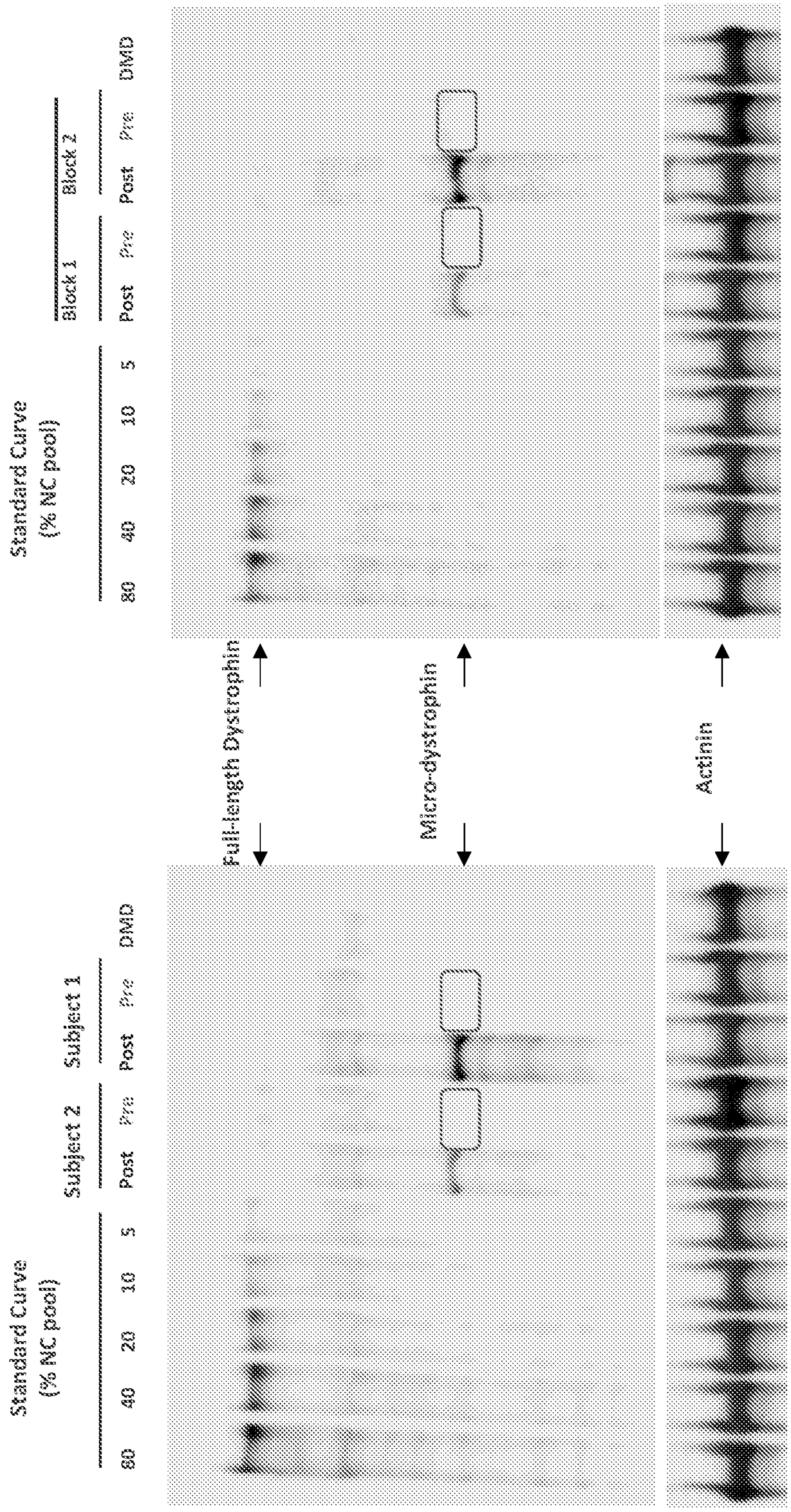
FIGS. 8A-8C provide Western blots demonstrating micro-dystrophin protein expression at the correct molecular weight.
Figure 8B:
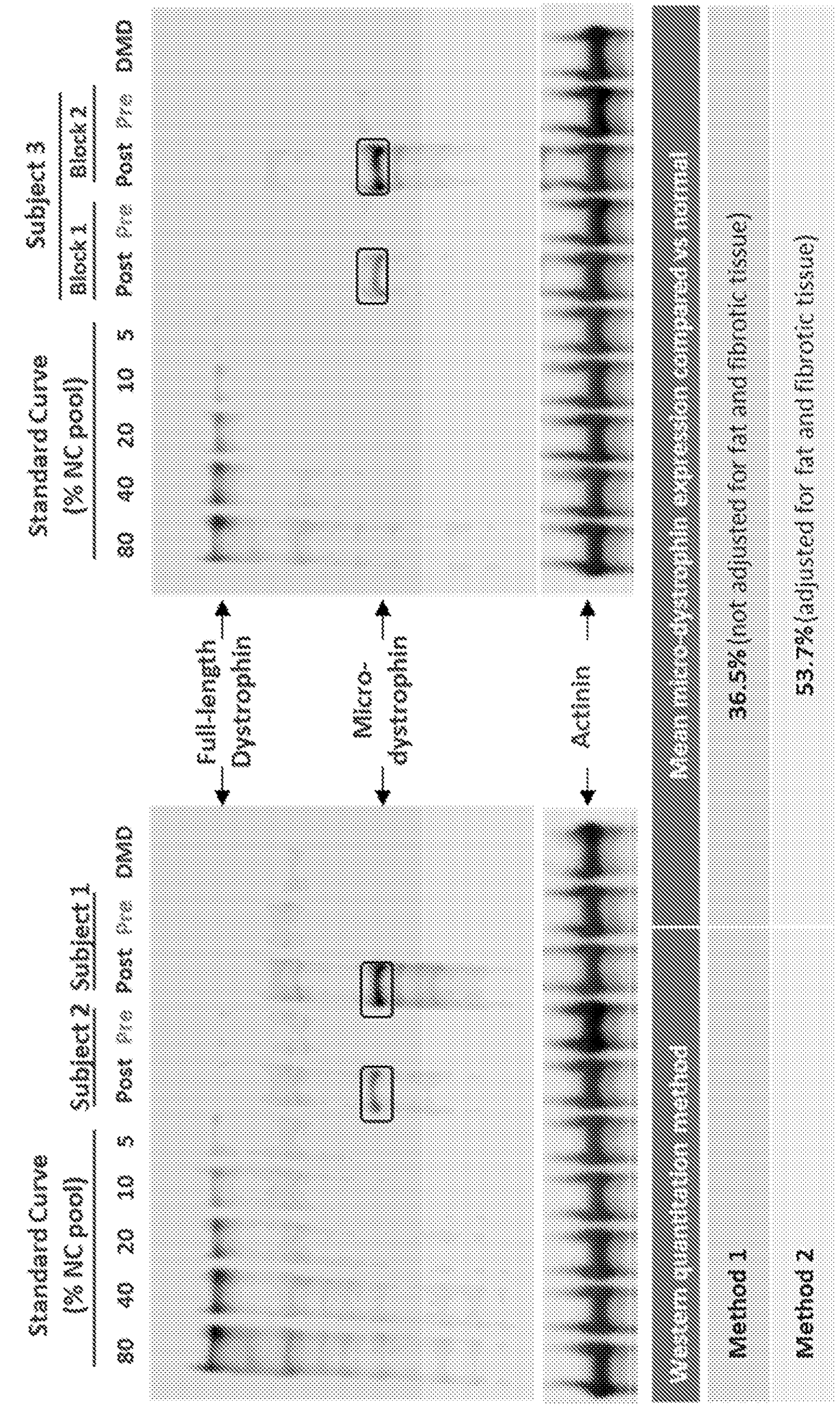
Figure 8C:
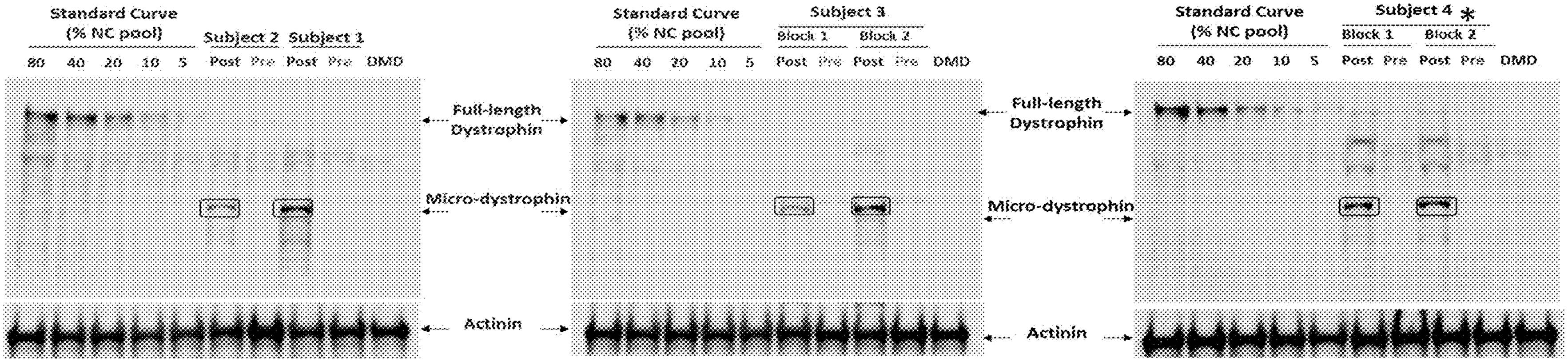

The change in micro-dystrophin gene expression from Baseline to Day 60 was also assessed by quantitating micro-dystrophin protein expression as measured by Western blot of biopsied muscle tissue. As shown in FIGS. 8A and 8B, Western blot analysis detected micro-dystrophin protein expression in Subject 1 (age 5), Subject 2 (age 4) and Subject 3 (age 6). FIG. 8C provides the Western Blot analysis detecting micro-dystrophin protein expression in Subject 4 (age 4). All post-treatment biopsies showed robust levels of micro-dystrophin as measured by Western blot, with a mean for Subjects 1-4 of 74.3 compared to normal utilizing method 1, and 95.8% compared to normal pursuant to method 2 that adjusts for fat and fibrotic tissue.

For each subject, the vector genome copy per nucleus of the muscle fibers were measured. As shown in Table 2, the vector genome copy per nuclease was greater than 1 for each of the subjects after administration of rAAVrh74.MHCK7.micro-dystrophin. One copy of the vector indicates approximately 50% expression of the micro-dystrophin gene. A mean of 1.6 vector copies per cell nucleus was measured in Subjects 1-3, consistent with the high micro-dystrophin expression levels observed. When the values for Subject 4 were included, the mean vectors copies/μg DNA is $>10^5$ with a mean of 3.3 vector copies per cell nucleus.

TABLE 2

| Subject | Vector copies/ μg DNA | Copies per Nuclei |
|---|---|---|
| 1 | $>10^5$ | 1.7 |
| 2 | $>10^5$ | 1.3 |
| 3 | $>10^5$ | 1.9 |

Figure 9A:
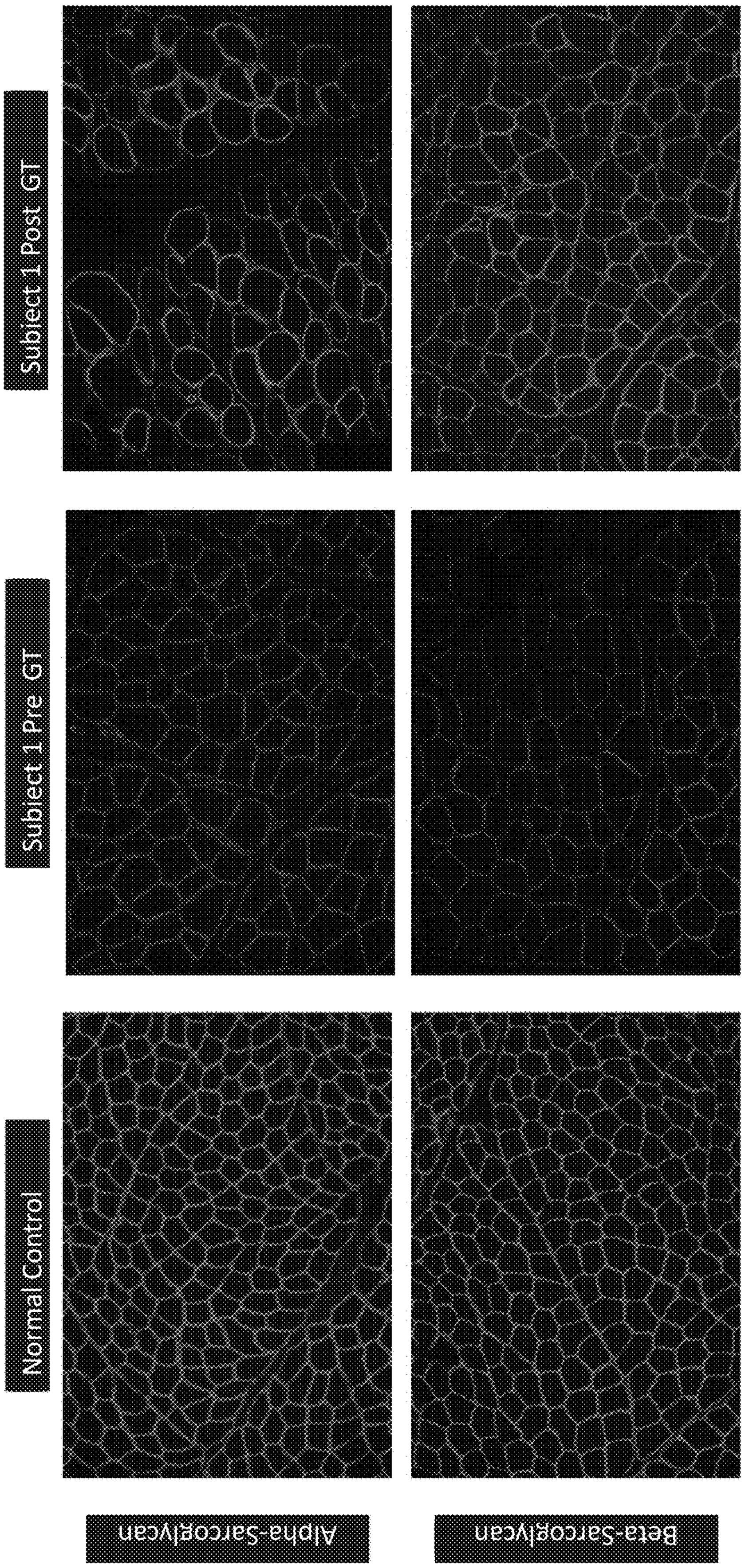
FIGS. 9A-9C demonstrates administration of rAAVrh74.MHCK7. micro-dystrophin upregulates expression of the DAPC proteins, alpha-sarcoglycan and beta-sarcoglycan.
Figure 9B:
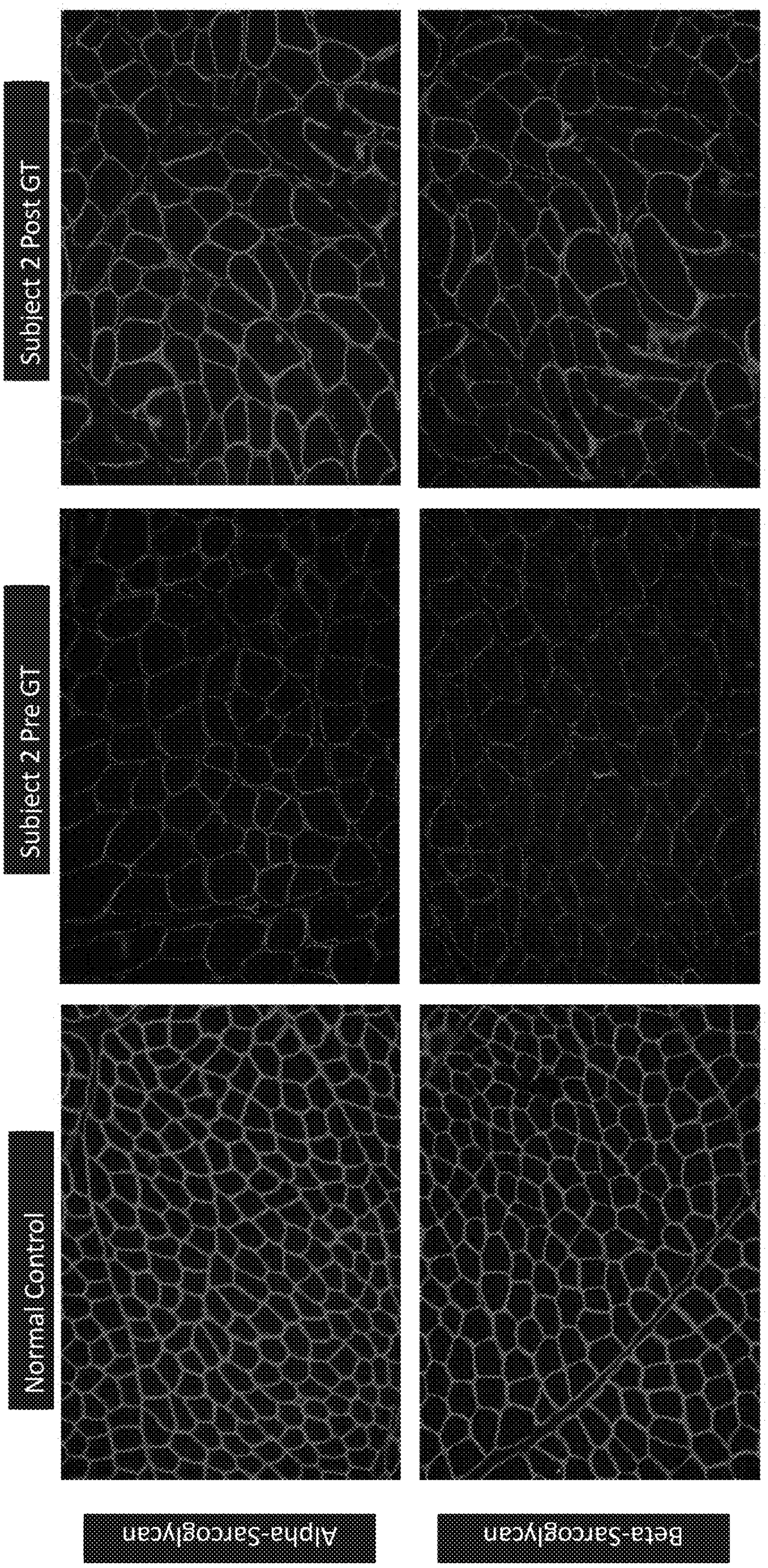
Figure 9C:
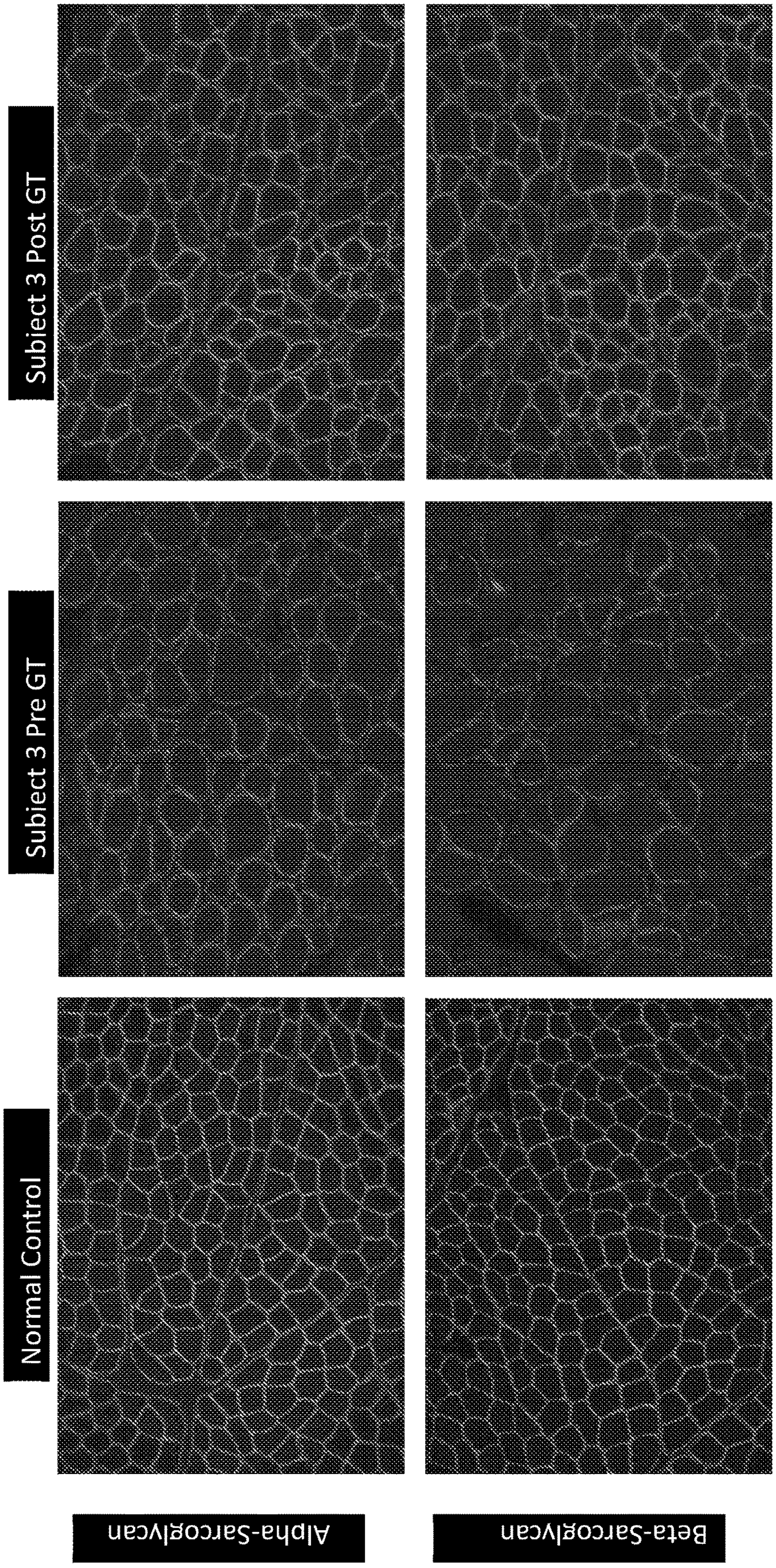

The protein levels of alpha-sarcoglycan and beta-sarcoglycan in muscle biopsy tissue were measured by immunohistochemistry before and after administration of rAAVrh74.MHCK7.micro-dystrophin. Administration of rAAVrh74.MHCK7 also resulted in upregulation of the DAPC proteins in the subjects. As shown in FIG. 9, expression of alpha-sarcoglycan and beta-sarcoglycan in muscle biopsy tissue was increased compared to the level so these proteins in muscle biopsies before administration of rAAVrh74.MHCK7 in Subjects 1 (FIG. 9A), Subject 2 (FIG. 9B) and Subject 3 (FIG. 9C).

Circulating Serum CK Levels

Figure 10:
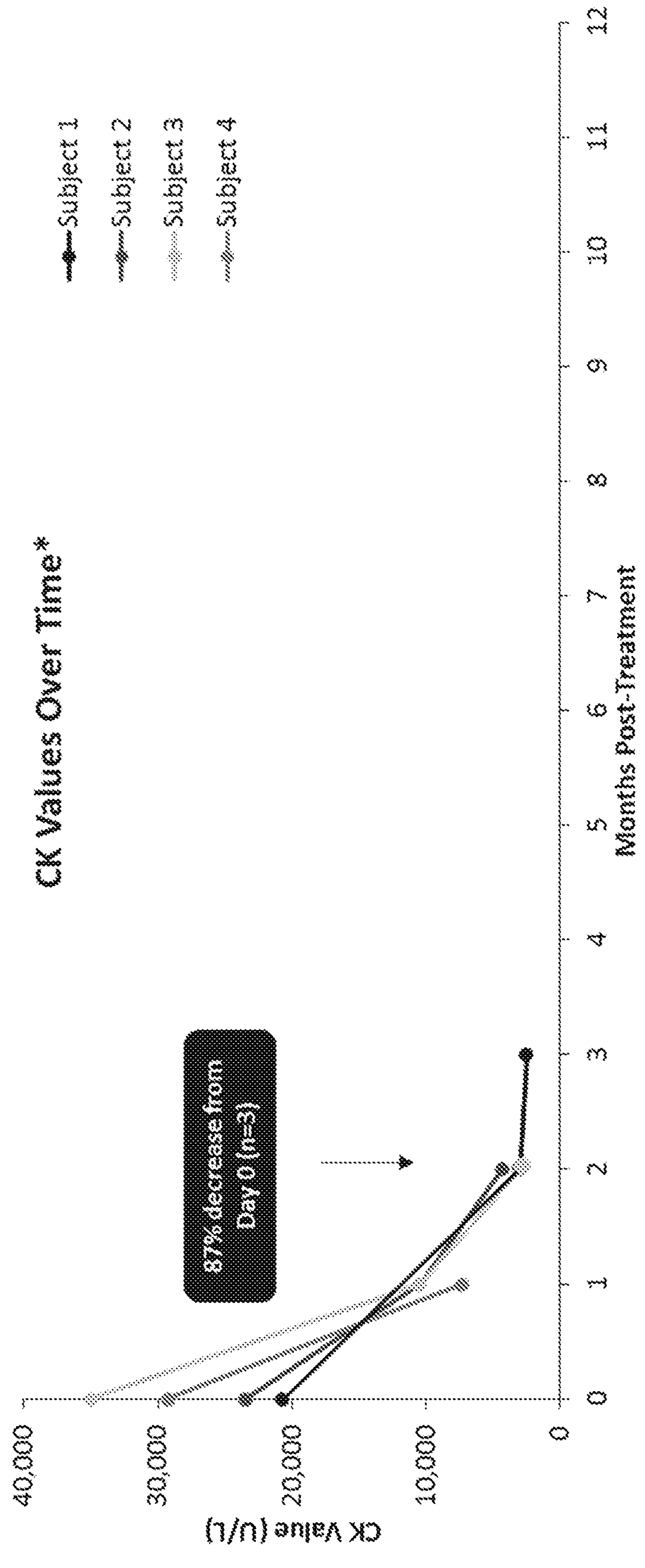
FIG. 10 demonstrates sustained dramatic reduction in Creatine Kinase (CK) with administration of rAAVrh74.MHCK7.micro-dystrophin.

Blood samples were obtained every 30 days after administration intravenous infusion of rAAVrh74.MHCK7.micro-dystrophin vector ($2\times10^{14}$ vg/kg in 10 mL/kg). CK levels were measured at each visit and compared to the baseline level obtained before administration of the rAAVrh74.MHCK7.micro-dystrophin (Visit Day 0). Baseline serum CK levels (Units/Liter) are provided in Table 3 below. As shown in FIG. 10, the level of circulating serum CK decreased about 87%, 2 months after administration of rAAVrh74.MHCK7.micro-dystrophin. All subjects showed significant decreases of serum creatine kinase (CK) levels, with a mean reduction of CK of over 87% at 2 months' post-treatment (n=3). CK is an enzyme associated with muscle damage and patients with DMD uniformly exhibit high levels of CK. Indeed, significantly elevated CK is often used as a preliminary diagnosis tool for DMD, which is then followed by confirmatory genetic testing.

Figure 11:
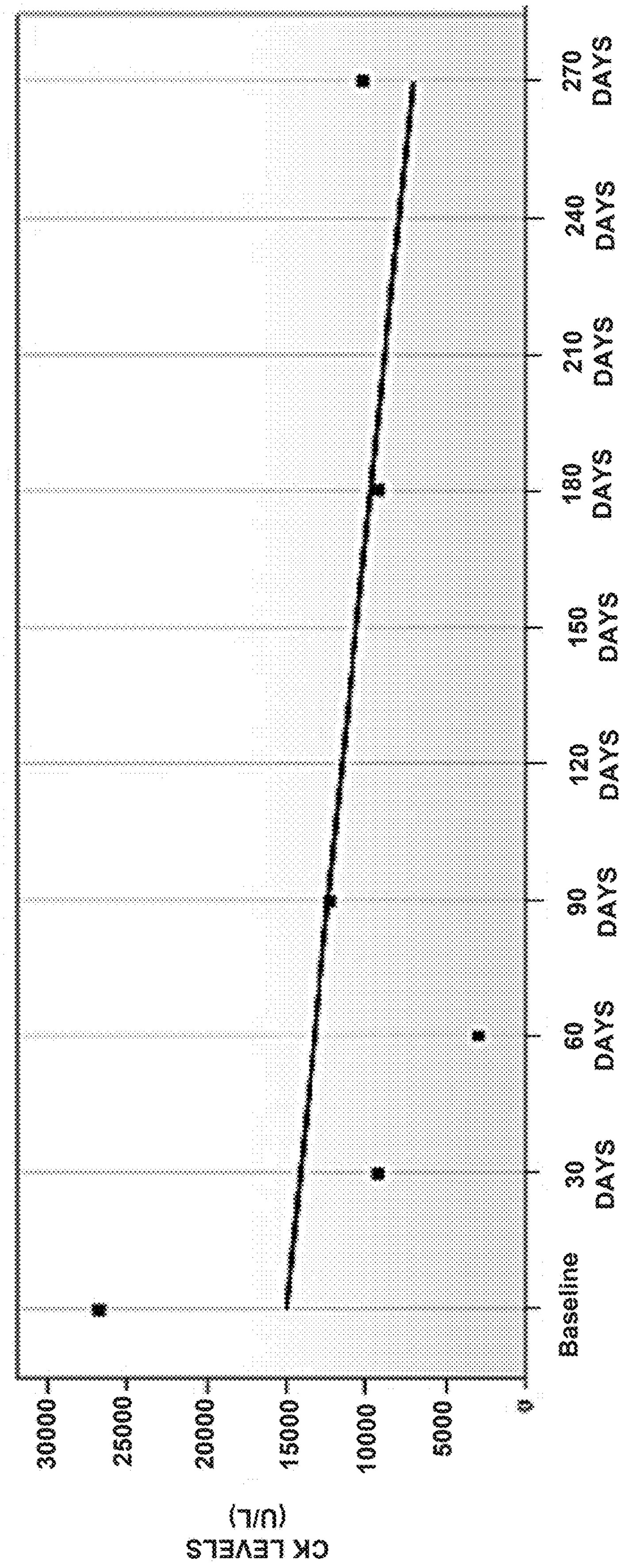
FIG. 11 provides the mean CK change from baseline to day 270. This data demonstrated that CK significantly decreases over time after administration of rAAVrh74.MHCK7.micro-dystrophin.

Table 4 and FIG. 10 provide the CK levels for each subject. FIG. 11 provides the mean CK levels over time, and demonstrates that the mean CK levels significantly decrease over time after administration of rAAVrh74.MHCK7.micro-dystrophin. The mean baseline CK level of 27,064 U/L (Mean for Table 3) is decreased by about 63% to a mean of 9,982 U/L (Mean, Day 270, Table 4).

TABLE 3

| Subject | Age (years) | CK Levels at Baseline Units/ Liter (U/L) |
|---|---|---|
| 1 | 5 | 20691 |
| 2 | 4 | 23414 |
| 3 | 6 | 34942 |
| 4 | 4 | 29210 |

TABLE 4

| Change in CK levels from Baseline to Day 270 | | | | | | | |
|---|---|---|---|---|---|---|---|
| Subject | Baseline | Day 30 | Day 60 | Day 90 | Day 180 | Day 270 | Day 360 |
| 1 | | — | 2984 | 2444 | 18476 | 6317 | — |
| 2 | 23414 | 10427 | 4283 | 41920 | 6209 | 10494 | — |
| 3 | 34942 | 10430 | 2966 | 2546 | 9650 | 18855 | 6410 |
| 4 | 29210 | 7215 | 908 | 1382 | 2580 | 4262 | — |

Efficacy Assessment

Figure 12:
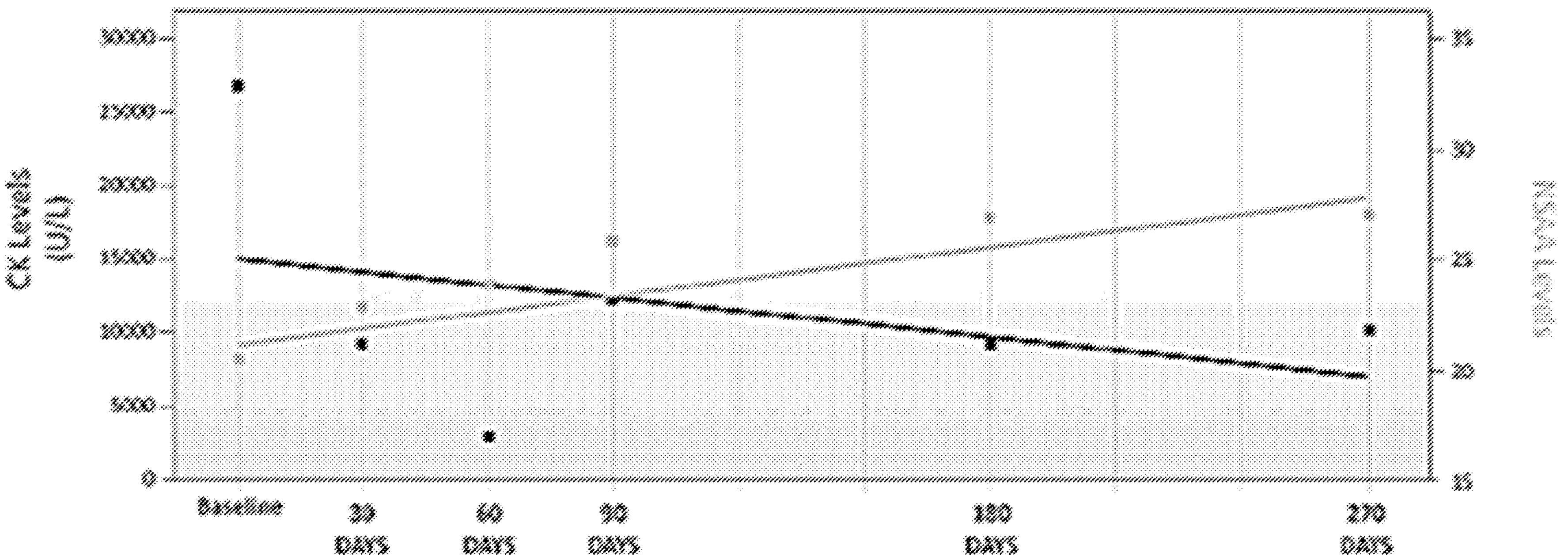
FIG. 12 provides the mean NSAA change and the mean CK change from baseline to day 270. This data demonstrated that NSAA significantly increased over time after administration of rAAVrh74.MHCK7.micro-dystrophin.

In addition to micro-dystrophin and CK levels, efficacy was measured by the following functional tests: Time to Rise from the floor, Ascend 4 steps, North Star Ambulatory Assessment (NSAA), Time to Rise Test, 4 Stairs Up Test, 10 Meter Timed Test (10 m), and 100 Meter Timed Test (100 m). The data is provided in Tables 5 and 6 below, and this data demonstrates consistent durable improvement at 9 months after administration of rAAVrh74.MHCK7.micro-dystrophin. The NSAA improvement over time is also provided in FIG. 12.

TABLE 5

| NSAA Change from Baseline to Day 270 | | | | | | | |
|---|---|---|---|---|---|---|---|
| Subject | Baseline | Day 30 | Day 60 | Day 90 | Day 180 | Day 270 | Change from Base-line |
| 1 | 18 | 22 | 24 | 23 | 25 | 26 | 8 |
| 2 | 19 | 21 | 23 | 25 | 27 | 27 | 8 |
| 3 | 26 | 28 | 28 | 30 | 30 | 28 | 2 |
| 4 | 19 | 20 | 20 | 25 | 25 | 27 | 8 |
| Mean Improve-ment | 20.5 | 22.75 | 23.75 | 25.75 | 26.75 | 27 | 6.5 |

TABLE 6

| Change from Baseline to Day 270 | | | | | | |
|---|---|---|---|---|---|---|
| Subject | Assessment | NSAA | Time to Rise | 4 Stairs Up | 100 m (sec) | 10 m |
| 1 | Baseline | 18 | 3.7 | 3.4 | 49.3 | 5.1 |
| | Day 270 | 26 | 3.0 | 2.3 | 43.2 | 4.3 |
| 2 | Baseline | 19 | 3.0 | 3.8 | 49.9 | 4.3 |
| | Day 180 | 27 | 3.7 | 2.6 | 48.6 | 3.9 |
| | Day 270 | 27 | 3.3 | 2.7 | 50.3 | |
| 3 | Baseline | 26 | 3.9 | 1.9 | 59.3 | 4.7 |
| | Day 180 | 30 | 3.4 | 1.8 | 48.4 | 4.1 |
| | Day 270 | 28 | 2.8 | 1.9 | 50.7 | |
| 4 | Baseline | 19 | 4.1 | 4.8 | 67.2 | 5.4 |
| | Day 90 | 25 | 2.3 | 2.2 | 50.7 | 4.4 |
| | Day 270 | 27 | 2.4 | 2.2 | 49.7 | |
| Average | Change from Baseline | 6.5 point improve-ment | .8 sec. improve-ment | 1.2 sec. improve-ment | 7.95 sec. improve-ment | 14% improve-ment |

Safety Assessment

No serious adverse events (SAEs) were observed in the study. Three subjects had elevated gamma-glutamyl transferase (GGT) that resolved with increased steroids within a week and returned to baseline levels. There were no other clinically significant laboratory findings. Patients had transient nausea generally during the first week of therapy coincident with increased steroid dosing. This did not correlate with liver enzyme elevations or any other abnormality.

Example 3

Randomized Double-Blind Placebo Controlled Systemic Gene Delivery Phase I/IIa Clinical Trial This is a randomized double-blind single-dose trial using rAAVrh74.MHCK7.micro-dystrophin for DMD subjects. The study includes twenty-four subjects ages 4 to 7 years old. Subjects are randomized to treatment or placebo at the time of enrollment. Twelve subjects receive intravenous rAAVrh74.MHCK7.micro-dystrophin vector ($2\times10^{14}$ vg/kg in approximately 10 mL/kg) and twelve subjects will receive 10 mL/kg placebo (lactated ringers). Placebo subjects will roll over to treatment which will be given in the same manner as the 12 previously treated subjects one year after the last treated subject is dosed. Subjects receive infusions of rAAV carrying micro-dystrophin or lactated ringers over approximately 1 hour. Pre and post-treatment (90 Day) needle muscle biopsies are done on gastrocnemius muscles.

The primary objective of this study is the assessment of the safety of intravenous administration of rAAVrh74.MHCK7.micro-dystrophin for DMD subjects via peripheral limb vein. Safety endpoints are assessed by changes in hematology, serum chemistry, urinalysis, immunologic response to rAAVrh74 and micro-dystrophin, and reported history and observations of symptoms. Dystrophin gene expression serves as a primary outcome measure along with safety. Quantification is carried out using validated immunofluorescence and immunoblot assays. A decrease in CK following gene therapy serves as a secondary outcome. Efficacy is measured by the following functional tests: Time to Rise, Ascend 4 steps, North Star Ambulatory Assessment (NSAA), 10 Meter Timed Test (10 m), 100 Meter Timed Test (100 m). Exploratory measures include hand-held dynamometry (HHD) for knee extensors and knee flexors, and elbow flexors and elbow extensors.

Inclusion criteria for the study are as follows:

Age of enrollment: between 4-7 years of age, inclusive.

Molecular characterization of the DMD gene with frameshift (deletion or duplication), or premature stop codon mutation between exons 18 to 58.

Indication of symptomatic muscular dystrophy: CK elevation>1000 U/L and Below mean percent predicted time on 100 meter walk test.

Males of any ethnic group will be eligible.

Ability to cooperate with motor assessment testing.

Stable dose equivalent of oral corticosteroids for at least 12 weeks prior to screening and the dose is expected to remain constant (except for potential modifications to accommodate changes in weight) throughout the study.

Exclusion criteria for the study are as follows:

Active viral infection based on clinical observations.

Signs of cardiomyopathy, including echocardiogram with ejection fraction below 40%.

Serological evidence of HIV infection, or Hepatitis B or C infection.

Diagnosis of (or ongoing treatment for) an autoimmune disease.

Abnormal laboratory values considered clinically significant (GGT>3XULN, bilirubin≥3.0 mg/dL, creatinine≥1.8 mg/dL, Hgb<8 or >18 g/Dl; WBC>18,500 per cmm), platelets≤50,000.

Concomitant illness or requirement for chronic drug treatment that in the opinion of the PI creates unnecessary risks for gene transfer.

Subjects with AAVrh74 or AAV8 antibody titers>1:400 as determined by ELISA immunoassay. If endpoint titer is positive at screening, testing may be repeated prior to exclusion.

Has a medical condition or extenuating circumstance that, in the opinion of the investigator, might compromise the subject's ability to comply with the protocol required testing or procedures or compromise the subject's wellbeing, safety, or clinical interpretability.

Severe infection (e.g., pneumonia, pyelonephritis, or meningitis) within 4 weeks before gene transfer visit (enrollment may be postponed).

Has received any investigational medication (other than corticosteroids) or exon skipping medications (including ExonDys 51®), experimental or otherwise, in the last 6 months prior to screening for this study.

Has had any type of gene therapy, cell based therapy (e.g. stem cell transplantation), or CRISPR/Cas9 therapy.

Family does not want to disclose patient's study participation with primary care physician and other medical providers.

Efficacy Assessments

Dystrophin gene expression serves as a primary outcome measure along with safety. Quantification is carried out using validated immunofluorescence and immunoblot assays. A decrease in CK following gene therapy serves as a secondary outcome. In addition, efficacy is measured by the following functional tests: Time to Rise from the floor, Ascend 4 steps, North Star Ambulatory Assessment (NSAA), 10 Meter Timed Test (10 m), 100 Meter Timed Test (100 m)]. Exploratory measures include hand-held dynamometry (HHD) for knee extensors and knee flexors, and elbow flexors and elbow extensors.

Muscle biopsies with ultrasound guidance are used to quantify transgene expression comparing baseline to Day 90. The biopsies are carried out on the same muscle as the original biopsies but on the opposite leg. One year after all subjects have been dosed, placebo crossover subjects will restart the study timeline at visit 1. Placebo subjects will not have the following performed at the second baseline screening: Cardiac MRI and Muscle Biopsy. Placebo subjects undergo a muscle biopsy at Day 90 (total of 3 muscle biopsies). Frozen sections are stained for dystrophin using indirect immunofluorescence (IF). Full slide scanning is performed and micro-dystrophin intensity and percent positive fibers is quantified using validated image scanning and MuscleMap™ analysis algorithm. Muscle morphometrics are performed blinded including fiber size histograms. Blinded frozen muscle biopsy shavings are used to perform quantitative protein analysis for micro-dystrophin using a validated western blot method.

Muscle needle biopsies of the gastrocnemius muscle (unless deemed contraindicated in a specific subject by the PI, in which case the PI will select an alternative muscle to biopsy) are used to quantify micro-dystrophin expression.

Efficacy Analyses

The primary efficacy endpoint is the change from Baseline to Day 90 in the quantity of micro-dystrophin protein expression as measured by Western blot of biopsied muscle tissue. Treatment group differences for the primary efficacy endpoint are assessed with an analysis of covariance (ANCOVA) model with treatment as the fixed factor and baseline value as the covariate. The Wilcoxon rank-sum test is performed as a supportive analysis. Change from Baseline in micro-dystrophin expression via immunofluorescence (IF) fiber intensity is analyzed similarly.

The supportive efficacy endpoints include change from Baseline to each scheduled assessment of Time to Rise from the floor, Ascend 4 steps, NSAA, Meter Timed Test (10 m), 100 Meter Timed Test (100 m), and change in CK. Exploratory measures include HHD for knee extensors and knee flexors, and elbow flexors and elbow extensors. Treatment group differences are assessed with ANCOVA model with treatment as the fixed factor and baseline value as the covariate. The Wilcoxon rank-sum test is performed as a supportive analysis.

Example 4

The trials and studies described in Examples 2 and 3 above are alternatively carried out utilizing the rAAVrh74.MHCK7.micro-dystrophin construct set forth in SEQ ID NO: 9; as set forth in SEQ ID NO: 8, nucleotides 1-4977; or as set forth in SEQ ID NO: 6; nucleotides 56-5022.

Example 5

Generation of the pAAV.MCK.Micro-Dystrophin Construct

The pAAV.MCK.micro-dystrophin plasmid was constructed by inserting the MCK expression cassette driving a codon optimized human micro-dystrophin cDNA sequence into the AAV cloning vector psub201 (Samulski et al., *J. Virol.* 61 (10): 3096-3101). A muscle-specific regulatory element was included in the construct to drive muscle-specific gene expression. This regulatory element comprised the mouse MCK core enhancer (206 bp) fused to the 351 bp MCK core promoter (proximal). After the core promoter, the construct comprises the 53 bp endogenous mouse MCK Exon1 (untranslated) for efficient transcription initiation, followed by the SV40 late 16S/19S splice signals (97 bp) and a small 5'UTR (61 bp). The intron and 5' UTR was derived from plasmid pCMVß (Clontech). The micro-dystrophin cassette has a consensus Kozak immediately in front of the ATG start and a small 53 bp synthetic polyA signal for mRNA termination. The human micro-dystrophin cassette contains the (R4-R23/Δ71-78) domains as previously described by Harper et al. *Nat. Med.* 8 (3): 253-61, 2002

Figure 5:
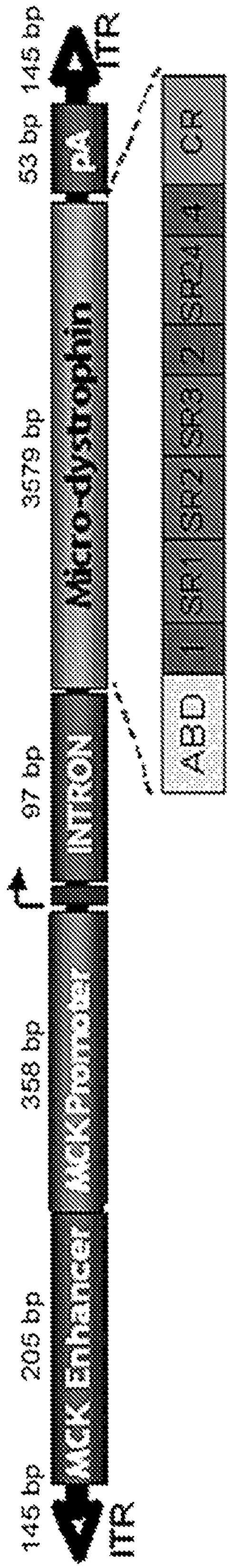
FIG. 5 illustrates the rAAV.MCK.micro-dystrophin plasmid construct.

The pAAV.MCK.micro-dystrophin plasmid contained the human micro-dystrophin cDNA expression cassette flanked by AAV2 inverted terminal repeat sequences (ITR) (see FIG. 5). This sequence was encapsidated into AAVrh.74 virions. The molecular clone of the AAVrh.74 serotype was cloned from a rhesus macaque lymph node and is described in Rodino-Klapac et al. *Journal of Tran. Med.* 45 (2007).

REFERENCES

1. Hoffman, E. P., Brown, R. H., Jr. & Kunkel, L. M. Dystrophin: the protein product of the Duchenne muscular dystrophy locus. *Cell* 51, 919-928 (1987).
2. Straub, V. & Campbell, K. P. Muscular dystrophies and the dystrophin-glycoprotein complex. *Curr Opin Neurol* 10, 168-175 (1997).
3. Sacco, A., et al. Short telomeres and stem cell exhaustion model Duchenne muscular dystrophy in mdx/mTR mice. *Cell* 143, 1059-1071 (2010).
4. Wallace, G. Q. & McNally, E. M. Mechanisms of muscle degeneration, regeneration, and repair in the muscular dystrophies. *Annu Rev Physiol* 71, 37-57 (2009).
5. Zhou, L. & Lu, H. Targeting fibrosis in Duchenne muscular dystrophy. *J Neuropathol Exp Neurol* 69, 771-776 (2010).
6. Desguerre, I., et al. Endomysial fibrosis in Duchenne muscular dystrophy: a marker of poor outcome associated with macrophage alternative activation. *J Neuropathol Exp Neurol* 68, 762-773 (2009).

7. DiPrimio, N., McPhee, S. W. & Samulski, R. J. Adeno-associated virus for the treatment of muscle diseases: toward clinical trials. *Curr Opin Mol Ther* 12, 553-560 (2010).
8. Mendell, J. R., et al. Sustained alpha-sarcoglycan gene expression after gene transfer in limb-girdle muscular dystrophy, type 2D. *Ann Neurol* 68, 629-638 (2010).
9. Mendell, J. R., et al. Limb-girdle muscular dystrophy type 2D gene therapy restores alpha-sarcoglycan and associated proteins. *Ann Neurol* 66, 290-297 (2009).
10. Mendell, J. R., et al. A phase 1/2a follistatin gene therapy trial for becker muscular dystrophy. *Molecular therapy: the journal of the American Society of Gene Therapy* 23, 192-201 (2015).
11. Carnwath, J. W. & Shotton, D. M. Muscular dystrophy in the mdx mouse: histopathology of the soleus and extensor digitorum longus muscles. *J Neurol Sci* 80, 39-54 (1987).
12. Coulton, G. R., Morgan, J. E., Partridge, T. A. & Sloper, J. C. The mdx mouse skeletal muscle myopathy: I. A histological, morphometric and biochemical investigation. *Neuropathol Appl Neurobiol* 14, 53-70 (1988).
13. Cullen, M. J. & Jaros, E. Ultrastructure of the skeletal muscle in the X chromosome-linked dystrophic (mdx) mouse. Comparison with Duchenne muscular dystrophy. *Acta Neuropathol* 77, 69-81 (1988).
14. Dupont-Versteegden, E. E. & McCarter, R. J. Differential expression of muscular dystrophy in diaphragm versus hindlimb muscles of mdx mice. *Muscle Nerve* 15, 1105-1110 (1992).
15. Stedman, H. H., et al. The mdx mouse diaphragm reproduces the degenerative changes of Duchenne muscular dystrophy. *Nature* 352, 536-539 (1991).
16. Deconinck, A. E., et al. Utrophin-dystrophin-deficient mice as a model for Duchenne muscular dystrophy. *Cell* 90, 717-727 (1997).
17. Grady, R. M., et al. Skeletal and cardiac myopathies in mice lacking utrophin and dystrophin: a model for Duchenne muscular dystrophy. *Cell* 90, 729-738 (1997).
18. Love, D. R., et al. An autosomal transcript in skeletal muscle with homology to dystrophin. *Nature* 339, 55-58 (1989).
19. Tinsley, J. M., et al. Primary structure of dystrophin-related protein. *Nature* 360, 591-593 (1992).
20. Tinsley, J., et al. Expression of full-length utrophin prevents muscular dystrophy in mdx mice. *Nat Med* 4, 1441-1444 (1998).
21. Squire, S., et al. Prevention of pathology in mdx mice by expression of utrophin: analysis using an inducible transgenic expression system. *Hum Mol Genet* 11, 3333-3344 (2002).
22. Rafael, J. A., Tinsley, J. M., Potter, A. C., Deconinck, A. E. & Davies, K. E. Skeletal muscle-specific expression of a utrophin transgene rescues utrophin-dystrophin deficient mice. *Nat Genet* 19, 79-82 (1998).
23. Zhou, L., et al. Haploinsufficiency of utrophin gene worsens skeletal muscle inflammation and fibrosis in mdx mice. *J Neurol Sci* 264, 106-111 (2008).
24. Gutpell, K. M., Hrinivich, W. T. & Hoffman, L. M. Skeletal Muscle Fibrosis in the mdx/utrn+/−Mouse Validates Its Suitability as a Murine Model of Duchenne Muscular Dystrophy. *PloS one* 10, e0117306 (2015).
25. Rodino-Klapac, L. R., et al. Micro-dystrophin and follistatin co-delivery restores muscle function in aged DMD model. *Human molecular genetics* 22, 4929-4937 (2013).
26. Nevo, Y., et al. The Ras antagonist, farnesylthiosalicylic acid (FTS), decreases fibrosis and improves muscle strength in dy/dy mouse model of muscular dystrophy. *PloS one* 6, e18049 (2011).
27. Rodino-Klapac, L. R., et al. A translational approach for limb vascular delivery of the micro-dystrophin gene without high volume or high pressure for treatment of Duchenne muscular dystrophy. *J Transl Med* 5, 45 (2007).
28. Mulieri, L. A., Hasenfuss, G., Ittleman, F., Blanchard, E. M. & Alpert, N. R. Protection of human left ventricular myocardium from cutting injury with 2,3-butanedione monoxime. *Circ Res* 65, 1441-1449 (1989).
29. Rodino-Klapac, L. R., et al. Persistent expression of FLAG-tagged micro dystrophin in nonhuman primates following intramuscular and vascular delivery. *Molecular therapy: the journal of the American Society of Gene Therapy* 18, 109-117 (2010).
30. Grose, W. E., et al. Homologous recombination mediates functional recovery of dysferlin deficiency following AAV5 gene transfer. *PloS one* 7, e39233 (2012).
31. Liu, M., et al. Adeno-associated virus-mediated micro-dystrophin expression protects young mdx muscle from contraction-induced injury. *Mol Ther* 11, 245-256 (2005).
32. Harper, S. Q., et al. Modular flexibility of dystrophin: implications for gene therapy of Duchenne muscular dystrophy. *Nature medicine* 8, 253-261 (2002).
33. Rodino-Klapac, L. R., et al. Persistent expression of FLAG-tagged micro dystrophin in nonhuman primates following intramuscular and vascular delivery. *Mol Ther* 18, 109-117 (2010).
34. Salva, M. Z., et al. Design of tissue-specific regulatory cassettes for high-level rAAV-mediated expression in skeletal and cardiac muscle. *Mol Ther* 15, 320-329 (2007).
35. Sondergaard, P. C., et al. AAV.Dysferlin Overlap Vectors Restore Function in Dysferlinopathy Animal Models. *Annals of clinical and translational neurology* 2, 256-270 (2015).
36. De, B. P., et al. High levels of persistent expression of alpha1-antitrypsin mediated by the nonhuman primate serotype rh.10 adeno-associated virus despite preexisting immunity to common human adeno-associated viruses. *Mol Ther* 13, 67-76 (2006).
37. Rodino-Klapac, L. R., et al. A translational approach for limb vascular delivery of the micro-dystrophin gene without high volume or high pressure for treatment of Duchenne muscular dystrophy. *Journal of translational medicine* 5, 45 (2007).
38. Bulfield et al., X chromosome-linked muscular dystrophy (mdx) in the mouse. *Proc Natl Acad Sci USA.* 1984; 81 (4): 1189-1192.
39. Sicinski et al., The molecular basis of muscular dystrophy in the mdx mouse: a point mutation. *Science.* 1989 30; 244 (4912): 1578-80

What is claimed:

1. A method of treating Duchenne muscular dystrophy in a human subject in need thereof comprising the step of administering a recombinant adeno-virus associated (rAAV) serotype rh.74 comprising a polynucleotide comprising the nucleotide sequence of SEQ ID NO: 1 operably linked to a promoter sequence of SEQ ID NO: 7, wherein the rAAV is administered intravenously at a dose of $5.0\times10^{12}$ vg/kg to $1.0\times10^{15}$ vg/kg.

2. The method of claim 1, wherein the dose of the rAAV administered is $2\times10^{14}$ vg/kg.

3. The method of claim 1, wherein the dose of rAAV is administered in about 10 mL/kg.

4. The method of claim 1, wherein the rAAV is administered by infusion over approximately one hour.

5. The method of claim 1, wherein the rAAV comprises a polynucleotide comprising the nucleotide sequence of SEQ ID NO: 9.

6. The method of claim 1, wherein the dose of rAAV is $2\times10^{14}$ vg/kg administered by intravenous infusion over approximately one hour, and wherein the rAAV comprises a polynucleotide comprising the nucleotide sequence of SEQ ID NO: 9.

7. The method of claim 1, wherein the level of micro-dystrophin gene expression in a muscle cell of the subject is increased after administration of the rAAV as compared to the level of micro-dystrophin gene expression before administration of the rAAV.

8. The method of claim 1, wherein the serum CK level in the subject is decreased after administration of the rAAV as compared to serum CK level before administration of the rAAV.

9. The method of claim 1, wherein the number of micro-dystrophin positive fibers in the muscle tissue of the subject is increased after administration of the rAAV as compared to the number of micro-dystrophin positive fibers before administration of the rAAV.

10. The method of claim 1, wherein the level of muscle alpha-sarcoglycan in the subject is increased after administration of the rAAV as compared to the level of muscle alpha-sarcoglycan before administration of the rAAV.

11. The method of claim 1, wherein the level of muscle beta-sarcoglycan in the subject is increased after administration of the rAAV as compared to the level of the muscle beta-sarcoglycan before administration of the rAAV.

12. The method of claim 1, wherein disease progression in the subject is delayed after administration of the rAAV as measured by any of: the six minute walk test, time to rise, ascend 4 steps, ascend and descend 4 steps, North Star Ambulatory Assessment (NSAA), 10 meter timed test, 100 meter timed test, hand held dynamometry (HHD), Timed Up and Go, and/or Gross Motor Subtest Scaled (Bayley-III) score.

13. The method of claim 2, wherein the dose of the rAAV is determined by utilizing a super-coiled DNA standard.

14. The method of claim 6, wherein the dose of the rAAV is determined by utilizing a super-coiled DNA standard.

* * * * *

SEQUENCE LISTING

<160> NUMBER OF SEQ ID NOS: 9

<210> SEQ ID NO 1
<211> LENGTH: 3579
<212> TYPE: DNA
<213> ORGANISM: Homo sapiens

<400> SEQUENCE: 1

```
atgctgtggt gggaggaggt ggaggattgt tatgaaaggg aggacgtgca gaagaagact     60
tttaccaagt gggtgaacgc tcagttcagc aaatttggga agcagcacat cgagaatctg    120
ttttccgacc tgcaggatgg gagacggctg ctggatctgc tggaaggact gactggccag    180
aagctgccca aagagaaggg gagcactagg gtgcacgccc tgaacaacgt gaacaaagct    240
ctgagagtgc tgcagaacaa caacgtggat ctggtgaata ttggcagtac tgatatcgtg    300
gacgggaacc acaaactgac actgggcctg atctggaaca ttattctgca ctggcaggtg    360
aaaaatgtga tgaagaacat catggccggg ctgcagcaga ccaattccga gaagatcctg    420
ctgtcttggg tgcggcagag cacccgcaac tatccccagg tgaacgtgat taacttcact    480
acatcctgga gcgacgggct ggccctgaat gctctgattc acagccacag gcctgatctg    540
ttcgactgga atagcgtggt gtgccagcag tctgccacac agcgcctgga acatgccttc    600
aatatcgctc ggtaccagct ggggatcgaa aaactgctgg acccagagga tgtggacact    660
acatacccag ataaaaagtc tattctgatg tacattacta gcctgttcca ggtgctgcca    720
cagcaggtgt ctattgaagc cattcaggag gtggaaatgc tgccccgccc ccccaaagtg    780
actaaagagg agcattttca gctgcatcat cagatgcatt acagccagca gattaccgtg    840
agcctggctc agggatatga gcgcaccagt agtccaaaac cacggttcaa gtcctacgct    900
tatacccagg ctgcctacgt gacaactagc gaccctacta gatcccccctt tccatcccag    960
cacctggagg ccccagagga caagagcttt gggtccagcc tgatggaaag cgaggtgaat   1020
ctggatcggt accagacagc cctggaggag gtgctgagct ggctgctgag tgctgaagac   1080
acactgcagg cccagggcga aatttccaat gacgtggaag tggtgaagga tcagttccac   1140
acacacgagg gctatatgat ggacctgaca gctcaccagg ggcgcgtggg caatatcctg   1200
cagctgggct ctaaactgat cggcaccggg aaactgagtg aggacgagga aacagaagtg   1260
caggagcaga tgaacctgct gaacagccgc tgggagtgtc tgagagtggc tagtatggag   1320
aagcagtcca acctgcaccg ggtgctgatg gacctgcaga accagaaact gaaagagctg   1380
aacgactggc tgacaaagac tgaggaacgc acaaggaaga tggaggagga gccactggga   1440
cccgacctgg aggatctgaa gagacaggtg cagcagcata aggtgctgca ggaggatctg   1500
gaacaggagc aggtgcgggt gaactccctg acacatatgg tggtggtggt ggacgaatct   1560
agtggagatc acgccaccgc cgccctggag gaacagctga aggtgctggg ggaccggtgg   1620
gccaacattt gccggtggac cgaggacagg tgggtgctgc tgcaggacat cctgctgaaa   1680
tggcagaggc tgaccgagga gcagtgtctg tttagtgctt ggctgagcga gaaagaggac   1740
gccgtgaaca agatccacac aaccggcttt aaggatcaga acgaaatgct gtctagcctg   1800
cagaaactgg ctgtgctgaa ggccgatctg gagaaaaaga agcagagcat gggcaaactg   1860
tatagcctga aacaggacct gctgagcacc ctgaagaaca agagcgtgac ccagaagaca   1920
gaagcctggc tggataactt tgcccgctgc tgggacaacc tggtgcagaa actggagaaa   1980
agtacagctc agatctctca ggctgtgacc acaacccagc ctagcctgac ccagacaacc   2040
gtgatggaaa ccgtgaccac cgtgacaacc cgcgaacaga tcctggtgaa acatgcccag   2100
```

gaagagctgc cacctccacc tccccagaag aagagaaccc tggagcggct gcaggagctg 2160
caggaagcca ctgacgaact ggacctgaag ctgaggcagg ccgaagtgat taaggggtct 2220
tggcagcctg tgggcgatct gctgattgat tccctgcagg accacctgga aaaggtgaag 2280
gctctgagag gcgaaattgc tccactgaag gagaacgtga gtcatgtgaa cgatctggct 2340
agacagctga caacactggg catccagctg agcccataca atctgagcac actggaggac 2400
ctgaatacca ggtggaagct gctgcaggtg gctgtggaag accgggtgcg gcagctgcat 2460
gaggcccatc gcgacttcgg accagccagc cagcactttc tgagcacatc cgtgcagggg 2520
ccctgggaga gggccatttc tcccaacaag gtgccctact atattaatca cgagacccag 2580
accacttgtt gggaccatcc caagatgaca gaactgtacc agtccctggc cgatctgaac 2640
aacgtgaggt ttagcgctta cagaaccgct atgaagctga gacggctgca gaaggccctg 2700
tgcctggatc tgctgtccct gtccgccgcc tgcgatgccc tggatcagca taatctgaag 2760
cagaacgatc agccaatgga tatcctgcag atcatcaact gcctgaccac tatctacgac 2820
aggctggagc aggagcacaa caacctggtg aacgtgcctc tgtgcgtgga tatgtgcctg 2880
aactggctgc tgaacgtgta tgacactggg cgcaccggcc ggatcagagt gctgagtttt 2940
aaaactggga ttatctccct gtgtaaggcc cacctggagg acaagtacag gtacctgttc 3000
aagcaggtgg ctagtagcac tggattttgt gaccagcgcc gcctgggact gctgctgcat 3060
gatagtatcc agattcctag acagctggga gaggtggcta gtttcggagg atctaacatc 3120
gaacccagcg tgcgcagctg tttccagttt gccaataaca aacctgaaat cgaggctgct 3180
ctgttcctgg attggatgcg cctggaacca cagagcatgg tgtggctgcc tgtgctgcac 3240
agagtggctg ccgccgaaac tgccaagcac caggctaaat gcaacatctg caaggaatgt 3300
cccattatcg gctttcgcta caggagtctg aaacatttta actacgatat ttgccagagc 3360
tgcttctttt ccggaagagt ggccaaagga cacaagatgc actaccctat ggtggaatat 3420
tgcaccccaa ctacatctgg cgaagatgtg cgcgattttg ccaaggtgct gaagaataag 3480
tttcggacta agaggtactt cgccaagcac ccccgcatgg ggtatctgcc agtgcagaca 3540
gtgctggaag gagacaatat ggagaccgat acaatgtga 3579

<210> SEQ ID NO 2
<211> LENGTH: 810
<212> TYPE: DNA
<213> ORGANISM: Artificial Sequence
<220> FEATURE:
<223> OTHER INFORMATION: Synthetic Promoter

<400> SEQUENCE: 2
gtttaaacaa gcttgcatgt ctaagctaga cccttcagat taaaaataac tgaggtaagg 60
gcctgggtag gggaggtggt gtgagacgct cctgtctctc ctctatctgc ccatcggccc 120
tttggggagg aggaatgtgc ccaaggacta aaaaaaggcc atggagccag aggggcgagg 180
gcaacagacc tttcatgggc aaaccttggg gccctgctgt ctagcatgcc ccactacggg 240
tctaggctgc ccatgtaagg aggcaaggcc tggggacacc cgagatgcct ggttataatt 300
aacccagaca tgtggctgcc cccccccccc caacacctgc tgcctctaaa aataaccctg 360
tccctggtgg atcccctgca tgcgaagatc ttcgaacaag gctgtggggg actgagggca 420
ggctgtaaca ggcttggggg ccagggctta tacgtgcctg ggactcccaa agtattactg 480
ttccatgttc ccggcgaagg gccagctgtc cccgccagc tagactcagc acttagttta 540

```
ggaaccagtg agcaagtcag ccccttggggc agcccataca aggccatggg gctgggcaag    600

ctgcacgcct gggtccgggg tgggcacggt gcccgggcaa cgagctgaaa gctcatctgc    660

tctcaggggc ccctccctgg ggacagcccc tcctggctag tcacaccctg taggctcctc    720

tatataaccc aggggcacag gggctgccct cattctacca ccacctccac agcacagaca    780

gacactcagg agccagccag cggcgcgccc                                     810
```

<210> SEQ ID NO 3
<211> LENGTH: 8562
<212> TYPE: DNA
<213> ORGANISM: Adeno-associated virus

<400> SEQUENCE: 3

```
gcccaatacg caaaccgcct ctccccgcgc gttggccgat tcattaatgc agctgcgcgc     60

tcgctcgctc actgaggccg cccgggcaaa gcccgggcgt cgggcgacct ttggtcgccc    120

ggcctcagtg agcgagcgag cgcgcagaga gggagtggcc aactccatca ctaggggttc    180

cttgtagtta atgattaacc cgccatgcta cttatctacg tagccatgct ctagagttta    240

aacaagcttg catgtctaag ctagaccctt cagattaaaa ataactgagg taagggcctg    300

ggtaggggag gtggtgtgag acgctcctgt ctctcctcta tctgcccatc ggccctttgg    360

ggaggaggaa tgtgcccaag gactaaaaaa aggccatgga gccagagggg cgagggcaac    420

agacctttca tgggcaaacc ttggggccct gctgtctagc atgccccact acgggtctag    480

gctgcccatg taaggaggca aggcctgggg acacccgaga tgcctggtta taattaaccc    540

agacatgtgg ctgccccccc cccccaaca cctgctgcct ctaaaaataa ccctgtccct    600

ggtggatccc ctgcatgcga agatcttcga acaaggctgt ggggggactga gggcaggctg    660

taacaggctt gggggccagg gcttatacgt gcctgggact cccaaagtat tactgttcca    720

tgttcccggc gaagggccag ctgtccccg ccagctagac tcagcactta gtttaggaac    780

cagtgagcaa gtcagccctt ggggcagccc atacaaggcc atggggctgg gcaagctgca    840

cgcctgggtc cggggtgggc acggtgcccg ggcaacgagc tgaaagctca tctgctctca    900

ggggcccctc cctggggaca gcccctcctg gctagtcaca ccctgtaggc tcctctatat    960

aacccagggg cacaggggct gccctcattc taccaccacc tccacagcac agacagacac   1020

tcaggagcag ccagcggcgc gcccaggtaa gtttagtctt tttgtctttt atttcaggtc   1080

ccggatccgg tggtggtgca aatcaaagaa ctgctcctca gtggatgttg cctttacttc   1140

taggcctgta cggaagtgtt acttctgctc taaaagctgc ggaattgtac ccgcggccgc   1200

caccatgctg tggtgggagg aggtggagga ttgttatgaa agggaggacg tgcagaagaa   1260

gacttttacc aagtgggtga acgctcagtt cagcaaattt gggaagcagc acatcgagaa   1320

tctgttttcc gacctgcagg atgggagacg gctgctggat ctgctggaag gactgactgg   1380

ccagaagctg cccaaagaga aggggagcac tagggtgcac gccctgaaca acgtgaacaa   1440

agctctgaga gtgctgcaga acaacaacgt ggatctggtg aatattggca gtactgatat   1500

cgtggacggg aaccacaaac tgacactggg cctgatctgg aacattattc tgcactggca   1560

ggtgaaaaat gtgatgaaga acatcatggc cgggctgcag cagaccaatt ccgagaagat   1620

cctgctgtct tgggtgcggc agagcacccg caactatccc caggtgaacg tgattaactt   1680

cactacatcc tggagcgacg ggctggccct gaatgctctg attcacagcc acaggcctga   1740

tctgttcgac tggaatagcg tggtgtgcca gcagtctgcc acacagcgcc tggaacatgc   1800

cttcaatatc gctcggtacc agctggggat cgaaaaactg ctggacccag aggatgtgga   1860
```

cactacatac ccagataaaa agtctattct gatgtacatt actagcctgt tccaggtgct 1920
gccacagcag gtgtctattg aagccattca ggaggtggaa atgctgcccc gcccccccaa 1980
agtgactaaa gaggagcatt ttcagctgca tcatcagatg cattacagcc agcagattac 2040
cgtgagcctg gctcagggat atgagcgcac cagtagtcca aaaccacggt tcaagtccta 2100
cgcttatacc caggctgcct acgtgacaac tagcgaccct actagatccc cctttccatc 2160
ccagcacctg gaggccccag aggacaagag ctttgggtcc agcctgatgg aaagcgaggt 2220
gaatctggat cggtaccaga cagccctgga ggaggtgctg agctggctgc tgagtgctga 2280
agacacactg caggcccagg gcgaaatttc caatgacgtg gaagtggtga aggatcagtt 2340
ccacacacac gagggctata tgatggacct gacagctcac caggggcgcg tgggcaatat 2400
cctgcagctg ggctctaaac tgatcggcac cgggaaactg agtgaggacg aggaaacaga 2460
agtgcaggag cagatgaacc tgctgaacag ccgctgggag tgtctgagag tggctagtat 2520
ggagaagcag tccaacctgc accgggtgct gatggacctg cagaaccaga aactgaaaga 2580
gctgaacgac tggctgacaa agactgagga acgcacaagg aagatggagg aggagccact 2640
gggacccgac ctggaggatc tgaagagaca ggtgcagcag cataaggtgc tgcaggagga 2700
tctggaacag gagcaggtgc gggtgaactc cctgacacat atggtggtgg tggtggacga 2760
atctagtgga gatcacgcca ccgccgccct ggaggaacag ctgaaggtgc tgggggaccg 2820
gtgggccaac atttgccggt ggaccgagga caggtgggtg ctgctgcagg acatcctgct 2880
gaaatggcag aggctgaccg aggagcagtg tctgtttagt gcttggctga gcgagaaaga 2940
ggacgccgtg aacaagatcc acacaaccgg ctttaaggat cagaacgaaa tgctgtctag 3000
cctgcagaaa ctggctgtgc tgaaggccga tctggagaaa aagaagcaga gcatgggcaa 3060
actgtatagc ctgaaacagg acctgctgag caccctgaag aacaagagcg tgacccagaa 3120
gacagaagcc tggctggata actttgcccg ctgctgggac aacctggtgc agaaactgga 3180
gaaaagtaca gctcagatct ctcaggctgt gaccacaacc cagcctagcc tgacccagac 3240
aaccgtgatg gaaaccgtga ccaccgtgac aacccgcgaa cagatcctgg tgaaacatgc 3300
ccaggaagag ctgccacctc cacctcccca gaagaagaga accctggagc ggctgcagga 3360
gctgcaggaa gccactgacg aactggacct gaagctgagg caggccgaag tgattaaggg 3420
gtcttggcag cctgtgggcg atctgctgat tgattccctg caggaccacc tggaaaaggt 3480
gaaggctctg agaggcgaaa ttgctccact gaaggagaac gtgagtcatg tgaacgatct 3540
ggctagacag ctgacaacac tgggcatcca gctgagccca tacaatctga gcacactgga 3600
ggacctgaat accaggtgga agctgctgca ggtggctgtg gaagaccggg tgcggcagct 3660
gcatgaggcc catcgcgact tcggaccagc cagccagcac tttctgagca catccgtgca 3720
ggggccctgg gagagggcca tttctcccaa caaggtgccc tactatatta atcacgagac 3780
ccagaccact tgttgggacc atcccaagat gacagaactg taccagtccc tggccgatct 3840
gaacaacgtg aggtttagcg cttacagaac cgctatgaag ctgagacggc tgcagaaggc 3900
cctgtgcctg gatctgctgt ccctgtccgc cgcctgcgat gccctggatc agcataatct 3960
gaagcagaac gatcagccaa tggatatcct gcagatcatc aactgcctga ccactatcta 4020
cgacaggctg gagcaggagc acaacaacct ggtgaacgtg cctctgtgcg tggatatgtg 4080
cctgaactgg ctgctgaacg tgtatgacac tgggcgcacc ggccggatca gagtgctgag 4140
ttttaaaact gggattatct ccctgtgtaa ggcccacctg gaggacaagt acaggtacct 4200

```
gttcaagcag gtggctagta gcactggatt ttgtgaccag cgccgcctgg gactgctgct   4260
gcatgatagt atccagattc ctagacagct gggagaggtg gctagtttcg gaggatctaa   4320
catcgaaccc agcgtgcgca gctgtttcca gtttgccaat aacaaacctg aaatcgaggc   4380
tgctctgttc ctggattgga tgcgcctgga accacagagc atggtgtggc tgcctgtgct   4440
gcacagagtg gctgccgccg aaactgccaa gcaccaggct aaatgcaaca tctgcaagga   4500
atgtcccatt atcggctttc gctacaggag tctgaaacat tttaactacg atatttgcca   4560
gagctgcttc ttttccggaa gagtggccaa aggacacaag atgcactacc ctatggtgga   4620
atattgcacc ccaactacat ctggcgaaga tgtgcgcgat tttgccaagg tgctgaagaa   4680
taagtttcgg actaagaggt acttcgccaa gcacccccgc atggggtatc tgccagtgca   4740
gacagtgctg gaaggagaca atatggagac cgatacaatg tgagcggccg caataaaaga   4800
tctttatttt cattagatct gtgtgttggt tttttgtgtg tctagagcat ggctacgtag   4860
ataagtagca tggcgggtta atcattaact acaaggaacc cctagtgatg gagttggcca   4920
ctccctctct gcgcgctcgc tcgctcactg aggccgggcg accaaaggtc gcccgacgcc   4980
cgggctttgc ccgggcggcc tcagtgagcg agcgagcgcg cagctggcgt aatagcgaag   5040
aggcccgcac cgatcgccct tcccaacagt tgcgcagcct gaatggcgaa tggcgattcc   5100
gttgcaatgg ctggcggtaa tattgttctg gatattacca gcaaggccga tagtttgagt   5160
tcttctactc aggcaagtga tgttattact aatcaaagaa gtattgcgac aacggttaat   5220
ttgcgtgatg gacagactct tttactcggt ggcctcactg attataaaaa cacttctcag   5280
gattctggcg taccgttcct gtctaaaatc cctttaatcg gcctcctgtt tagctcccgc   5340
tctgattcta acgaggaaag cacgttatac gtgctcgtca aagcaaccat agtacgcgcc   5400
ctgtagcggc gcattaagcg cggcgggtgt ggtggttacg cgcagcgtga ccgctacact   5460
tgccagcgcc ctagcgcccg ctcctttcgc tttcttccct tcctttctcg ccacgttcgc   5520
cggctttccc cgtcaagctc taaatcgggg gctcccttta gggttccgat ttagtgcttt   5580
acggcacctc gaccccaaaa aacttgatta gggtgatggt tcacgtagtg ggccatcgcc   5640
ctgatagacg gtttttcgcc ctttgacgtt ggagtccacg ttctttaata gtggactctt   5700
gttccaaact ggaacaacac tcaaccctat ctcggtctat tcttttgatt tataagggat   5760
tttgccgatt tcggcctatt ggttaaaaaa tgagctgatt taacaaaaat ttaacgcgaa   5820
ttttaacaaa atattaacgc ttacaattta aatatttgct tatacaatct tcctgttttt   5880
ggggcttttc tgattatcaa ccggggtaca tatgattgac atgctagttt tacgattacc   5940
gttcatcgat tctcttgttt gctccagact ctcaggcaat gacctgatag cctttgtaga   6000
gacctctcaa aaatagctac cctctccggc atgaatttat cagctagaac ggttgaatat   6060
catattgatg gtgatttgac tgtctccggc ctttctcacc cgtttgaatc tttacctaca   6120
cattactcag gcattgcatt taaaatatat gagggttcta aaaattttta tccttgcgtt   6180
gaaataaagg cttctcccgc aaaagtatta cagggtcata atgtttttgg tacaaccgat   6240
ttagctttat gctctgaggc tttattgctt aattttgcta attctttgcc ttgcctgtat   6300
gatttattgg atgttggaat cgcctgatgc ggtattttct ccttacgcat ctgtgcggta   6360
tttcacaccg catatggtgc actctcagta caatctgctc tgatgccgca tagttaagcc   6420
agccccgaca cccgccaaca cccgctgacg cgccctgacg ggcttgtctg ctcccggcat   6480
ccgcttacag acaagctgtg accgtctccg ggagctgcat gtgtcagagg ttttcaccgt   6540
catcaccgaa acgcgcgaga cgaaagggcc tcgtgatacg cctattttta taggttaatg   6600
```

```
tcatgataat aatggtttct tagacgtcag gtggcacttt tcggggaaat gtgcgcggaa   6660
cccctatttg tttatttttc taaatacatt caaatatgta tccgctcatg agacaataac   6720
cctgataaat gcttcaataa tattgaaaaa ggaagagtat gagtattcaa catttccgtg   6780
tcgcccttat tccctttttt gcggcatttt gccttcctgt ttttgctcac ccagaaacgc   6840
tggtgaaagt aaaagatgct gaagatcagt tgggtgcacg agtgggttac atcgaactgg   6900
atctcaacag cggtaagatc cttgagagtt ttcgccccga agaacgtttt ccaatgatga   6960
gcacttttaa agttctgcta tgtggcgcgg tattatcccg tattgacgcc gggcaagagc   7020
aactcggtcg ccgcatacac tattctcaga atgacttggt tgagtactca ccagtcacag   7080
aaaagcatct tacggatggc atgacagtaa gagaattatg cagtgctgcc ataaccatga   7140
gtgataacac tgcggccaac ttacttctga caacgatcgg aggaccgaag gagctaaccg   7200
cttttttgca caacatgggg gatcatgtaa ctcgccttga tcgttgggaa ccggagctga   7260
atgaagccat accaaacgac gagcgtgaca ccacgatgcc tgtagcaatg gcaacaacgt   7320
tgcgcaaact attaactggc gaactactta ctctagcttc ccggcaacaa ttaatagact   7380
ggatggaggc ggataaagtt gcaggaccac ttctgcgctc ggcccttccg gctggctggt   7440
ttattgctga taaatctgga gccggtgagc gtgggtctcg cggtatcatt gcagcactgg   7500
ggccagatgg taagccctcc cgtatcgtag ttatctacac gacggggagt caggcaacta   7560
tggatgaacg aaatagacag atcgctgaga taggtgcctc actgattaag cattggtaac   7620
tgtcagacca agtttactca tatatacttt agattgattt aaaacttcat ttttaattta   7680
aaaggatcta ggtgaagatc ctttttgata atctcatgac caaaatccct taacgtgagt   7740
tttcgttcca ctgagcgtca gaccccgtag aaaagatcaa aggatcttct tgagatcctt   7800
tttttctgcg cgtaatctgc tgcttgcaaa caaaaaaacc accgctacca gcggtggttt   7860
gtttgccgga tcaagagcta ccaactcttt ttccgaaggt aactggcttc agcagagcgc   7920
agataccaaa tactgttctt ctagtgtagc cgtagttagg ccaccacttc aagaactctg   7980
tagcaccgcc tacatacctc gctctgctaa tcctgttacc agtggctgct gccagtggcg   8040
ataagtcgtg tcttaccggg ttggactcaa gacgatagtt accggataag gcgcagcggt   8100
cgggctgaac ggggggttcg tgcacacagc ccagcttgga gcgaacgacc tacaccgaac   8160
tgagatacct acagcgtgag ctatgagaaa gcgccacgct tcccgaaggg agaaaggcgg   8220
acaggtatcc ggtaagcggc agggtcggaa caggagagcg cacgagggag cttccagggg   8280
gaaacgcctg gtatctttat agtcctgtcg ggtttcgcca cctctgactt gagcgtcgat   8340
ttttgtgatg ctcgtcaggg gggcggagcc tatggaaaaa cgccagcaac gcggcctttt   8400
tacggttcct ggccttttgc tggccttttg ctcacatgtt ctttcctgcg ttatcccctg   8460
attctgtgga taaccgtatt accgcctttg agtgagctga taccgctcgc cgcagccgaa   8520
cgaccgagcg cagcgagtca gtgagcgagg aagcggaaga gc                      8562
```

<210> SEQ ID NO 4
<211> LENGTH: 564
<212> TYPE: DNA
<213> ORGANISM: Artificial Sequence
<220> FEATURE:
<223> OTHER INFORMATION: Synthetic Promoter

<400> SEQUENCE: 4

```
cagccactat gggtctaggc tgcccatgta aggaggcaag gcctggggac acccgagatg     60
```

cctggttata attaacccag acatgtggct gctccccccc cccaacacct gctgcctgag 120
cctcaccccc accccggtgc ctgggtctta ggctctgtac accatggagg agaagctcgc 180
tctaaaaata accctgtccc tggtgggctg tgggggactg agggcaggct gtaacaggct 240
tgggggccag ggcttatacg tgcctgggac tcccaaagta ttactgttcc atgttcccgg 300
cgaagggcca gctgtccccc gccagctaga ctcagcactt agtttaggaa ccagtgagca 360
agtcagccct tggggcagcc catacaaggc catggggctg ggcaagctgc acgcctgggt 420
ccggggtggg cacggtgccc gggcaacgag ctgaaagctc atctgctctc aggggcccct 480
ccctggggac agcccctcct ggctagtcac accctgtagg ctcctctata taacccaggg 540
gcacaggggc tgcccccggg tcac 564

<210> SEQ ID NO 5
<211> LENGTH: 8409
<212> TYPE: DNA
<213> ORGANISM: Adeno-associated virus

<400> SEQUENCE: 5
gcccaatacg caaaccgcct ctccccgcgc gttggccgat tcattaatgc agctggcgcg 60
ctcgctcgct cactgaggcc gcccgggcaa agcccgggcg tcgggcgacc tttggtcgcc 120
cggcctcagt gagcgagcga gcgcgcagag agggagtggc caactccatc actaggggtt 180
ccttgtagtt aatgattaac ccgccatgct aattatctac gtagccatgt ctagacagcc 240
actatgggtc taggctgccc atgtaaggag gcaaggcctg gggacacccg agatgcctgg 300
ttataattaa cccagacatg tggctgctcc cccccccaa cacctgctgc ctgagcctca 360
cccccacccc ggtgcctggg tcttaggctc tgtacaccat ggaggagaag ctcgctctaa 420
aaataaccct gtccctggtg ggctgtgggg gactgagggc aggctgtaac aggcttgggg 480
gccagggctt atacgtgcct gggactccca aagtattact gttccatgtt cccggcgaag 540
ggccagctgt cccccgccag ctagactcag cacttagttt aggaaccagt gagcaagtca 600
gcccttgggg cagcccatac aaggccatgg ggctgggcaa gctgcacgcc tgggtccggg 660
gtgggcacgg tgcccgggca acgagctgaa agctcatctg ctctcagggg cccctccctg 720
gggacagccc ctcctggcta gtcacaccct gtaggctcct ctatataacc caggggcaca 780
ggggctgccc ccgggtcacc accacctcca cagcacagac agacactcag gagccagcca 840
gccaggtaag tttagtcttt ttgtctttta tttcaggtcc cggatccggt ggtggtgcaa 900
atcaaagaac tgctcctcag tggatgttgc ctttacttct aggcctgtac ggaagtgtta 960
cttctgctct aaaagctgcg gaattgtacc cgcggccgcc accatgctgt ggtgggagga 1020
ggtggaggat tgttatgaaa gggaggacgt gcagaagaag acttttacca agtgggtgaa 1080
cgctcagttc agcaaatttg ggaagcagca catcgagaat ctgttttccg acctgcagga 1140
tgggagacgg ctgctggatc tgctggaagg actgactggc cagaagctgc ccaaagagaa 1200
ggggagcact agggtgcacg ccctgaacaa cgtgaacaaa gctctgagag tgctgcagaa 1260
caacaacgtg gatctggtga atattggcag tactgatatc gtggacggga accacaaact 1320
gacactgggc ctgatctgga acattattct gcactggcag gtgaaaaatg tgatgaagaa 1380
catcatggcc gggctgcagc agaccaattc cgagaagatc ctgctgtctt gggtgcggca 1440
gagcacccgc aactatcccc aggtgaacgt gattaacttc actacatcct ggagcgacgg 1500
gctggccctg aatgctctga ttcacagcca caggcctgat ctgttcgact ggaatagcgt 1560
ggtgtgccag cagtctgcca cacagcgcct ggaacatgcc ttcaatatcg ctcggtacca 1620

-continued

```
gctggggatc gaaaaactgc tggacccaga ggatgtggac actacatacc cagataaaaa   1680
gtctattctg atgtacatta ctagcctgtt ccaggtgctg ccacagcagg tgtctattga   1740
agccattcag gaggtggaaa tgctgccccg cccccccaaa gtgactaaag aggagcattt   1800
tcagctgcat catcagatgc attacagcca gcagattacc gtgagcctgg ctcagggata   1860
tgagcgcacc agtagtccaa aaccacggtt caagtcctac gcttataccc aggctgccta   1920
cgtgacaact agcgacccta ctagatcccc ctttccatcc cagcacctgg aggccccaga   1980
ggacaagagc tttgggtcca gcctgatgga aagcgaggtg aatctggatc ggtaccagac   2040
agccctggag gaggtgctga gctggctgct gagtgctgaa gacacactgc aggcccaggg   2100
cgaaatttcc aatgacgtgg aagtggtgaa ggatcagttc cacacacacg agggctatat   2160
gatggacctg acagctcacc aggggcgcgt gggcaatatc ctgcagctgg gctctaaact   2220
gatcggcacc gggaaactga gtgaggacga ggaaacagaa gtgcaggagc agatgaacct   2280
gctgaacagc cgctgggagt gtctgagagt ggctagtatg gagaagcagt ccaacctgca   2340
ccgggtgctg atggacctgc agaaccagaa actgaaagag ctgaacgact ggctgacaaa   2400
gactgaggaa cgcacaagga agatggagga ggagccactg ggacccgacc tggaggatct   2460
gaagagacag gtgcagcagc ataaggtgct gcaggaggat ctggaacagg agcaggtgcg   2520
ggtgaactcc ctgacacata tggtggtggt ggtggacgaa tctagtggag atcacgccac   2580
cgccgccctg gaggaacagc tgaaggtgct gggggaccgg tgggccaaca tttgccggtg   2640
gaccgaggac aggtgggtgc tgctgcagga catcctgctg aaatggcaga ggctgaccga   2700
ggagcagtgt ctgtttagtg cttggctgag cgagaaagag gacgccgtga acaagatcca   2760
cacaaccggc tttaaggatc agaacgaaat gctgtctagc ctgcagaaac tggctgtgct   2820
gaaggccgat ctggagaaaa agaagcagag catgggcaaa ctgtatagcc tgaaacagga   2880
cctgctgagc accctgaaga acaagagcgt gacccagaag acagaagcct ggctggataa   2940
ctttgcccgc tgctgggaca acctggtgca gaaactggag aaaagtacag ctcagatctc   3000
tcaggctgtg accacaaccc agcctagcct gacccagaca accgtgatgg aaaccgtgac   3060
caccgtgaca acccgcgaac agatcctggt gaaacatgcc caggaagagc tgccacctcc   3120
acctccccag aagaagagaa ccctggagcg gctgcaggag ctgcaggaag ccactgacga   3180
actggacctg aagctgaggc aggccgaagt gattaagggg tcttggcagc ctgtgggcga   3240
tctgctgatt gattccctgc aggaccacct ggaaaaggtg aaggctctga gaggcgaaat   3300
tgctccactg aaggagaacg tgagtcatgt gaacgatctg gctagacagc tgacaacact   3360
gggcatccag ctgagcccat acaatctgag cacactggag gacctgaata ccaggtggaa   3420
gctgctgcag gtggctgtgg aagaccgggt gcggcagctg catgaggccc atcgcgactt   3480
cggaccagcc agccagcact ttctgagcac atccgtgcag gggccctggg agagggccat   3540
ttctcccaac aaggtgccct actatattaa tcacgagacc cagaccactt gttgggacca   3600
tcccaagatg acagaactgt accagtccct ggccgatctg aacaacgtga ggtttagcgc   3660
ttacagaacc gctatgaagc tgagacggct gcagaaggcc ctgtgcctgg atctgctgtc   3720
cctgtccgcc gcctgcgatg ccctggatca gcataatctg aagcagaacg atcagccaat   3780
ggatatcctg cagatcatca actgcctgac cactatctac gacaggctgg agcaggagca   3840
caacaacctg gtgaacgtgc ctctgtgcgt ggatatgtgc ctgaactggc tgctgaacgt   3900
gtatgacact gggcgcaccg gccggatcag agtgctgagt tttaaaactg ggattatctc   3960
```

```
cctgtgtaag gcccacctgg aggacaagta caggtacctg ttcaagcagg tggctagtag   4020
cactggattt tgtgaccagc gccgcctggg actgctgctg catgatagta tccagattcc   4080
tagacagctg ggagaggtgg ctagtttcgg aggatctaac atcgaaccca gcgtgcgcag   4140
ctgtttccag tttgccaata acaaacctga aatcgaggct gctctgttcc tggattggat   4200
gcgcctggaa ccacagagca tggtgtggct gcctgtgctg cacagagtgg ctgccgccga   4260
aactgccaag caccaggcta aatgcaacat ctgcaaggaa tgtcccatta tcggctttcg   4320
ctacaggagt ctgaaacatt ttaactacga tatttgccag agctgcttct tttccggaag   4380
agtggccaaa ggacacaaga tgcactaccc tatggtggaa tattgcaccc caactacatc   4440
tggcgaagat gtgcgcgatt ttgccaaggt gctgaagaat aagtttcgga ctaagaggta   4500
cttcgccaag cacccccgca tggggtatct gccagtgcag acagtgctgg aaggagacaa   4560
tatggagacc gatacaatgt gagcggccgc aataaaagat ctttattttc attagatctg   4620
tgtgttggtt ttttgtgtgt ctagagcatg gctacgtaga taagtagcat ggcgggttaa   4680
tcattaacta caaggaaccc ctagtgatgg agttggccac tccctctctg cgcgctcgct   4740
cgctcactga ggccgggcga ccaaaggtcg cccgacgccc gggctttgcc cgggcggcct   4800
cagtgagcga gcgagcgcgc cagctggcgt aatagcgaag aggcccgcac cgatcgccct   4860
tcccaacagt tgcgcagcct gaatggcgaa tggaagttcc agacgattga gcgtcaaaat   4920
gtaggtattt ccatgagcgt ttttcctgtt gcaatggctg gcggtaatat tgttctggat   4980
attaccagca aggccgatag tttgagttct tctactcagg caagtgatgt tattactaat   5040
caaagaagta ttgcgacaac ggttaatttg cgtgatggac agactctttt actcggtggc   5100
ctcactgatt ataaaaacac ttctcaggat tctggcgtac cgttcctgtc taaaatccct   5160
ttaatcggcc tcctgtttag ctcccgctct gattctaacg aggaaagcac gttatacgtg   5220
ctcgtcaaag caaccatagt acgcgccctg tagcggcgca ttaagcgcgg cgggtgtggt   5280
ggttacgcgc agcgtgaccg ctacacttgc cagcgcccta gcgcccgctc ctttcgcttt   5340
cttcccttcc tttctcgcca cgttcgccgg ctttccccgt caagctctaa atcgggggct   5400
ccctttaggg ttccgattta gtgatttacg gcacctcgac cccaaaaaac ttgattaggg   5460
tgatggttca cgtagtgggc catcgccctg atagacggtt tttcgccctt tgacgttgga   5520
gtccacgttc tttaatagtg gactcttgtt ccaaactgga acaacactca accctatctc   5580
ggtctattct tttgatttat aagggatttt gccgatttcg gcctattggt taaaaaatga   5640
gctgatttaa caaaaattta acgcgaattt taacaaaata ttaacgttta caatttaaat   5700
atttgcttat acaatcttcc tgtttttggg gcttttctga ttatcaaccg gggtacatat   5760
gattgacatg ctagttttac gattaccgtt catcgattct cttgtttgct ccagactctc   5820
aggcaatgac ctgatagcct ttgtagagac ctctcaaaaa tagctaccct ctccggcatg   5880
aatttatcag ctagaacggt tgaatatcat attgatggtg atttgactgt ctccggcctt   5940
tctcacccgt ttgaatcttt acctacacat tactcaggca ttgcatttaa aatatatgag   6000
ggttctaaaa atttttatcc ttgcgttgaa ataaaggctt ctcccgcaaa agtattacag   6060
ggtcataatg tttttggtac aaccgattta gctttatgct ctgaggcttt attgcttaat   6120
tttgctaatt ctttgccttg cctgtatgat ttattggatg ttggaagttc ctgatgcggt   6180
attttctcct tacgcatctg tgcggtattt cacaccgcat atggtgcact ctcagtacaa   6240
tctgctctga tgccgcatag ttaagccagc cccgacaccc gccaacaccc gctgacgcgc   6300
cctgacgggc ttgtctgctc ccggcatccg cttacagaca agctgtgacc gtctccggga   6360
```

gctgcatgtg tcagaggttt tcaccgtcat caccgaaacg cgcgagacga aagggcctcg 6420
tgatacgcct atttttatag gttaatgtca tgataataat ggtttcttag acgtcaggtg 6480
gcacttttcg gggaaatgtg cgcggaaccc ctatttgttt atttttctaa atacattcaa 6540
atatgtatcc gctcatgaga caataaccct gataaatgct tcaataatat tgaaaaagga 6600
agagtatgag tattcaacat ttccgtgtcg cccttattcc cttttttgcg gcattttgcc 6660
ttcctgtttt tgctcaccca gaaacgctgg tgaaagtaaa agatgctgaa gatcagttgg 6720
gtgcacgagt gggttacatc gaactggatc tcaacagcgg taagatcctt gagagttttc 6780
gccccgaaga acgttttcca atgatgagca cttttaaagt tctgctatgt ggcgcggtat 6840
tatcccgtat tgacgccggg caagagcaac tcggtcgccg catacactat tctcagaatg 6900
acttggttga gtactcacca gtcacagaaa agcatcttac ggatggcatg acagtaagag 6960
aattatgcag tgctgccata accatgagtg ataacactgc ggccaactta cttctgacaa 7020
cgatcggagg accgaaggag ctaaccgctt ttttgcacaa catgggggat catgtaactc 7080
gccttgatcg ttgggaaccg gagctgaatg aagccatacc aaacgacgag cgtgacacca 7140
cgatgcctgt agcaatggca acaacgttgc gcaaactatt aactggcgaa ctacttactc 7200
tagcttcccg gcaacaatta atagactgga tggaggcgga taaagttgca ggaccacttc 7260
tgcgctcggc ccttccggct ggctggttta ttgctgataa atctggagcc ggtgagcgtg 7320
ggtctcgcgg tatcattgca gcactggggc cagatggtaa gccctcccgt atcgtagtta 7380
tctacacgac ggggagtcag gcaactatgg atgaacgaaa tagacagatc gctgagatag 7440
gtgcctcact gattaagcat tggtaactgt cagaccaagt ttactcatat atactttaga 7500
ttgatttaaa acttcatttt taatttaaaa ggatctaggt gaagatcctt tttgataatc 7560
tcatgaccaa aatcccttaa cgtgagtttt cgttccactg agcgtcagac cccgtagaaa 7620
agatcaaagg atcttcttga gatccttttt ttctgcgcgt aatctgctgc ttgcaaacaa 7680
aaaaaccacc gctaccagcg gtggtttgtt tgccggatca agagctacca actctttttc 7740
cgaaggtaac tggcttcagc agagcgcaga taccaaatac tgtccttcta gtgtagccgt 7800
agttaggcca ccacttcaag aactctgtag caccgcgtac atacctcgct ctgctaatcc 7860
tgttaccagt ggctgctgcc agtggcgata agtcgtgtct taccgggttg gactcaagac 7920
gatagttacc ggataaggcg cagcggtcgg gctgaacggg gggttcgtgc acacagccca 7980
gcttggagcg aacgacctac accgaactga gatacctaca gcgtgagcta tgagaaagcg 8040
ccacgcttcc cgaagggaga aaggcggaca ggtatccggt aagcggcagg gtcggaacag 8100
gagagcgcac gagggagctt ccagggggaa acgcctggta tctttatagt cctgtcgggt 8160
ttcgccacct ctgacttgag cgtcgatttt tgtgatgctc gtcagggggg cggagcctat 8220
ggaaaaacgc cagcaacgcg gcctttttac ggttcctggc cttttgctgg ccttttgctc 8280
acatgttctt tcctgcgtta tcccctgatt ctgtggataa ccgtattacc gggtttgagt 8340
gagctgatac cgctcgccgc agccgaacga ccgagcgcag cgagtcagtg agcgaccaag 8400
cggaagagc 8409

<210> SEQ ID NO 6
<211> LENGTH: 8611
<212> TYPE: DNA
<213> ORGANISM: Adeno-associated virus

<400> SEQUENCE: 6

```
gcccaatacg caaaccgcct ctccccgcgc gttggccgat tcattaatgc agctggcgcg     60
ctcgctcgct cactgaggcc gcccgggcaa agcccgggcg tcgggcgacc tttggtcgcc    120
cggcctcagt gagcgagcga gcgcgcagag agggagtggc caactccatc actaggggtt    180
ccttgtagtt aatgattaac ccgccatgct aattatctac gtagccatgt ctagagttta    240
aacaagcttg catgtctaag ctagaccctt cagattaaaa ataactgagg taagggcctg    300
ggtaggggag gtggtgtgag acgctcctgt ctctcctcta tctgcccatc ggccctttgg    360
ggaggaggaa tgtgcccaag gactaaaaaa aggccatgga gccagagggg cgagggcaac    420
agacctttca tgggcaaacc ttggggccct gctgtctagc atgccccact acgggtctag    480
gctgcccatg taaggaggca aggcctgggg acacccgaga tgcctggtta taattaaccc    540
agacatgtgg ctgccccccc ccccccaaca cctgctgcct ctaaaaataa ccctgtccct    600
ggtggatccc ctgcatgcga agatcttcga acaaggctgt gggggactga gggcaggctg    660
taacaggctt gggggccagg gcttatacgt gcctgggact cccaaagtat tactgttcca    720
tgttcccggc gaagggccag ctgtcccccg ccagctagac tcagcactta gtttaggaac    780
cagtgagcaa gtcagccctt ggggcagccc atacaaggcc atggggctgg gcaagctgca    840
cgcctgggtc cggggtgggc acggtgcccg ggcaacgagc tgaaagctca tctgctctca    900
ggggcccctc cctggggaca gcccctcctg gctagtcaca ccctgtaggc tcctctatat    960
aacccagggg cacaggggct gccctcattc taccaccacc tccacagcac agacagacac   1020
tcaggagcca gccagcggcg cgcccaggta agtttagtct tttgtcttt tatttcaggt   1080
cccggatccg gtggtggtgc aaatcaaaga actgctcctc agtggatgtt gcctttactt   1140
ctaggcctgt acggaagtgt tacttctgct ctaaaagctg cggaattgta cccgcggccg   1200
ccaccatgct gtggtgggag gaggtggagg attgttatga aagggaggac gtgcagaaga   1260
agacttttac caagtgggtg aacgctcagt tcagcaaatt tgggaagcag cacatcgaga   1320
atctgttttc cgacctgcag gatgggagac ggctgctgga tctgctggaa ggactgactg   1380
gccagaagct gcccaaagag aaggggagca ctagggtgca cgccctgaac aacgtgaaca   1440
aagctctgag agtgctgcag aacaacaacg tggatctggt gaatattggc agtactgata   1500
tcgtggacgg gaaccacaaa ctgacactgg gcctgatctg gaacattatt ctgcactggc   1560
aggtgaaaaa tgtgatgaag aacatcatgg ccgggctgca gcagaccaat tccgagaaga   1620
tcctgctgtc ttgggtgcgg cagagcaccc gcaactatcc ccaggtgaac gtgattaact   1680
tcactacatc ctggagcgac gggctggccc tgaatgctct gattcacagc cacaggcctg   1740
atctgttcga ctggaatagc gtggtgtgcc agcagtctgc cacacagcgc ctggaacatg   1800
ccttcaatat cgctcggtac cagctgggga tcgaaaaact gctggaccca gaggatgtgg   1860
acactacata cccagataaa aagtctattc tgatgtacat tactagcctg ttccaggtgc   1920
tgccacagca ggtgtctatt gaagccattc aggaggtgga aatgctgccc cgcccccca   1980
aagtgactaa agaggagcat tttcagctgc atcatcagat gcattacagc cagcagatta   2040
ccgtgagcct ggctcaggga tatgagcgca ccagtagtcc aaaaccacgg ttcaagtcct   2100
acgcttatac ccaggctgcc tacgtgacaa ctagcgaccc tactagatcc cccttttccat   2160
cccagcacct ggaggcccca gaggacaaga gctttgggtc cagcctgatg gaaagcgagg   2220
tgaatctgga tcggtaccag acagccctgg aggaggtgct gagctggctg ctgagtgctg   2280
aagacacact gcaggcccag ggcgaaattt ccaatgacgt ggaagtggtg aaggatcagt   2340
tccacacaca cgagggctat atgatggacc tgacagctca ccaggggcgc gtgggcaata   2400
```

-continued

```
tcctgcagct gggctctaaa ctgatcggca ccgggaaact gagtgaggac gaggaaacag   2460
aagtgcagga gcagatgaac ctgctgaaca gccgctggga gtgtctgaga gtggctagta   2520
tggagaagca gtccaacctg caccgggtgc tgatggacct gcagaaccag aaactgaaag   2580
agctgaacga ctggctgaca aagactgagg aacgcacaag gaagatggag gaggagccac   2640
tgggacccga cctggaggat ctgaagagac aggtgcagca gcataaggtg ctgcaggagg   2700
atctggaaca ggagcaggtg cgggtgaact ccctgacaca tatggtggtg gtggtggacg   2760
aatctagtgg agatcacgcc accgccgccc tggaggaaca gctgaaggtg ctgggggacc   2820
ggtgggccaa catttgccgg tggaccgagg acaggtgggt gctgctgcag gacatcctgc   2880
tgaaatggca gaggctgacc gaggagcagt gtctgtttag tgcttggctg agcgagaaag   2940
aggacgccgt gaacaagatc cacacaaccg gctttaagga tcagaacgaa atgctgtcta   3000
gcctgcagaa actggctgtg ctgaaggccg atctggagaa aaagaagcag agcatgggca   3060
aactgtatag cctgaaacag gacctgctga gcaccctgaa gaacaagagc gtgacccaga   3120
agacagaagc ctggctggat aactttgccc gctgctggga caacctggtg cagaaactgg   3180
agaaaagtac agctcagatc tctcaggctg tgaccacaac ccagcctagc ctgacccaga   3240
caaccgtgat ggaaaccgtg accaccgtga caacccgcga acagatcctg gtgaaacatg   3300
cccaggaaga gctgccacct ccacctcccc agaagaagag aaccctggag cggctgcagg   3360
agctgcagga agccactgac gaactggacc tgaagctgag gcaggccgaa gtgattaagg   3420
ggtcttggca gcctgtgggc gatctgctga ttgattccct gcaggaccac ctggaaaagg   3480
tgaaggctct gagaggcgaa attgctccac tgaaggagaa cgtgagtcat gtgaacgatc   3540
tggctagaca gctgacaaca ctgggcatcc agctgagccc atacaatctg agcacactgg   3600
aggacctgaa taccaggtgg aagctgctgc aggtggctgt ggaagaccgg gtgcggcagc   3660
tgcatgaggc ccatcgcgac ttcggaccag ccagccagca ctttctgagc acatccgtgc   3720
aggggccctg ggagagggcc atttctccca acaaggtgcc ctactatatt aatcacgaga   3780
cccagaccac ttgttgggac catcccaaga tgacagaact gtaccagtcc ctggccgatc   3840
tgaacaacgt gaggtttagc gcttacagaa ccgctatgaa gctgagacgg ctgcagaagg   3900
ccctgtgcct ggatctgctg tccctgtccg ccgcctgcga tgccctggat cagcataatc   3960
tgaagcagaa cgatcagcca atggatatcc tgcagatcat caactgcctg accactatct   4020
acgacaggct ggagcaggag cacaacaacc tggtgaacgt gcctctgtgc gtggatatgt   4080
gcctgaactg gctgctgaac gtgtatgaca ctgggcgcac cggccggatc agagtgctga   4140
gttttaaaac tgggattatc tccctgtgta aggcccacct ggaggacaag tacaggtacc   4200
tgttcaagca ggtggctagt agcactggat tttgtgacca gcgccgcctg ggactgctgc   4260
tgcatgatag tatccagatt cctagacagc tgggagaggt ggctagtttc ggaggatcta   4320
acatcgaacc cagcgtgcgc agctgtttcc agtttgccaa taacaaacct gaaatcgagg   4380
ctgctctgtt cctggattgg atgcgcctgg aaccacagag catggtgtgg ctgcctgtgc   4440
tgcacagagt ggctgccgcc gaaactgcca agcaccaggc taaatgcaac atctgcaagg   4500
aatgtcccat tatcggcttt cgctacagga gtctgaaaca ttttaactac gatatttgcc   4560
agagctgctt cttttccgga agagtggcca aaggacacaa gatgcactac cctatggtgg   4620
aatattgcac cccaactaca tctggcgaag atgtgcgcga ttttgccaag gtgctgaaga   4680
ataagtttcg gactaagagg tacttcgcca agcacccccg catggggtat ctgccagtgc   4740
```

agacagtgct ggaaggagac aatatggaga ccgatacaat gtgagcggcc gcaataaaag 4800
atctttattt tcattagatc tgtgtgttgg ttttttgtgt gtctagagca tggctacgta 4860
gataagtagc atggcgggtt aatcattaac tacaaggaac ccctagtgat ggagttggcc 4920
actccctctc tgcgcgctcg ctcgctcact gaggccgggc gaccaaaggt cgcccgacgc 4980
ccgggctttg cccgggcggc ctcagtgagc gagcgagcgc gccagctggc gtaatagcga 5040
agaggcccgc accgatcgcc cttcccaaca gttgcgcagc ctgaatggcg aatggaagtt 5100
ccagacgatt gagcgtcaaa atgtaggtat ttccatgagc gtttttcctg ttgcaatggc 5160
tggcggtaat attgttctgg atattaccag caaggccgat agtttgagtt cttctactca 5220
ggcaagtgat gttattacta atcaaagaag tattgcgaca acggttaatt tgcgtgatgg 5280
acagactctt ttactcggtg gcctcactga ttataaaaac acttctcagg attctggcgt 5340
accgttcctg tctaaaatcc ctttaatcgg cctcctgttt agctcccgct ctgattctaa 5400
cgaggaaagc acgttatacg tgctcgtcaa agcaaccata gtacgcgccc tgtagcggcg 5460
cattaagcgc ggcgggtgtg gtggttacgc gcagcgtgac cgctacactt gccagcgccc 5520
tagcgcccgc tcctttcgct ttcttccctt cctttctcgc cacgttcgcc ggctttcccc 5580
gtcaagctct aaatcggggg ctccctttag ggttccgatt tagtgattta cggcacctcg 5640
accccaaaaa acttgattag ggtgatggtt cacgtagtgg gccatcgccc tgatagacgg 5700
tttttcgccc tttgacgttg gagtccacgt tctttaatag tggactcttg ttccaaactg 5760
gaacaacact caaccctatc tcggtctatt cttttgattt ataagggatt ttgccgattt 5820
cggcctattg gttaaaaaat gagctgattt aacaaaaatt taacgcgaat tttaacaaaa 5880
tattaacgtt tacaatttaa atatttgctt atacaatctt cctgtttttg gggcttttct 5940
gattatcaac cggggtacat atgattgaca tgctagtttt acgattaccg ttcatcgatt 6000
ctcttgtttg ctccagactc tcaggcaatg acctgatagc ctttgtagag acctctcaaa 6060
aatagctacc ctctccggca tgaatttatc agctagaacg gttgaatatc atattgatgg 6120
tgatttgact gtctccggcc tttctcaccc gtttgaatct ttacctacac attactcagg 6180
cattgcattt aaaatatatg agggttctaa aaatttttat ccttgcgttg aaataaaggc 6240
ttctcccgca aaagtattac agggtcataa tgtttttggt acaaccgatt tagctttatg 6300
ctctgaggct ttattgctta attttgctaa ttctttgcct tgcctgtatg atttattgga 6360
tgttggaagt tcctgatgcg gtattttctc cttacgcatc tgtgcggtat ttcacaccgc 6420
atatggtgca ctctcagtac aatctgctct gatgccgcat agttaagcca gccccgacac 6480
ccgccaacac ccgctgacgc gccctgacgg gcttgtctgc tcccggcatc cgcttacaga 6540
caagctgtga ccgtctccgg gagctgcatg tgtcagaggt tttcaccgtc atcaccgaaa 6600
cgcgcgagac gaaagggcct cgtgatacgc ctatttttat aggttaatgt catgataata 6660
atggtttctt agacgtcagg tggcactttt cggggaaatg tgcgcggaac ccctatttgt 6720
ttatttttct aaatacattc aaatatgtat ccgctcatga gacaataacc ctgataaatg 6780
cttcaataat attgaaaaag gaagagtatg agtattcaac atttccgtgt cgcccttatt 6840
ccctttttttg cggcattttg ccttcctgtt tttgctcacc cagaaacgct ggtgaaagta 6900
aaagatgctg aagatcagtt gggtgcacga gtgggttaca tcgaactgga tctcaacagc 6960
ggtaagatcc ttgagagttt tcgccccgaa gaacgttttc caatgatgag cacttttaaa 7020
gttctgctat gtggcgcggt attatcccgt attgacgccg ggcaagagca actcggtcgc 7080
cgcatacact attctcagaa tgacttggtt gagtactcac cagtcacaga aaagcatctt 7140

```
acggatggca tgacagtaag agaattatgc agtgctgcca taaccatgag tgataacact   7200
gcggccaact tacttctgac aacgatcgga ggaccgaagg agctaaccgc tttttgcac    7260
aacatggggg atcatgtaac tcgccttgat cgttgggaac cggagctgaa tgaagccata   7320
ccaaacgacg agcgtgacac cacgatgcct gtagcaatgg caacaacgtt gcgcaaacta   7380
ttaactggcg aactacttac tctagcttcc cggcaacaat taatagactg gatggaggcg   7440
gataaagttg caggaccact tctgcgctcg gcccttccgg ctggctggtt tattgctgat   7500
aaatctggag ccggtgagcg tgggtctcgc ggtatcattg cagcactggg gccagatggt   7560
aagccctccc gtatcgtagt tatctacacg acggggagtc aggcaactat ggatgaacga   7620
aatagacaga tcgctgagat aggtgcctca ctgattaagc attggtaact gtcagaccaa   7680
gtttactcat atatacttta gattgattta aaacttcatt tttaatttaa aaggatctag   7740
gtgaagatcc tttttgataa tctcatgacc aaaatccctt aacgtgagtt ttcgttccac   7800
tgagcgtcag accccgtaga aaagatcaaa ggatcttctt gagatccttt ttttctgcgc   7860
gtaatctgct gcttgcaaac aaaaaaacca ccgctaccag cggtggtttg tttgccggat   7920
caagagctac caactctttt tccgaaggta actggcttca gcagagcgca gataccaaat   7980
actgtccttc tagtgtagcc gtagttaggc caccacttca agaactctgt agcaccgcgt   8040
acatacctcg ctctgctaat cctgttacca gtggctgctg ccagtggcga taagtcgtgt   8100
cttaccgggt tggactcaag acgatagtta ccggataagg cgcagcggtc gggctgaacg   8160
gggggttcgt gcacacagcc cagcttggag cgaacgacct acaccgaact gagataccta   8220
cagcgtgagc tatgagaaag cgccacgctt cccgaaggga gaaaggcgga caggtatccg   8280
gtaagcggca gggtcggaac aggagagcgc acgagggagc ttccaggggg aaacgcctgg   8340
tatctttata gtcctgtcgg gtttcgccac ctctgacttg agcgtcgatt tttgtgatgc   8400
tcgtcagggg ggcggagcct atggaaaaac gccagcaacg cggccttttt acggttcctg   8460
gccttttgct ggccttttgc tcacatgttc tttcctgcgt tatcccctga ttctgtggat   8520
aaccgtatta ccgggtttga gtgagctgat accgctcgcc gcagccgaac gaccgagcgc   8580
agcgagtcag tgagcgacca agcggaagag c                                  8611
```

```
<210> SEQ ID NO 7
<211> LENGTH: 792
<212> TYPE: DNA
<213> ORGANISM: Artificial Sequence
<220> FEATURE:
<223> OTHER INFORMATION: Synthetic Promoter

<400> SEQUENCE: 7

aagcttgcat gtctaagcta gacccttcag attaaaaata actgaggtaa gggcctgggt     60
aggggaggtg gtgtgagacg ctcctgtctc tcctctatct gcccatcggc cctttgggga    120
ggaggaatgt gcccaaggac taaaaaaagg ccatggagcc agaggggcga gggcaacaga    180
cctttcatgg gcaaaccttg gggccctgct gtctagcatg ccccactacg ggtctaggct    240
gcccatgtaa ggaggcaagg cctggggaca cccgagatgc ctggttataa ttaacccaga    300
catgtggctg cccccccccc cccaacacct gctgcctcta aaaataaccc tgtccctggt    360
ggatcccctg catgcgaaga tcttcgaaca aggctgtggg ggactgaggg caggctgtaa    420
caggcttggg ggccagggct tatacgtgcc tgggactccc aaagtattac tgttccatgt    480
tcccggcgaa gggccagctg tcccccgcca gctagactca gcacttagtt taggaaccag    540
```

tgagcaagtc agcccttggg gcagcccata caaggccatg ggctgggca agctgcacgc 600 ctgggtccgg ggtgggcacg gtgcccgggc aacgagctga aagctcatct gctctcaggg 660
gcccctccct ggggacagcc cctcctggct agtcacaccc tgtaggctcc tctatataac 720
ccaggggcac aggggctgcc ctcattctac caccacctcc acagcacaga cagacactca 780
ggagcagcca gc 792

<210> SEQ ID NO 8
<211> LENGTH: 8629
<212> TYPE: DNA
<213> ORGANISM: Adeno-associated virus

<400> SEQUENCE: 8
gcgcgctcgc tcgctcactg aggccgcccg ggcaaagccc gggcgtcggg cgacctttgg 60
tcgcccggcc tcagtgagcg agcgagcgcg cagagaggga gtggccaact ccatcactag 120
gggttccttg tagttaatga ttaacccgcc atgctactta tctacgtagc catgctctag 180
agtttaaaca agcttgcatg tctaagctag acccttcaga ttaaaaataa ctgaggtaag 240
ggcctgggta ggggaggtgg tgtgagacgc tcctgtctct cctctatctg cccatcggcc 300
ctttggggag gaggaatgtg cccaaggact aaaaaaaggc catggagcca gaggggcgag 360
ggcaacagac ctttcatggg caaaccttgg ggccctgctg tctagcatgc cccactacgg 420
gtctaggctg cccatgtaag gaggcaaggc ctggggacac ccgagatgcc tggttataat 480
taacccagac atgtggctgc ccccccccc ccaacacctg ctgcctctaa aaataaccct 540
gtccctggtg gatcccctgc atgcgaagat cttcgaacaa ggctgtgggg gactgagggc 600
aggctgtaac aggcttgggg gccagggctt atacgtgcct gggactccca aagtattact 660
gttccatgtt cccggcgaag ggccagctgt cccccgccag ctagactcag cacttagttt 720
aggaaccagt gagcaagtca gcccttgggg cagcccatac aaggccatgg ggctgggcaa 780
gctgcacgcc tgggtccggg gtgggcacgg tgcccgggca acgagctgaa agctcatctg 840
ctctcagggg cccctccctg gggacagccc ctcctggcta gtcacaccct gtaggctcct 900
ctatataacc caggggcaca ggggctgccc tcattctacc accacctcca cagcacagac 960
agacactcag gagcagccag cggcgcgccc aggtaagttt agtctttttg tcttttattt 1020
caggtcccgg atccggtggt ggtgcaaatc aaagaactgc tcctcagtgg atgttgcctt 1080
tacttctagg cctgtacgga agtgttactt ctgctctaaa agctgcggaa ttgtacccgc 1140
ggccgccacc atgctgtggt gggaggaggt ggaggattgt tatgaaaggg aggacgtgca 1200
gaagaagact tttaccaagt gggtgaacgc tcagttcagc aaatttggga agcagcacat 1260
cgagaatctg ttttccgacc tgcaggatgg gagacggctg ctggatctgc tggaaggact 1320
gactggccag aagctgccca aagagaaggg gagcactagg gtgcacgccc tgaacaacgt 1380
gaacaaagct ctgagagtgc tgcagaacaa caacgtggat ctggtgaata ttggcagtac 1440
tgatatcgtg gacgggaacc acaaactgac actgggcctg atctggaaca ttattctgca 1500
ctggcaggtg aaaaatgtga tgaagaacat catggccggg ctgcagcaga ccaattccga 1560
gaagatcctg ctgtcttggg tgcggcagag cacccgcaac tatccccagg tgaacgtgat 1620
taacttcact acatcctgga gcgacgggct ggccctgaat gctctgattc acagccacag 1680
gcctgatctg ttcgactgga atagcgtggt gtgccagcag tctgccacac agcgcctgga 1740
acatgccttc aatatcgctc ggtaccagct ggggatcgaa aaactgctgg acccagagga 1800
tgtggacact acatacccag ataaaaagtc tattctgatg tacattacta gcctgttcca 1860

-continued

```
ggtgctgcca cagcaggtgt ctattgaagc cattcaggag gtggaaatgc tgccccgccc   1920
ccccaaagtg actaaagagg agcattttca gctgcatcat cagatgcatt acagccagca   1980
gattaccgtg agcctggctc agggatatga gcgcaccagt agtccaaaac cacggttcaa   2040
gtcctacgct tatacccagg ctgcctacgt gacaactagc gaccctacta gatcccccctt   2100
tccatcccag cacctggagg ccccagagga caagagcttt gggtccagcc tgatggaaag   2160
cgaggtgaat ctggatcggt accagacagc cctggaggag gtgctgagct ggctgctgag   2220
tgctgaagac acactgcagg cccagggcga aatttccaat gacgtggaag tggtgaagga   2280
tcagttccac acacacgagg gctatatgat ggacctgaca gctcaccagg ggcgcgtggg   2340
caatatcctg cagctgggct ctaaactgat cggcaccggg aaactgagtg aggacgagga   2400
aacagaagtg caggagcaga tgaacctgct gaacagccgc tgggagtgtc tgagagtggc   2460
tagtatggag aagcagtcca acctgcaccg ggtgctgatg gacctgcaga accagaaact   2520
gaaagagctg aacgactggc tgacaaagac tgaggaacgc acaaggaaga tggaggagga   2580
gccactggga cccgacctgg aggatctgaa gagacaggtg cagcagcata aggtgctgca   2640
ggaggatctg gaacaggagc aggtgcgggt gaactccctg acacatatgg tggtggtggt   2700
ggacgaatct agtggagatc acgccaccgc cgccctggag gaacagctga aggtgctggg   2760
ggaccggtgg gccaacattt gccggtggac cgaggacagg tgggtgctgc tgcaggacat   2820
cctgctgaaa tggcagaggc tgaccgagga gcagtgtctg tttagtgctt ggctgagcga   2880
gaaagaggac gccgtgaaca agatccacac aaccggcttt aaggatcaga acgaaatgct   2940
gtctagcctg cagaaactgg ctgtgctgaa ggccgatctg gagaaaaaga agcagagcat   3000
gggcaaactg tatagcctga aacaggacct gctgagcacc ctgaagaaca agagcgtgac   3060
ccagaagaca gaagcctggc tggataactt tgcccgctgc tgggacaacc tggtgcagaa   3120
actggagaaa agtacagctc agatctctca ggctgtgacc acaacccagc ctagcctgac   3180
ccagacaacc gtgatggaaa ccgtgaccac cgtgacaacc cgcgaacaga tcctggtgaa   3240
acatgcccag gaagagctgc cacctccacc tccccagaag aagagaaccc tggagcggct   3300
gcaggagctg caggaagcca ctgacgaact ggacctgaag ctgaggcagg ccgaagtgat   3360
taaggggtct tggcagcctg tgggcgatct gctgattgat tccctgcagg accacctgga   3420
aaaggtgaag gctctgagag gcgaaattgc tccactgaag gagaacgtga gtcatgtgaa   3480
cgatctggct agacagctga caacactggg catccagctg agcccataca atctgagcac   3540
actggaggac ctgaatacca ggtggaagct gctgcaggtg gctgtggaag accgggtgcg   3600
gcagctgcat gaggcccatc gcgacttcgg accagccagc cagcactttc tgagcacatc   3660
cgtgcagggg ccctgggaga gggccatttc tcccaacaag gtgccctact atattaatca   3720
cgagacccag accacttgtt gggaccatcc caagatgaca gaactgtacc agtccctggc   3780
cgatctgaac aacgtgaggt ttagcgctta cagaaccgct atgaagctga gacggctgca   3840
gaaggccctg tgcctggatc tgctgtccct gtccgccgcc tgcgatgccc tggatcagca   3900
taatctgaag cagaacgatc agccaatgga tatcctgcag atcatcaact gcctgaccac   3960
tatctacgac aggctggagc aggagcacaa caacctggtg aacgtgcctc tgtgcgtgga   4020
tatgtgcctg aactggctgc tgaacgtgta tgacactggg cgcaccggcc ggatcagagt   4080
gctgagtttt aaaactggga ttatctccct gtgtaaggcc cacctggagg acaagtacag   4140
gtacctgttc aagcaggtgg ctagtagcac tggattttgt gaccagcgcc gcctgggact   4200
```

-continued

```
gctgctgcat gatagtatcc agattcctag acagctggga gaggtggcta gtttcggagg   4260
atctaacatc gaacccagcg tgcgcagctg tttccagttt gccaataaca aacctgaaat   4320
cgaggctgct ctgttcctgg attggatgcg cctggaacca cagagcatgg tgtggctgcc   4380
tgtgctgcac agagtggctg ccgccgaaac tgccaagcac caggctaaat gcaacatctg   4440
caaggaatgt cccattatcg gctttcgcta caggagtctg aaacatttta actacgatat   4500
ttgccagagc tgcttctttt ccggaagagt ggccaaagga cacaagatgc actaccctat   4560
ggtggaatat tgcaccccaa ctacatctgg cgaagatgtg cgcgattttg ccaaggtgct   4620
gaagaataag tttcggacta agaggtactt cgccaagcac ccccgcatgg ggtatctgcc   4680
agtgcagaca gtgctggaag gagacaatat ggagaccgat acaatgtgag cggccgcaat   4740
aaaagatctt tattttcatt agatctgtgt gttggttttt tgtgtgtcta gagtcgacca   4800
gagcatggct acgtagataa gtagcatggc gggttaatca ttaactacaa ggaaccccta   4860
gtgatggagt tggccactcc ctctctgcgc gctcgctcgc tcactgaggc cgggcgacca   4920
aaggtcgccc gacgcccggg ctttgcccgg gcggcctcag tgagcgagcg agcgcgcagc   4980
tgcattaatg aatcggccaa cgcgcgggga gaggcggttt gcgtattggg cgctcttccg   5040
cttcctcgct cactgactcg ctgcgctcgg tcgttcggct gcggcgagcg gtatcagctc   5100
actcaaaggc ggtaatacgg ttatccacag aatcagggga taacgcagga aagaacatgt   5160
gagcaaaagg ccagcaaaag gccaggaacc gtaaaaaggc cgcgttgctg gcgtttttcc   5220
ataggctccg cccccctgac gagcatcaca aaaatcgacg ctcaagtcag aggtggcgaa   5280
acccgacagg actataaaga taccaggcgt ttccccctgg aagctccctc gtgcgctctc   5340
ctgttccgac cctgccgctt accggatacc tgtccgcctt tctcccttcg ggaagcgtgg   5400
cgctttctca tagctcacgc tgtaggtatc tcagttcggt gtaggtcgtt cgctccaagc   5460
tgggctgtgt gcacgaaccc cccgttcagc ccgaccgctg cgccttatcc ggtaactatc   5520
gtcttgagtc caacccggta agacacgact tatcgccact ggcagcagcc actggtaaca   5580
ggattagcag agcgaggtat gtaggcggtg ctacagagtt cttgaagtgg tggcctaact   5640
acggctacac tagaagaaca gtatttggta tctgcgctct gctgaagcca gttaccttcg   5700
gaaaaagagt tggtagctct tgatccggca aacaaaccac cgctggtagc ggtggttttt   5760
ttgtttgcaa gcagcagatt acgcgcagaa aaaaaggatc tcaagaagat cctttgatct   5820
tttctacggg gtctgacgct cagtggaacg aaaactcacg ttaagggatt ttggtcatga   5880
gattatcaaa aaggatcttc acctagatcc ttttaaatta aaaatgaagt tttaaatcaa   5940
tctaaagtat atatgagtaa aaatattccg gaattgccag ctggggcgcc ctctggtaag   6000
gttgggaagc cctgcaaagt aaactggatg gctttcttgc cgccaaggat ctgatggcgc   6060
aggggatcaa gatctgatca agagacagga tgaggatcgt ttcgcatgat tgaacaagat   6120
ggattgcacg caggttctcc ggccgcttgg gtggagaggc tattcggcta tgactgggca   6180
caacagacaa tcggctgctc tgatgccgcc gtgttccggc tgtcagcgca ggggcgcccg   6240
gttctttttg tcaagaccga cctgtccggt gccctgaatg aactgcagga cgaggcagcg   6300
cggctatcgt ggctggccac gacgggcgtt ccttgcgcag ctgtgctcga cgttgtcact   6360
gaagcgggaa gggactggct gctattgggc gaagtgccgg ggcaggatct cctgtcatcc   6420
caccttgctc ctgccgagaa agtatccatc atggctgatg caatgcggcg gctgcatacg   6480
cttgatccgg ctacctgccc attcgaccac caagcgaaac atcgcatcga gcgagcacgt   6540
actcggatgg aagccggtct tgtcgatcag gatgatctgg acgaagagca tcaggggctc   6600
```

gcgccagccg aactgttcgc caggctcaag gcgcgcatgc ccgacggcga ggatctcgtc 6660
gtgacccatg gcgatgcctg cttgccgaat atcatggtgg aaaatggccg cttttctgga 6720
ttcatcgact gtggccggct gggtgtggcg gaccgctatc aggacatagc gttggctacc 6780
cgtgatattg ctgaagagct tggcggcgaa tgggctgacc gcttcctcgt gctttacggt 6840
atcgccgctc ccgattcgca gcgcatcgcc ttctatcgcc ttcttgacga gttcttctga 6900
accggtaata ttattgaagc atttatcagg gttattgtct catgagcgga tacatatttg 6960
aatgtattta gaaaaataaa caaatagggg ttccgcgcac atttccccga aaagtgccac 7020
ctgacgtcta agaaaccatt attatcatga cattaaccta taaaaatagg cgtatcacga 7080
ggccctttcg tctcgcgcgt ttcggtgatg acggtgaaaa cctctgacac atgcagctcc 7140
cggagacggt cacagcttgt ctgtaagcgg atgccgggag cagacaagcc cgtcagggcg 7200
cgtcagcggg tgttggcggg tgtcggggct ggcttaacta tgcggcatca gagcagattg 7260
tactgagagt gcaccatatg cggtgtgaaa taccgcacag atgcgtaagg agaaaatacc 7320
gcatcaggcg attccaacat ccaataaatc atacaggcaa ggcaaagaat tagcaaaatt 7380
aagcaataaa gcctcagagc ataaagctaa atcggttgta ccaaaaacat tatgaccctg 7440
taatactttt gcgggagaag cctttatttc aacgcaagga taaaaatttt tagaaccctc 7500
atatatttta aatgcaatgc ctgagtaatg tgtaggtaaa gattcaaacg ggtgagaaag 7560
gccggagaca gtcaaatcac catcaatatg atattcaacc gttctagctg ataaattcat 7620
gccggagagg gtagctattt ttgagaggtc tctacaaagg ctatcaggtc attgcctgag 7680
agtctggagc aaacaagaga atcgatgaac ggtaatcgta aaactagcat gtcaatcata 7740
tgtaccccgg ttgataatca gaaaagcccc aaaaacagga agattgtata agcaaatatt 7800
taaattgtaa gcgttaatat tttgttaaaa ttcgcgttaa atttttgtta aatcagctca 7860 tttttaacc aataggccga aatcggcaaa atcccttata aatcaaaaga atagaccgag 7920
atagggttga gtgttgttcc agtttggaac aagagtccac tattaaagaa cgtggactcc 7980
aacgtcaaag ggcgaaaaac cgtctatcag ggcgatggcc cactacgtga accatcaccc 8040
taatcaagtt ttttggggtc gaggtgccgt aaagcactaa atcggaaccc taaagggagc 8100
ccccgattta gagcttgacg gggaaagccg gcgaacgtgg cgagaaagga agggaagaaa 8160
gcgaaaggag cgggcgctag ggcgctggca agtgtagcgg tcacgctgcg cgtaaccacc 8220
acacccgccg cgcttaatgc gccgctacag ggcgcgtact atggttgctt tgacgagcac 8280
gtataacgtg ctttcctcgt tagaatcaga gcgggagcta aacaggaggc cgattaaagg 8340
gattttagac aggaacggta cgccagaatc ctgagaagtg tttttataat cagtgaggcc 8400
accgagtaaa agagtctgtc catcacgcaa attaaccgtt gtcgcaatac ttctttgatt 8460
agtaataaca tcacttgcct gagtagaaga actcaaacta tcggccttgc tggtaatatc 8520
cagaacaata ttaccgccag ccattgcaac ggaatcgcca ttcgccattc aggctgcgca 8580
actgttggga agggcgatcg gtgcgggcct cttcgctatt acgccagct 8629

<210> SEQ ID NO 9
<211> LENGTH: 4977
<212> TYPE: DNA
<213> ORGANISM: Adeno-associated virus

<400> SEQUENCE: 9
gcgcgctcgc tcgctcactg aggccgcccg ggcaaagccc gggcgtcggg cgacctttgg 60

```
tcgcccggcc tcagtgagcg agcgagcgcg cagagaggga gtggccaact ccatcactag    120
gggttccttg tagttaatga ttaacccgcc atgctactta tctacgtagc catgctctag    180
agtttaaaca agcttgcatg tctaagctag acccttcaga ttaaaaataa ctgaggtaag    240
ggcctgggta ggggaggtgg tgtgagacgc tcctgtctct cctctatctg cccatcggcc    300
ctttggggag gaggaatgtg cccaaggact aaaaaaaggc catggagcca gaggggcgag    360
ggcaacagac ctttcatggg caaaccttgg ggccctgctg tctagcatgc cccactacgg    420
gtctaggctg cccatgtaag gaggcaaggc ctggggacac ccgagatgcc tggttataat    480
taacccagac atgtggctgc cccccccccc ccaacacctg ctgcctctaa aaataaccct    540
gtccctggtg gatcccctgc atgcgaagat cttcgaacaa ggctgtgggg gactgagggc    600
aggctgtaac aggcttgggg gccagggctt atacgtgcct gggactccca aagtattact    660
gttccatgtt cccggcgaag ggccagctgt cccccgccag ctagactcag cacttagttt    720
aggaaccagt gagcaagtca gcccttgggg cagcccatac aaggccatgg ggctgggcaa    780
gctgcacgcc tgggtccggg gtgggcacgg tgcccgggca acgagctgaa agctcatctg    840
ctctcagggg cccctccctg ggacagcccc ctcctggcta gtcacaccct gtaggctcct    900
ctatataacc caggggcaca ggggctgccc tcattctacc accacctcca cagcacagac    960
agacactcag gagcagccag cggcgcgccc aggtaagttt agtctttttg tcttttattt   1020
caggtcccgg atccggtggt ggtgcaaatc aaagaactgc tcctcagtgg atgttgcctt   1080
tacttctagg cctgtacgga agtgttactt ctgctctaaa agctgcggaa ttgtacccgc   1140
ggccgccacc atgctgtggt gggaggaggt ggaggattgt tatgaaaggg aggacgtgca   1200
gaagaagact tttaccaagt gggtgaacgc tcagttcagc aaatttggga agcagcacat   1260
cgagaatctg ttttccgacc tgcaggatgg gagacggctg ctggatctgc tggaaggact   1320
gactggccag aagctgccca aagagaaggg gagcactagg gtgcacgccc tgaacaacgt   1380
gaacaaagct ctgagagtgc tgcagaacaa caacgtggat ctggtgaata ttggcagtac   1440
tgatatcgtg gacgggaacc acaaactgac actgggcctg atctggaaca ttattctgca   1500
ctggcaggtg aaaaatgtga tgaagaacat catggccggg ctgcagcaga ccaattccga   1560
gaagatcctg ctgtcttggg tgcggcagag cacccgcaac tatccccagg tgaacgtgat   1620
taacttcact acatcctgga gcgacgggct ggccctgaat gctctgattc acagccacag   1680
gcctgatctg ttcgactgga atagcgtggt gtgccagcag tctgccacac agcgcctgga   1740
acatgccttc aatatcgctc ggtaccagct ggggatcgaa aaactgctgg acccagagga   1800
tgtggacact acatacccag ataaaaagtc tattctgatg tacattacta gcctgttcca   1860
ggtgctgcca cagcaggtgt ctattgaagc cattcaggag gtggaaatgc tgccccgccc   1920
ccccaaagtg actaaagagg agcattttca gctgcatcat cagatgcatt acagccagca   1980
gattaccgtg agcctggctc agggatatga gcgcaccagt agtccaaaac cacggttcaa   2040
gtcctacgct tatacccagg ctgcctacgt gacaactagc gaccctacta gatcccccct   2100
tccatcccag cacctggagg ccccagagga caagagcttt gggtccagcc tgatggaaag   2160
cgaggtgaat ctggatcggt accagacagc cctggaggag gtgctgagct ggctgctgag   2220
tgctgaagac acactgcagg cccagggcga aatttccaat gacgtggaag tggtgaagga   2280
tcagttccac acacacgagg gctatatgat ggacctgaca gctcaccagg ggcgcgtggg   2340
caatatcctg cagctgggct ctaaactgat cggcaccggg aaactgagtg aggacgagga   2400
aacagaagtg caggagcaga tgaacctgct gaacagccgc tgggagtgtc tgagagtggc   2460
```

```
tagtatggag aagcagtcca acctgcaccg ggtgctgatg gacctgcaga accagaaact   2520
gaaagagctg aacgactggc tgacaaagac tgaggaacgc acaaggaaga tggaggagga   2580
gccactggga cccgacctgg aggatctgaa gagacaggtg cagcagcata aggtgctgca   2640
ggaggatctg gaacaggagc aggtgcgggt gaactccctg acacatatgg tggtggtggt   2700
ggacgaatct agtggagatc acgccaccgc cgccctggag gaacagctga aggtgctggg   2760
ggaccggtgg gccaacattt gccggtggac cgaggacagg tgggtgctgc tgcaggacat   2820
cctgctgaaa tggcagaggc tgaccgagga gcagtgtctg tttagtgctt ggctgagcga   2880
gaaagaggac gccgtgaaca agatccacac aaccggcttt aaggatcaga acgaaatgct   2940
gtctagcctg cagaaactgg ctgtgctgaa ggccgatctg gagaaaaaga agcagagcat   3000
gggcaaactg tatagcctga aacaggacct gctgagcacc ctgaagaaca agagcgtgac   3060
ccagaagaca gaagcctggc tggataactt tgcccgctgc tgggacaacc tggtgcagaa   3120
actggagaaa agtacagctc agatctctca ggctgtgacc acaacccagc ctagcctgac   3180
ccagacaacc gtgatggaaa ccgtgaccac cgtgacaacc cgcgaacaga tcctggtgaa   3240
acatgcccag gaagagctgc cacctccacc tccccagaag aagagaaccc tggagcggct   3300
gcaggagctg caggaagcca ctgacgaact ggacctgaag ctgaggcagg ccgaagtgat   3360
taaggggtct tggcagcctg tgggcgatct gctgattgat tccctgcagg accacctgga   3420
aaaggtgaag gctctgagag gcgaaattgc tccactgaag gagaacgtga gtcatgtgaa   3480
cgatctggct agacagctga caacactggg catccagctg agcccataca atctgagcac   3540
actggaggac ctgaatacca ggtggaagct gctgcaggtg gctgtggaag accgggtgcg   3600
gcagctgcat gaggcccatc gcgacttcgg accagccagc cagcactttc tgagcacatc   3660
cgtgcagggg ccctgggaga gggccatttc tcccaacaag gtgccctact atattaatca   3720
cgagacccag accacttgtt gggaccatcc caagatgaca gaactgtacc agtccctggc   3780
cgatctgaac aacgtgaggt ttagcgctta cagaaccgct atgaagctga gacggctgca   3840
gaaggccctg tgcctggatc tgctgtccct gtccgccgcc tgcgatgccc tggatcagca   3900
taatctgaag cagaacgatc agccaatgga tatcctgcag atcatcaact gcctgaccac   3960
tatctacgac aggctggagc aggagcacaa caacctggtg aacgtgcctc tgtgcgtgga   4020
tatgtgcctg aactggctgc tgaacgtgta tgacactggg cgcaccggcc ggatcagagt   4080
gctgagtttt aaaactggga ttatctccct gtgtaaggcc cacctggagg acaagtacag   4140
gtacctgttc aagcaggtgg ctagtagcac tggattttgt gaccagcgcc gcctgggact   4200
gctgctgcat gatagtatcc agattcctag acagctggga gaggtggcta gtttcggagg   4260
atctaacatc gaacccagcg tgcgcagctg tttccagttt gccaataaca aacctgaaat   4320
cgaggctgct ctgttcctgg attggatgcg cctggaacca cagagcatgg tgtggctgcc   4380
tgtgctgcac agagtggctg ccgccgaaac tgccaagcac caggctaaat gcaacatctg   4440
caaggaatgt cccattatcg gctttcgcta caggagtctg aaacatttta actacgatat   4500
ttgccagagc tgcttctttt ccggaagagt ggccaaagga cacaagatgc actaccctat   4560
ggtggaatat tgcaccccaa ctacatctgg cgaagatgtg cgcgattttg ccaaggtgct   4620
gaagaataag tttcggacta agaggtactt cgccaagcac ccccgcatgg ggtatctgcc   4680
agtgcagaca gtgctggaag gagacaatat ggagaccgat acaatgtgag cggccgcaat   4740
aaaagatctt tattttcatt agatctgtgt gttggttttt tgtgtgtcta gagtcgacca   4800
```

-continued

| | | | | | | |
|---|---|---|---|---|---|---|
| gagcatggct | acgtagataa | gtagcatggc | gggttaatca | ttaactacaa | ggaacccta | 4860 |
| gtgatggagt | tggccactcc | ctctctgcgc | gctcgctcgc | tcactgaggc | cgggcgacca | 4920 |
| aaggtcgccc | gacgcccggg | ctttgcccgg | gcggcctcag | tgagcgagcg | agcgcgc | 4977 |